United States Patent
Brogdon et al.

(10) Patent No.: US 11,028,177 B2
(45) Date of Patent: Jun. 8, 2021

(54) EFFECTIVE TARGETING OF PRIMARY HUMAN LEUKEMIA USING ANTI-CD123 CHIMERIC ANTIGEN RECEPTOR ENGINEERED T CELLS

(71) Applicants: Novartis AG, Basel (CH); The Trustees of the University of Pennsylvania, Philadelphia, PA (US)

(72) Inventors: Jennifer Brogdon, Cambridge, MA (US); Saar Gill, Philadelphia, PA (US); Carl H. June, Merion Station, PA (US); Michael D. Kalos, New York, NY (US); Andreas Loew, Cambridge, MA (US); John Scholler, Narberth, PA (US)

(73) Assignees: Novartis AG, Basel (CH); The Trustees of the University of Pennsylvania, Philadelphia, PA (US)

( * ) Notice: Subject to any disclaimer, the term of this patent is extended or adjusted under 35 U.S.C. 154(b) by 405 days.

(21) Appl. No.: 15/400,096

(22) Filed: Jan. 6, 2017

(65) Prior Publication Data

US 2017/0183415 A1   Jun. 29, 2017

Related U.S. Application Data

(62) Division of application No. 14/184,895, filed on Feb. 20, 2014, now Pat. No. 9,573,988.

(60) Provisional application No. 61/865,856, filed on Aug. 14, 2013, provisional application No. 61/767,058, filed on Feb. 20, 2013.

(51) Int. Cl.

| | |
|---|---|
| *C07K 16/22* | (2006.01) |
| *C07K 16/28* | (2006.01) |
| *C07K 14/725* | (2006.01) |
| *C07K 14/705* | (2006.01) |
| *A61K 35/17* | (2015.01) |
| *A61K 35/28* | (2015.01) |
| *A61K 38/17* | (2006.01) |
| *A61K 39/395* | (2006.01) |
| *A61K 39/00* | (2006.01) |

(52) U.S. Cl.
CPC .......... *C07K 16/2866* (2013.01); *A61K 35/17* (2013.01); *A61K 35/28* (2013.01); *A61K 38/1774* (2013.01); *A61K 39/3955* (2013.01); *C07K 14/7051* (2013.01); *C07K 14/70517* (2013.01); *C07K 16/2803* (2013.01); *A61K 2039/505* (2013.01); *A61K 2039/507* (2013.01); *A61K 2039/5158* (2013.01); *C07K 2317/24* (2013.01); *C07K 2317/53* (2013.01); *C07K 2317/622* (2013.01); *C07K 2317/73* (2013.01); *C07K 2319/00* (2013.01); *C07K 2319/30* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,359,046 A | 10/1994 | Capon et al. |
| 5,541,063 A | 7/1996 | Kitamura et al. |
| 5,639,605 A | 6/1997 | Kitamura et al. |
| 5,686,281 A | 11/1997 | Roberts |
| 5,712,149 A | 1/1998 | Roberts |
| 5,874,240 A | 2/1999 | Ni et al. |
| 5,906,936 A | 5/1999 | Eshhar et al. |
| 6,103,521 A | 8/2000 | Capon et al. |
| 6,177,078 B1 | 1/2001 | Lopez |
| 6,319,494 B1 | 11/2001 | Capon et al. |
| 6,355,779 B1 | 3/2002 | Goodwin et al. |
| 6,410,319 B1 | 6/2002 | Raubitschek et al. |
| 6,569,997 B1 | 5/2003 | Kwon |
| 7,049,136 B2 | 5/2006 | Seed et al. |
| 7,052,906 B1 | 5/2006 | Lawson et al. |
| 7,070,995 B2 | 7/2006 | Jensen |
| 7,265,209 B2 | 9/2007 | Jensen |
| 7,319,143 B2 | 1/2008 | Gross et al. |
| 7,320,787 B2 | 1/2008 | Seed et al. |
| 7,446,190 B2 | 11/2008 | Sadelain et al. |
| 7,446,191 B2 | 11/2008 | Jensen |
| 7,514,537 B2 | 4/2009 | Jensen |
| 7,627,643 B1 | 12/2009 | Ignatoff et al. |
| 7,638,326 B2 | 12/2009 | June et al. |
| 7,741,465 B1 | 6/2010 | Eshhar et al. |
| 7,745,140 B2 | 6/2010 | June et al. |
| 7,754,482 B2 | 7/2010 | Riley et al. |
| 7,994,298 B2 | 8/2011 | Zhang et al. |
| 8,211,422 B2 | 7/2012 | Eshhar et al. |
| 8,252,914 B2 | 8/2012 | Zhang et al. |

(Continued)

FOREIGN PATENT DOCUMENTS

| | | |
|---|---|---|
| CN | 102796198 A | 11/2012 |
| CN | 103492406 A | 1/2014 |

(Continued)

OTHER PUBLICATIONS

International Search Report and Written Opinion from PCT/CN2014/084696, dated May 25, 2015.

(Continued)

*Primary Examiner* — Michael D Pak
(74) *Attorney, Agent, or Firm* — Lando & Anastasi, LLP

(57) ABSTRACT

The invention provides compositions and methods for treating leukemia, for example, acute myeloid leukemia (AML) and B-cell acute lymphoid leukemia (B-ALL). The invention also relates to at least one chimeric antigen receptor (CAR) specific to CD123, vectors comprising the same, and recombinant T cells comprising the CD123 CAR. The invention also includes methods of administering a genetically modified T cell expressing a CAR that comprises a CD123 binding domain. The invention also includes methods of bone marrow ablation for use in treatments necessitating bone marrow reconditioning or transplant.

47 Claims, 49 Drawing Sheets

Specification includes a Sequence Listing.

(56) References Cited

U.S. PATENT DOCUMENTS

| | | |
|---|---|---|
| 8,389,282 B2 | 3/2013 | Sadelain et al. |
| 8,399,645 B2 | 3/2013 | Campana et al. |
| 8,465,743 B2 | 6/2013 | Rosenberg et al. |
| 8,492,119 B2 | 7/2013 | Tawara et al. |
| 8,637,307 B2 | 1/2014 | June et al. |
| 8,722,400 B2 | 5/2014 | Riley et al. |
| 8,852,551 B2 | 10/2014 | Jordan |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,101,584 B2 | 8/2015 | June et al. |
| 9,102,760 B2 | 8/2015 | June et al. |
| 9,102,761 B2 | 8/2015 | June et al. |
| 9,394,368 B2 | 7/2016 | Brogdon et al. |
| 9,573,988 B2 | 2/2017 | Brogdon et al. |
| 9,745,368 B2 | 8/2017 | Milone et al. |
| 9,777,061 B2 | 10/2017 | Ebersbach et al. |
| 9,815,901 B2 | 11/2017 | Brogdon et al. |
| 2003/0039611 A1 | 2/2003 | Jordan |
| 2003/0060444 A1 | 3/2003 | Finney et al. |
| 2003/0077249 A1 | 4/2003 | Bebbington et al. |
| 2003/0148982 A1 | 8/2003 | Brenner et al. |
| 2003/0224520 A1 | 12/2003 | June et al. |
| 2004/0038886 A1 | 2/2004 | Finney et al. |
| 2004/0043401 A1 | 3/2004 | Sadelain et al. |
| 2005/0113564 A1 | 5/2005 | Campana et al. |
| 2005/0129671 A1 | 6/2005 | Cooper et al. |
| 2007/0036773 A1 | 2/2007 | Cooper et al. |
| 2008/0131415 A1 | 6/2008 | Riddell et al. |
| 2009/0252742 A1 | 10/2009 | Bergstein |
| 2009/0257994 A1 | 10/2009 | Jensen |
| 2011/0052554 A1 | 3/2011 | Zakrzewski et al. |
| 2011/0052574 A1 | 3/2011 | Dick et al. |
| 2012/0070448 A1 | 3/2012 | Tawara et al. |
| 2012/0070450 A1 | 3/2012 | Ishikawa et al. |
| 2012/0148552 A1 | 6/2012 | Jensen |
| 2012/0189540 A1 | 7/2012 | Bergstein |
| 2012/0244116 A1 | 9/2012 | Hiwase et al. |
| 2012/0321667 A1 | 12/2012 | Sentman |
| 2012/0328619 A1 | 12/2012 | Fey et al. |
| 2013/0071409 A1 | 3/2013 | Riley et al. |
| 2013/0071414 A1 | 3/2013 | Dotti et al. |
| 2013/0149303 A1 | 6/2013 | Drane et al. |
| 2013/0149337 A1 | 6/2013 | Cooper et al. |
| 2013/0155909 A1 | 6/2013 | Jackson et al. |
| 2013/0230510 A1 | 9/2013 | Dick et al. |
| 2013/0287748 A1 | 10/2013 | June et al. |
| 2014/0050708 A1 | 2/2014 | Powell et al. |
| 2014/0099309 A1 | 4/2014 | Powell, Jr. et al. |
| 2014/0099340 A1 | 4/2014 | June et al. |
| 2014/0106449 A1 | 4/2014 | June et al. |
| 2014/0186947 A1 | 7/2014 | June et al. |
| 2014/0212446 A1 | 7/2014 | Riley et al. |
| 2014/0219975 A1 | 8/2014 | June et al. |
| 2014/0227237 A1 | 8/2014 | June et al. |
| 2014/0271635 A1 | 9/2014 | Brogdon et al. |
| 2014/0322169 A1 | 10/2014 | Harper et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0370045 A1 | 12/2014 | June et al. |
| 2015/0017141 A1 | 1/2015 | June et al. |
| 2015/0119555 A1 | 4/2015 | Jung et al. |
| 2015/0140019 A1 | 5/2015 | June et al. |
| 2015/0190428 A1 | 7/2015 | June et al. |
| 2015/0202286 A1 | 7/2015 | June et al. |
| 2015/0283178 A1 | 10/2015 | June et al. |
| 2015/0290244 A1 | 10/2015 | June et al. |
| 2015/0342994 A1 | 12/2015 | Riley et al. |
| 2016/0046724 A1 | 2/2016 | Brogdon et al. |
| 2016/0051651 A1 | 2/2016 | Brogdon et al. |
| 2016/0068601 A1 | 3/2016 | Brogdon et al. |
| 2016/0096892 A1 | 4/2016 | Brogdon et al. |
| 2016/0185861 A1 | 6/2016 | Bedoya et al. |
| 2016/0311907 A1 | 10/2016 | Brogdon et al. |
| 2016/0311917 A1 | 10/2016 | Beatty et al. |
| 2016/0340406 A1 | 11/2016 | Zhao et al. |
| 2016/0362472 A1 | 12/2016 | Bitter et al. |
| 2017/0008963 A1 | 1/2017 | Brogdon et al. |
| 2017/0081411 A1 | 3/2017 | Engels et al. |
| 2017/0137783 A1 | 5/2017 | Bedoya et al. |
| 2017/0209492 A1 | 7/2017 | June et al. |
| 2017/0211055 A1 | 7/2017 | Brogdon et al. |
| 2017/0226495 A1 | 8/2017 | Guimaraes |
| 2017/0239294 A1 | 8/2017 | Thomas-Tikhonenko et al. |
| 2017/0260268 A1 | 9/2017 | Beatty et al. |
| 2017/0274014 A1 | 9/2017 | Brogdon et al. |
| 2017/0306416 A1 | 10/2017 | Bedoya et al. |
| 2017/0335281 A1 | 11/2017 | Loew et al. |
| 2018/0022795 A1 | 1/2018 | Milone et al. |
| 2018/0044423 A1 | 2/2018 | Ebersbach et al. |
| 2018/0044424 A1 | 2/2018 | June et al. |
| 2018/0118834 A1 | 5/2018 | Brogdon et al. |
| 2018/0125892 A1 | 5/2018 | Brannetti et al. |
| 2018/0133296 A1 | 5/2018 | Barrett et al. |
| 2018/0140602 A1 | 5/2018 | Angst et al. |
| 2018/0230193 A1 | 8/2018 | Loew et al. |
| 2018/0252727 A1 | 9/2018 | Garfall et al. |
| 2018/0258149 A1 | 9/2018 | Motz et al. |
| 2018/0298068 A1 | 10/2018 | Albelda |
| 2018/0312595 A1 | 11/2018 | Brogdon et al. |
| 2019/0000880 A1 | 1/2019 | Motz et al. |
| 2019/0000944 A1 | 1/2019 | Brogdon et al. |
| 2019/0135940 A1 | 5/2019 | Brogdon et al. |
| 2019/0151365 A1 | 5/2019 | Anak et al. |
| 2019/0153061 A1 | 5/2019 | Brogdon et al. |
| 2019/0161542 A1 | 5/2019 | Gill et al. |
| 2019/0263914 A1 | 8/2019 | Brogdon et al. |
| 2019/0292238 A1 | 9/2019 | Bitter et al. |
| 2019/0292257 A1 | 9/2019 | Bedoya et al. |
| 2019/0298715 A1 | 10/2019 | Motz et al. |
| 2019/0330356 A1 | 10/2019 | Brogdon et al. |
| 2019/0336504 A1 | 11/2019 | Gill et al. |
| 2019/0375815 A1 | 12/2019 | Engels et al. |
| 2019/0382500 A1 | 12/2019 | Abujoub et al. |
| 2019/0388471 A1 | 12/2019 | June et al. |
| 2019/0389928 A1 | 12/2019 | Posey et al. |

FOREIGN PATENT DOCUMENTS

| | | |
|---|---|---|
| EP | 0574512 A1 | 12/1993 |
| EP | 0871495 A1 | 10/1998 |
| EP | 1226244 A2 | 7/2002 |
| WO | 1992015322 A1 | 9/1992 |
| WO | 199530014 A1 | 11/1995 |
| WO | 9623814 A1 | 8/1996 |
| WO | 9624671 A1 | 8/1996 |
| WO | 1997015669 A1 | 5/1997 |
| WO | 9723613 A2 | 7/1997 |
| WO | 1997024373 A1 | 7/1997 |
| WO | 9818809 A1 | 5/1998 |
| WO | 9900494 A2 | 1/1999 |
| WO | 9957268 A1 | 11/1999 |
| WO | 0014257 A1 | 3/2000 |
| WO | 2002033101 A1 | 4/2002 |
| WO | 02077029 A2 | 10/2002 |
| WO | 02088334 A1 | 11/2002 |
| WO | 2003057171 A2 | 7/2003 |
| WO | 2005019429 A2 | 3/2005 |
| WO | 2005044996 A2 | 5/2005 |
| WO | 2005/118788 A2 | 12/2005 |
| WO | 2006060878 A1 | 6/2006 |
| WO | 2008045437 A2 | 4/2008 |
| WO | 2008127735 A1 | 10/2008 |
| WO | 2010085660 A2 | 7/2010 |
| WO | 2010126066 A1 | 11/2010 |
| WO | 2011059836 A2 | 5/2011 |
| WO | 2011070109 A1 | 6/2011 |
| WO | 2011097477 A1 | 8/2011 |
| WO | 2011156860 A1 | 12/2011 |
| WO | 2012033885 A1 | 3/2012 |
| WO | 2012058460 A2 | 5/2012 |

(56) References Cited

FOREIGN PATENT DOCUMENTS

| | | |
|---|---|---|
| WO | 2012079000 A1 | 6/2012 |
| WO | 2012082841 A2 | 6/2012 |
| WO | 2012/099973 A2 | 7/2012 |
| WO | 2012127464 A2 | 9/2012 |
| WO | 2012129514 A1 | 9/2012 |
| WO | 2012135854 A2 | 10/2012 |
| WO | 2012138858 A1 | 10/2012 |
| WO | 2013019615 A2 | 2/2013 |
| WO | 2013033626 A2 | 3/2013 |
| WO | 2013040371 A2 | 3/2013 |
| WO | 2013040557 A2 | 3/2013 |
| WO | 2013059593 A1 | 4/2013 |
| WO | 2013092001 A1 | 6/2013 |
| WO | 2013/126712 A1 | 8/2013 |
| WO | 2013126726 A1 | 8/2013 |
| WO | 2013126729 A1 | 8/2013 |
| WO | 2013126733 A1 | 8/2013 |
| WO | 2013173820 A2 | 11/2013 |
| WO | 2014/011984 A1 | 1/2014 |
| WO | 2014/011987 A1 | 1/2014 |
| WO | 2014/011993 A2 | 1/2014 |
| WO | 2014/012001 A1 | 1/2014 |
| WO | 2014011988 A2 | 1/2014 |
| WO | 2014011996 A1 | 1/2014 |
| WO | 2014031687 A1 | 2/2014 |
| WO | 2014039513 A2 | 3/2014 |
| WO | 2014/055442 A2 | 4/2014 |
| WO | 2014055657 A1 | 4/2014 |
| WO | 2014130635 A1 | 8/2014 |
| WO | 2014130657 A1 | 8/2014 |
| WO | 2014/145252 A2 | 9/2014 |
| WO | 2014138805 A1 | 9/2014 |
| WO | 2014138819 A1 | 9/2014 |
| WO | 2014144622 A2 | 9/2014 |
| WO | 2014153270 A1 | 9/2014 |
| WO | 2015044386 A1 | 4/2015 |
| WO | 2015090229 A1 | 6/2015 |
| WO | 2015090230 A1 | 6/2015 |
| WO | 2015/105522 A1 | 7/2015 |
| WO | 2015112626 A1 | 7/2015 |
| WO | 2015124715 A1 | 8/2015 |
| WO | 2015/142661 A1 | 9/2015 |
| WO | 2015140268 A1 | 9/2015 |
| WO | 2015142675 A2 | 9/2015 |
| WO | 2015157252 A1 | 10/2015 |
| WO | 2016014501 A1 | 1/2016 |
| WO | 2016014530 A1 | 1/2016 |
| WO | 2016014535 A1 | 1/2016 |
| WO | 2016014553 A1 | 1/2016 |
| WO | 2016014565 A2 | 1/2016 |
| WO | 2016014576 A1 | 1/2016 |
| WO | 2016019300 A1 | 2/2016 |
| WO | 2016025880 A1 | 2/2016 |
| WO | 2016028896 A1 | 2/2016 |
| WO | 2016044605 A1 | 3/2016 |

OTHER PUBLICATIONS

International Search Report for PCT/US2015/045898 dated Nov. 4, 2015.
International Search Report from PCT/US2011/064191 dated Jan. 5, 2012.
International Search Report including Written Opinon for PCT/US2014/017328 dated Jun. 26, 2014.
International Search Reporting and Written Opinion for PCT/CN2014/084695 dated May 21, 2015.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Jin et al, "Monoclonal Antibody-Mediated Targeting of CD123, IL-3 Receptor a Chain, Eliminates Human Acute Myeloid Leukemic Stem Cells" Cell Stem Cell (2009) vol. 5 pp. 31-42.
Johnson et al., "Gene therapy with human and mouse T-cell receptors mediates cancer regression and targets normal tissues expressing cognate antigen" Blood (2009) vol. 114 No. 3 pp. 535-545.
Jordan et al, "The interleukin-3 receptor alpha chain is a unique marker for human acute myelogenous leukaemia stem cells," Leukaemia (2000) vol. 14 pp. 1777-1784.
Jordan et al. "Targeting Myeloid Leukemia Stem Cells" Cancer (2010) vol. 2 No. 31 31ps21.
June et al., "Engineering lymphocyte subsets: tools, trials and tribulations" Nat Rev Immunol (2009) vol. 9 No. 10 pp. 704-716.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Kitamura et al. "Expression Cloning of the Human IL-3 Receptor cDNA Reveals a Shared Subunit for the Human IL-3 and GM-CSF Receptors" Cell (1991) vol. 66 pp. 1165-1174.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH), Orlando, FL, USA; Dec. 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letourneur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.

(56) References Cited

OTHER PUBLICATIONS

Macallan et al., "Measurement and modeling of human T cell kinetics" European Journal of Immunology (2003) vol. 33 pp. 2316-2326.
MacCallum R.M. et al, Antibody-antigen interactions: Contact analysis and binding site topography. J. Mol. Bioi., 1998, vol. 262, p. 732-745.
Maher et al., "Human T lymphocyte cytotoxicity and proliferation directed by a single chimeric TCRzeta/CD28 receptor," Nat. Biotechnol. 20: 70-75 (2002).
Mardiros et al. "T cells expressing CD123-specific chimeric antigen receptors exhibit specific cytolytic effector functions and antitumor effects against human acute myeloid leukemia," Blood (2013) vol. 122 No. 18 pp. 3138-3148.
Mardiros et al., "CD123-Specific Chimeric Antigen Receptor Redirected T Cells Exhibit Potent Cytolytic Activity and Multiple Effector Functions Against Acute Myeloid Leukemia without Altering Normal Hematopoietic Colony Formation in Vitro" Blood 120(21): abstract 950 (2011).
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Miyamoto et al. "AML1yETO-expressing nonleukemic stem cells in acute myelogenous leukemia with 8;21 chromosomal translocation" PNAS (2000) vol. 97 No. 13 pp. 7521-7526.
Molina, "A Decade of Rituximab: Improving Survival Outcomes in Non-Hodgkin's Lymphoma" Annu. Rev. Med. (2008) vol. 59 pp. 237-250.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Munoz et al, "Interleukin-3 receptor chain (CD123) is widely expresssed in hematologic malignancies, Haematologica" (2001), vol. 86 pp. 1261-1269.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.
NCBI Reference Sequence NM_000734.3 accessed Oct. 27, 2015 from http://www.ncbi.nlm.nih.gov/nuccore/NM_000734.3.
Nicholson et al., "Construction and Characterisation of a Function CD19 Specific Single Chain Fv Fragment for Immunotherapy of B Lineage Leukaemia and Lymphoma," Molecular Immunology 34(I6-I7): 1157-1165 (1997).
Nilsson et al, "Involvement and functional impairment of the CD34_CD38_Thy-1_hematopoietic stem cell pool in myelodysplastic syndromes with trisomy 8" Blood (2002) vol. 100 No. 1 pp. 259-267.
Pang et al, "Human bone marrow hematopoietic stem cells are increased in frequency and myeloid-biased with age" PNAS (2011) vol. 108 No. 50 pp. 20012-20017.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Baeksgaard & Sorensen, "Acute tumor lysis syndrome in solid tumors—a case report and review of the literature" Cancer Chemotherapy Pharmacology (2003) vol. 51 pp. 187-192.
Bendig, M.M. Humanization of rodent monoclonal antibodies by CDR grafting. Methods: A Companion to Methods in Enzymology, 1995; vol. 8, p. 83-93.
Bondanza et al. "Suicide gene therapy of graft-versus-host disease induced by central memory human T lymphocytes" Blood (2006) vol. 107 No. 5 pp. 1828-1836.
Brentjens et al. "Genetically Targeted T Cells Eradicate Systemic Acute Lymphoblastic Leukemia Xenografts", Clinical Cancer Research(2007) vol. 13, No. 18, pp. 5426-5435.
Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.
Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Call & Wucherpfennig, "The T Cell Receptor: Critical Role of the Membrane Environment in Receptor Assembly and Function" Annu. Rev. Immunol. (2005) vol. 23 pp. 101-125.
Cao et al. "Development and Application of a Multiplexable Flow cytometry-Based Assay to Quantify Cell-Mediated Cytolysis" Cytometry Part A (2010) vol. 77A pp. 534-545.
Carpenito et al. "Control of large, established tumor xenografts with genetically retargeted human T cells containing CD28 and CD137 domains", Proc Natl Acad Sci USA (2009) vol. 106 pp. 3360-3365.
Casset F, et al. A peptide mimetic of an anti-CD4 monoclonal antibody by rational design. Biochemical and Biophysical Research Communications, 2003, vol. 307, p. 198-205.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Du et al., "New Immunotoxins Targeting CD123, a Stem Cell Antigen on Acute Myeloid Leukemia Cells" J. Immunother. vol. 30, No. 6 pp. 607-613 (2007).
Dull et al, "A Third-Generation Lentivirus Vector with a Conditional Packaging System" Journal of Virology (1998) vol. 12 No. 11 pp. 8463-8471.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).

(56) References Cited

OTHER PUBLICATIONS

Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That Is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBan Acc. No. BAG36664.1 accessed Oct. 13, 2015 from http://www.ncbi.nlm.nih.gov/protein/BAG36664.1.
GenBank Acc. No. AAA62478.2 accessed Oct. 13, 2015 from http://www.ncbi.nlm.nih.gov/protein/AAA62478.2.
GenBank Accession No. M74782 accessed Oct. 27, 2015 from <http://www.ncbi.nlm.nih.gov/nuccore/M74782>.
Genbank Accession No. NM 005191 accessed Oct. 27, 2015 from <http://www.ncbi.nlm.nih.gov/nuccore/nm_005191>.
Genbank Accession No. NP 002174 accessed Oct. 27, 2015 from <http://www.ncbi.nlm.nih.gov/protein/NP_002174>.
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gill et al. "Preclinical targeting of human acute myeloid leukemia and myeloablation using chimeric antigen receptor-modified T cells", Blood (2014) vol. 123 No. 23 pp. 2343-2345.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hekele et al., "Growth Retardation of Tumors by Adoptive Transfer of Cytotoxic T Lymphocytes Reprogrammed by CD44V6-Specific SCFV:~-Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.

Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Hong et al. "Initiating and Cancer-Propagating Cells in TEL-AML1-Associated Childhood Leukemia" Science (2008) vol. 319 pp. 336-339.
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.
International Search Report and Written Opinion for PCT/CN2014/090505 dated May 6, 2015.
International Search Report and Written Opinion for PCT/CN2014/090508 dated May 22, 2015.
Gill et al. "Effective targeting of primary human acute myeloid leukemia using anti-CD123 chimeric antigen receptor engineered T cells" Cytotherapy, (2013) vol. 15, No. 4, pp. S13-S14.
John et al. "Blockade of PD-1 immunosuppression boosts CAR T-cell therapy" Oncoimmunology (2013) vol. 2, No. 10, pp. e26286:1-3.
Pizzitola et al. "Chimeric antigen receptors against CD33/CD123 antigens efficiently target primary acute myeloid leukemia cells in vivo" Leukemia (2014) vol. 28, No. 8, pp. 1596-1605.
Singapore Search Report and Written Opinion for Singapore Application No. 11201700770P dated Nov. 10, 2017.
Patel et al., "Impact of chimeric immune receptor extracellular protein domains on T cell function" Gene Therapy (1999) vol. 6 pp. 412-419.
Paul, W.E. Fundamental Immunology, 3rd Edition, 1993, pp. 292-295.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 aostimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Radhika et al., "Targeting Leukemias by CD123 Specific Chimerica Antigen Receptor" Blood(ASH Annual Meeting Abstracts) 118(21): abstract 1908 (2011).
Rapoport et al., "Restoration of immunity in lymphopenic individuals with cancer by vaccination and adoptive T-cell transfer" Nature Medicine (2005) vol. 11 No. 11 pp. 1230-1237.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Ruella et al. "Anti-CD123 Chimeric Antigen Receptor Redirected T Cells for Relapsed B-Cell Acute Lymphoblastic Leukemuia" Cytotherapy, vol. 16 No. 4 Suppl. S, (2014), p. s8.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Sato et al, "Expression and factor-dependent modulation of the interleukin-3 receptor subunits on human hematopoietic cells" Blood (1993) vol. 82 No. 3 pp. 752-761.

(56) References Cited

OTHER PUBLICATIONS

Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 146-452.
Testa et al, Elevated expression of IL-3R_ in acute myelogenous leukemia is associated with enhanced blast proliferation, increased cellularity, and poor prognosis Blood (2002) vol. 100 No. 8 pp. 2980-2988.
Tettamanti et al., "Targeting of the acute myeloid leukemia stem cells through immunotherapy: development of novel chimeric receptors specific for the CD123 antigen," OMICS group conference 2nd world congress on biotechology (2011) retrieved from internet www.omicsonline.org/biotechnology2011.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
UniProtKB Accession No. P26951 accessed Oct. 27, 2015 from <http://www.uniprot.org/uniprot/P26951>.
Vinay & Kwon, "Role of 4-1BB in immune responses" Immunology (1998) vol. 10 pp. 481-489.
Walter et al, "Clonal Architecture of Secondary Acute Myeloid Leukemia" The New England Journal of Medicine (2012) vol. 366 No. 12 pp. 1090-1098.
Weissman, "Paths to Cancer Therapies and Regerative Medicine," JAMA (2005) vol. 294 pp. 1359-1366.
Welch et al. "The origin and evolution of mutations in Acute Myeloid Leukemia" Cell (2012) vol. 150 No. 2 pp. 264-278.
Willemsen et al., "Genetic Engineering of T Cell Specificity for Immunotherapy of Cancer" Human Immunology (2003) vol. 64 pp. 56-68.
Wunderlich et al, "AML xenograft efficiency is significantly improved in NOD/SCID-IL2RG mice constitutively expressing human SCF, GM-CSF and IL-3" Leukemia (2010) vol. 24 pp. 1785-1788.
Yalcintepe et al, "Expression of interleukin-3 receptor subunits on defined subpopulations of acute myeloid leukemia blasts predicts the cytotoxicity of diphtheria toxin interleukin-3fusion protein against malignant progenitors that engraft in immunodeficient mice" Blood (2006), vol. 108 No. 10:3530-7.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Abaza et al. "Effects of Amino Acid Substitutions Outside an Antigenic Site on Protein Binding to Monoclonal Antibodies of Predictive Specificity Obtained by Peptide Immunization: Demonstration with Region 94-100 (Antigenic Site 3) of Myoglobin" Journal of Protein Chemistry (1992) vol. 11, No. 5, pp. 433-444.
Bonini et al. "Adoptive T-cell therapy for cancer: The era of engineered T cells" Eur J Immunol (2015) vol. 45, pp. 2457-2469.
Colman "Effects of amino acid sequence changes on antibody-antigen interactions" Research in Immunology (1994) vol. 145, No. 1, pp. 33-36.
Ibragimova et al. "Stability of the B-sheet of the WW Domain: A Molecular Dynamics Simulation Study" Biophysical Journal (1999) vol. 77, pp. 2191-2198.
Kochenderfer et al. "Treating B-cell cancer with T cells expressing anti-CD19 chimeric antigen receptors" Nature Reviews Clinical Oncology (2013) vol. 10, pp. 267-276.
Prazma et al. "Dendritic cell CD83: A therapeutic target or innocent bystander?" Immunology Letters (2008) vol. 115, pp. 1-8.
Rudikoff et al. "Single amino acid subsitution altering antigen-binding specificity" PNAS (1982) vol. 79, pp. 1979-1983.
Sznol "Blockade of the B7-H1/PD-1 Pathway as a Basis for Combination Anticancer Therapy" The Cancer Journal (2014) vol. 20, No. 4, pp. 290-295.
Testa et al. "CD123 is a membrane biomarker and a therapeutic target in hematologic malignancies" Biomarker Research (2014) vol. 2, No. 4, pp. 1-11.
Extended European Search Report for European Application No. 20177540.0 dated Oct. 5, 2020.

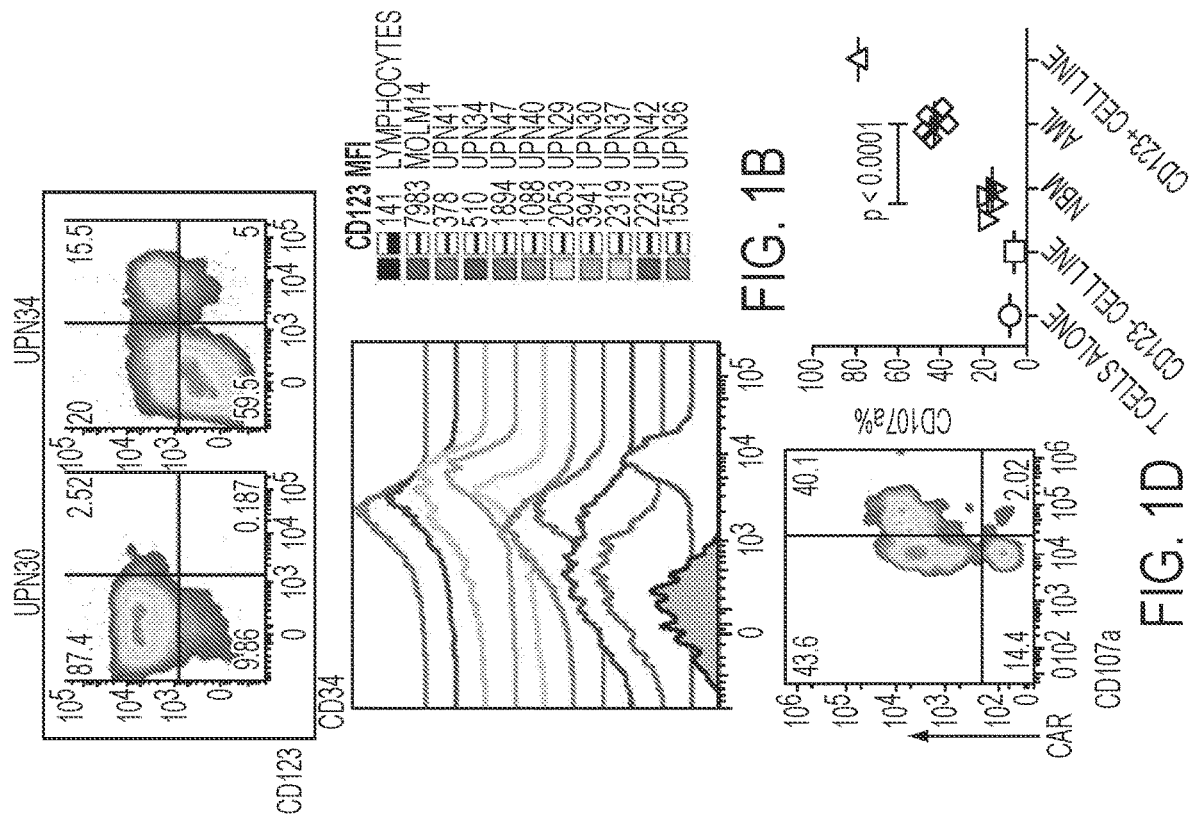

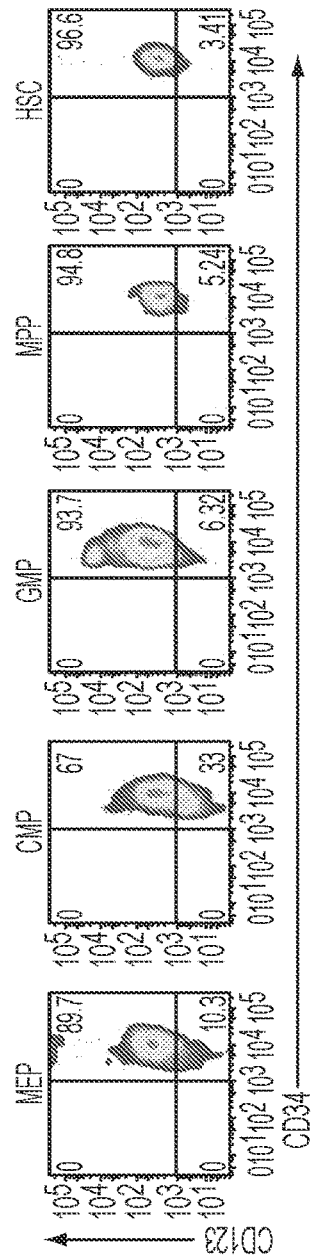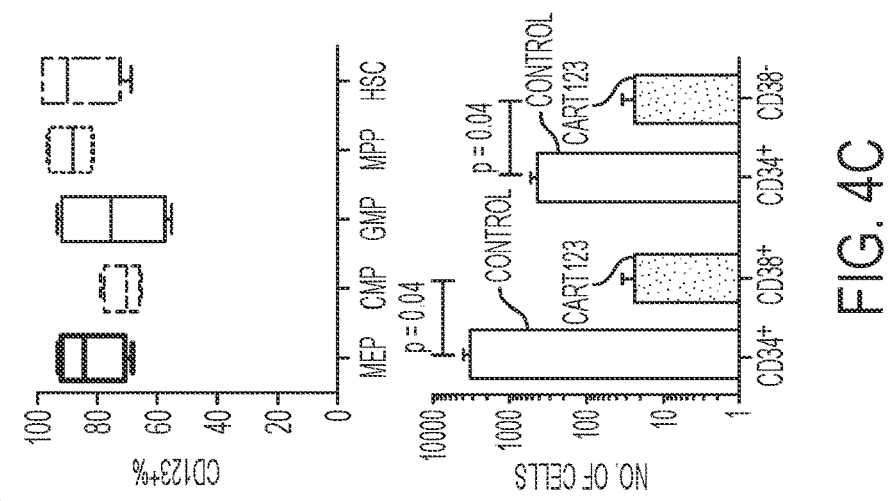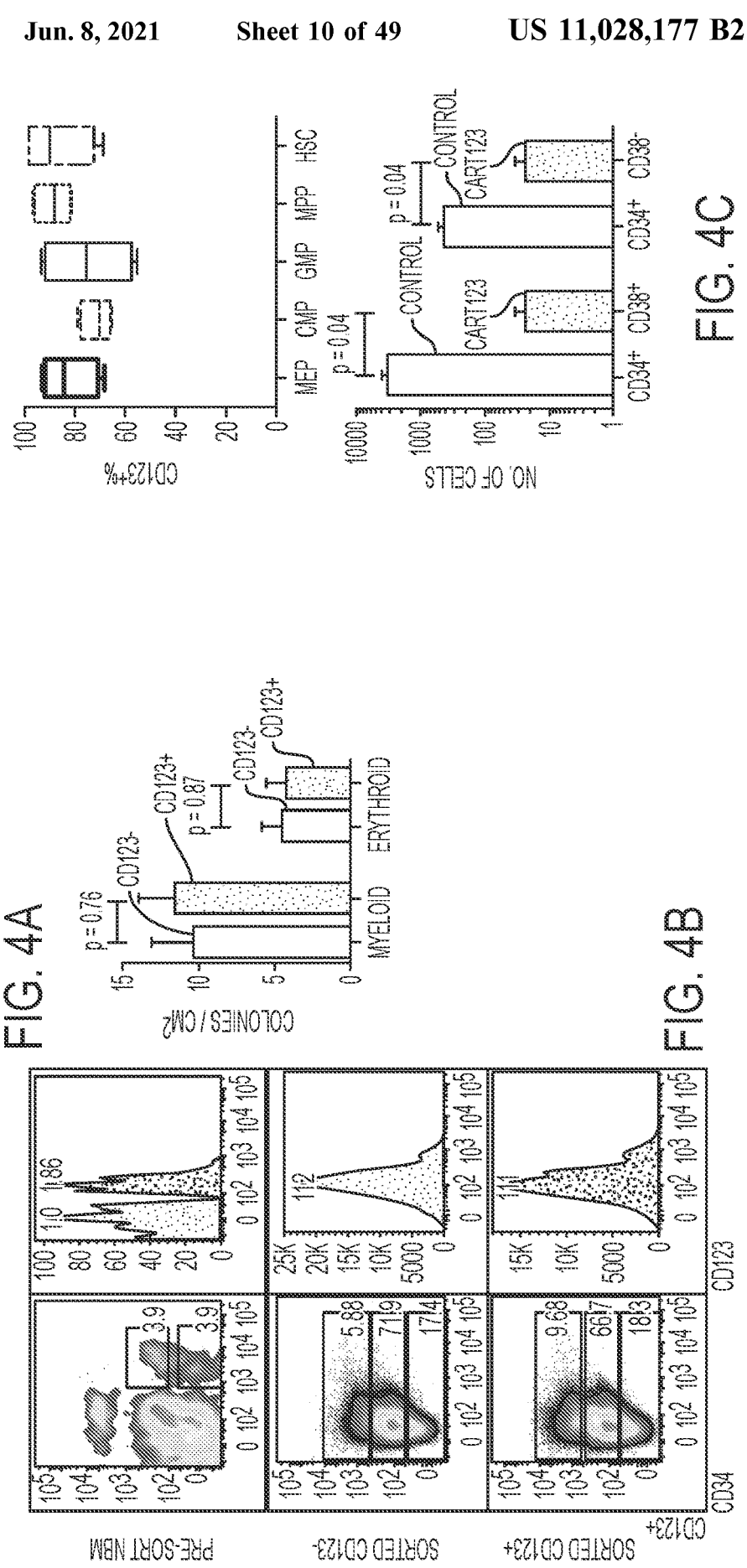
FIG. 4A
FIG. 4B
FIG. 4C

FIG. 7A

HUMANIZATION VH

FR1 (Kabat numbering 1–30; Chothia numbering has gap at position 7):

| CDR DEFINITION | | | | | | | | | | | | | | | | | | | | | | | | | | | CDR1 | | | |
|---|---|---|---|---|---|---|---|---|---|---|---|---|---|---|---|---|---|---|---|---|---|---|---|---|---|---|---|---|---|---|
| Kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| Chothia | 1 | 2 | 3 | 4 | 5 | 6 | 7 | – | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
| murine | Q | I | Q | L | V | Q | S | G | P | E | L | K | K | P | G | E | T | V | K | I | S | C | K | A | S | G | Y | I | F | T |
| NH1_1-03/Hz1 | Q | I | Q | L | V | Q | S | G | A | E | V | K | K | P | G | A | S | V | K | V | S | C | K | V | S | G | Y | I | F | T |
| NH_7.4.1/Hz1 | Q | I | Q | L | V | Q | S | G | S | E | L | K | K | P | G | A | S | V | K | V | S | C | K | V | S | G | Y | I | F | T |

FR3 (positions 66–94, with Kabat insertions 82a, 82b, 82c):

| Kabat | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| Chothia | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
| murine | R | E | A | F | S | L | E | T | S | A | S | T | A | Y | L | H | I | N | D | L | K | N | E | D | T | A | T | Y | F | C | A | R |
| NH1_1-03/Hz1 | R | V | T | I | T | D | T | S | A | S | T | A | Y | M | E | L | S | S | L | R | S | E | D | T | A | V | Y | Y | C | A | R | |
| NH_7.4.1/Hz1 | R | F | V | F | S | I | D | T | S | V | S | T | A | Y | L | Q | I | N | A | L | K | A | E | D | T | A | V | Y | Y | C | A | R |

DAY 21 IMAGING

DAY 28 IMAGING

SEQUENCE LISTING

```
<160> NUMBER OF SEQ ID NOS: 136

<210> SEQ ID NO 1
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Ala
                20                  25                  30

Ser Leu Ala Val Ser Leu Gly Gln Arg Ala Thr Ile Ser Cys Arg Ala
            35                  40                  45

Ser Glu Ser Val Asp Asn Tyr Gly Asn Thr Phe Met His Trp Tyr Gln
        50                  55                  60

Gln Lys Pro Gly Gln Pro Pro Lys Leu Leu Ile Tyr Arg Ala Ser Asn
65                  70                  75                  80

Leu Glu Ser Gly Ile Pro Ala Arg Phe Ser Gly Ser Gly Ser Arg Thr
                85                  90                  95

Asp Phe Thr Leu Thr Ile Asn Pro Val Glu Ala Asp Val Ala Thr
                100                 105                 110

Tyr Tyr Cys Gln Gln Ser Asn Glu Asp Pro Thr Phe Gly Ala Gly
            115                 120                 125

Thr Lys Leu Glu Leu Lys Gly Gly Gly Ser Gly Gly Gly Gly Ser
        130                 135                 140

Ser Gly Gly Gly Ser Gln Ile Gln Leu Val Gln Ser Gly Pro Glu Leu
145                 150                 155                 160
```

```
Lys Lys Pro Gly Glu Thr Val Lys Ile Ser Cys Lys Ala Ser Gly Tyr
            165                 170                 175

Ile Phe Thr Asn Tyr Gly Met Asn Trp Val Lys Gln Ala Pro Gly Lys
            180                 185                 190

Ser Phe Lys Trp Met Gly Trp Ile Asn Thr Tyr Thr Gly Glu Ser Thr
            195                 200                 205

Tyr Ser Ala Asp Phe Lys Gly Arg Phe Ala Phe Ser Leu Glu Thr Ser
            210                 215                 220

Ala Ser Thr Ala Tyr Leu His Ile Asn Asp Leu Lys Asn Glu Asp Thr
225                 230                 235                 240

Ala Thr Tyr Phe Cys Ala Arg Ser Gly Gly Tyr Asp Pro Met Asp Tyr
            245                 250                 255

Trp Gly Gln Gly Thr Ser Val Thr Val Ser Ser Ala Ser Ser Gly Thr
            260                 265                 270

Thr Thr Pro Ala Pro Arg Pro Pro Thr Pro Ala Pro Thr Ile Ala Ser
            275                 280                 285

Gln Pro Leu Ser Leu Arg Pro Glu Ala Cys Arg Pro Ala Ala Gly Gly
            290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
            325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
            355                 360                 365

Ser Cys Arg Phe Pro Glu Glu Glu Gly Gly Cys Glu Leu Arg Val
            370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 2
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30
```

```
Gly Asn Thr Phe Met His Trp Tyr Gln Gln Lys Pro Gly Gln Pro
            35                  40                  45

Lys Leu Leu Ile Tyr Arg Ala Ser Asn Leu Glu Ser Gly Ile Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Pro Thr Phe Gly Ala Gly Thr Lys Leu Glu Leu Lys Gly
                100                 105                 110

Gly Gly Gly Ser Gly Gly Gly Ser Ser Gly Gly Ser Gln Ile
            115                 120                 125

Gln Leu Val Gln Ser Gly Pro Glu Leu Lys Lys Pro Gly Glu Thr Val
    130                 135                 140

Lys Ile Ser Cys Lys Ala Ser Gly Tyr Ile Phe Thr Asn Tyr Gly Met
145                 150                 155                 160

Asn Trp Val Lys Gln Ala Pro Gly Lys Ser Phe Lys Trp Met Gly Trp
                165                 170                 175

Ile Asn Thr Tyr Thr Gly Glu Ser Thr Tyr Ser Ala Asp Phe Lys Gly
                180                 185                 190

Arg Phe Ala Phe Ser Leu Glu Thr Ser Ala Ser Thr Ala Tyr Leu His
            195                 200                 205

Ile Asn Asp Leu Lys Asn Glu Asp Thr Ala Thr Tyr Phe Cys Ala Arg
    210                 215                 220

Ser Gly Gly Tyr Asp Pro Met Asp Tyr Trp Gly Gln Gly Thr Ser Val
225                 230                 235                 240

Thr Val Ser Ser

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ala Leu Pro Val Thr Ala Leu Leu Leu Pro Leu Ala Leu Leu Leu
 1               5                  10                  15

His Ala Ala Arg Pro
             20

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45
```

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 7
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 8
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atggccctgc ctgtgacagc cctgctgctg cctctggctc tgctgctgca tgccgctaga    60
cccggatccg acatcgtgct gacacagagc cctgcttccc tggccgtgtc cctgggacag   120
agagccacaa tcagctgcag ggccagcgag agcgtggaca actacggcaa caccttcatg   180
cactggtatc agcagaagcc cggccagccc cccaagctgc tgatctacag agccagcaac   240
ctggaaagcg gcatccccgc cagatttttc cggcagcggc agcagaaccga cttcaccctg   300 accatcaacc ccgtggaagc cgacgacgtg gccacctact actgccagca gagcaacgag   360 gacccccccca catttggagc cggcaccaag ctggaactga agggcggagg cggatctggc   420
ggcggaggat cttctggggg aggctctcag attcagctgg tgcagagcgg cccagagctg   480
aagaaacccg gcgagacagt gaagatctcc tgcaaggcct ccggctacat cttcaccaat   540
tacggcatga actgggtcaa gcaggcccct ggcaagagct caagtggat gggctggatc     600 aacacctaca ccggcgagag cacctacagc gccgacttca agggcagatt cgccttcagc   660
ctggaaacca cgccagcac cgcctacctg cacatcaacg acctgaagaa cgaggacacc    720
gccacctatt tctgcgccag aagcggcggc tacgacccca tggattattg gggccagggc   780
accagcgtga ccgtgtcctc tgctagctcc ggaaccacga cgccagcgcc gcgaccacca   840
acaccggcgc ccaccatcgc gtcgcagccc ctgtccctgc gcccagaggc gtgccggcca   900
gcggcggggg gcgcagtgca cacgaggggg ctggacttcg cctgtgatat ctacatctgg   960
gcgcccttgg ccgggacttg tggggtcctt ctcctgtcac tggttatcac cctttactgc  1020
aaacggggca gaaagaaact cctgtatata ttcaaacaac catttatgag accagtacaa  1080
actactcaag aggaagatgg ctgtagctgc cgatttccag aagaagaaga aggaggatgt  1140
gaactgagag tgaagttcag caggagcgca gacgcccccg cgtacaagca gggccagaac  1200
cagctctata cgagctcaa tctaggacga agagaggagt acgatgtttt ggacaagaga   1260
cgtggccggg accctgagat ggggggaaag ccgagaagga agaaccctca ggaaggcctg   1320
tacaatgaac tgcagaaaga taagatggcg gaggcctaca gtgagattgg gatgaaaggc   1380
gagcgccgga ggggcaaggg gcacgatggc ctttaccagg gtctcagtac agccaccaag  1440
gacacctacg acgcccttca catgcaggcc ctgccccctc gc                      1482

<210> SEQ ID NO 9
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacatcgtgc tgacacagag ccctgcttcc ctggccgtgt ccctgggaca gagagccaca    60
atcagctgca gggccagcga gagcgtggac aactacggca acaccttcat gcactggtat   120
cagcagaagc ccggccagcc ccccaagctg ctgatctaca gagccagcaa cctggaaagc   180
ggcatccccg ccagattttc cggcagcggc agcagaaccg acttcaccct gaccatcaac   240
cccgtggaag ccgacgacgt ggccacctac tactgccagc agagcaacga gaccccccc    300 acatttggag ccggcaccaa gctggaactg aagggcggag gcggatctgg cggcggagga   360
tcttctgggg gaggctctca gattcagctg gtgcagagcg gcccagagct gaagaaaccc   420
ggcgagacag tgaagatctc ctgcaaggcc tccggctaca tcttcaccaa ttacggcatg   480
aactgggtca gcaggcccc tggcaagagc ttcaagtgga tgggctggat caacacctac    540
```

```
accggcgaga gcacctacag cgccgacttc aagggcagat tcgccttcag cctggaaacc    600
agcgccagca ccgcctacct gcacatcaac gacctgaaga cgaggacac cgccacctat     660 ttctgcgcca aagcggcgg ctacgacccc atggattatt ggggccaggg caccagcgtg    720
accgtgtcct ct                                                        732
```

```
<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atggccctgc ctgtgacagc cctgctgctg cctctggctc tgctgctgca tgccgctaga    60
ccc                                                                  63
```

```
<210> SEQ ID NO 11
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
accacgacgc cagcgccgcg accaccaaca ccggcgccca ccatcgcgtc gcagcccctg    60
tccctgcgcc cagaggcgtg ccggccagcg gcggggggcg cagtgcacac gaggggctg    120 gacttcgcct gtgat                                                    135
```

```
<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atctacatct gggcgccctt ggccgggact tgtggggtcc ttctcctgtc actggttatc    60 acccttttact gc                                                       72
```

```
<210> SEQ ID NO 13
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

```
<210> SEQ ID NO 14
<211> LENGTH: 336
<212> TYPE: DNA
<213> ORGANISM: Artificial Sequence
<220> FEATURE:
```

```
<223> OTHER INFORMATION: Description of Artificial Sequence: Synthetic
      polynucleotide

<400> SEQUENCE: 14
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggg aaagccgaga aggaagaacc ctcaggaagg cctgtacaat      180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                               336

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser
        115

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Tyr Gly Met Asn
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Ile Asn Thr Tyr Thr Gly Glu Ser Thr Tyr Ser Ala Asp Phe Lys
1               5                   10                  15
```

Gly

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Gly Gly Tyr Asp Pro Met Asp Tyr
1               5

<210> SEQ ID NO 19
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys
            100                 105                 110

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ala Ser Glu Ser Val Asp Asn Tyr Gly Asn Thr Phe Met His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Asn Leu Glu Ser
1               5

<210> SEQ ID NO 22

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Ser Asn Glu Asp Pro Pro Thr
1               5

<210> SEQ ID NO 23
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
            35                  40                  45

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Tyr Ile Phe Thr Asn Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Thr Tyr Thr Gly Glu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Gly Gly Tyr Asp Pro Met Asp Tyr
1               5

<210> SEQ ID NO 27
<211> LENGTH: 123
<212> TYPE: DNA
<213> ORGANISM: Artificial Sequence
```

-continued

<220> FEATURE:
<223> OTHER INFORMATION: Description of Artificial Sequence: Synthetic
      polynucleotide

<400> SEQUENCE: 27
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Glu Ser Val Asp Asn Tyr Gly Asn Thr Phe
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser
1

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Asn Glu Asp Pro Pro
1               5

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
            85                  90                  95

Glu Asp Pro Pro Thr Phe Gly Gln Gly Thr Lys Leu Glu Ile Lys
            100                 105                 110

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
            85                  90                  95

Glu Asp Pro Pro Thr Phe Gly Gln Gly Thr Lys Leu Glu Ile Lys
            100                 105                 110

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ser Tyr Ser Ala Asp Phe
    50                  55                  60

Arg Val Thr Ile Thr Leu Asp Thr Ser Ala Ser Thr Ala Tyr Met Glu
65                  70                  75                  80

Leu Ser Ser Leu Arg Ser Glu Asp Thr Ala Val Tyr Tyr Cys Ala Arg
            85                  90                  95

Ser Gly Gly Tyr Asp Pro Met Asp Tyr Trp Gly Gln Gly Thr Thr Val
            100                 105                 110

Thr Val Ser Ser
        115

<210> SEQ ID NO 34
<211> LENGTH: 116
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 34

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Tyr Ser Ala Asp Phe
    50                  55                  60

Arg Phe Val Phe Ser Leu Asp Thr Ser Val Ser Thr Ala Tyr Leu Gln
65                  70                  75                  80

Ile Asn Ala Leu Lys Ala Glu Asp Thr Ala Val Tyr Tyr Cys Ala Arg
                85                  90                  95

Ser Gly Gly Tyr Asp Pro Met Asp Tyr Trp Gly Gln Gly Thr Thr Val
            100                 105                 110

Thr Val Ser Ser
        115

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser
1               5

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125
```

```
Gly Gly Ser Gln Ile Gln Leu Val Gln Ser Gly Ser Glu Leu Lys Lys
        130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245
```

<210> SEQ ID NO 37
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
gacatcgtgc tgacccaatc cccggacagc ctcgcagtct cactcggaga acgcgccact    60
atcaattgta gggcgtcgga gtccgtggac aattacggaa acaccttcat gcactggtac   120
caacaaaaac ctggtcagcc acctaagctg ctgatctacc gcgcctcgaa tctggaatca   180
ggagtgccgg acagattctc ggggtccggc tccggacgg atttcacttt gaccatctcg    240
tcacttcaag ctgaggacgt cgcggtgtac tactgccagc agagcaacga agatccaccc   300
acgttcggac aaggcaccaa gctggagatt aaaggaggcg gaggctccgg tggaggagga   360
tcgggaggag gcggctccgg cggaggtgga tcgcagattc agctggtgca gtcgggttca   420
gaattgaaga aaccaggagc ctcggtgaag gtcagctgca aggcatcagg gtacatcttc   480
actaactacg gcatgaactg ggtgcgccag gctccgggac aggggctgga gtggatggga   540
tggatcaaca cttacaccgg ggagtcaact tactcggctg actttaaggg ccggtttgtg   600
ttctccctcg acactagcgt gagcaccgcc tatcttcaaa tcaacgccct caaggcggaa   660
gataccgccg tctactactg cgcaagatcc ggtgggtacg atccgatgga ttattgggga   720
cagggaacca ctgtcaccgt gagcagc                                      747
```

<210> SEQ ID NO 38
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

```
atggccctcc ctgtcaccgc cctgctgctt ccgctggctc ttctgctcca cgccgctcgg    60
cccgacatcg tgctgaccca atccccggac agcctcgcag tctcactcgg agaacgcgcc   120
actatcaatt gtagggcgtc ggagtccgtg gacaattacg gaaacacctt catgcactgg   180
taccaacaaa aacctggtca gccacctaag ctgctgatct accgcgcctc gaatctggaa   240
```

```
tcaggagtgc cggacagatt ctcggggtcc ggctcccgga cggatttcac tttgaccatc    300
tcgtcacttc aagctgagga cgtcgcggtg tactactgcc agcagagcaa cgaagatcca    360
cccacgttcg gacaaggcac caagctggag attaaaggag gcggaggctc cggtggagga    420
ggatcgggag gaggcggctc cggcggaggt ggatcgcaga ttcagctggt gcagtcgggt    480
tcagaattga agaaaccagg agcctcggtg aaggtcagct gcaaggcatc agggtacatc    540
ttcactaact acggcatgaa ctgggtgcgc caggctccgg acaggggct ggagtggatg     600 ggatggatca acacttacac cggggagtca acttactcgg ctgactttaa gggccggttt    660
gtgttctccc tcgacactag cgtgagcacc gcctatcttc aaatcaacgc cctcaaggcg    720
gaagataccg ccgtctacta ctgcgcaaga tccggtgggt acgatccgat ggattattgg    780
ggacagggaa ccactgtcac cgtgagcagc ggctcgcacc accatcacca tcatcatcac    840
cac                                                                  843
```

```
<210> SEQ ID NO 39
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Asp Ser Leu
            20                  25                  30

Ala Val Ser Leu Gly Glu Arg Ala Thr Ile Asn Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Pro Pro Lys Leu Leu Ile Tyr Arg Ala Ser Asn Leu Glu
65                  70                  75                  80

Ser Gly Val Pro Asp Arg Phe Ser Gly Ser Gly Ser Arg Thr Asp Phe
                85                  90                  95

Thr Leu Thr Ile Ser Ser Leu Gln Ala Glu Asp Val Ala Val Tyr Tyr
            100                 105                 110

Cys Gln Gln Ser Asn Glu Asp Pro Pro Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Ser Gln Ile Gln Leu Val Gln Ser Gly
145                 150                 155                 160

Ser Glu Leu Lys Lys Pro Gly Ala Ser Val Lys Val Ser Cys Lys Ala
                165                 170                 175

Ser Gly Tyr Ile Phe Thr Asn Tyr Gly Met Asn Trp Val Arg Gln Ala
            180                 185                 190

Pro Gly Gln Gly Leu Glu Trp Met Gly Trp Ile Asn Thr Tyr Thr Gly
        195                 200                 205

Glu Ser Thr Tyr Ser Ala Asp Phe Lys Gly Arg Phe Val Phe Ser Leu
    210                 215                 220

Asp Thr Ser Val Ser Thr Ala Tyr Leu Gln Ile Asn Ala Leu Lys Ala
225                 230                 235                 240
```

Glu Asp Thr Ala Val Tyr Tyr Cys Ala Arg Ser Gly Gly Tyr Asp Pro
            245                 250                 255

Met Asp Tyr Trp Gly Gln Gly Thr Thr Val Thr Val Ser Ser Gly Ser
        260                 265                 270

His His His His His His His His His
        275                 280

<210> SEQ ID NO 40
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

| | | |
|---|---|---|
| atggccctcc ctgtcaccgc cctgctgctt ccgctggctc ttctgctcca cgccgctcgg | 60 |
| cccgacatcg tgctgaccca atccccggac agcctcgcag tctcactcgg agaacgcgcc | 120 |
| actatcaatt gtagggcgtc ggagtccgtg acaattacg gaaacacctt catgcactgg | 180 |
| taccaacaaa aacctggtca gccacctaag ctgctgatct accgcgcctc gaatctggaa | 240 |
| tcaggagtgc cggacagatt ctcggggtcc ggctcccgga cggatttcac tttgaccatc | 300 |
| tcgtcacttc aagctgagga cgtcgcggtg tactactgcc agcagagcaa cgaagatcca | 360 |
| cccacgttcg gacaaggcac caagctggag attaaaggag gcgaggctc cggtggagga | 420 |
| ggatcgggag gaggcggctc cggcggaggt ggatcgcaga ttcagctggt gcagtcgggt | 480 |
| tcagaattga gaaaccagg agcctcggtg aaggtcagct gcaaggcatc agggtacatc | 540 |
| ttcactaact acggcatgaa ctgggtgcgc caggctccgg acaggggct ggagtggatg | 600 |
| ggatggatca cacttacac cggggagtca acttactcgg ctgactttaa gggccggttt | 660 |
| gtgttctccc tcgacactag cgtgagcacc gcctatcttc aaatcaacgc cctcaaggcg | 720 |
| gaagataccg ccgtctacta ctgcgcaaga tccggtgggt acgatccgat ggattattgg | 780 |
| ggacagggaa ccactgtcac cgtgagcagc accactaccc cagcaccgag gccacccacc | 840 |
| ccggctccta ccatcgcctc ccagcctctg tccctgcgtc cggaggcatg tagacccgca | 900 |
| gctggtgggg ccgtgcatac ccgggggtctt gacttcgcct gcgatatcta catttgggcc | 960 |
| cctctggctg gtacttgcgg ggtcctgctg ctttcactcg tgatcactct ttactgtaag | 1020 |
| cgcggtcgga agaagctgct gtacatcttt aagcaaccct tcatgaggcc tgtgcagact | 1080 |
| actcaagagg aggacggctg ttcatgccgg ttcccagagg aggaggaagg cggctgcgaa | 1140 |
| ctgcgcgtga aattcagccg cagcgcagat gctccagcct acaagcaggg gcagaaccag | 1200 |
| ctctacaacg aactcaatct tggtcggaga gaggagtacg acgtgctgga caagcggaga | 1260 |
| ggacgggacc cagaaatggg cgggaagccg cgcagaaaga tccccaaga gggcctgtac | 1320 |
| aacgagctcc aaaaggataa gatgcagaa gcctatagcg agattggtat gaaagggaa | 1380 |
| cgcagaagag gcaaaggcca cgacggactg taccagggac tcagcaccgc caccaaggac | 1440 |
| acctatgacg ctcttcacat gcaggccctg ccgcctcgg | 1479 |

<210> SEQ ID NO 41
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Met Ala Leu Pro Val Thr Ala Leu Leu Leu Pro Leu Ala Leu Leu Leu
1               5                   10                  15
His Ala Ala Arg Pro Asp Ile Val Leu Thr Gln Ser Pro Asp Ser Leu
                20                  25                  30
Ala Val Ser Leu Gly Glu Arg Ala Thr Ile Asn Cys Arg Ala Ser Glu
            35                  40                  45
Ser Val Asp Asn Tyr Gly Asn Thr Phe Met His Trp Tyr Gln Gln Lys
50                  55                  60
Pro Gly Gln Pro Pro Lys Leu Leu Ile Tyr Arg Ala Ser Asn Leu Glu
65                  70                  75                  80
Ser Gly Val Pro Asp Arg Phe Ser Gly Ser Gly Ser Arg Thr Asp Phe
                85                  90                  95
Thr Leu Thr Ile Ser Ser Leu Gln Ala Glu Asp Val Ala Val Tyr Tyr
            100                 105                 110
Cys Gln Gln Ser Asn Glu Asp Pro Pro Thr Phe Gly Gln Gly Thr Lys
            115                 120                 125
Leu Glu Ile Lys Gly Gly Gly Gly Ser Gly Gly Gly Ser Gly Gly
130                 135                 140
Gly Gly Ser Gly Gly Gly Gly Ser Gln Ile Gln Leu Val Gln Ser Gly
145                 150                 155                 160
Ser Glu Leu Lys Lys Pro Gly Ala Ser Val Lys Val Ser Cys Lys Ala
                165                 170                 175
Ser Gly Tyr Ile Phe Thr Asn Tyr Gly Met Asn Trp Val Arg Gln Ala
            180                 185                 190
Pro Gly Gln Gly Leu Glu Trp Met Gly Trp Ile Asn Thr Tyr Thr Gly
            195                 200                 205
Glu Ser Thr Tyr Ser Ala Asp Phe Lys Gly Arg Phe Val Phe Ser Leu
210                 215                 220
Asp Thr Ser Val Ser Thr Ala Tyr Leu Gln Ile Asn Ala Leu Lys Ala
225                 230                 235                 240
Glu Asp Thr Ala Val Tyr Tyr Cys Ala Arg Ser Gly Gly Tyr Asp Pro
                245                 250                 255
Met Asp Tyr Trp Gly Gln Gly Thr Thr Val Thr Val Ser Ser Thr Thr
            260                 265                 270
Thr Pro Ala Pro Arg Pro Pro Thr Pro Ala Pro Thr Ile Ala Ser Gln
            275                 280                 285
Pro Leu Ser Leu Arg Pro Glu Ala Cys Arg Pro Ala Ala Gly Gly Ala
290                 295                 300
Val His Thr Arg Gly Leu Asp Phe Ala Cys Asp Ile Tyr Ile Trp Ala
305                 310                 315                 320
Pro Leu Ala Gly Thr Cys Gly Val Leu Leu Leu Ser Leu Val Ile Thr
                325                 330                 335
Leu Tyr Cys Lys Arg Gly Arg Lys Lys Leu Leu Tyr Ile Phe Lys Gln
            340                 345                 350
Pro Phe Met Arg Pro Val Gln Thr Thr Gln Glu Glu Asp Gly Cys Ser
            355                 360                 365
Cys Arg Phe Pro Glu Glu Glu Gly Gly Cys Glu Leu Arg Val Lys
            370                 375                 380
Phe Ser Arg Ser Ala Asp Ala Pro Ala Tyr Lys Gln Gly Gln Asn Gln
385                 390                 395                 400
Leu Tyr Asn Glu Leu Asn Leu Gly Arg Arg Glu Glu Tyr Asp Val Leu
                405                 410                 415
```

-continued

```
Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 42
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ala Glu Val Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
        195                 200                 205

Thr Ala Tyr Met Glu Leu Ser Ser Leu Arg Ser Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 43
<211> LENGTH: 747
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 43

```
gatattgtcc tcactcaatc gccggactca ctggcggtgt ccctcggaga gagggcgacg    60
atcaattgcc gggcttccga atccgtcgat aactacggaa acacctttat gcactggtac   120
caacagaagc caggacagcc accaaagctg ttgatctacc gcgcttcaaa ccttgagtcg   180
ggtgtgccgg accgcttcag cggcagcggt tccagaaccg actttaccct caccatcagc   240
tcgctgcagg ccgaagatgt cgccgtctat tactgccaac agagcaacga agatccgcct   300
actttcggac aggggactaa actggaaatc aagggcggag gaggctcggg tggaggagga   360
tcgggaggag gcgggtccgg tggtggcgga tcgcaaatcc agctggtgca gtccggcgca   420
gaagtgaaga agccgggagc gtccgtgaaa gtgagctgca aggcctcagg gtacatcttc   480
accaattacg gcatgaattg ggtgcggcag gcacccggac agcgcctgga gtggatgggc   540
tggatcaaca cttacaccgg gaaagcacg tactcggccg acttcaaagg acgggtgacc   600
attccctgg atacctcggc ctcaaccgct tacatggagc tctcatcact tagatccgag   660
gacactgccg tctactactg tgcaaggagc ggaggctacg accctatgga ctattgggga   720
caaggcacta ctgtgactgt gtcgtcc                                       747
```

<210> SEQ ID NO 44
<211> LENGTH: 843
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
atggccctcc ctgtcaccgc cctgctgctt ccgctggctc ttctgctcca cgccgctcgg    60
cccgatattg tcctcactca atcgccggac tcactggcgg tgtccctcgg agagagggcg   120
acgatcaatt gccgggcttc cgaatccgtc gataactacg gaaacacctt tatgcactgg   180
taccaacaga agccaggaca gccaccaaag ctgttgatct accgcgcttc aaaccttgag   240
tcgggtgtgc cggaccgctt cagcggcagc ggttccagaa ccgactttac cctcaccatc   300
agctcgctgc aggccgaaga tgtcgccgtc tattactgcc aacagagcaa cgaagatccg   360
cctactttcg gacaggggac taaactggaa atcaagggcg gaggaggctc gggtggagga   420
ggatcgggag gaggcgggtc cggtggtggc ggatcgcaaa tccagctggt gcagtccggc   480
gcagaagtga agaagccggg agcgtccgtg aaagtgagct gcaaggcctc agggtacatc   540
ttcaccaatt acggcatgaa ttgggtgcgg caggcacccg acagcgcct ggagtggatg   600
ggctggatca cacttacac cggggaaagc acgtactcgg ccgacttcaa aggacgggtg   660
accattaccc tggatacctc ggcctcaacc gcttacatgg agctctcatc acttagatcc   720
gaggacactg ccgtctacta ctgtgcaagg agcggaggct acgaccctat ggactattgg   780
ggacaaggca ctactgtgac tgtgtcgtcc ggctcgcacc accatcacca tcatcatcac   840
cac                                                                 843
```

<210> SEQ ID NO 45
<211> LENGTH: 281
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 45

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Asp Ser Leu
            20                  25                  30

Ala Val Ser Leu Gly Glu Arg Ala Thr Ile Asn Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Pro Pro Lys Leu Leu Ile Tyr Arg Ala Ser Asn Leu Glu
65                  70                  75                  80

Ser Gly Val Pro Asp Arg Phe Ser Gly Ser Gly Ser Arg Thr Asp Phe
                85                  90                  95

Thr Leu Thr Ile Ser Ser Leu Gln Ala Glu Asp Val Ala Val Tyr Tyr
            100                 105                 110

Cys Gln Gln Ser Asn Glu Asp Pro Pro Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gln Ile Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Ile Phe Thr Asn Tyr Gly Met Asn Trp Val Arg Gln Ala
            180                 185                 190

Pro Gly Gln Arg Leu Glu Trp Met Gly Trp Ile Asn Thr Tyr Thr Gly
        195                 200                 205

Glu Ser Thr Tyr Ser Ala Asp Phe Lys Gly Arg Val Thr Ile Thr Leu
    210                 215                 220

Asp Thr Ser Ala Ser Thr Ala Tyr Met Glu Leu Ser Ser Leu Arg Ser
225                 230                 235                 240

Glu Asp Thr Ala Val Tyr Tyr Cys Ala Arg Ser Gly Gly Tyr Asp Pro
                245                 250                 255

Met Asp Tyr Trp Gly Gln Gly Thr Thr Val Thr Val Ser Ser Gly Ser
            260                 265                 270

His His His His His His His His
        275                 280

<210> SEQ ID NO 46
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggccctcc ctgtcaccgc cctgctgctt ccgctggctc ttctgctcca cgccgctcgg      60
cccgatattg tcctcactca atcgccggac tcactggcgg tgtccctcgg agagagggcg     120
acgatcaatt gccgggcttc cgaatccgtc gataactacg gaaacacctt atgcactgg      180 taccaacaga agccaggaca gccaccaaag ctgttgatct accgcgcttc aaaccttgag     240
```

```
tcgggtgtgc cggaccgctt cagcggcagc ggttccagaa ccgactttac cctcaccatc      300
agctcgctgc aggccgaaga tgtcgccgtc tattactgcc aacagagcaa cgaagatccg      360
cctactttcg gacaggggac taaactggaa atcaagggcg aggaggctc gggtggagga       420 ggatcgggag gaggcgggtc cggtggtggc ggatcgcaaa tccagctggt gcagtccggc      480
gcagaagtga agaagccggg agcgtccgtg aaagtgagct gcaaggcctc agggtacatc      540
ttcaccaatt acggcatgaa ttgggtgcgg caggcacccg acagcgcct ggagtggatg       600 ggctggatca acacttacac cggggaaagc acgtactcgg ccgacttcaa aggacgggtg      660
accattaccc tggatacctc ggcctcaacc gcttacatgg agctctcatc acttagatcc      720
gaggacactg ccgtctacta ctgtgcaagg agcggaggct acgaccctat ggactattgg      780
ggacaaggca ctactgtgac tgtgtcgtcc accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga tccccaaga gggcctgtac      1320 aacgagctcc aaaaggataa gatggcagaa gcctatagcg agattggtat gaaaggggaa     1380
cgcagaagag gcaaaggcca cgacggactg taccagggac tcagcaccgc caccaaggac     1440
acctatgacg ctcttcacat gcaggccctg ccgcctcgg                            1479
```

<210> SEQ ID NO 47
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Asp Ser Leu
            20                  25                  30

Ala Val Ser Leu Gly Glu Arg Ala Thr Ile Asn Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Pro Pro Lys Leu Leu Ile Tyr Arg Ala Ser Asn Leu Glu
65                  70                  75                  80

Ser Gly Val Pro Asp Arg Phe Ser Gly Ser Gly Ser Arg Thr Asp Phe
                85                  90                  95

Thr Leu Thr Ile Ser Ser Leu Gln Ala Glu Asp Val Ala Val Tyr Tyr
            100                 105                 110

Cys Gln Gln Ser Asn Glu Asp Pro Pro Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Ser Gln Ile Gln Leu Val Gln Ser Gly
145                 150                 155                 160

Ala Glu Val Lys Lys Pro Gly Ala Ser Val Lys Val Ser Cys Lys Ala
            165                 170                 175

Ser Gly Tyr Ile Phe Thr Asn Tyr Gly Met Asn Trp Val Arg Gln Ala
            180                 185                 190

Pro Gly Gln Arg Leu Glu Trp Met Gly Trp Ile Asn Thr Tyr Thr Gly
        195                 200                 205

Glu Ser Thr Tyr Ser Ala Asp Phe Lys Gly Arg Val Thr Ile Thr Leu
    210                 215                 220

Asp Thr Ser Ala Ser Thr Ala Tyr Met Glu Leu Ser Ser Leu Arg Ser
225                 230                 235                 240

Glu Asp Thr Ala Val Tyr Tyr Cys Ala Arg Ser Gly Gly Tyr Asp Pro
                245                 250                 255

Met Asp Tyr Trp Gly Gln Gly Thr Thr Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 48
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Ile Val Leu Thr Gln Ser Pro Ala Thr Leu Ser Leu Ser Pro Gly

```
 1               5                  10                 15
Glu Arg Ala Thr Leu Ser Cys Arg Ala Ser Glu Ser Val Asp Asn Tyr
            20                  25                 30

Gly Asn Thr Phe Met His Trp Tyr Gln Gln Lys Pro Gly Gln Ala Pro
            35                  40                 45

Arg Leu Leu Ile Tyr Arg Ala Ser Asn Leu Glu Ser Gly Ile Pro Ala
 50                      55                 60

Arg Phe Ser Gly Ser Gly Ser Arg Thr Asp Phe Thr Leu Thr Ile Ser
 65                  70                  75                 80

Ser Leu Glu Pro Glu Asp Val Ala Val Tyr Tyr Cys Gln Gln Ser Asn
                 85                  90                  95

Glu Asp Pro Pro Thr Phe Gly Gln Gly Thr Lys Leu Glu Ile Lys Gly
             100                 105                110

Gly Gly Gly Ser Gly Gly Gly Gly Ser Gly Gly Gly Ser Gly Gly
             115                 120                 125

Gly Gly Ser Gln Ile Gln Leu Val Gln Ser Gly Ser Glu Leu Lys Lys
         130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                 165                 170                 175

Glu Trp Met Gly Trp Ile Asn Thr Tyr Thr Gly Glu Ser Thr Tyr Ser
             180                 185                 190

Ala Asp Phe Lys Gly Arg Phe Val Phe Ser Leu Asp Thr Ser Val Ser
         195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 49
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaaattgtgc tcacgcaatc acccgccact ctgtcgcttt ccccgggaga gcgggccacc      60
ctctcctgcc gcgcttcgga atcggtcgac aattacggaa atactttttat gcactggtac     120 caacagaagc cagggcaggc gccaaggctg ctgatctaca gagcctcgaa cctcgaaagc     180
ggcatccctg cgcggttcag cggtagcgga agccgcaccg atttcaccct gaccatctca     240
tcactggagc cggaggatgt ggcagtgtac tattgtcagc agtcgaacga gacccgccg      300 actttcgggc agggaaccaa gctggaaatc aagggtggag gagggagcgg cggaggagga     360
tcgggaggag gaggcagcgg aggcggagga tcgcaaatcc aacttgtcca gtcgggctcc     420
gaactcaaaa agcctggcgc gtccgtgaag gtcagctgca agcatcagg atacatcttc      480 actaactacg gtatgaattg ggtcagacag gctccgggtc agggtctgga gtggatggga     540
tggattaaca cctacactgg ggaatcgact tactccgcgg acttcaaagg gcggttcgtg     600
ttttcactgg acaccagcgt gtccaccgct tacttgcaaa tcaacgccct caaggccgag     660
```

```
gacaccgccg tgtactactg cgcacgctca ggcggatacg atccaatgga ctactgggga    720
cagggcacta cggtgactgt gtcctcc                                        747
```

<210> SEQ ID NO 50
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
atggccctcc ctgtcaccgc cctgctgctt ccgctggctc ttctgctcca cgccgctcgg     60
cccgaaattg tgctcacgca atcacccgcc actctgtcgc tttccccggg agagcgggcc    120
accctctcct gccgcgcttc ggaatcggtc gacaattacg gaaatacttt tatgcactgg    180
taccaacaga agccagggca ggcgccaagg ctgctgatct acagagcctc gaacctcgaa    240
agcggcatcc ctgcgcggtt cagcggtagc ggaagccgca ccgatttcac cctgaccatc    300
tcatcactgg agccggagga tgtggcagtg tactattgtc agcagtcgaa cgaggacccg    360
ccgactttcg gcagggaac caagctggaa atcaagggtg gaggagggag cggcggagga    420
ggatcgggag gaggaggcag cggaggcgga ggatcgcaaa tccaacttgt ccagtcgggc    480
tccgaactca aaaagcctgg cgcgtccgtg aaggtcagct gcaaagcatc aggatacatc    540
ttcactaact acggtatgaa ttgggtcaga caggctccgg gtcagggtct ggagtggatg    600
ggatggatta cacctacac tggggaatcg acttactccg cggacttcaa agggcggttc    660
gtgttttcac tggacaccag cgtgtccacc gcttacttgc aaatcaacgc cctcaaggcc    720
gaggacaccg ccgtgtacta ctgcgcacgc tcaggcggat acgatccaat ggactactgg    780
ggacagggca ctacggtgac tgtgtcctcc ggctcgcacc accatcacca tcatcatcac    840
cac                                                                  843
```

<210> SEQ ID NO 51
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Ala Pro Arg Leu Leu Ile Tyr Arg Ala Ser Asn Leu Glu
65                  70                  75                  80

Ser Gly Ile Pro Ala Arg Phe Ser Gly Ser Gly Ser Arg Thr Asp Phe
                85                  90                  95

Thr Leu Thr Ile Ser Ser Leu Glu Pro Glu Asp Val Ala Val Tyr Tyr
            100                 105                 110

Cys Gln Gln Ser Asn Glu Asp Pro Pro Thr Phe Gly Gln Gly Thr Lys
```

```
                  115                 120                 125
Leu Glu Ile Lys Gly Gly Gly Ser Gly Gly Gly Ser Gly Gly
            130                 135                 140

Gly Gly Ser Gly Gly Gly Ser Gln Ile Gln Leu Val Gln Ser Gly
145                 150                 155                 160

Ser Glu Leu Lys Lys Pro Gly Ala Ser Val Lys Val Ser Cys Lys Ala
                165                 170                 175

Ser Gly Tyr Ile Phe Thr Asn Tyr Gly Met Asn Trp Val Arg Gln Ala
            180                 185                 190

Pro Gly Gln Gly Leu Glu Trp Met Gly Trp Ile Asn Thr Tyr Thr Gly
                195                 200                 205

Glu Ser Thr Tyr Ser Ala Asp Phe Lys Gly Arg Phe Val Phe Ser Leu
            210                 215                 220

Asp Thr Ser Val Ser Thr Ala Tyr Leu Gln Ile Asn Ala Leu Lys Ala
225                 230                 235                 240

Glu Asp Thr Ala Val Tyr Tyr Cys Ala Arg Ser Gly Gly Tyr Asp Pro
                245                 250                 255

Met Asp Tyr Trp Gly Gln Gly Thr Thr Val Thr Val Ser Ser Gly Ser
            260                 265                 270

His His His His His His His
        275                 280

<210> SEQ ID NO 52
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
atggccctcc ctgtcaccgc cctgctgctt ccgctggctc ttctgctcca cgccgctcgg      60
cccgaaattg tgctcacgca atcacccgcc actctgtcgc tttccccggg agagcgggcc     120
accctctcct gccgcgcttc ggaatcggtc gacaattacg gaaatacttt tatgcactgg     180
taccaacaga agccagggca ggcgccaagg ctgctgatct acagagcctc gaacctcgaa     240
agcggcatcc ctgcgcggtt cagcggtagc ggaagccgca ccgatttcac cctgaccatc     300
tcatcactgg agccggagga tgtggcagtg tactattgtc agcagtcgaa cgaggacccg     360
ccgactttcg gcagggaac caagctggaa atcaagggtg gaggagggag cggcggagga     420
ggatcgggag gaggaggcag cggaggcgga ggatcgcaaa tccaacttgt ccagtcgggc     480
tccgaactca aaaagcctgg cgcgtccgtg aaggtcagct gcaaagcatc aggatacatc     540
ttcactaact acggtatgaa ttgggtcaga caggctccgg gtcagggtct ggagtggatg     600
ggatggatta cacctacac tggggaatcg acttactccg cggacttcaa agggcggttc     660
gtgttttcac tggacaccag cgtgtccacc gcttacttgc aaatcaacgc cctcaaggcc     720
gaggacaccg ccgtgtacta ctgcgcacgc tcaggcggat acgatccaat ggactactgg     780
ggacagggca ctacggtgac tgtgtcctcc accactaccc cagcaccgag gccacccacc     840
ccggctccta ccatcgcctc ccagcctctg tcctgcgtc ggaggcatg tagacccgca     900 gctggtgggg ccgtgcatac ccggggtctt gacttcgcct gcgatatcta catttgggcc     960
cctctggctg gtacttgcgg ggtcctgctg ctttcactcg tgatcactct ttactgtaag    1020
cgcggtcgga agaagctgct gtacatcttt aagcaaccct tcatgaggcc tgtgcagact    1080
```

```
actcaagagg aggacggctg ttcatgccgg ttcccagagg aggaggaagg cggctgcgaa    1140
ctgcgcgtga aattcagccg cagcgcagat gctccagcct acaagcaggg gcagaaccag    1200
ctctacaacg aactcaatct tggtcggaga gaggagtacg acgtgctgga caagcggaga    1260
ggacgggacc cagaaatggg cgggaagccg cgcagaaaga atccccaaga gggcctgtac    1320
aacgagctcc aaaaggataa gatggcagaa gcctatagcg agattggtat gaaaggggaa    1380
cgcagaagag gcaaaggcca cgacggactg taccagggac tcagcaccgc caccaaggac    1440
acctatgacg ctcttcacat gcaggccctg ccgcctcgg                          1479
```

<210> SEQ ID NO 53
<211> LENGTH: 493
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 53

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Ala Pro Arg Leu Leu Ile Tyr Arg Ala Ser Asn Leu Glu
65                  70                  75                  80

Ser Gly Ile Pro Ala Arg Phe Ser Gly Ser Gly Ser Arg Thr Asp Phe
                85                  90                  95

Thr Leu Thr Ile Ser Ser Leu Glu Pro Glu Asp Val Ala Val Tyr Tyr
            100                 105                 110

Cys Gln Gln Ser Asn Glu Asp Pro Pro Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gln Ile Gln Leu Val Gln Ser Gly
145                 150                 155                 160

Ser Glu Leu Lys Lys Pro Gly Ala Ser Val Lys Val Ser Cys Lys Ala
                165                 170                 175

Ser Gly Tyr Ile Phe Thr Asn Tyr Gly Met Asn Trp Val Arg Gln Ala
            180                 185                 190

Pro Gly Gln Gly Leu Glu Trp Met Gly Trp Ile Asn Thr Tyr Thr Gly
        195                 200                 205

Glu Ser Thr Tyr Ser Ala Asp Phe Lys Gly Arg Phe Val Phe Ser Leu
    210                 215                 220

Asp Thr Ser Val Ser Thr Ala Tyr Leu Gln Ile Asn Ala Leu Lys Ala
225                 230                 235                 240

Glu Asp Thr Ala Val Tyr Tyr Cys Ala Arg Ser Gly Gly Tyr Asp Pro
                245                 250                 255

Met Asp Tyr Trp Gly Gln Gly Thr Thr Val Thr Val Ser Ser Thr Thr
            260                 265                 270

Thr Pro Ala Pro Arg Pro Pro Thr Pro Ala Pro Thr Ile Ala Ser Gln
        275                 280                 285
```

```
Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
                325                 330                 335

Leu Tyr Cys Lys Arg Gly Arg Lys Leu Leu Tyr Ile Phe Lys Gln
            340                 345                 350

Pro Phe Met Arg Pro Val Gln Thr Thr Gln Glu Asp Gly Cys Ser
        355                 360                 365

Cys Arg Phe Pro Glu Glu Glu Gly Gly Cys Glu Leu Arg Val Lys
370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 54
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ala Glu Val Lys Lys
    130                 135                 140

Pro Gly Ala Ser Val Lys Val Ser Cys Lys Ala Ser Gly Tyr Ile Phe
145                 150                 155                 160
```

Thr Asn Tyr Gly Met Asn Trp Val Arg Gln Ala Pro Gly Gln Arg Leu
            165                 170                 175

Glu Trp Met Gly Trp Ile Asn Thr Tyr Thr Gly Glu Ser Thr Tyr Ser
        180                 185                 190

Ala Asp Phe Lys Gly Arg Val Thr Ile Thr Leu Asp Thr Ser Ala Ser
    195                 200                 205

Thr Ala Tyr Met Glu Leu Ser Ser Leu Arg Ser Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245

<210> SEQ ID NO 55
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
gagatcgtct tgacgcaatc gccagccacc ctgtccctga gcccaggcga gcgcgccacc      60
ctcagctgtc gggcgagcga aagcgtggac aattacggaa acacctttat gcactggtac     120
caacagaaac cggggcaggc tccgcgcctc ctcatctacc gcgcatccaa tctggaatca     180
ggaatccccg cgaggttctc cggtagcgga tcgcggactg actttactct gaccatctcg     240
tcccttgaac cggaggatgt ggctgtgtat tactgccagc agtcaaacga ggaccctcca     300
actttcgggc agggaaccaa gctcgaaatc aaggcggtg gcgaagcgg aggaggagga      360 tcaggcggag gcggctcagg cggtggaggt tcacaaattc aactggtgca gtcgggagcg     420
gaggtcaaga agccgggagc ctcagtgaaa gtgagctgca aggcttcggg ttacattttc     480
actaattacg gcatgaactg ggtgaggcag gcccctggcc aacggttgga atggatggga     540
tggatcaaca cctacaccgg ggagtcgact tactccgcgg acttcaaggg agagtcacg      600 atcaccctgg atacgtccgc aagcactgcc tacatggaac tgtcctccct cgcgtcggaa     660
gataccgcag tctactactg cgccagatcg ggcggatatg acccgatgga ctactgggga     720
cagggaacta ctgtcaccgt gtcctcg                                        747

<210> SEQ ID NO 56
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggccctcc ctgtcaccgc cctgctgctt ccgctggctc ttctgctcca cgccgctcgg      60
cccgagatcg tcttgacgca atcgccagcc accctgtccc tgagcccagg cgagcgcgcc     120
accctcagct gtcgggcgag cgaaagcgtg gacaattacg gaaacacctt tatgcactgg     180
taccaacaga aaccggggca ggctccgcgc ctcctcatct accgcgcatc caatctggaa     240
tcaggaatcc ccgcgaggtt ctccggtagc ggatcgcgga ctgactttac tctgaccatc     300
tcgtcccttg aacggagga tgtggctgtg tattactgcc agcagtcaaa cgaggaccct     360

-continued

```
ccaactttcg ggcagggaac caagctcgaa atcaagggcg gtggcggaag cggaggagga      420
ggatcaggcg gaggcggctc aggcggtgga ggttcacaaa ttcaactggt gcagtcggga      480
gcggaggtca agaagccggg agcctcagtg aaagtgagct gcaaggcttc gggttacatt      540
ttcactaatt acggcatgaa ctgggtgagg caggcccctg gccaacggtt ggaatggatg      600
ggatggatca acacctacac cggggagtcg acttactccg cggacttcaa ggggagagtc      660
acgatcaccc tggatacgtc cgcaagcact gcctacatgg aactgtcctc cctgcgctcg      720
gaagataccg cagtctacta ctgcgccaga tcgggcggat atgacccgat ggactactgg      780
ggacagggaa ctactgtcac cgtgtcctcg ggctcgcacc accatcacca tcatcatcac      840
cac                                                                   843
```

<210> SEQ ID NO 57
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Glu
        35                  40                  45

Ser Val Asp Asn Tyr Gly Asn Thr Phe Met His Trp Tyr Gln Gln Lys
    50                  55                  60

Pro Gly Gln Ala Pro Arg Leu Leu Ile Tyr Arg Ala Ser Asn Leu Glu
65                  70                  75                  80

Ser Gly Ile Pro Ala Arg Phe Ser Gly Ser Gly Ser Arg Thr Asp Phe
                85                  90                  95

Thr Leu Thr Ile Ser Ser Leu Glu Pro Glu Asp Val Ala Val Tyr Tyr
            100                 105                 110

Cys Gln Gln Ser Asn Glu Asp Pro Pro Thr Phe Gly Gln Gly Thr Lys
        115                 120                 125

Leu Glu Ile Lys Gly Gly Gly Gly Ser Gly Gly Gly Gly Ser Gly Gly
    130                 135                 140

Gly Gly Ser Gly Gly Gly Gly Ser Gln Ile Gln Leu Val Gln Ser Gly
145                 150                 155                 160

Ala Glu Val Lys Lys Pro Gly Ala Ser Val Lys Val Ser Cys Lys Ala
                165                 170                 175

Ser Gly Tyr Ile Phe Thr Asn Tyr Gly Met Asn Trp Val Arg Gln Ala
            180                 185                 190

Pro Gly Gln Arg Leu Glu Trp Met Gly Trp Ile Asn Thr Tyr Thr Gly
        195                 200                 205

Glu Ser Thr Tyr Ser Ala Asp Phe Lys Gly Arg Val Thr Ile Thr Leu
    210                 215                 220

Asp Thr Ser Ala Ser Thr Ala Tyr Met Glu Leu Ser Ser Leu Arg Ser
225                 230                 235                 240

Glu Asp Thr Ala Val Tyr Tyr Cys Ala Arg Ser Gly Gly Tyr Asp Pro
                245                 250                 255

Met Asp Tyr Trp Gly Gln Gly Thr Thr Val Thr Val Ser Ser Gly Ser
            260                 265                 270
```

His His His His His His His His His
            275                 280

<210> SEQ ID NO 58
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

| | | | | |
|---|---|---|---|---|
| atggccctcc | ctgtcaccgc | cctgctgctt | ccgctggctc | ttctgctcca cgccgctcgg | 60 |
| cccgagatcg | tcttgacgca | atcgccagcc | accctgtccc | tgagcccagg cgagcgcgcc | 120 |
| accctcagct | gtcgggcgag | cgaaagcgtg | gacaattacg | gaaacacctt tatgcactgg | 180 |
| taccaacaga | aaccggggca | ggctccgcgc | ctcctcatct | accgcgcatc caatctggaa | 240 |
| tcaggaatcc | ccgcgaggtt | ctccggtagc | ggatcgcgga | ctgactttac tctgaccatc | 300 |
| tcgtcccttg | aaccggagga | tgtggctgtg | tattactgcc | agcagtcaaa cgaggaccct | 360 |
| ccaactttcg | gcagggaac | caagctcgaa | atcaagggcg | gtggcggaag cggaggagga | 420 |
| ggatcaggcg | gaggcggctc | aggcggtgga | ggttcacaaa | ttcaactggt gcagtcggga | 480 |
| gcggaggtca | agaagccggg | agcctcagtg | aaagtgagct | gcaaggcttc gggttacatt | 540 |
| ttcactaatt | acggcatgaa | ctgggtgagg | caggcccctg | gccaacggtt ggaatggatg | 600 |
| ggatggatca | acacctacac | cggggagtcg | acttactccg | cggacttcaa ggggagagtc | 660 |
| acgatcaccc | tggatacgtc | cgcaagcact | gcctacatgg | aactgtcctc cctgcgctcg | 720 |
| gaagataccg | cagtctacta | ctgcgccaga | tcgggcggat | atgacccgat ggactactgg | 780 |
| ggacagggaa | ctactgtcac | cgtgtcctcg | accactaccc | cagcaccgag gccacccacc | 840 |
| ccggctccta | ccatcgcctc | ccagcctctg | tccctgcgtc | cggaggcatg tagacccgca | 900 |
| gctggtgggg | ccgtgcatac | ccgggggtctt | gacttcgcct | gcgatatcta catttgggcc | 960 |
| cctctggctg | gtacttgcgg | ggtcctgctg | ctttcactcg | tgatcactct ttactgtaag | 1020 |
| cgcggtcgga | agaagctgct | gtacatcttt | aagcaaccct | tcatgaggcc tgtgcagact | 1080 |
| actcaagagg | aggacggctg | ttcatgccgg | ttcccagagg | aggaggaagg cggctgcgaa | 1140 |
| ctgcgcgtga | aattcagccg | cagcgcagat | gctccagcct | acaagcaggg gcagaaccag | 1200 |
| ctctacaacg | aactcaatct | tggtcggaga | gaggagtacg | acgtgctgga caagcggaga | 1260 |
| ggacgggacc | cagaaatggg | cgggaagccg | cgcagaaaga | tccccaaga gggcctgtac | 1320 |
| aacgagctcc | aaaaggataa | gatggcagaa | gcctatagcg | agattggtat gaaaggggaa | 1380 |
| cgcagaagag | gcaaaggcca | cgacggactg | taccagggac | tcagcaccgc caccaaggac | 1440 |
| acctatgacg | ctcttcacat | gcaggccctg | ccgcctcgg | | 1479 |

<210> SEQ ID NO 59
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Ala Leu Pro Val Thr Ala Leu Leu Leu Pro Leu Ala Leu Leu Leu
1               5                   10                  15

-continued

```
His Ala Ala Arg Pro Glu Ile Val Leu Thr Gln Ser Pro Ala Thr Leu
             20                  25                  30
Ser Leu Ser Pro Gly Glu Arg Ala Thr Leu Ser Cys Arg Ala Ser Glu
         35                  40                  45
Ser Val Asp Asn Tyr Gly Asn Thr Phe Met His Trp Tyr Gln Gln Lys
     50                  55                  60
Pro Gly Gln Ala Pro Arg Leu Leu Ile Tyr Arg Ala Ser Asn Leu Glu
 65                  70                  75                  80
Ser Gly Ile Pro Ala Arg Phe Ser Gly Ser Gly Ser Arg Thr Asp Phe
                 85                  90                  95
Thr Leu Thr Ile Ser Ser Leu Glu Pro Glu Asp Val Ala Val Tyr Tyr
            100                 105                 110
Cys Gln Gln Ser Asn Glu Asp Pro Pro Thr Phe Gly Gln Gly Thr Lys
        115                 120                 125
Leu Glu Ile Lys Gly Gly Gly Gly Ser Gly Gly Gly Gly Ser Gly Gly
    130                 135                 140
Gly Gly Ser Gly Gly Gly Ser Gln Ile Gln Leu Val Gln Ser Gly
145                 150                 155                 160
Ala Glu Val Lys Lys Pro Gly Ala Ser Val Lys Val Ser Cys Lys Ala
                165                 170                 175
Ser Gly Tyr Ile Phe Thr Asn Tyr Gly Met Asn Trp Val Arg Gln Ala
            180                 185                 190
Pro Gly Gln Arg Leu Glu Trp Met Gly Trp Ile Asn Thr Tyr Thr Gly
        195                 200                 205
Glu Ser Thr Tyr Ser Ala Asp Phe Lys Gly Arg Val Thr Ile Thr Leu
    210                 215                 220
Asp Thr Ser Ala Ser Thr Ala Tyr Met Glu Leu Ser Ser Leu Arg Ser
225                 230                 235                 240
Glu Asp Thr Ala Val Tyr Tyr Cys Ala Arg Ser Gly Tyr Asp Pro
                245                 250                 255
Met Asp Tyr Trp Gly Gln Gly Thr Thr Val Thr Val Ser Ser Thr Thr
            260                 265                 270
Thr Pro Ala Pro Arg Pro Pro Thr Pro Ala Pro Thr Ile Ala Ser Gln
        275                 280                 285
Pro Leu Ser Leu Arg Pro Glu Ala Cys Arg Pro Ala Ala Gly Gly Ala
    290                 295                 300
Val His Thr Arg Gly Leu Asp Phe Ala Cys Asp Ile Tyr Ile Trp Ala
305                 310                 315                 320
Pro Leu Ala Gly Thr Cys Gly Val Leu Leu Leu Ser Leu Val Ile Thr
                325                 330                 335
Leu Tyr Cys Lys Arg Gly Arg Lys Lys Leu Leu Tyr Ile Phe Lys Gln
            340                 345                 350
Pro Phe Met Arg Pro Val Gln Thr Thr Gln Glu Glu Asp Gly Cys Ser
        355                 360                 365
Cys Arg Phe Pro Glu Glu Glu Gly Gly Cys Glu Leu Arg Val Lys
    370                 375                 380
Phe Ser Arg Ser Ala Asp Ala Pro Ala Tyr Lys Gln Gly Gln Asn Gln
385                 390                 395                 400
Leu Tyr Asn Glu Leu Asn Leu Gly Arg Arg Glu Glu Tyr Asp Val Leu
                405                 410                 415
Asp Lys Arg Arg Gly Arg Asp Pro Glu Met Gly Gly Lys Pro Arg Arg
            420                 425                 430
Lys Asn Pro Gln Glu Gly Leu Tyr Asn Glu Leu Gln Lys Asp Lys Met
```

```
                    435                 440                 445
Ala Glu Ala Tyr Ser Glu Ile Gly Met Lys Gly Glu Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 60
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ser Ala Asp Phe
    50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Ser Asp Ile Val Leu Thr Gln
    130                 135                 140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
            180                 185                 190

Ala Ser Asn Leu Glu Ser Gly Val Pro Asp Arg Phe Ser Gly Ser Gly
        195                 200                 205

Ser Arg Thr Asp Phe Thr Leu Thr Ile Ser Ser Leu Gln Ala Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245

<210> SEQ ID NO 61
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 61

```
cagatccagt tggtccagtc aggctccgaa ctgaaaaagc cgggtgcatc cgtcaaggtg      60
tcgtgcaaag cctccggtta cattttcacc aactacggca tgaactgggt ccgccaggcc     120
cctgggcagg gactcgaatg gatggggtgg atcaacactt acaccggaga gtcgacttac     180
tcggccgatt tcaagggacg gttcgtgttt ccctggaca cttcagtctc gaccgcatat      240
ctccaaatca acgcgcttaa ggcggaagat actgctgtct actactgcgc cagatcagga     300
ggttacgatc caatggacta ctggggacag ggcaccactg tgacggtgtc gtcgggagga     360
ggaggatcgg gcggaggcgg gtccggcggt ggagggagcg gaggaggcgg aagcgacatc     420
gtgctgaccc agtcgccaga tagcctggcg gtgtccttgg gtgagagggc taccatcaat     480
tgtcgcgcgt cagagtccgt ggacaattac gggaatacct tcatgcactg gtaccaacaa    540
aagcccggac aaccgccgaa gctgctgatc tacagagcaa gcaacctcga atcaggagtg    600
ccggaccgct ttagcgggtc aggaagccgg actgacttca ccctgactat ctcctcgctc    660
caggccgagg acgtggccgt gtattactgc cagcagagca cgaagatcc tccaacgttc    720
ggccaaggaa ccaaactgga gattaag                                         747
```

<210> SEQ ID NO 62
<211> LENGTH: 843
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62

```
atggccctcc ctgtcaccgc cctgctgctt ccgctggctc ttctgctcca cgccgctcgg     60
ccccagatcc agttggtcca gtcaggctcc gaactgaaaa agccgggtgc atccgtcaag    120
gtgtcgtgca aagcctccgg ttacattttc accaactacg gcatgaactg gtccgccag    180
gcccctgggc agggactcga atggatgggg tggatcaaca cttacaccgg agagtcgact    240
tactcggccg atttcaaggg acggttcgtg ttttccctgg acacttcagt ctcgaccgca    300
tatctccaaa tcaacgcgct taaggcgaa gatactgctg tctactactg cgccagatca    360
ggaggttacg atccaatgga ctactgggga cagggcacca ctgtgacggt gtcgtcggga    420
ggaggaggat cgggcggagg cgggtccggc ggtggaggga gcggaggagg cggaagcgac    480
atcgtgctga cccagtcgcc agatagcctg gcggtgtcct tgggtgagag ggctaccatc    540
aattgtcgcg cgtcagagtc cgtggacaat tacgggaata ccttcatgca ctggtaccaa    600
caaaagcccg acaaccgcc gaagctgctg atctacagag caagcaacct cgaatcagga    660
gtgccggacc gctttagcgg gtcaggaagc cggactgact tcaccctgac tatctcctcg    720
ctccaggccg aggacgtggc cgtgtattac tgccagcaga gcaacgaaga tcctccaacg    780
ttcggccaag gaaccaaact ggagattaag gctcgcacc accatcacca tcatcatcac    840
cac                                                                  843
```

<210> SEQ ID NO 63
<211> LENGTH: 281
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ser Glu Leu
                20                  25                  30

Lys Lys Pro Gly Ala Ser Val Lys Val Ser Cys Lys Ala Ser Gly Tyr
            35                  40                  45

Ile Phe Thr Asn Tyr Gly Met Asn Trp Val Arg Gln Ala Pro Gly Gln
        50                  55                  60

Gly Leu Glu Trp Met Gly Trp Ile Asn Thr Tyr Thr Gly Glu Ser Thr
65              70                  75                  80

Tyr Ser Ala Asp Phe Lys Gly Arg Phe Val Phe Ser Leu Asp Thr Ser
                85                  90                  95

Val Ser Thr Ala Tyr Leu Gln Ile Asn Ala Leu Lys Ala Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Gly Gly Gly Gly Ser Asp
145                 150                 155                 160

Ile Val Leu Thr Gln Ser Pro Asp Ser Leu Ala Val Ser Leu Gly Glu
            165                 170                 175

Arg Ala Thr Ile Asn Cys Arg Ala Ser Glu Ser Val Asp Asn Tyr Gly
        180                 185                 190

Asn Thr Phe Met His Trp Tyr Gln Gln Lys Pro Gly Gln Pro Pro Lys
    195                 200                 205

Leu Leu Ile Tyr Arg Ala Ser Asn Leu Glu Ser Gly Val Pro Asp Arg
210                 215                 220

Phe Ser Gly Ser Gly Ser Arg Thr Asp Phe Thr Leu Thr Ile Ser Ser
225                 230                 235                 240

Leu Gln Ala Glu Asp Val Ala Val Tyr Tyr Cys Gln Gln Ser Asn Glu
            245                 250                 255

Asp Pro Pro Thr Phe Gly Gln Gly Thr Lys Leu Glu Ile Lys Gly Ser
        260                 265                 270

His His His His His His His His
        275                 280

<210> SEQ ID NO 64
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
atggccctcc ctgtcaccgc cctgctgctt ccgctggctc ttctgctcca cgccgctcgg     60
ccccagatcc agttggtcca gtcaggctcc gaactgaaaa agccgggtgc atccgtcaag    120
gtgtcgtgca agcctccgg ttacattttc accaactacg gcatgaactg ggtccgccag    180
gcccctgggc agggactcga atggatgggg tggatcaaca cttacaccgg agagtcgact    240
tactcggccg atttcaaggg acggttcgtg ttttccctgg acacttcagt ctcgaccgca    300
tatctccaaa tcaacgcgct taaggcgaa gatactgctg tctactactg cgccagatca    360
ggaggttacg atccaatgga ctactgggga cagggcacca ctgtgacggt gtcgtcggga    420

-continued

```
ggaggaggat cgggcggagg cgggtccggc ggtggaggga gcggaggagg cggaagcgac    480
atcgtgctga cccagtcgcc agatagcctg gcggtgtcct tgggtgagag ggctaccatc    540
aattgtcgcg cgtcagagtc cgtggacaat tacgggaata ccttcatgca ctggtaccaa    600
caaaagcccg gacaaccgcc gaagctgctg atctacagag caagcaacct cgaatcagga    660
gtgccggacc gctttagcgg gtcaggaagc cggactgact tcaccctgac tatctcctcg    720
ctccaggccg aggacgtggc cgtgtattac tgccagcaga gcaacgaaga tcctccaacg    780
ttcggccaag gaaccaaact ggagattaag accactaccc cagcaccgag gccacccacc    840
ccggctccta ccatcgcctc ccagcctctg tccctgcgtc cggaggcatg tagacccgca    900
gctggtgggg ccgtgcatac ccggggtctt gacttcgcct gcgatatcta catttgggcc    960
cctctggctg gtacttgcgg ggtcctgctg ctttcactcg tgatcactct ttactgtaag   1020
cgcggtcgga agaagctgct gtacatcttt aagcaaccct tcatgaggcc tgtgcagact   1080
actcaagagg aggacggctg ttcatgccgg ttcccagagg aggaggaagg cggctgcgaa   1140
ctgcgcgtga aattcagccg cagcgcagat gctccagcct acaagcaggg gcagaaccag   1200
ctctacaacg aactcaatct tggtcggaga gaggagtacg acgtgctgga caagcgggaga  1260 ggacgggacc cagaaatggg cgggaagccg cgcagaaaga tccccaaga gggcctgtac    1320 aacgagctcc aaaaggataa gatggcagaa gcctatagcg agattggtat gaaaggggaa   1380
cgcagaagag gcaaaggcca cgacggactg taccagggac tcagcaccgc caccaaggac   1440
acctatgacg ctcttcacat gcaggccctg ccgcctcgg                          1479
```

<210> SEQ ID NO 65
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ser Glu Leu
                20                  25                  30

Lys Lys Pro Gly Ala Ser Val Lys Val Ser Cys Lys Ala Ser Gly Tyr
            35                  40                  45

Ile Phe Thr Asn Tyr Gly Met Asn Trp Val Arg Gln Ala Pro Gly Gln
        50                  55                  60

Gly Leu Glu Trp Met Gly Trp Ile Asn Thr Tyr Thr Gly Glu Ser Thr
65                  70                  75                  80

Tyr Ser Ala Asp Phe Lys Gly Arg Phe Val Phe Ser Leu Asp Thr Ser
                85                  90                  95

Val Ser Thr Ala Tyr Leu Gln Ile Asn Ala Leu Lys Ala Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Gly Gly Gly Gly Ser Asp
145                 150                 155                 160

Ile Val Leu Thr Gln Ser Pro Asp Ser Leu Ala Val Ser Leu Gly Glu
```

-continued

```
                165                 170                 175
Arg Ala Thr Ile Asn Cys Arg Ala Ser Glu Ser Val Asp Asn Tyr Gly
            180                 185                 190

Asn Thr Phe Met His Trp Tyr Gln Gln Lys Pro Gly Gln Pro Pro Lys
        195                 200                 205

Leu Leu Ile Tyr Arg Ala Ser Asn Leu Glu Ser Gly Val Pro Asp Arg
    210                 215                 220

Phe Ser Gly Ser Gly Ser Arg Thr Asp Phe Thr Leu Thr Ile Ser Ser
225                 230                 235                 240

Leu Gln Ala Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 66
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 66

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30
```

Gly Met Asn Trp Val Arg Gln Ala Pro Gly Gln Gly Leu Glu Trp Met
            35                  40                  45

Gly Trp Ile Asn Thr Tyr Thr Gly Glu Ser Thr Tyr Ser Ala Asp Phe
 50                  55                  60

Lys Gly Arg Phe Val Phe Ser Leu Asp Thr Ser Val Ser Thr Ala Tyr
 65                  70                  75                  80

Leu Gln Ile Asn Ala Leu Lys Ala Glu Asp Thr Ala Val Tyr Tyr Cys
                 85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
            115                 120                 125

Gly Gly Gly Gly Ser Gly Gly Gly Ser Glu Ile Val Leu Thr Gln
            130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
            180                 185                 190

Ala Ser Asn Leu Glu Ser Gly Ile Pro Ala Arg Phe Ser Gly Ser Gly
            195                 200                 205

Ser Arg Thr Asp Phe Thr Leu Thr Ile Ser Ser Leu Glu Pro Glu Asp
            210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
            245

<210> SEQ ID NO 67
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
cagatccaac tggtgcaatc aggatcggag ctgaagaagc ctggggcttc agtgaaagtc         60
agctgcaaag cctccggtta catcttcacc aactacggca tgaactgggt gcgccaggcc        120
cctggacagg gactcgaatg gatggggtgg atcaacacct ataccgggga atccacgtac        180
tcagcagatt tcaagggacg cttcgtcttt cgctggata cctccgtgtc cactgcgtac         240
ctccaaatca tgccctcaa agccgaagat actgcggtct actactgcgc acggagcgga        300
ggctacgacc cgatggacta ctggggacag ggaaccacgg tgaccgtgtc cagcggagga        360
ggcggatcgg gaggcggtgg ttcaggcggt ggaggcagcg gcgaggtgg aagcgaaatc         420 gtcttgactc agagcccagc gactttgtcc ctgtcgcccg gagagcgggc aactctgtca        480
tgccgcgctt cggaatcggt ggacaactat ggaaacacct ttatgcactg gtaccaacag        540
aagccgggac aagccccgag acttctgatc taccgggcct cgaatctcga agcggcatc         600 ccggctagat tctcggggtc gggatcaagg accgacttca ctcttactat ttcctcactg        660
gagccagaag atgtggcggt gtactactgt cagcagtcca atgaggaccc gccaactttc        720
gggcagggca ccaagctgga gattaag                                            747

<210> SEQ ID NO 68
<211> LENGTH: 843
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
atggccctcc ctgtcaccgc cctgctgctt ccgctggctc ttctgctcca cgccgctcgg      60
ccccagatcc aactggtgca atcaggatcg gagctgaaga agcctggggc ttcagtgaaa     120
gtcagctgca agcctccgg ttacatcttc accaactacg gcatgaactg ggtgcgccag      180
gcccctggac agggactcga atggatgggg tggatcaaca cctataccgg ggaatccacg     240
tactcagcag atttcaaggg acgcttcgtc ttttcgctgg ataccagt gtccactgcg       300
tacctccaaa tcaatgccct caaagccgaa gatactgcgg tctactactg cgcacggagc     360
ggaggctacg acccgatgga ctactgggga caggaaacca cggtgaccgt gtccagcgga     420
ggaggcggat cgggaggcgg tggttcaggc ggtggaggca gcggcggagg tggaagcgaa     480
atcgtcttga ctcagagccc agcgactttg tccctgtcgc ccggagagcg ggcaactctg     540
tcatgccgcg cttcggaatc ggtggacaac tatggaaaca cctttatgca ctggtaccaa     600
cagaagccgg acaagcccc gagacttctg atctaccggg cctcgaatct cgaaagcggc     660
atcccggcta gattctcggg gtcgggatca aggaccgact tcactcttac tatttcctca     720
ctggagccag aagatgtggc ggtgtactac tgtcagcagt ccaatgagga cccgccaact     780
ttcgggcagg gcaccaagct ggagattaag ggctcgcacc accatcacca tcatcatcac     840
cac                                                                   843
```

<210> SEQ ID NO 69
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ser Glu Leu
            20                  25                  30

Lys Lys Pro Gly Ala Ser Val Lys Val Ser Cys Lys Ala Ser Gly Tyr
        35                  40                  45

Ile Phe Thr Asn Tyr Gly Met Asn Trp Val Arg Gln Ala Pro Gly Gln
    50                  55                  60

Gly Leu Glu Trp Met Gly Trp Ile Asn Thr Tyr Thr Gly Glu Ser Thr
65                  70                  75                  80

Tyr Ser Ala Asp Phe Lys Gly Arg Phe Val Phe Ser Leu Asp Thr Ser
                85                  90                  95

Val Ser Thr Ala Tyr Leu Gln Ile Asn Ala Leu Lys Ala Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140
```

Gly Gly Gly Ser Gly Gly Gly Ser Gly Gly Gly Ser Glu
145                 150                 155                 160

Ile Val Leu Thr Gln Ser Pro Ala Thr Leu Ser Leu Ser Pro Gly Glu
                165                 170                 175

Arg Ala Thr Leu Ser Cys Arg Ala Ser Glu Ser Val Asp Asn Tyr Gly
            180                 185                 190

Asn Thr Phe Met His Trp Tyr Gln Gln Lys Pro Gly Gln Ala Pro Arg
        195                 200                 205

Leu Leu Ile Tyr Arg Ala Ser Asn Leu Glu Ser Gly Ile Pro Ala Arg
    210                 215                 220

Phe Ser Gly Ser Gly Ser Arg Thr Asp Phe Thr Leu Thr Ile Ser Ser
225                 230                 235                 240

Leu Glu Pro Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Gly Ser
            260                 265                 270

His His His His His His His His
        275                 280

<210> SEQ ID NO 70
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atggccctcc ctgtcaccgc cctgctgctt ccgctggctc ttctgctcca cgccgctcgg      60
ccccagatcc aactggtgca atcaggatcg gagctgaaga agcctggggc ttcagtgaaa     120
gtcagctgca aagcctccgg ttacatcttc accaactacg gcatgaactg ggtgcgccag     180
gcccctggac agggactcga atggatgggg tggatcaaca cctataccgg gaatccacg      240 tactcagcag atttcaaggg acgcttcgtc ttttcgctgg ataccctcgt gtccactgcg     300
tacctccaaa tcaatgccct caaagccgaa gatactgcgg tctactactg cgcacggagc     360
ggaggctacg acccgatgga ctactgggga cagggaacca cggtgaccgt gtccagcgga     420
ggaggcggat cggaggcggt tggttcaggc ggtggaggca gcggcggagg tggaagcgaa     480
atcgtcttga ctcagagccc agcgactttg tccctgtcgc ccggagagcg ggcaactctg     540
tcatgccgcg cttcggaatc ggtggacaac tatggaaaca cctttatgca ctggtaccaa     600
cagaagccgg acaagccccc gagacttctg atctaccggg cctcgaatct cgaaagcggc     660
atcccggcta gattctcggg gtcgggatca aggaccgact tcactcttac tatttcctca     720
ctggagccag aagatgtggc ggtgtactac tgtcagcagt ccaatgagga cccgccaact     780
ttcgggcagg gcaccaagct ggagattaag accactaccc cagcaccgag gccacccacc     840
ccggctccta ccatcgcctc ccagcctctg tccctgcgtc cggaggcatg tagacccgca     900
gctggtgggg ccgtgcatac ccggggtctt gacttcgcct gcgatatcta catttgggcc     960
cctctggctg gtacttgcgg ggtcctgctg ctttcactcg tgatcactct ttactgtaag    1020
cgcggtcgga agaagctgct gtacatcttt aagcaaccct tcatgaggcc tgtgcagact    1080
actcaagagg aggacggctg ttcatgccgg ttcccagagg aggaggaagg cggctgcgaa    1140
ctgcgcgtga aattcagccg cagcgcagat gctccagcct acaagcaggg gcagaaccag    1200
ctctacaacg aactcaatct tggtcggaga gaggagtacg acgtgctgga caagcggaga    1260

```
ggacgggacc cagaaatggg cgggaagccg cgcagaaaga atccccaaga gggcctgtac   1320
aacgagctcc aaaaggataa gatggcagaa gcctatagcg agattggtat gaaaggggaa   1380
cgcagaagag gcaaaggcca cgacggactg taccagggac tcagcaccgc caccaaggac   1440
acctatgacg ctcttcacat gcaggccctg ccgcctcgg                          1479
```

<210> SEQ ID NO 71
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ser Glu Leu
            20                  25                  30

Lys Lys Pro Gly Ala Ser Val Lys Val Ser Cys Lys Ala Ser Gly Tyr
        35                  40                  45

Ile Phe Thr Asn Tyr Gly Met Asn Trp Val Arg Gln Ala Pro Gly Gln
    50                  55                  60

Gly Leu Glu Trp Met Gly Trp Ile Asn Thr Tyr Thr Gly Glu Ser Thr
65                  70                  75                  80

Tyr Ser Ala Asp Phe Lys Gly Arg Phe Val Phe Ser Leu Asp Thr Ser
                85                  90                  95

Val Ser Thr Ala Tyr Leu Gln Ile Asn Ala Leu Lys Ala Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Ala Thr Leu Ser Leu Ser Pro Gly Glu
                165                 170                 175

Arg Ala Thr Leu Ser Cys Arg Ala Ser Glu Ser Val Asp Asn Tyr Gly
            180                 185                 190

Asn Thr Phe Met His Trp Tyr Gln Gln Lys Pro Gly Gln Ala Pro Arg
        195                 200                 205

Leu Leu Ile Tyr Arg Ala Ser Asn Leu Glu Ser Gly Ile Pro Ala Arg
    210                 215                 220

Phe Ser Gly Ser Gly Ser Arg Thr Asp Phe Thr Leu Thr Ile Ser Ser
225                 230                 235                 240

Leu Glu Pro Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320
```

Pro Leu Ala Gly Thr Cys Gly Val Leu Leu Ser Leu Val Ile Thr
            325                 330                 335

Leu Tyr Cys Lys Arg Gly Arg Lys Leu Leu Tyr Ile Phe Lys Gln
            340                 345                 350

Pro Phe Met Arg Pro Val Gln Thr Thr Gln Glu Glu Asp Gly Cys Ser
            355                 360                 365

Cys Arg Phe Pro Glu Glu Glu Gly Gly Cys Glu Leu Arg Val Lys
            370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
            405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
            450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490

<210> SEQ ID NO 72
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
            35                  40                  45

Gly Trp Ile Asn Thr Tyr Thr Gly Glu Ser Thr Tyr Ser Ala Asp Phe
        50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Ser Gly Gly Gly Gly Ser
            115                 120                 125

Gly Gly Gly Gly Ser Gly Gly Gly Ser Asp Ile Val Leu Thr Gln
        130                 135                 140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
            165                 170                 175

Trp Tyr Gln Gln Lys Pro Gly Gln Pro Pro Lys Leu Leu Ile Tyr Arg

```
              180                 185                 190
Ala Ser Asn Leu Glu Ser Gly Val Pro Asp Arg Phe Ser Gly Ser Gly
            195                 200                 205

Ser Arg Thr Asp Phe Thr Leu Thr Ile Ser Ser Leu Gln Ala Glu Asp
        210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245
```

<210> SEQ ID NO 73
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73

```
cagatccagc tggtgcagtc gggagctgaa gtgaaaaagc cgggagcatc ggtgaaggtg    60
tcatgcaaag ccagcggtta catcttcact aactacggta tgaactgggt gagacaagcg   120
cctggccaga gattggaatg gatgggatgg atcaatacct acaccgggga atcaacttac   180
agcgccgact tcaagggacg cgtgaccatc acgctggaca cctccgcgtc cactgcctac   240
atggagctct cgtcattgcg gagcgaggac accgccgtct actactgcgc acggtcagga   300
gggtacgatc cgatggacta ctggggacag ggcactaccg tcaccgtgag ctccggtgga   360
ggcggcagcg gcggtggcgg atcaggtgga ggaggatcag gaggaggagg gtccgatatc   420
gtgcttactc agtcacccga ttcgctggca gtctccctcg gagaacgcgc caccatcaat   480
tgtcgcgcgt ccgaatccgt cgacaactac ggcaacacct ttatgcactg gtaccaacag   540
aagcctggac aaccgccaaa actgctgatc taccgcgcta gcaacctcga atcgggcgtg   600
ccagataggt tctcgggctc ggggagccgg acggatttta ctctgactat ttcgtccctc   660
caagcagagg acgtcgccgt gtattactgc cagcaatcga atgaggaccc gccaactttc   720
ggacagggga ccaagctgga gattaag                                       747
```

<210> SEQ ID NO 74
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
atggccctcc ctgtcaccgc cctgctgctt ccgctggctc ttctgctcca cgccgctcgg    60
ccccagatcc agctggtgca gtcgggagct gaagtgaaaa agccgggagc atcggtgaag   120
gtgtcatgca aagccagcgg ttacatcttc actaactacg gtatgaactg ggtgagacaa   180
gcgcctggcc agagattgga atggatggga tggatcaata cctacaccgg gaatcaact    240 tacagcgccg acttcaaggg acgcgtgacc atcacgctgg acacctccgc gtccactgcc   300
tacatggagc tctcgtcatt gcggagcgag gacaccgccg tctactactg cgcacggtca   360
ggagggtacg atccgatgga ctactgggga cagggcacta ccgtcaccgt gagctccggt   420
ggaggcggca gcggcggtgg cggatcaggt ggaggaggat caggaggagg agggtccgat   480
atcgtgctta ctcagtcacc cgattcgctg gcagtctccc tcggagaacg cgccaccatc   540
```

```
aattgtcgcg cgtccgaatc cgtcgacaac tacggcaaca cctttatgca ctggtaccaa    600
cagaagcctg gacaaccgcc aaaactgctg atctaccgcg ctagcaacct cgaatcgggc    660
gtgccagata ggttctcggg ctcggggagc cggacggatt ttactctgac tatttcgtcc    720
ctccaagcag aggacgtcgc cgtgtattac tgccagcaat cgaatgagga cccgccaact    780
ttcggacagg ggaccaagct ggagattaag ggctcgcacc accatcacca tcatcatcac    840
cac                                                                  843
```

```
<210> SEQ ID NO 75
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75
```

Met Ala Leu Pro Val Thr Ala Leu Leu Pro Leu Ala Leu Leu Leu
1               5                   10                  15

His Ala Ala Arg Pro Gln Ile Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

Ile Phe Thr Asn Tyr Gly Met Asn Trp Val Arg Gln Ala Pro Gly Gln
    50                  55                  60

Arg Leu Glu Trp Met Gly Trp Ile Asn Thr Tyr Thr Gly Glu Ser Thr
65                  70                  75                  80

Tyr Ser Ala Asp Phe Lys Gly Arg Val Thr Ile Thr Leu Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Gly Gly Gly Gly Ser Asp
145                 150                 155                 160

Ile Val Leu Thr Gln Ser Pro Asp Ser Leu Ala Val Ser Leu Gly Glu
                165                 170                 175

Arg Ala Thr Ile Asn Cys Arg Ala Ser Glu Ser Val Asp Asn Tyr Gly
            180                 185                 190

Asn Thr Phe Met His Trp Tyr Gln Gln Lys Pro Gly Gln Pro Pro Lys
        195                 200                 205

Leu Leu Ile Tyr Arg Ala Ser Asn Leu Glu Ser Gly Val Pro Asp Arg
    210                 215                 220

Phe Ser Gly Ser Gly Ser Arg Thr Asp Phe Thr Leu Thr Ile Ser Ser
225                 230                 235                 240

Leu Gln Ala Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Gly Ser
            260                 265                 270

His His His His His His His His
        275                 280

<210> SEQ ID NO 76
<211> LENGTH: 1479
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

| | | | | | |
|---|---|---|---|---|---|
| atggccctcc | ctgtcaccgc | cctgctgctt | ccgctggctc | ttctgctcca | cgccgctcgg | 60 |
| ccccagatcc | agctggtgca | gtcgggagct | gaagtgaaaa | agccgggagc | atcggtgaag | 120 |
| gtgtcatgca | aagccagcgg | ttacatcttc | actaactacg | gtatgaactg | ggtgagacaa | 180 |
| gcgcctggcc | agagattgga | atggatggga | tggatcaata | cctacaccgg | ggaatcaact | 240 |
| tacagcgccg | acttcaaggg | acgcgtgacc | atcacgctgg | acacctccgc | gtccactgcc | 300 |
| tacatggagc | tctcgtcatt | gcggagcgag | gacaccgccg | tctactactg | cgcacggtca | 360 |
| ggagggtacg | atccgatgga | ctactgggga | caggcactac | cgtcaccgt | gagctccggt | 420 |
| ggaggcggca | gcggcggtgg | cggatcaggt | ggaggaggat | caggaggagg | agggtccgat | 480 |
| atcgtgctta | ctcagtcacc | cgattcgctg | gcagtctccc | tcggagaacg | cgccaccatc | 540 |
| aattgtcgcg | cgtccgaatc | cgtcgacaac | tacggcaaca | cctttatgca | ctggtaccaa | 600 |
| cagaagcctg | gacaaccgcc | aaaactgctg | atctaccgcg | ctagcaacct | cgaatcgggc | 660 |
| gtgccagata | ggttctcggg | ctcggggagc | cggacggatt | ttactctgac | tatttcgtcc | 720 |
| ctccaagcag | aggacgtcgc | cgtgtattac | tgccagcaat | cgaatgagga | cccgccaact | 780 |
| ttcggacagg | ggaccaagct | ggagattaag | accactaccc | cagcaccgag | gccacccacc | 840 |
| ccggctccta | ccatcgcctc | ccagcctctg | tccctgcgtc | cggaggcatg | tagacccgca | 900 |
| gctggtgggg | ccgtgcatac | ccggggtctt | gacttcgcct | gcgatatcta | catttgggcc | 960 |
| cctctggctg | gtacttgcgg | ggtcctgctg | ctttcactcg | tgatcactct | ttactgtaag | 1020 |
| cgcggtcgga | agaagctgct | gtacatcttt | aagcaaccct | tcatgaggcc | tgtgcagact | 1080 |
| actcaagagg | aggacggctg | ttcatgccgg | ttcccagagg | aggaggaagg | cggctgcgaa | 1140 |
| ctgcgcgtga | aattcagccg | cagcgcagat | gctccagcct | acaagcaggg | gcagaaccag | 1200 |
| ctctacaacg | aactcaatct | tggtcggaga | gaggagtacg | acgtgctgga | caagcggaga | 1260 |
| ggacgggacc | cagaaatggg | cgggaagccg | cgcagaaaga | atccccaaga | gggcctgtac | 1320 |
| aacgagctcc | aaaaggataa | gatggcagaa | gcctatagcg | agattggtat | gaaagggggaa | 1380 |
| cgcagaagag | gcaaaggcca | cgacggactg | taccagggac | tcagcaccgc | caccaaggac | 1440 |
| acctatgacg | ctcttcacat | gcaggccctg | ccgcctcgg | | | 1479 |

<210> SEQ ID NO 77
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ala Glu Val
            20                  25                  30

Lys Lys Pro Gly Ala Ser Val Lys Val Ser Cys Lys Ala Ser Gly Tyr
        35                  40                  45

```
Ile Phe Thr Asn Tyr Gly Met Asn Trp Val Arg Gln Ala Pro Gly Gln
 50                  55                  60

Arg Leu Glu Trp Met Gly Trp Ile Asn Thr Tyr Thr Gly Glu Ser Thr
 65                  70                  75                  80

Tyr Ser Ala Asp Phe Lys Gly Arg Val Thr Ile Thr Leu Asp Thr Ser
                 85                  90                  95

Ala Ser Thr Ala Tyr Met Glu Leu Ser Ser Leu Arg Ser Glu Asp Thr
                100                 105                 110

Ala Val Tyr Tyr Cys Ala Arg Ser Gly Tyr Asp Pro Met Asp Tyr
                115                 120                 125

Trp Gly Gln Gly Thr Thr Val Thr Val Ser Ser Gly Gly Gly Ser
                130                 135                 140

Gly Gly Gly Gly Ser Gly Gly Gly Ser Gly Gly Gly Ser Asp
145                 150                 155                 160

Ile Val Leu Thr Gln Ser Pro Asp Ser Leu Ala Val Ser Leu Gly Glu
                165                 170                 175

Arg Ala Thr Ile Asn Cys Arg Ala Ser Glu Ser Val Asp Asn Tyr Gly
                180                 185                 190

Asn Thr Phe Met His Trp Tyr Gln Gln Lys Pro Gly Gln Pro Pro Lys
                195                 200                 205

Leu Leu Ile Tyr Arg Ala Ser Asn Leu Glu Ser Gly Val Pro Asp Arg
210                 215                 220

Phe Ser Gly Ser Gly Ser Arg Thr Asp Phe Thr Leu Thr Ile Ser Ser
225                 230                 235                 240

Leu Gln Ala Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Thr Thr
                260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
                290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Glu Gly Gly Cys Glu Leu Arg Val Lys
                370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
450                 455                 460
```

```
Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490
```

<210> SEQ ID NO 78
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ser Tyr Ser Ala Asp Phe
    50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
            180                 185                 190

Ala Ser Asn Leu Glu Ser Gly Ile Pro Ala Arg Phe Ser Gly Ser Gly
        195                 200                 205

Ser Arg Thr Asp Phe Thr Leu Thr Ile Ser Ser Leu Glu Pro Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245
```

<210> SEQ ID NO 79
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
cagatccagc tggtgcaatc gggagctgaa gtgaagaagc ccggagcttc agtcaaagtc     60
agctgcaagg cgtcgggcta tatcttcacc aactacggga tgaactgggt gcggcaggcc    120
```

```
cctggacaaa gactggaatg gatgggatgg atcaacactt atactggcga gagcacgtac    180
tcagccgact ttaagggacg ggtgactatc accctcgata cctccgcctc cactgcgtac    240
atggaactct cgtccttgcg ctccgaggac actgccgtgt actactgcgc caggtcgggt    300
ggctacgatc cgatggatta ctggggtcaa ggaaccaccg tcactgtgtc gtccggcgga    360
ggcgggagcg gaggtggtgg ttcgggagga ggagggtcag gcggaggagg cagcgaaatc    420
gtgctgaccc aaagcccggc aactctgtca ctcagcccag ggagagggc aaccctgtca    480 tgtcgggcta gcgaatccgt ggacaattac ggaaacacgt ttatgcactg gtaccaacag    540
aaaccaggac aggcgcctag acttctcatc taccgcgcga gcaatttgga atccggcatc    600
ccagcccgct ctccgggtc ggggtcacgc accgatttca ctctgaccat tcctccctg    660 gaacccgagg acgtggcagt ctactactgc cagcagtcga atgaggaccc gccgaccttc    720
ggacagggca ccaagctgga gattaag                                       747
```

```
<210> SEQ ID NO 80
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
atggccctcc ctgtcaccgc cctgctgctt ccgctggctc ttctgctcca cgccgctcgg    60
ccccagatcc agctggtgca atcgggagct gaagtgaaga agcccggagc ttcagtcaaa    120
gtcagctgca aggcgtcggg ctatatcttc accaactacg ggatgaactg ggtgcggcag    180 gccctggac aaagactgga atggatggga tggatcaaca cttatactgg cgagagcacg    240
tactcagccg actttaaggg acgggtgact atcaccctcg ataccctcgc ctccactgcg    300
tacatggaac tctcgtcctt gcgctccgag gacactgccg tgtactactg cgccaggtcg    360
ggtggctacg atccgatgga ttactggggt caaggaacca ccgtcactgt gtcgtccggc    420
ggaggcggga gcggaggtgg tggttcggga ggaggagggt caggcggagg aggcagcgaa    480
atcgtgctga cccaaagccc ggcaactctg tcactcagcc aggggagag gcaaccctg    540 tcatgtcggg ctagcgaatc cgtggacaat tacggaaaca cgtttatgca ctggtaccaa    600
cagaaaccag gacaggcgcc tagacttctc atctaccgcg cgagcaattt ggaatccggc    660
atcccagccc gcttctccgg gtcggggtca cgcaccgatt tcactctgac catttcctcc    720
ctggaacccg aggacgtggc agtctactac tgccagcagt cgaatgagga cccgccgacc    780
ttcggacagg gcaccaagct ggagattaag ggctcgcacc accatcacca tcatcatcac    840
cac                                                                 843
```

```
<210> SEQ ID NO 81
<211> LENGTH: 281
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ala Glu Val
```

```
                    20                  25                  30
Lys Lys Pro Gly Ala Ser Val Lys Val Ser Cys Lys Ala Ser Gly Tyr
            35                  40                  45
Ile Phe Thr Asn Tyr Gly Met Asn Trp Val Arg Gln Ala Pro Gly Gln
    50                  55                  60
Arg Leu Glu Trp Met Gly Trp Ile Asn Thr Tyr Thr Gly Glu Ser Thr
65                  70                  75                  80
Tyr Ser Ala Asp Phe Lys Gly Arg Val Thr Ile Thr Leu Asp Thr Ser
                85                  90                  95
Ala Ser Thr Ala Tyr Met Glu Leu Ser Ser Leu Arg Ser Glu Asp Thr
            100                 105                 110
Ala Val Tyr Tyr Cys Ala Arg Ser Gly Gly Tyr Asp Pro Met Asp Tyr
        115                 120                 125
Trp Gly Gln Gly Thr Thr Val Thr Val Ser Ser Gly Gly Gly Gly Ser
        130                 135                 140
Gly Gly Gly Gly Ser Gly Gly Gly Ser Gly Gly Gly Ser Glu
145                 150                 155                 160
Ile Val Leu Thr Gln Ser Pro Ala Thr Leu Ser Leu Ser Pro Gly Glu
                165                 170                 175
Arg Ala Thr Leu Ser Cys Arg Ala Ser Glu Ser Val Asp Asn Tyr Gly
            180                 185                 190
Asn Thr Phe Met His Trp Tyr Gln Gln Lys Pro Gly Gln Ala Pro Arg
        195                 200                 205
Leu Leu Ile Tyr Arg Ala Ser Asn Leu Glu Ser Gly Ile Pro Ala Arg
    210                 215                 220
Phe Ser Gly Ser Gly Ser Arg Thr Asp Phe Thr Leu Thr Ile Ser Ser
225                 230                 235                 240
Leu Glu Pro Glu Asp Val Ala Val Tyr Tyr Cys Gln Gln Ser Asn Glu
                245                 250                 255
Asp Pro Pro Thr Phe Gly Gln Gly Thr Lys Leu Glu Ile Lys Gly Ser
            260                 265                 270
His His His His His His His His His
        275                 280

<210> SEQ ID NO 82
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
atggccctcc ctgtcaccgc cctgctgctt ccgctggctc ttctgctcca cgccgctcgg      60
ccccagatcc agctggtgca atcgggagct gaagtgaaga agcccggagc ttcagtcaaa     120
gtcagctgca aggcgtcggg ctatatcttc accaactacg ggatgaactg ggtgcgcag     180 gccccctgga caaagactgg aatggatggga tggatcaaca cttatactgg cgagagcacg     240
tactcagccg actttaaggg acgggtgact atcaccctcg atacctccgc ctccactgcg     300
tacatggaac tctcgtcctt gcgctccgag gacactgccg tgtactactg cgccaggtcg     360
ggtggctacg atccgatgga ttactggggt caaggaacca ccgtcactgt gtcgtccggc     420
ggaggcggga gcggaggtgg tggttcggga ggagagggt caggcggagg aggcagcgaa     480
atcgtgctga cccaaagccc ggcaactctg tcactcagcc caggggagag ggcaaccctg     540
```

```
tcatgtcggg ctagcgaatc cgtggacaat tacggaaaca cgtttatgca ctggtaccaa      600
cagaaaccag gacaggcgcc tagacttctc atctaccgcg cgagcaattt ggaatccggc      660
atcccagccc gcttctccgg gtcggggtca cgcaccgatt tcactctgac catttcctcc      720
ctggaacccg aggacgtggc agtctactac tgccagcagt cgaatgagga cccgccgacc      780
ttcggacagg gcaccaagct ggagattaag accactaccc cagcaccgag gccacccacc      840
ccggctccta ccatcgcctc ccagcctctg tccctgcgtc cggaggcatg tagacccgca      900
gctggtgggg ccgtgcatac ccggggtctt gacttcgcct gcgatatcta catttgggcc      960
cctctggctg gtacttgcgg ggtcctgctg ctttcactcg tgatcactct ttactgtaag     1020
cgcggtcgga agaagctgct gtacatcttt aagcaaccct tcatgaggcc tgtgcagact     1080
actcaagagg aggacggctg ttcatgccgg ttcccagagg aggaggaagg cggctgcgaa     1140
ctgcgcgtga aattcagccg cagcgcagat gctccagcct acaagcaggg gcagaaccag     1200
ctctacaacg aactcaatct tggtcggaga gaggagtacg acgtgctgga caagcggaga     1260
ggacgggacc cagaaatggg cgggaagccg cgcagaaaga atccccaaga gggcctgtac     1320
aacgagctcc aaaaggataa gatggcagaa gcctatagcg agattggtat gaaaggggaa     1380
cgcagaagag gcaaaggcca cgacggactg taccagggac tcagcaccgc caccaaggac     1440
acctatgacg ctcttcacat gcaggccctg ccgcctcgg                            1479
```

<210> SEQ ID NO 83
<211> LENGTH: 493
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Ile Phe Thr Asn Tyr Gly Met Asn Trp Val Arg Gln Ala Pro Gly Gln
        50                  55                  60

Arg Leu Glu Trp Met Gly Trp Ile Asn Thr Tyr Thr Gly Glu Ser Thr
65                  70                  75                  80

Tyr Ser Ala Asp Phe Lys Gly Arg Val Thr Ile Thr Leu Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Ser Gly Gly Tyr Asp Pro Met Asp Tyr
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Gly Ser Gly Gly Gly Gly Ser Glu
145                 150                 155                 160

Ile Val Leu Thr Gln Ser Pro Ala Thr Leu Ser Leu Ser Pro Gly Glu
                165                 170                 175

Arg Ala Thr Leu Ser Cys Arg Ala Ser Glu Ser Val Asp Asn Tyr Gly
            180                 185                 190
```

```
Asn Thr Phe Met His Trp Tyr Gln Gln Lys Pro Gly Gln Ala Pro Arg
            195                 200                 205

Leu Leu Ile Tyr Arg Ala Ser Asn Leu Glu Ser Gly Ile Pro Ala Arg
210                 215                 220

Phe Ser Gly Ser Gly Ser Arg Thr Asp Phe Thr Leu Thr Ile Ser Ser
225                 230                 235                 240

Leu Glu Pro Glu Asp Val Ala Val Tyr Tyr Cys Gln Gln Ser Asn Glu
                245                 250                 255

Asp Pro Pro Thr Phe Gly Gln Gly Thr Lys Leu Glu Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 84
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 84

Ser Tyr Trp Met Asn
1               5

<210> SEQ ID NO 85
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 85
```

Arg Ile Asp Pro Tyr Asp Ser Glu Thr His Tyr Asn Gln Lys Phe Lys
1               5                   10                  15

Asp

<210> SEQ ID NO 86
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 86

Gly Asn Trp Asp Asp Tyr
1               5

<210> SEQ ID NO 87
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 87

Arg Ala Ser Lys Ser Ile Ser Lys Asp Leu Ala
1               5                   10

<210> SEQ ID NO 88
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 88

Ser Gly Ser Thr Leu Gln Ser
1               5

<210> SEQ ID NO 89
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 89

Gln Gln His Asn Lys Tyr Pro Tyr Thr
1               5

<210> SEQ ID NO 90
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(400)
<223> OTHER INFORMATION: This sequence may encompass between 100 and 400
      nucleotides

<400> SEQUENCE: 90
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180

| | | |
|---|---|---|
| aaaaaaaaaa aaaaaaaaaa aaaaaaaaaa aaaaaaaaaa aaaaaaaaaa aaaaaaaaaa | 240 | |
| aaaaaaaaaa aaaaaaaaaa aaaaaaaaaa aaaaaaaaaa aaaaaaaaaa aaaaaaaaaa | 300 | |
| aaaaaaaaaa aaaaaaaaaa aaaaaaaaaa aaaaaaaaaa aaaaaaaaaa aaaaaaaaaa | 360 | |
| aaaaaaaaaa aaaaaaaaaa aaaaaaaaaa aaaaaaaaaa | 400 | |

<210> SEQ ID NO 91
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

| | |
|---|---|
| atggccctgc ctgtgacagc cctgctgctg cctctggctc tgctgctgca cgccgctaga | 60 |
| cctggatccc aggtgcagct gcagcagcct ggcgctgaac tcgtgcggcc aggcgcttct | 120 |
| gtgaagctga gctgtaaagc cagcggctac accttcacca gctactggat gaactgggtc | 180 |
| aagcagcggc ccgaccaggg cctggagtgg atcggcagaa tcgacccta cgacagcgag | 240 |
| acacactaca accagaagtt caaggacaag gccatcctga ccgtggacaa gagcagcagc | 300 |
| accgcctaca tgcagctgtc cagcctgacc agcgaggaca cgccgtgta ctactgcgcc | 360 |
| aggggcaact gggacgacta ttggggccag ggcaccaccc tgacagtgtc tagcggaggc | 420 |
| ggaggatctg gcggcggagg aagttctggc ggaggctccg acgtgcagat cacccagagc | 480 |
| cctagctacc tggccgcctc tcctggcgag acaatcacca tcaactgccg ggccagcaag | 540 |
| agcatctcca aggacctggc ctggtatcag aaaagcccg gcaagaccaa caagctgctg | 600 |
| atctacagcg gcagcaccct gcagagcggc atccccagca gattttccgg cagcggctcc | 660 |
| ggcaccgact tcaccctgac catcagctcc ctggaacccg aggactttgc catgtactat | 720 |
| tgccagcagc acaacaagta cccttacacc ttcggcggag gcaccaagct ggaaatcaag | 780 |
| gccagctccg agagagcaa gtacggccct ccctgccccc cttgccctgc ccccgagttc | 840 |
| ctgggcggac ccagcgtgtt cctgttcccc cccaagccca aggacaccct gatgatcagc | 900 |
| cggacccccg aggtgacctg tgtggtggtg gacgtgtccc aggaggaccc cgaggtccag | 960 |
| ttcaactggt acgtggacgg cgtggaggtg cacaacgcca agaccaagcc ccgggaggag | 1020 |
| cagttcaata gcacctaccg ggtggtgtcc gtgctgaccg tgctgcacca ggactggctg | 1080 |
| aacggcaaga atacaagtg taaggtgtcc aacaagggcc tgcccagcag catcgagaaa | 1140 |
| accatcagca aggccaaggg ccagcctcgg gagccccagg tgtacaccct gccccctagc | 1200 |
| caagaggaga tgaccaagaa ccaggtgtcc ctgacctgcc tggtgaaggg cttctacccc | 1260 |
| agcgacatcg ccgtggagtg ggagagcaac ggccagcccg agaacaacta caagaccacc | 1320 |
| cccctgtgc tggacagcga cggcagcttc ttcctgtaca gccggctgac cgtggacaag | 1380 |
| agccggtggc aggagggcaa cgtctttagc tgctccgtga tgcacgaggc cctgcacaac | 1440 |
| cactacaccc agaagagcct gagcctgtcc ctgggcaaga tggatatcta catctgggcg | 1500 |
| cccttggccg ggacttgtgg ggtccttctc ctgtcactgg ttatcaccct ttactgcaaa | 1560 |
| cggggcagaa agaaactcct gtatatattc aaacaaccat ttatgagacc agtacaaact | 1620 |
| actcaagagg aagatggctg tagctgccga tttccagaag aagaagaagg aggatgtgaa | 1680 |
| ctgagagtga agttcagcag gagcgcagac gcccccgcgt acaagcaggg ccagaaccag | 1740 |
| ctctataacg agctcaatct aggacgaaga gaggagtacg atgtttggga caagagacgt | 1800 |

```
ggccgggacc ctgagatggg gggaaagccg agaaggaaga accctcagga aggcctgtac    1860
aatgaactgc agaagataa gatggcgag gcctacagtg agattgggat gaaaggcgag     1920
cgccggaggg gcaaggggca cgatggcctt taccagggtc tcagtacagc caccaaggac    1980
acctacgacg cccttcacat gcaggccctg ccccctcgc                           2019
```

<210> SEQ ID NO 92
<211> LENGTH: 111
<212> TYPE: PRT
<213> ORGANISM: Mus musculus

<400> SEQUENCE: 92

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys
            100                 105                 110
```

<210> SEQ ID NO 93
<211> LENGTH: 118
<212> TYPE: PRT
<213> ORGANISM: Mus musculus

<400> SEQUENCE: 93

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser
        115
```

<210> SEQ ID NO 94
<211> LENGTH: 2003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

```
ggcagcggag agggcagagg aagtcttcta acatgcggtg acgtggagga gaatcccggc      60
cctagagcca ccatggccct gcctgtgaca gccctgctgc tgcctctggc tctgctgctg     120
catgccgcta acccggatc cgacatcgtg ctgacacaga gccctgcttc cctggccgtg      180
tccctgggac agagagccac aatcagctgc agggccagcg agagcgtgga caactacggc     240
aacaccttca tgcactggta tcagcagaag cccggccagc cccccaagct gctgatctac     300
agagccagca acctggaaag cggcatcccc gccagatttt ccggcagcgg cagcagaacc     360
gacttcaccc tgaccatcaa ccccgtggaa gccgacgacg tggccaccta ctactgccag     420
cagagcaacg aggacccccc cacatttgga gccggcacca agctggaact gaagggcgga     480
ggcggatctg gcggcggagg atcttctggg ggaggctctc agattcagct ggtgcagagc     540
ggcccagagc tgaagaaacc cggcgagaca gtgaagatct cctgcaaggc ctccggctac     600
atcttcacca attacggcat gaactgggtc aagcaggccc tggcaagag cttcaagtgg     660
atgggctgga tcaacaccta caccggcgag agcacctaca cgccgactt caagggcaga     720
ttcgccttca gcctggaaac cagcgccagc accgcctacc tgcacatcaa cgacctgaag     780
aacgaggaca ccgccaccta tttctgcgcc agaagcggcg gctacgaccc catggattat     840
tggggccagg gcaccagcgt gaccgtgtcc tctgctagct ccggaaccac gacgccagcg     900
ccgcgaccac caacaccggc gcccaccatc gcgtcgcagc cctgtccct gcgcccagag     960
gcgtgccggc cagcggcggg gggcgcagtg cacacgaggg ggctggactt cgcctgtgat    1020
atctacatct gggcgccctt ggccgggact tgtgggtcc ttctcctgtc actggttatc    1080
acccttact gcaaacgggg cagaaagaaa ctcctgtata tattcaaaca accatttatg    1140
agaccagtac aaactactca agaggaagat ggctgtagct gccgatttcc agaagaagaa   1200
gaaggaggat gtgaactgag agtgaagttc agcaggagcg cagacgcccc cgcgtacaag   1260
cagggccaga accagctcta taacgagctc aatctaggac gaagagagga gtacgatgtt   1320
ttggacaaga cgtggccg ggaccctgag atggggggaa agccgagaag gaagaaccct    1380
caggaaggcc tgtacaatga actgcagaaa gataagatgg cggaggccta cagtgagatt   1440
gggatgaaag gcgagcgccg gaggggcaag gggcacgatg gcctttacca gggtctcagt   1500
acagccacca aggacaccta cgacgccctt cacatgcagg ccctgccccc tcgctaagtc   1560
gacagctcgc tttcttgctg tccaatttct attaaaggtt cctttgttcc ctaagtccaa   1620
ctactaaact gggggatatt atgaagggcc ttgagcatct ggattctgcc taataaaaaa   1680
catttatttt cattgctgcg tcgagagctc gctttcttgc tgtccaattt ctattaaagg   1740
ttcctttgtt ccctaagtcc aactactaaa ctgggggata ttatgaaggg ccttgagcat   1800
ctggattctg cctaataaaa acatttatt ttcattgctg cctcgacgaa ttcaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaa                                           2003
```

<210> SEQ ID NO 95
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Ala
            20                  25                  30

Ser Leu Ala Val Ser Leu Gly Gln Arg Ala Thr Ile Ser Cys Arg Ala
        35                  40                  45

Ser Glu Ser Val Asp Asn Tyr Gly Asn Thr Phe Met His Trp Tyr Gln
    50                  55                  60

Gln Lys Pro Gly Gln Pro Pro Lys Leu Leu Ile Tyr Arg Ala Ser Asn
65                  70                  75                  80

Leu Glu Ser Gly Ile Pro Ala Arg Phe Ser Gly Ser Gly Ser Arg Thr
                85                  90                  95

Asp Phe Thr Leu Thr Ile Asn Pro Val Glu Ala Asp Asp Val Ala Thr
            100                 105                 110

Tyr Tyr Cys Gln Gln Ser Asn Glu Asp Pro Pro Thr Phe Gly Ala Gly
        115                 120                 125

Thr Lys Leu Glu Leu Lys Gly Gly Gly Gly Ser Gly Gly Gly Gly Ser
    130                 135                 140

Ser Gly Gly Gly Ser Gln Ile Gln Leu Val Gln Ser Gly Pro Glu Leu
145                 150                 155                 160

Lys Lys Pro Gly Glu Thr Val Lys Ile Ser Cys Lys Ala Ser Gly Tyr
                165                 170                 175

Ile Phe Thr Asn Tyr Gly Met Asn Trp Val Lys Gln Ala Pro Gly Lys
            180                 185                 190

Ser Phe Lys Trp Met Gly Trp Ile Asn Thr Tyr Thr Gly Glu Ser Thr
        195                 200                 205

Tyr Ser Ala Asp Phe Lys Gly Arg Phe Ala Phe Ser Leu Glu Thr Ser
    210                 215                 220

Ala Ser Thr Ala Tyr Leu His Ile Asn Asp Leu Lys Asn Glu Asp Thr
225                 230                 235                 240

Ala Thr Tyr Phe Cys Ala Arg Ser Gly Gly Tyr Asp Pro Met Asp Tyr
                245                 250                 255

Trp Gly Gln Gly Thr Ser Val Thr Val Ser Ser Ala Ser Ser Gly Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415
```

Leu Asp Lys Arg Arg Gly Arg Asp Pro Glu Met Gly Gly Lys Pro Arg
                420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 96
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atggccctgc ctgtgacagc cctgctgctg cctctggctc tgctgctgca cgccgctaga        60
cctggatccc aggtgcagct gcagcagcct ggcgctgaac tcgtgcggcc aggcgcttct       120
gtgaagctga gctgtaaagc cagcggctac accttcacca gctactggat gaactgggtc       180
aagcagcggc ccgaccaggg cctggagtgg atcggcagaa tcgaccccta cgacagcgag       240
acacactaca accagaagtt caaggacaag gccatcctga ccgtggacaa gagcagcagc       300
accgcctaca tgcagctgtc cagcctgacc agcgaggaca cgccgtgta ctactgcgcc        360 agggcaact gggacgacta ttggggccag ggcaccaccc tgacagtgtc tagcggaggc       420
ggaggatctg gcggcggagg aagttctggc ggaggctccg acgtgcagat cacccagagc       480
cctagctacc tggccgcctc tcctggcgag acaatcacca tcaactgccg ggccagcaag       540
agcatctcca aggacctggc ctggtatcag gaaaagcccg gcaagaccaa caagctgctg       600
atctacagcg gcagcaccct gcagagcggc atccccagca gattttccgg cagcggctcc       660
ggcaccgact tcaccctgac catcagctcc ctggaacccg aggactttgc catgtactat       720
tgccagcagc acaacaagta cccttacacc ttcggcggag gcaccaagct ggaaatcaag       780
gccagctccg gagagagcaa gtacggccct cctgccccc cttgccctgc ccccgagttc       840
ctgggcggac ccagcgtgtt cctgttcccc cccaagccca aggacaccct gatgatcagc       900 cggaccccg aggtgacctg tgtggtggtg gacgtgtccc aggaggaccc cgaggtccag       960
ttcaactggt acgtggacgg cgtggaggtg cacaacgcca agaccaagcc ccggaggag      1020 cagttcaata gcacctaccg ggtggtgtcc gtgctgaccg tgctgcacca ggactggctg      1080
aacggcaagg aatacaagtg taaggtgtcc aacaagggcc tgcccagcag catcgagaaa      1140
accatcagca aggccaaggg ccagcctcgg gagcccagg tgtacaccct gcccctagc       1200 caagaggaga tgaccaagaa ccaggtgtcc ctgacctgcc tggtgaaggg cttctacccc      1260
agcgacatcg ccgtggagtg ggagagcaac ggccagcccg agaacaacta caagaccacc      1320 cccctgtgc tggacagcga cggcagcttc ttcctgtaca gccggctgac cgtggacaag      1380
agccggtggc aggagggcaa cgtctttagc tgctccgtga tgcacgaggc cctgcacaac      1440
cactacaccc agaagagcct gagcctgtcc ctgggcaaga tggatatcta catctgggcg      1500
cccttggccg ggacttgtgg ggtccttctc ctgtcactgg ttatcaccct ttactgcaaa      1560

-continued

```
cggggcagaa agaaactcct gtatatattc aaacaaccat ttatgagacc agtacaaact    1620
actcaagagg aagatggctg tagctgccga tttccagaag aagaagaagg aggatgtgaa    1680
ctgagagtga agttcagcag gagcgcagac gcccccgcgt acaagcaggg ccagaaccag    1740
ctctataacg agctcaatct aggacgaaga gaggagtacg atgttttgga caagagacgt    1800
ggccgggacc ctgagatggg gggaaagccg agaaggaaga accctcagga aggcctgtac    1860
aatgaactgc agaaagataa gatggcggag gcctacagtg agattgggat gaaaggcgag    1920
cgccggaggg gcaaggggca cgatggcctt taccagggtc tcagtacagc caccaaggac    1980
acctacgacg cccttcacat gcaggccctg ccccctcgc                           2019
```

<210> SEQ ID NO 97
<211> LENGTH: 673
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Pro Gly Ala
            20                  25                  30

Glu Leu Val Arg Pro Gly Ala Ser Val Lys Leu Ser Cys Lys Ala Ser
        35                  40                  45

Gly Tyr Thr Phe Thr Ser Tyr Trp Met Asn Trp Val Lys Gln Arg Pro
    50                  55                  60

Asp Gln Gly Leu Glu Trp Ile Gly Arg Ile Asp Pro Tyr Asp Ser Glu
65                  70                  75                  80

Thr His Tyr Asn Gln Lys Phe Lys Asp Lys Ala Ile Leu Thr Val Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Gly Asn Trp Asp Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Ser Gly Gly Gly Ser Asp Val Gln Ile Thr Gln Ser
145                 150                 155                 160

Pro Ser Tyr Leu Ala Ala Ser Pro Gly Glu Thr Ile Thr Ile Asn Cys
                165                 170                 175

Arg Ala Ser Lys Ser Ile Ser Lys Asp Leu Ala Trp Tyr Gln Glu Lys
            180                 185                 190

Pro Gly Lys Thr Asn Lys Leu Leu Ile Tyr Ser Gly Ser Thr Leu Gln
        195                 200                 205

Ser Gly Ile Pro Ser Arg Phe Ser Gly Ser Gly Ser Gly Thr Asp Phe
    210                 215                 220

Thr Leu Thr Ile Ser Ser Leu Glu Pro Glu Asp Phe Ala Met Tyr Tyr
225                 230                 235                 240

Cys Gln Gln His Asn Lys Tyr Pro Tyr Thr Phe Gly Gly Gly Thr Lys
                245                 250                 255

Leu Glu Ile Lys Ala Ser Ser Gly Glu Ser Lys Tyr Gly Pro Pro Cys
            260                 265                 270

Pro Pro Cys Pro Ala Pro Glu Phe Leu Gly Gly Pro Ser Val Phe Leu
```

```
                275                 280                 285
Phe Pro Pro Lys Pro Lys Asp Thr Leu Met Ile Ser Arg Thr Pro Glu
290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
                355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
                435                 440                 445

Ser Phe Phe Leu Tyr Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Met Asp Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
                515                 520                 525

Ile Phe Lys Gln Pro Phe Met Arg Pro Val Gln Thr Thr Gln Glu Glu
530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Lys Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
                595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 98
<211> LENGTH: 112
```

<212> TYPE: PRT
<213> ORGANISM: Homo sapiens

<400> SEQUENCE: 98

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 99
<211> LENGTH: 336
<212> TYPE: DNA
<213> ORGANISM: Homo sapiens

<400> SEQUENCE: 99

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga agataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca ggccctgccc cctcgc                              336
```

<210> SEQ ID NO 100
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Met Ala Leu Pro Val Thr Ala Leu Leu Leu Pro Leu Ala Leu Leu Leu
1               5                   10                  15

His Ala Ala Arg Pro Gly Ser Asp Val Gln Ile Thr Gln Ser Pro Ser
            20                  25                  30

Tyr Leu Ala Ala Ser Pro Gly Glu Thr Ile Thr Ile Asn Cys Arg Ala
        35                  40                  45

Ser Lys Ser Ile Ser Lys Asp Leu Ala Trp Tyr Gln Glu Lys Pro Gly
    50                  55                  60

Lys Thr Asn Lys Leu Leu Ile Tyr Ser Gly Ser Thr Leu Gln Ser Gly
65                  70                  75                  80

Ile Pro Ser Arg Phe Ser Gly Ser Gly Ser Gly Thr Asp Phe Thr Leu
                85                  90                  95

Thr Ile Ser Ser Leu Glu Pro Glu Asp Phe Ala Met Tyr Tyr Cys Gln
            100                 105                 110

Gln His Asn Lys Tyr Pro Tyr Thr Phe Gly Gly Gly Thr Lys Leu Glu
```

```
                115                 120                 125
Ile Lys Gly Gly Gly Ser Gly Gly Gly Ser Ser Gly Gly Gly
        130                 135                 140
Ser Gln Val Gln Leu Gln Gln Pro Gly Ala Glu Leu Val Arg Pro Gly
145                 150                 155                 160
Ala Ser Val Lys Leu Ser Cys Lys Ala Ser Gly Tyr Thr Phe Thr Ser
                165                 170                 175
Tyr Trp Met Asn Trp Val Lys Gln Arg Pro Asp Gln Gly Leu Glu Trp
            180                 185                 190
Ile Gly Arg Ile Asp Pro Tyr Asp Ser Glu Thr His Tyr Asn Gln Lys
        195                 200                 205
Phe Lys Asp Lys Ala Ile Leu Thr Val Asp Lys Ser Ser Thr Ala
210                 215                 220
Tyr Met Gln Leu Ser Ser Leu Thr Ser Glu Asp Ser Ala Val Tyr Tyr
225                 230                 235                 240
Cys Ala Arg Gly Asn Trp Asp Asp Tyr Trp Gly Gln Gly Thr Thr Leu
                245                 250                 255
Thr Val Ser Ser Ala Ser Ser Gly Thr Thr Thr Pro Ala Pro Arg Pro
            260                 265                 270
Pro Thr Pro Ala Pro Thr Ile Ala Ser Gln Pro Leu Ser Leu Arg Pro
        275                 280                 285
Glu Ala Cys Arg Pro Ala Ala Gly Gly Ala Val His Thr Arg Gly Leu
290                 295                 300
Asp Phe Ala Cys Asp Ile Tyr Ile Trp Ala Pro Leu Ala Gly Thr Cys
305                 310                 315                 320
Gly Val Leu Leu Leu Ser Leu Val Ile Thr Leu Tyr Cys Lys Arg Gly
                325                 330                 335
Arg Lys Lys Leu Leu Tyr Ile Phe Lys Gln Pro Phe Met Arg Pro Val
            340                 345                 350
Gln Thr Thr Gln Glu Glu Asp Gly Cys Ser Cys Arg Phe Pro Glu Glu
        355                 360                 365
Glu Glu Gly Gly Cys Glu Leu Arg Val Lys Phe Ser Arg Ser Ala Asp
370                 375                 380
Ala Pro Ala Tyr Lys Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
            420                 425                 430
Leu Tyr Asn Glu Leu Gln Lys Asp Lys Met Ala Glu Ala Tyr Ser Glu
        435                 440                 445
Ile Gly Met Lys Gly Glu Arg Arg Gly Lys Gly His Asp Gly Leu
        450                 455                 460
Tyr Gln Gly Leu Ser Thr Ala Thr Lys Asp Thr Tyr Asp Ala Leu His
465                 470                 475                 480
Met Gln Ala Leu Pro Pro Arg
                485

<210> SEQ ID NO 101
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 101

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Ser Gly Gly Ser Gln Val Gln Leu Gln Gln
        115                 120                 125

Pro Gly Ala Glu Leu Val Arg Pro Gly Ala Ser Val Lys Leu Ser Cys
    130                 135                 140

Lys Ala Ser Gly Tyr Thr Phe Thr Ser Tyr Trp Met Asn Trp Val Lys
145                 150                 155                 160

Gln Arg Pro Asp Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Gly Asn Trp Asp
    210                 215                 220

Asp Tyr Trp Gly Gln Gly Thr Thr Leu Thr Val Ser Ser
225                 230                 235
```

<210> SEQ ID NO 102
<211> LENGTH: 1461
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
atggccctgc ctgtgacagc cctgctgctg cctctggctc tgctgctgca cgccgctaga      60
cccggatccg acgtgcagat cacacagagc cctagctacc tggccgccag ccctggcgag     120
acaatcacca tcaactgccg ggccagcaag agcatcagca aggacctggc ctggtatcag     180
gaaaagcccg gcaagaccaa caagctgctg atctacagcg gcagcaccct gcagagcggc     240
atccccagca gattttccgg cagcggctcc ggcaccgact caccctgac aatcagcagc      300
ctggaacccg aggacttcgc catgtactac tgccagcagc acaacaagta cccctacacc     360
ttcggcggag gcaccaagct ggaaatcaag ggcggaggcg gatctggcgg cggaggaagt     420
tctggcggag gatctcaggt gcagctgcag cagccaggcg ctgaactcgt gcggcctggc     480
gcttctgtga agctgagctg taaagccagc ggctacacct ttaccagcta ctggatgaac     540
tgggtcaagc agcggcccga ccagggcctg gagtggatcg gcagaatcga ccccacgac     600
```

```
agcgagacac actacaacca gaagttcaag gacaaggcca tcctgaccgt ggacaagagc    660
agctccaccg cctacatgca gctgtccagc ctgaccagcg aggacagcgc cgtgtactat    720
tgcgccaggg gcaactggga cgactactgg ggccagggca acccctgac agtgtcctct    780 gctagctccg gaaccacgac gccagcgccg accaccaa caccggcgcc caccatcgcg    840
tcgcagcccc tgtccctgcg cccagaggcg tgccggccag cggcgggggg cgcagtgcac    900 acgaggggc tggacttcgc ctgtgatatc tacatctggg cgcccttggc cgggacttgt    960
ggggtccttc tcctgtcact ggttatcacc ctttactgca aacggggcag aagaaactc    1020 ctgtatatat tcaaacaacc atttatgaga ccagtacaaa ctactcaaga ggaagatggc    1080
tgtagctgcc gatttccaga agaagaagaa ggaggatgtg aactgagagt gaagttcagc    1140
aggagcgcag acgccccgc gtacaagcag ggccagaacc agctctataa cgagctcaat    1200
ctaggacgaa gagaggagta cgatgttttg gacaagagac gtggccggga ccctgagatg    1260
gggggaaagc cgagaaggaa gaaccctcag gaaggcctgt acaatgaact gcagaaagat    1320
aagatggcgg aggcctacag tgagattggg atgaaaggcg agcgccggag gggcaagggg    1380
cacgatggcc tttaccaggg tctcagtaca gccaccaagg acacctacga cgcccttcac    1440
atgcaggccc tgcccctcg c                                             1461

<210> SEQ ID NO 103
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gacgtgcaga tcacacagag ccctagctac ctggccgcca gccctggcga gacaatcacc     60
atcaactgcc gggccagcaa gagcatcagc aaggacctgg cctggtatca ggaaaagccc    120
ggcaagacca acaagctgct gatctacagc ggcagcaccc tgcagagcgg catccccagc    180
agattttccg gcagcggctc cggcaccgac ttcaccctga caatcagcag cctggaaccc    240
gaggacttcg ccatgtacta ctgccagcag cacaacaagt accctacac cttcggcgga    300 ggcaccaagc tggaaatcaa gggcggaggc ggatctggcg gcggaggaag ttctggcgga    360
ggatctcagg tgcagctgca gcagccaggc gctgaactcg tgcggcctgg cgcttctgtg    420
aagctgagct gtaaagccag cggctacacc tttaccagct actggatgaa ctgggtcaag    480
cagcggcccg accagggcct ggagtggatc ggcagaatcg acccctacga cagcgagaca    540
cactacaacc agaagttcaa ggacaaggcc atcctgaccg tggacaagag cagctccacc    600
gcctacatgc agctgtccag cctgaccagc gaggacagcc cgtgtacta ttgcgccagg    660 ggcaactggg acgactactg ggccagggc acaaccctga cagtgtcctc t              711

<210> SEQ ID NO 104
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Ser Lys Tyr Gly Pro Pro Cys Pro Pro Cys Pro Ala Pro Glu Phe
1               5                   10                  15
```

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 105
<211> LENGTH: 690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gagagcaagt acggccctcc ctgccccct tgccctgccc ccgagttcct gggcggaccc     60
agcgtgttcc tgttcccccc caagcccaag acaccctga tgatcagccg gaccccgag   120 gtgacctgtg tggtggtgga cgtgtcccag gaggaccccg aggtccagtt caactggtac   180
gtggacggcg tggaggtgca caacgccaag accaagcccc gggaggagca gttcaatagc   240
acctaccggg tggtgtccgt gctgaccgtg ctgcaccagg actggctgaa cggcaaggaa   300
tacaagtgta aggtgtccaa caagggcctg cccagcagca tcgagaaaac catcagcaag   360
gccaagggcc agcctcggga gccccaggtg tacaccctgc ccctagcca agaggagatg   420 accaagaacc aggtgtccct gacctgcctg gtgaagggct tctaccccag cgacatcgcc   480
gtggagtggg agagcaacgg ccagcccgag aacaactaca agaccacccc cctgtgctg   540 gacagcgacg gcagcttctt cctgtacagc cggctgaccg tggacaagag ccggtggcag   600
gagggcaacg tctttagctg ctccgtgatg cacgaggccc tgcacaacca ctacacccag   660
aagagcctga gcctgtccct gggcaagatg                                   690

<210> SEQ ID NO 106

<211> LENGTH: 2684
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106

| | | | | | |
|---|---|---|---|---|---|
| cgtgaggctc | cggtgcccgt | cagtgggcag | agcgcacatc | gcccacagtc | cccgagaagt | 60 |
| tgggggagg | ggtcggcaat | tgaaccggtg | cctagagaag | gtggcgcggg | gtaaactggg | 120 |
| aaagtgatgt | cgtgtactgg | ctccgccttt | ttcccgaggg | tgggggagaa | ccgtatataa | 180 |
| gtgcagtagt | cgccgtgaac | gttcttttc | gcaacgggtt | tgccgccaga | acacaggtaa | 240 |
| gtgccgtgtg | tggttcccgc | gggcctggcc | tctttacggg | ttatggccct | tgcgtgcctt | 300 |
| gaattacttc | cacctggctg | cagtacgtga | ttcttgatcc | cgagcttcgg | gttggaagtg | 360 |
| ggtgggagag | ttcgaggcct | tgcgcttaag | gagccccttc | gcctcgtgct | tgagttgagg | 420 |
| cctggcctgg | gcgctgggc | cgccgcgtgc | gaatctggtg | gcaccttcgc | gcctgtctcg | 480 |
| ctgctttcga | taagtctcta | gccatttaaa | attttgatg | acctgctgcg | acgctttttt | 540 |
| tctggcaaga | tagtcttgta | aatgcgggcc | aagatctgca | cactggtatt | tcggtttttg | 600 |
| gggccgcggg | cggcgacggg | gcccgtgcgt | cccagcgcac | atgttcggcg | aggcggggcc | 660 |
| tgcgagcgcg | gccaccgaga | atcggacggg | ggtagtctca | agctggccgg | cctgctctgg | 720 |
| tgcctggcct | cgcgccgccg | tgtatcgccc | cgccctgggc | ggcaaggctg | gcccggtcgg | 780 |
| caccagttgc | gtgagcggaa | agatggccgc | ttccccggccc | tgctgcaggg | agctcaaaat | 840 |
| ggaggacgcg | gcgctcggga | gagcgggcgg | gtgagtcacc | cacacaaagg | aaaagggcct | 900 |
| ttccgtcctc | agccgtcgct | tcatgtgact | ccactgagta | ccgggcgccg | tccaggcacc | 960 |
| tcgattagtt | ctcgtgcttt | tggagtacgt | cgtctttagg | ttgggggag | gggttttatg | 1020 |
| cgatggagtt | tccccacact | gagtgggtgg | agactgaagt | taggccagct | tggcacttga | 1080 |
| tgtaattctc | cttggaattt | gccctttttg | agtttggatc | ttggttcatt | ctcaagcctc | 1140 |
| agacagtggt | tcaaagtttt | tttcttccat | ttcaggtgtc | gtgagctagc | tctagagcca | 1200 |
| ccatggccct | gcctgtgaca | gccctgctgc | tgcctctggc | tctgctgctg | catgccgcta | 1260 |
| gacccggatc | cgacatcgtg | ctgacacaga | gccctgcttc | cctggccgtg | tccctgggac | 1320 |
| agagagccac | aatcagctgc | agggccgcg | agagcgtgga | caactacggc | aacaccttca | 1380 |
| tgcactggta | tcagcagaag | cccggccagc | cccccaagct | gctgatctac | agagccagca | 1440 |
| acctggaaag | cggcatcccc | gccagatttt | ccggcagcgg | cagcagaacc | gacttcaccc | 1500 |
| tgaccatcaa | ccccgtggaa | gccgacgacg | tggccaccta | ctactgccag | cagagcaacg | 1560 |
| aggaccccc | cacatttgga | gccggcacca | agctggaact | gaagggcgga | ggcggatctg | 1620 |
| gcggcggagg | atcttctggg | ggaggctctc | agattcagct | ggtgcagagc | ggcccagagc | 1680 |
| tgaagaaacc | cggcgagaca | gtgaagatct | cctgcaaggc | ctccggctac | atcttcacca | 1740 |
| attacggcat | gaactgggtc | aagcaggccc | ctggcaagag | cttcaagtgg | atgggctgga | 1800 |
| tcaacaccta | caccggcgag | agcacctaca | gcgccgactt | caagggcaga | ttcgccttca | 1860 |
| gcctggaaac | cagcgccagc | accgcctacc | tgcacatcaa | cgacctgaag | aacgaggaca | 1920 |
| ccgccaccta | tttctgcgcc | agaagcggcg | gctacgaccc | catggattat | tggggccagg | 1980 |
| gcaccagcgt | gaccgtgtcc | tctgctagct | ccggaaccac | gacgccagcg | ccgcgaccac | 2040 |
| caacaccggc | gcccaccatc | gcgtcgcagc | ccctgtccct | gcgcccagag | gcgtgccggc | 2100 |

```
cagcggcggg gggcgcagtg cacacgaggg ggctggactt cgcctgtgat atctacatct   2160
gggcgccctt ggccgggact tgtggggtcc ttctcctgtc actggttatc acccttact    2220 gcaaacgggg cagaaagaaa ctcctgtata tattcaaaca accatttatg agaccagtac   2280
aaactactca agaggaagat ggctgtagct gccgatttcc agaagaagaa gaaggaggat   2340
gtgaactgag agtgaagttc agcaggagcg cagacgcccc cgcgtacaag cagggccaga   2400
accagctcta taacgagctc aatctaggac gaagagagga gtacgatgtt ttggacaaga   2460
gacgtggccg ggaccctgag atggggggaa agccgagaag gaagaaccct caggaaggcc   2520
tgtacaatga actgcagaaa gataagatgg cggaggccta cagtgagatt gggatgaaag   2580
gcgagcgccg gaggggcaag gggcacgatg gcctttacca gggtctcagt acagccacca   2640
aggacaccta cgacgccctt cacatgcagg ccctgccccc tcgc                    2684
```

<210> SEQ ID NO 107
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Ala
            20                  25                  30

Ser Leu Ala Val Ser Leu Gly Gln Arg Ala Thr Ile Ser Cys Arg Ala
        35                  40                  45

Ser Glu Ser Val Asp Asn Tyr Gly Asn Thr Phe Met His Trp Tyr Gln
    50                  55                  60

Gln Lys Pro Gly Gln Pro Pro Lys Leu Leu Ile Tyr Arg Ala Ser Asn
65                  70                  75                  80

Leu Glu Ser Gly Ile Pro Ala Arg Phe Ser Gly Ser Gly Ser Arg Thr
                85                  90                  95

Asp Phe Thr Leu Thr Ile Asn Pro Val Glu Ala Asp Asp Val Ala Thr
            100                 105                 110

Tyr Tyr Cys Gln Gln Ser Asn Glu Asp Pro Pro Thr Phe Gly Ala Gly
        115                 120                 125

Thr Lys Leu Glu Leu Lys Gly Gly Gly Ser Gly Gly Gly Gly Ser
    130                 135                 140

Ser Gly Gly Gly Ser Gln Ile Gln Leu Val Gln Ser Gly Pro Glu Leu
145                 150                 155                 160

Lys Lys Pro Gly Glu Thr Val Lys Ile Ser Cys Lys Ala Ser Gly Tyr
                165                 170                 175

Ile Phe Thr Asn Tyr Gly Met Asn Trp Val Lys Gln Ala Pro Gly Lys
            180                 185                 190

Ser Phe Lys Trp Met Gly Trp Ile Asn Thr Tyr Thr Gly Glu Ser Thr
        195                 200                 205

Tyr Ser Ala Asp Phe Lys Gly Arg Phe Ala Phe Ser Leu Glu Thr Ser
    210                 215                 220

Ala Ser Thr Ala Tyr Leu His Ile Asn Asp Leu Lys Asn Glu Asp Thr
225                 230                 235                 240

Ala Thr Tyr Phe Cys Ala Arg Ser Gly Gly Tyr Asp Pro Met Asp Tyr
                245                 250                 255
```

```
Trp Gly Gln Gly Thr Ser Val Thr Val Ser Ser Ala Ser Ser Gly Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 108
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atggccctgc tgtgacagc cctgctgctg cctctggctc tgctgctgca tgccgctaga      60
cccggatccg acatcgtgct gacacagagc cctgcttccc tggccgtgtc cctgggacag    120
agagccacaa tcagctgcag ggccagcgag agcgtggaca actacggcaa caccttcatg    180
cactggtatc agcagaagcc cggccagccc cccaagctgc tgatctacag agccagcaac    240
ctggaaagcg gcatccccgc cagatttttc ggcagcggca gcagaaccga cttcaccctg    300
accatcaacc ccgtggaagc cgacgacgtg gccacctact actgccagca gagcaacgag    360
gaccccccca catttggagc cggcaccaag ctggaactga agggcggagg cggatctggc    420
ggcggaggat cttctggggg aggctctcag attcagctgg tgcagagcgg cccagagctg    480
aagaaacccg gcgagacagt gaagatctcc tgcaaggcct ccggctacat cttcaccaat    540
tacggcatga actgggtcaa gcaggcccct ggcaagagct tcaagtggat gggctggatc    600
aacacctaca ccgcgagag cacctacagc gccgacttca gggcagatt cgccttcagc    660 ctggaaacca gcgccagcac cgcctacctg cacatcaacg acctgaagaa cgaggacacc    720
```

```
gccacctatt tctgcgccag aagcggcggc tacgacccca tggattattg gggccagggc    780
accagcgtga ccgtgtcctc tgctagctcc ggaaccacga cgccagcgcc gcgaccacca    840
acaccggcgc ccaccatcgc gtcgcagccc ctgtccctgc cccagaggc gtgccggcca     900 gcggcggggg gcgcagtgca cacgagggg ctggacttcg cctgtgatat ctacatctgg    960
gcgcccttgg ccgggacttg tggggtcctt ctcctgtcac tggttatcac cctttactgc   1020
aaacggggca gaaagaaact cctgtatata ttcaaacaac catttatgag accagtacaa   1080
actactcaag aggaagatgg ctgtagctgc cgatttccag aagaagaaga aggaggatgt   1140
gaactgagag tgaagttcag caggagcgca gacgcccccg cgtacaagca gggccagaac   1200
cagctctata cgagctcaa tctaggacga agagaggagt acgatgtttt ggacaagaga    1260
cgtggccggg accctgagat gggggaaag ccgagaagga agaaccctca ggaaggcctg    1320
tacaatgaac tgcagaaaga taagatggcg gaggcctaca gtgagattgg gatgaaaggc   1380
gagcgccgga ggggcaaggg gcacgatggc ctttaccagg gtctcagtac agccaccaag   1440
gacacctacg acgcccttca catgcaggcc ctgccccctc gc                      1482
```

<210> SEQ ID NO 109
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Met Ala Leu Pro Val Thr Ala Leu Leu Leu Pro Leu Ala Leu Leu Leu
1               5                   10                  15

His Ala Ala Arg Pro Gly Ser Asp Ile Val Leu Thr Gln Ser Pro Ala
                20                  25                  30

Ser Leu Ala Val Ser Leu Gly Gln Arg Ala Thr Ile Ser Cys Arg Ala
            35                  40                  45

Ser Glu Ser Val Asp Asn Tyr Gly Asn Thr Phe Met His Trp Tyr Gln
        50                  55                  60

Gln Lys Pro Gly Gln Pro Pro Lys Leu Leu Ile Tyr Arg Ala Ser Asn
65                  70                  75                  80

Leu Glu Ser Gly Ile Pro Ala Arg Phe Ser Gly Ser Gly Ser Arg Thr
                85                  90                  95

Asp Phe Thr Leu Thr Ile Asn Pro Val Glu Ala Asp Asp Val Ala Thr
                100                 105                 110

Tyr Tyr Cys Gln Gln Ser Asn Glu Asp Pro Pro Thr Phe Gly Ala Gly
            115                 120                 125

Thr Lys Leu Glu Leu Lys Gly Gly Gly Ser Gly Gly Gly Gly Ser
        130                 135                 140

Ser Gly Gly Gly Ser Gln Ile Gln Leu Val Gln Ser Gly Pro Glu Leu
145                 150                 155                 160

Lys Lys Pro Gly Glu Thr Val Lys Ile Ser Cys Lys Ala Ser Gly Tyr
                165                 170                 175

Ile Phe Thr Asn Tyr Gly Met Asn Trp Val Lys Gln Ala Pro Gly Lys
                180                 185                 190

Ser Phe Lys Trp Met Gly Trp Ile Asn Thr Tyr Thr Gly Glu Ser Thr
            195                 200                 205

Tyr Ser Ala Asp Phe Lys Gly Arg Phe Ala Phe Ser Leu Glu Thr Ser
        210                 215                 220
```

```
Ala Ser Thr Ala Tyr Leu His Ile Asn Asp Leu Lys Asn Glu Asp Thr
225                 230                 235                 240

Ala Thr Tyr Phe Cys Ala Arg Ser Gly Gly Tyr Asp Pro Met Asp Tyr
            245                 250                 255

Trp Gly Gln Gly Thr Ser Val Thr Val Ser Ser Ala Ser Ser Gly Glu
        260                 265                 270

Ser Lys Tyr Gly Pro Pro Cys Pro Pro Cys Pro Ala Pro Glu Phe Leu
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Asp Val Ser
305                 310                 315                 320

Gln Glu Asp Pro Glu Val Gln Phe Asn Trp Tyr Val Asp Gly Val Glu
                325                 330                 335

Val His Asn Ala Lys Thr Lys Pro Arg Glu Glu Gln Phe Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Gly Leu Pro Ser Ser
370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Arg Leu Thr
    450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Leu Gly Lys Met Asp Ile Tyr Ile Trp Ala Pro Leu Ala Gly Thr
            500                 505                 510

Cys Gly Val Leu Leu Leu Ser Leu Val Ile Thr Leu Tyr Cys Lys Arg
        515                 520                 525

Gly Arg Lys Lys Leu Leu Tyr Ile Phe Lys Gln Pro Phe Met Arg Pro
    530                 535                 540

Val Gln Thr Thr Gln Glu Glu Asp Gly Cys Ser Cys Arg Phe Pro Glu
545                 550                 555                 560

Glu Glu Glu Gly Gly Cys Glu Leu Arg Val Lys Phe Ser Arg Ser Ala
                565                 570                 575

Asp Ala Pro Ala Tyr Lys Gln Gly Gln Asn Gln Leu Tyr Asn Glu Leu
            580                 585                 590

Asn Leu Gly Arg Arg Glu Glu Tyr Asp Val Leu Asp Lys Arg Arg Gly
        595                 600                 605

Arg Asp Pro Glu Met Gly Gly Lys Pro Arg Arg Lys Asn Pro Gln Glu
    610                 615                 620

Gly Leu Tyr Asn Glu Leu Gln Lys Asp Lys Met Ala Glu Ala Tyr Ser
625                 630                 635                 640
```

```
Glu Ile Gly Met Lys Gly Glu Arg Arg Gly Lys Gly His Asp Gly
                645                 650                 655

Leu Tyr Gln Gly Leu Ser Thr Ala Thr Lys Asp Thr Tyr Asp Ala Leu
            660                 665                 670

His Met Gln Ala Leu Pro Pro Arg
            675             680

<210> SEQ ID NO 110
<211> LENGTH: 2040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
atggccctgc ctgtgacagc cctgctgctg cctctggctc tgctgctgca tgccgctaga      60
cccggatccg acatcgtgct gacacagagc cctgcttccc tggccgtgtc cctgggacag     120
agagccacaa tcagctgcag ggccagcgag agcgtggaca ctacggcaa caccttcatg      180 cactggtatc agcagaagcc cggccagccc ccaagctgc tgatctacag agccagcaac      240
ctggaaagcg gcatccccgc cagattttcc ggcagcggga gcagaaccga cttcaccctg     300
accatcaacc ccgtggaagc cgacgacgtg gccacctact actgccagca gagcaacgag     360
gaccccccca catttggagc cggcaccaag ctggaactga agggcggagg cggatctggc     420
ggcggaggat cttctggggg aggctctcag attcagctgg tgcagagcgg cccagagctg     480
aagaaacccg gcgagacagt gaagatctcc tgcaaggcct ccggctacat cttcaccaat     540
tacggcatga actgggtcaa gcaggcccct ggcaagagct caagtggat gggctggatc      600 aacacctaca ccgccgagag cacctacagc gccgacttca agggcagatt cgccttcagc     660
ctggaaacca gcgccagcac cgcctacctg cacatcaacg acctgaagaa cgaggacacc     720
gccacctatt tctgcgccag aagcggcggc tacgacccca tggattattg gggccagggc     780
accagcgtga ccgtgtcctc tgctagctcc ggagagagca agtacggccc tcctgccccc     840
ccttgccctg cccccgagtt cctgggcgga cccagcgtgt tcctgttccc ccaagcccc     900 aaggacaccc tgatgatcag ccggacccc gaggtgacct gtgtggtggt ggacgtgtcc      960
caggaggacc ccgaggtcca gttcaactgg tacgtggacg gcgtggaggt gcacaacgcc     1020
aagaccaagc ccgggagga gcagttcaat agcacctacc gggtggtgtc cgtgctgacc     1080
gtgctgcacc aggactggct gaacggcaag gaatacaagt gtaaggtgtc caacaagggc     1140
ctgcccagca gcatcgagaa aaccatcagc aaggccaagg gccagcctcg ggagcccag     1200 gtgtacaccc tgcccctag ccaagaggag atgaccaaga accaggtgtc cctgacctgc     1260
ctggtgaagg gcttctaccc cagcgacatc gccgtggagt gggagagcaa cggccagccc     1320
gagaacaact acaagaccac ccccctgtg ctggacagcg acggcagctt cttcctgtac     1380
agccggctga ccgtggacaa gagccggtgg caggaggca acgtctttag ctgctccgtg     1440
atgcacgagg ccctgcacaa ccactacacc cagaagagcc tgagcctgtc cctgggcaag     1500
atggatatct acatctgggc gcccttggcc gggacttgtg gggtccttct cctgtcactg     1560
gttatcaccc tttactgcaa acggggcaga aagaaactcc tgtatatatt caaacaacca     1620
tttatgagac cagtacaaac tactcaagag gaagatggct gtagctgccg atttccagaa     1680
gaagaagaag gaggatgtga actgagagtg aagttcagca ggagcgcaga cgcccccgcg     1740
tacaagcagg gccagaacca gctctataac gagctcaatc taggacgaag agaggagtac     1800
```

```
gatgttttgg acaagagacg tggccgggac cctgagatgg ggggaaagcc gagaaggaag    1860
aaccctcagg aaggcctgta caatgaactg cagaaagata agatggcgga ggcctacagt    1920
gagattggga tgaaaggcga gcgccggagg ggcaaggggc acgatggcct ttaccagggt    1980
ctcagtacag ccaccaagga cacctacgac gcccttcaca tgcaggccct gccccctcgc    2040
```

<210> SEQ ID NO 111
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Met Ala Leu Pro Val Thr Ala Leu Leu Leu Pro Leu Ala Leu Leu Leu
1               5                   10                  15

His Ala Ala Arg Pro Gly Ser Gln Ile Gln Leu Val Gln Ser Gly Pro
            20                  25                  30

Glu Leu Lys Lys Pro Gly Glu Thr Val Lys Ile Ser Cys Lys Ala Ser
        35                  40                  45

Gly Tyr Ile Phe Thr Asn Tyr Gly Met Asn Trp Val Lys Gln Ala Pro
    50                  55                  60

Gly Lys Ser Phe Lys Trp Met Gly Trp Ile Asn Thr Tyr Thr Gly Glu
65                  70                  75                  80

Ser Thr Tyr Ser Ala Asp Phe Lys Gly Arg Phe Ala Phe Ser Leu Glu
                85                  90                  95

Thr Ser Ala Ser Thr Ala Tyr Leu His Ile Asn Asp Leu Lys Asn Glu
            100                 105                 110

Asp Thr Ala Thr Tyr Phe Cys Ala Arg Ser Gly Gly Tyr Asp Pro Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Ser Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Asn Thr Phe
            180                 185                 190

Met His Trp Tyr Gln Gln Lys Pro Gly Gln Pro Pro Lys Leu Leu Ile
        195                 200                 205

Tyr Arg Ala Ser Asn Leu Glu Ser Gly Ile Pro Ala Arg Phe Ser Gly
    210                 215                 220

Ser Gly Ser Arg Thr Asp Phe Thr Leu Thr Ile Asn Pro Val Glu Ala
225                 230                 235                 240

Asp Asp Val Ala Thr Tyr Tyr Cys Gln Gln Ser Asn Glu Asp Pro Pro
                245                 250                 255

Thr Phe Gly Ala Gly Thr Lys Leu Glu Leu Lys Ala Ser Ser Gly Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320
```

```
Ala Pro Leu Ala Gly Thr Cys Gly Val Leu Leu Ser Leu Val Ile
            325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
            355                 360                 365

Ser Cys Arg Phe Pro Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
            435                 440                 445

Met Ala Glu Ala Tyr Ser Glu Ile Gly Met Lys Gly Glu Arg Arg Arg
        450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490
```

<210> SEQ ID NO 112
<211> LENGTH: 1482
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
atggccctgc ctgtgacagc cctgctgctg cctctggctc tgctgctgca tgccgctaga      60
cccggatccc agatccagct ggtgcagtct ggccccgagc tgaagaaacc cggcgagaca     120
gtgaagatca gctgcaaggc cagcggctac atcttcacca actacggcat gaactgggtc     180
aagcaggccc ctggcaagag cttcaagtgg atgggctgga tcaacaccta caccggcgag     240
agcacctaca gcgccgactt caagggcaga ttcgccttca gctggaaaac cagcgccagc     300
accgcctacc tgcacatcaa cgacctgaag aacgaggaca ccgccaccta cttttgcgcc     360
agaagcggcg gctacgaccc catggattat tggggccagg gcaccagcgt gaccgtgtct     420
agcggaggcg gaggatctgg cggaggggga tcttctggcg gcggaagcga tatcgtgctg     480
acccagtctc ctgccagcct ggccgtgtct ctgggacaga gagccacaat cagctgccgg     540
gcctctgaga gcgtggacaa ttacggcaac accttcatgc actggtatca gcagaagccc     600
ggccagcccc ccaagctgct gatctacaga gccagcaacc tggaaagcgg catccccgcc     660
agattttccg gcagcggcag cagaaccgac ttcaccctga ccatcaaccc cgtggaagcc     720
gacgacgtgg ccacctatta ctgccagcag agcaacgagg accccctac ctttggagcc     780 ggcaccaagc tggaactgaa ggctagctcc ggaaccacga cgccagcgcc gcgaccacca     840
acaccggcgc ccaccatcgc gtcgcagccc ctgtccctgc gcccagaggc gtgccggcca     900
gcggcggggg gcgcagtgca cacgagggggg ctggacttcg cctgtgatat ctacatctgg     960
gcgcccttgg ccgggacttg tggggtcctt ctcctgtcac tggttatcac cctttactgc    1020
```

-continued

```
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgccccg cgtacaagca gggccagaac     1200
cagctctata acgagctcaa tctaggacga agagaggagt acgatgtttt ggacaagaga    1260
cgtggccggg accctgagat ggggggaaag ccgagaagga agaaccctca ggaaggcctg    1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gc                       1482
```

<210> SEQ ID NO 113
<211> LENGTH: 680
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Met Ala Leu Pro Val Thr Ala Leu Leu Leu Pro Leu Ala Leu Leu Leu
1               5                   10                  15

His Ala Ala Arg Pro Gly Ser Gln Ile Gln Leu Val Gln Ser Gly Pro
            20                  25                  30

Glu Leu Lys Lys Pro Gly Glu Thr Val Lys Ile Ser Cys Lys Ala Ser
        35                  40                  45

Gly Tyr Ile Phe Thr Asn Tyr Gly Met Asn Trp Val Lys Gln Ala Pro
    50                  55                  60

Gly Lys Ser Phe Lys Trp Met Gly Trp Ile Asn Thr Tyr Thr Gly Glu
65                  70                  75                  80

Ser Thr Tyr Ser Ala Asp Phe Lys Gly Arg Phe Ala Phe Ser Leu Glu
                85                  90                  95

Thr Ser Ala Ser Thr Ala Tyr Leu His Ile Asn Asp Leu Lys Asn Glu
            100                 105                 110

Asp Thr Ala Thr Tyr Phe Cys Ala Arg Ser Gly Gly Tyr Asp Pro Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Ser Gly Gly Gly Ser Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Asn Thr Phe
            180                 185                 190

Met His Trp Tyr Gln Gln Lys Pro Gly Gln Pro Pro Lys Leu Leu Ile
        195                 200                 205

Tyr Arg Ala Ser Asn Leu Glu Ser Gly Ile Pro Ala Arg Phe Ser Gly
    210                 215                 220

Ser Gly Ser Arg Thr Asp Phe Thr Leu Thr Ile Asn Pro Val Glu Ala
225                 230                 235                 240

Asp Asp Val Ala Thr Tyr Tyr Cys Gln Gln Ser Asn Glu Asp Pro Pro
                245                 250                 255

Thr Phe Gly Ala Gly Thr Lys Leu Glu Leu Lys Ala Ser Ser Gly Glu
            260                 265                 270

Ser Lys Tyr Gly Pro Pro Cys Pro Pro Cys Pro Ala Pro Glu Phe Leu
```

```
                275                 280                 285
Gly Gly Pro Ser Val Phe Leu Phe Pro Pro Lys Pro Lys Asp Thr Leu
290                 295                 300
Met Ile Ser Arg Thr Pro Glu Val Thr Cys Val Val Val Asp Val Ser
305                 310                 315                 320
Gln Glu Asp Pro Glu Val Gln Phe Asn Trp Tyr Val Asp Gly Val Glu
                325                 330                 335
Val His Asn Ala Lys Thr Lys Pro Arg Glu Glu Gln Phe Asn Ser Thr
            340                 345                 350
Tyr Arg Val Val Ser Val Leu Thr Val Leu His Gln Asp Trp Leu Asn
        355                 360                 365
Gly Lys Glu Tyr Lys Cys Lys Val Ser Asn Lys Gly Leu Pro Ser Ser
    370                 375                 380
Ile Glu Lys Thr Ile Ser Lys Ala Lys Gly Gln Pro Arg Glu Pro Gln
385                 390                 395                 400
Val Tyr Thr Leu Pro Pro Ser Gln Glu Glu Met Thr Lys Asn Gln Val
                405                 410                 415
Ser Leu Thr Cys Leu Val Lys Gly Phe Tyr Pro Ser Asp Ile Ala Val
            420                 425                 430
Glu Trp Glu Ser Asn Gly Gln Pro Glu Asn Asn Tyr Lys Thr Thr Pro
        435                 440                 445
Pro Val Leu Asp Ser Asp Gly Ser Phe Phe Leu Tyr Ser Arg Leu Thr
    450                 455                 460
Val Asp Lys Ser Arg Trp Gln Glu Gly Asn Val Phe Ser Cys Ser Val
465                 470                 475                 480
Met His Glu Ala Leu His Asn His Tyr Thr Gln Lys Ser Leu Ser Leu
                485                 490                 495
Ser Leu Gly Lys Met Asp Ile Tyr Ile Trp Ala Pro Leu Ala Gly Thr
            500                 505                 510
Cys Gly Val Leu Leu Leu Ser Leu Val Ile Thr Leu Tyr Cys Lys Arg
        515                 520                 525
Gly Arg Lys Lys Leu Leu Tyr Ile Phe Lys Gln Pro Phe Met Arg Pro
    530                 535                 540
Val Gln Thr Thr Gln Glu Glu Asp Gly Cys Ser Cys Arg Phe Pro Glu
545                 550                 555                 560
Glu Glu Glu Gly Gly Cys Glu Leu Arg Val Lys Phe Ser Arg Ser Ala
                565                 570                 575
Asp Ala Pro Ala Tyr Lys Gln Gly Gln Asn Gln Leu Tyr Asn Glu Leu
            580                 585                 590
Asn Leu Gly Arg Arg Glu Glu Tyr Asp Val Leu Asp Lys Arg Arg Gly
        595                 600                 605
Arg Asp Pro Glu Met Gly Gly Lys Pro Arg Arg Lys Asn Pro Gln Glu
    610                 615                 620
Gly Leu Tyr Asn Glu Leu Gln Lys Asp Lys Met Ala Glu Ala Tyr Ser
625                 630                 635                 640
Glu Ile Gly Met Lys Gly Glu Arg Arg Arg Gly Lys Gly His Asp Gly
                645                 650                 655
Leu Tyr Gln Gly Leu Ser Thr Ala Thr Lys Asp Thr Tyr Asp Ala Leu
            660                 665                 670
His Met Gln Ala Leu Pro Pro Arg
        675                 680

<210> SEQ ID NO 114
```

<211> LENGTH: 2040
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

```
atggccctgc ctgtgacagc cctgctgctg cctctggctc tgctgctgca tgccgctaga      60
cccggatccc agatccagct ggtgcagtct ggccccgagc tgaagaaacc cggcgagaca     120
gtgaagatca gctgcaaggc cagcggctac atcttcacca actacggcat gaactgggtc     180
aagcaggccc ctggcaagag cttcaagtgg atgggctgga tcaacaccta caccggcgag     240
agcacctaca cgccgactt caagggcaga ttcgccttca gcctggaaac cagcgccagc     300
accgcctacc tgcacatcaa cgacctgaag aacgaggaca ccgccaccta cttttgcgcc     360
agaagcggcg gctacgaccc catggattat tggggccagg gcaccagcgt gaccgtgtct     420
agcggaggcg gaggatctgg cggaggggga tcttctggcg gcgaagcga tatcgtgctg     480
acccagtctc ctgccagcct ggccgtgtct ctgggacaga gagccacaat cagctgccgg     540
gcctctgaga gcgtggacaa ttacggcaac accttcatgc actggtatca gcagaagccc     600
ggccagcccc ccaagctgct gatctacaga gccagcaacc tggaaagcgg catccccgcc     660
agattttccg gcagcggcag cagaaccgac ttcaccctga ccatcaaccc cgtgaagcc     720
gacgacgtgg ccacctatta ctgccagcag agcaacgagg acccccctac ctttggagcc     780
ggcaccaagc tggaactgaa ggctagctcc ggagagagca gtacggccc tccctgcccc     840
ccttgccctg ccccgagtt cctgggcgga cccagcgtgt tcctgttccc ccccaagccc     900
aaggacaccc tgatgatcag ccggaccccc gaggtgacct gtgtggtggt ggacgtgtcc     960
caggaggacc ccgaggtcca gttcaactgg tacgtggacg gcgtggaggt gcacaacgcc    1020
aagaccaagc ccgggagga gcagttcaat agcacctacc gggtggtgtc cgtgctgacc    1080
gtgctgcacc aggactggct gaacggcaag gaatacaagt gtaaggtgtc caacaagggc    1140
ctgcccagca gcatcgagaa aaccatcagc aaggccaagg gccagcctcg ggagccccag    1200
gtgtacaccc tgcccccta gccaagaggag atgaccaaga accaggtgtc cctgacctgc    1260
ctggtgaagg gcttctaccc cagcgacatc gccgtggagt gggagagcaa cggccagccc    1320
gagaacaact acaagaccac cccccctgtg ctggacagcg acggcagctt cttcctgtac    1380
agccggctga ccgtggacaa gagccggtgg caggagggca acgtctttag ctgctccgtg    1440
atgcacgagg ccctgcacaa ccactacacc cagaagagcc tgagcctgtc cctgggcaag    1500
atggatatct acatctgggc gcccttggcc gggacttgtg gggtccttct cctgtcactg    1560
gttatcaccc tttactgcaa acggggcaga aagaaactcc tgtatatatt caaacaacca    1620
tttatgagac cagtacaaac tactcaagag gaagatggct gtagctgccg atttccagaa    1680
gaagaagaag aggatgtgaa actgagagtg aagttcagca ggagcgcaga cgcccccgcg    1740
tacaagcagg gccagaacca gctctataac gagctcaatc taggacgaag agaggagtac    1800
gatgttttgg acaagagacg tggccgggac cctgagatgg ggggaaagcc gagaaggaag    1860
aaccctcagg aaggcctgta caatgaactg cagaaagata gatggcgga ggcctacagt    1920
gagattggga tgaaaggcga gcgccggagg ggcaaggggc acgatggcct ttaccagggt    1980
ctcagtacag ccaccaagga cacctacgac gcccttcaca tgcaggccct gccccctcgc    2040
```

<210> SEQ ID NO 115

```
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Ala Leu Pro Val Thr Ala Leu Leu Leu Pro Leu Ala Leu Leu Leu
1               5                   10                  15

His Ala Ala Arg Pro Gly Ser Asp Val Gln Ile Thr Gln Ser Pro Ser
            20                  25                  30

Tyr Leu Ala Ala Ser Pro Gly Glu Thr Ile Thr Ile Asn Cys Arg Ala
        35                  40                  45

Ser Lys Ser Ile Ser Lys Asp Leu Ala Trp Tyr Gln Glu Lys Pro Gly
50                  55                  60

Lys Thr Asn Lys Leu Leu Ile Tyr Ser Gly Ser Thr Leu Gln Ser Gly
65                  70                  75                  80

Ile Pro Ser Arg Phe Ser Gly Ser Gly Ser Gly Thr Asp Phe Thr Leu
                85                  90                  95

Thr Ile Ser Ser Leu Glu Pro Glu Asp Phe Ala Met Tyr Tyr Cys Gln
            100                 105                 110

Gln His Asn Lys Tyr Pro Tyr Thr Phe Gly Gly Gly Thr Lys Leu Glu
        115                 120                 125

Ile Lys Gly Gly Gly Gly Ser Gly Gly Gly Gly Ser Gly Gly Gly Gly
130                 135                 140

Ser Gln Val Gln Leu Gln Gln Pro Gly Ala Glu Leu Val Arg Pro Gly
145                 150                 155                 160

Ala Ser Val Lys Leu Ser Cys Lys Ala Ser Gly Tyr Thr Phe Thr Ser
                165                 170                 175

Tyr Trp Met Asn Trp Val Lys Gln Arg Pro Asp Gln Gly Leu Glu Trp
            180                 185                 190

Ile Gly Arg Ile Asp Pro Tyr Asp Ser Glu Thr His Tyr Asn Gln Lys
        195                 200                 205

Phe Lys Asp Lys Ala Ile Leu Thr Val Asp Lys Ser Ser Ser Thr Ala
210                 215                 220

Tyr Met Gln Leu Ser Ser Leu Thr Ser Glu Asp Ser Ala Val Tyr Tyr
225                 230                 235                 240

Cys Ala Arg Gly Asn Trp Asp Asp Tyr Trp Gly Gln Gly Thr Thr Leu
                245                 250                 255

Thr Val Ser Ser Ala Ser Ser Gly Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
```

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 116
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

```
atggccctgc ctgtgacagc cctgctgctg cctctggctc tgctgctgca cgccgctaga      60
cccggatccg acgtgcagat cacacagagc cctagctacc tggccgccag ccctggcgag     120
acaatcacca tcaactgccg ggccagcaag agcatcagca aggacctggc ctggtatcag     180
gaaaagcccg gcaagaccaa caagctgctg atctacagcg cagcaccct gcagagcggc     240
atccccagca gattttccgg cagcggctcc ggcaccgact tcaccctgac aatcagcagc     300
ctggaacccg aggacttcgc catgtactac tgccagcagc acaacaagta ccctacacc     360
ttcggcggag gcaccaagct ggaaatcaag ggcggaggcg gatctggcgg cggaggaagt     420
tctggcggag gatctcaggt gcagctgcag cagccaggcg ctgaactcgt gcggcctggc     480
gcttctgtga agctgagctg taaagccagc ggctacacct ttaccagcta ctggatgaac     540
tgggtcaagc agcggcccga ccagggcctg agtggatcg cagaatcga cccctacgac     600
agcgagacac actacaacca gaagttcaag gacaaggcca tcctgaccgt ggacaagagc     660
agctccaccg cctacatgca gctgtccagc ctgaccagcg aggacagcgc cgtgtactat     720
tgcgccaggg gcaactggga cgactactgg ggccagggca acccctgac agtgtcctct     780
gctagctccg gaaccacgac gccagcgccg cgaccaccaa caccggcgcc caccatcgcg     840
tcgcagcccc tgtccctgcg cccagaggcg tgccggccag cggcgggggg cgcagtgcac     900
acgagggggc tggacttcgc ctgtgatatc tacatctggg cgcccttggc cgggacttgt     960
ggggtccttc tcctgtcact ggttatcacc ctttactgca acggggcag aagaaactc    1020
ctgtatatat tcaaacaacc atttatgaga ccagtacaaa ctactcaaga ggaagatggc    1080
tgtagctgcc gatttccaga agaagaagaa ggaggatgtg aactgagagt gaagttcagc    1140
aggagcgcag acgcccccgc gtacaagcag ggccagaacc agctctataa cgagctcaat    1200
ctaggacgaa gagaggagta cgatgttttg acaagagac gtggccggga ccctgagatg    1260
gggggaaagc cgagaggaa gaaccctcag gaaggcctgt acaatgaact gcagaaagat    1320
aagatggcgg aggcctacag tgagattggg atgaaaggcg agcgccggag gggcaagggg    1380
```

```
cacgatggcc tttaccaggg tctcagtaca gccaccaagg acacctacga cgcccttcac      1440
atgcaggccc tgcccccccg c                                                1461
```

<210> SEQ ID NO 117
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Met Ala Leu Pro Val Thr Ala Leu Leu Leu Pro Leu Ala Leu Leu Leu
1               5                   10                  15

His Ala Ala Arg Pro Gly Ser Asp Val Gln Ile Thr Gln Ser Pro Ser
            20                  25                  30

Tyr Leu Ala Ala Ser Pro Gly Glu Thr Ile Thr Ile Asn Cys Arg Ala
        35                  40                  45

Ser Lys Ser Ile Ser Lys Asp Leu Ala Trp Tyr Gln Glu Lys Pro Gly
    50                  55                  60

Lys Thr Asn Lys Leu Leu Ile Tyr Ser Gly Ser Thr Leu Gln Ser Gly
65                  70                  75                  80

Ile Pro Ser Arg Phe Ser Gly Ser Gly Ser Gly Thr Asp Phe Thr Leu
                85                  90                  95

Thr Ile Ser Ser Leu Glu Pro Glu Asp Phe Ala Met Tyr Tyr Cys Gln
            100                 105                 110

Gln His Asn Lys Tyr Pro Tyr Thr Phe Gly Gly Gly Thr Lys Leu Glu
        115                 120                 125

Ile Lys Gly Gly Gly Gly Ser Gly Gly Gly Gly Ser Gly Gly Gly Gly
    130                 135                 140

Ser Gln Val Gln Leu Gln Gln Pro Gly Ala Glu Leu Val Arg Pro Gly
145                 150                 155                 160

Ala Ser Val Lys Leu Ser Cys Lys Ala Ser Gly Tyr Thr Phe Thr Ser
                165                 170                 175

Tyr Trp Met Asn Trp Val Lys Gln Arg Pro Asp Gln Gly Leu Glu Trp
            180                 185                 190

Ile Gly Arg Ile Asp Pro Tyr Asp Ser Glu Thr His Tyr Asn Gln Lys
        195                 200                 205

Phe Lys Asp Lys Ala Ile Leu Thr Val Asp Lys Ser Ser Ser Thr Ala
    210                 215                 220

Tyr Met Gln Leu Ser Ser Leu Thr Ser Glu Asp Ser Ala Val Tyr Tyr
225                 230                 235                 240

Cys Ala Arg Gly Asn Trp Asp Asp Tyr Trp Gly Gln Gly Thr Thr Leu
                245                 250                 255

Thr Val Ser Ser Ala Ser Ser Gly Glu Ser Lys Tyr Gly Pro Pro Cys
            260                 265                 270

Pro Pro Cys Pro Ala Pro Glu Phe Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335
```

```
Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
    450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Met Asp Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
        515                 520                 525

Ile Phe Lys Gln Pro Phe Met Arg Pro Val Gln Thr Thr Gln Glu Glu
    530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Lys Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
    610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 118
<211> LENGTH: 2019
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
atggccctgc ctgtgacagc cctgctgctg cctctggctc tgctgctgca cgccgctaga      60
cccggatccg acgtgcagat cacacagagc cctagctacc tggccgccag ccctggcgag     120
```

```
acaatcacca tcaactgccg ggccagcaag agcatcagca aggacctggc ctggtatcag    180
gaaaagcccg gcaagaccaa caagctgctg atctacagcg cagcaccct  gcagagcggc    240 atccccagca gattttccgg cagcggctcc ggcaccgact tcaccctgac aatcagcagc    300
ctggaacccg aggacttcgc catgtactac tgccagcagc acaacaagta ccctacacc    360 ttcggcggag gcaccaagct ggaaatcaag ggcggaggcg gatctggcgg cggaggaagt    420
tctggcggag gatctcaggt gcagctgcag cagccaggcg ctgaactcgt gcggcctggc    480
gcttctgtga agctgagctg taaagccagc ggctacacct ttaccagcta ctggatgaac    540
tgggtcaagc agcggcccga ccagggcctg gagtggatcg gcagaatcga ccctacgac    600 agcgagacac actacaacca gaagttcaag gacaaggcca tcctgaccgt ggacaagagc    660
agctccaccg cctacatgca gctgtccagc ctgaccagcg aggacagcgc cgtgtactat    720
tgcgccaggg gcaactggga cgactactgg ggccagggca acccctgac  agtgtcctct    780 gctagctccg agagagcaa  gtacggccct ccctgccccc cttgccctgc ccccgagttc    840
ctgggcggac cagcgtgtt  cctgttcccc ccaagcccca aggacaccct gatgatcagc    900 cggaccccccg aggtgacctg tgtggtggtg gacgtgtccc aggaggaccc cgaggtccag    960
ttcaactggt acgtggacgg cgtggaggtg cacaacgcca agaccaagcc ccgggaggag   1020
cagttcaata gcacctaccg ggtggtgtcc gtgctgaccg tgctgcacca ggactggctg   1080
aacggcaagg aatacaagtg taaggtgtcc aacaagggcc tgcccagcag catcgagaaa   1140
accatcagca aggccaaggg ccagcctcgg gagccccagg tgtacacccc tgcccccctagc   1200 caagaggaga tgaccaagaa ccaggtgtcc ctgacctgcc tggtgaaggg cttctacccc   1260
agcgacatcg ccgtggagtg ggagagcaac ggccagcccg agaacaacta caagaccacc   1320 cccctgtgc  tggacagcga cggcagcttc ttcctgtaca gcggctgac  cgtggacaag   1380 agccggtggc aggagggcaa cgtctttagc tgctccgtga tgcacgaggc cctgcacaac   1440
cactacaccc agaagagcct gagcctgtcc ctgggcaaga tggatatcta catctgggcg   1500
cccttggccg ggacttgtgg ggtccttctc ctgtcactgg ttatcaccct ttactgcaaa   1560
cggggcagaa agaaactcct gtatatattc aaacaaccat ttatgagacc agtacaaact   1620
actcaagagg aagatggctg tagctgccga tttccagaag aagaagaagg aggatgtgaa   1680
ctgagagtga agttcagcag gagcgcagac gcccccgcgt acaagcaggg ccagaaccag   1740
ctctataacg agctcaatct aggacgaaga gaggagtacg atgttttgga caagagacgt   1800
ggccgggacc ctgagatggg gggaaagccg agaaggaaga accctcagga aggcctgtac   1860
aatgaactgc agaaagataa gatggcggag gcctacagtg agattgggat gaaaggcgag   1920
cgccggaggg gcaaggggca cgatggcctt taccagggtc tcagtacagc caccaaggac   1980
acctacgacg cccttcacat gcaggccctg ccccctcgc                         2019
```

<210> SEQ ID NO 119
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Pro Gly Ala
            20                  25                  30
Glu Leu Val Arg Pro Gly Ala Ser Val Lys Leu Ser Cys Lys Ala Ser
        35                  40                  45
Gly Tyr Thr Phe Thr Ser Tyr Trp Met Asn Val Lys Gln Arg Pro
    50                  55                  60
Asp Gln Gly Leu Glu Trp Ile Gly Arg Ile Asp Pro Tyr Asp Ser Glu
65                  70                  75                  80
Thr His Tyr Asn Gln Lys Phe Lys Asp Lys Ala Ile Leu Thr Val Asp
                85                  90                  95
Lys Ser Ser Ser Thr Ala Tyr Met Gln Leu Ser Ser Leu Thr Ser Glu
            100                 105                 110
Asp Ser Ala Val Tyr Tyr Cys Ala Arg Gly Asn Trp Asp Asp Tyr Trp
        115                 120                 125
Gly Gln Gly Thr Thr Leu Thr Val Ser Ser Gly Gly Gly Gly Ser Gly
    130                 135                 140
Gly Gly Gly Ser Ser Gly Gly Gly Ser Asp Val Gln Ile Thr Gln Ser
145                 150                 155                 160
Pro Ser Tyr Leu Ala Ala Ser Pro Gly Glu Thr Ile Thr Ile Asn Cys
                165                 170                 175
Arg Ala Ser Lys Ser Ile Ser Lys Asp Leu Ala Trp Tyr Gln Glu Lys
            180                 185                 190
Pro Gly Lys Thr Asn Lys Leu Leu Ile Tyr Ser Gly Ser Thr Leu Gln
        195                 200                 205
Ser Gly Ile Pro Ser Arg Phe Ser Gly Ser Gly Ser Gly Thr Asp Phe
    210                 215                 220
Thr Leu Thr Ile Ser Ser Leu Glu Pro Glu Asp Phe Ala Met Tyr Tyr
225                 230                 235                 240
Cys Gln Gln His Asn Lys Tyr Pro Tyr Thr Phe Gly Gly Gly Thr Lys
                245                 250                 255
Leu Glu Ile Lys Ala Ser Ser Gly Thr Thr Thr Pro Ala Pro Arg Pro
            260                 265                 270
Pro Thr Pro Ala Pro Thr Ile Ala Ser Gln Pro Leu Ser Leu Arg Pro
        275                 280                 285
Glu Ala Cys Arg Pro Ala Ala Gly Gly Ala Val His Thr Arg Gly Leu
    290                 295                 300
Asp Phe Ala Cys Asp Ile Tyr Ile Trp Ala Pro Leu Ala Gly Thr Cys
305                 310                 315                 320
Gly Val Leu Leu Leu Ser Leu Val Ile Thr Leu Tyr Cys Lys Arg Gly
                325                 330                 335
Arg Lys Lys Leu Leu Tyr Ile Phe Lys Gln Pro Phe Met Arg Pro Val
            340                 345                 350
Gln Thr Thr Gln Glu Glu Asp Gly Cys Ser Cys Arg Phe Pro Glu Glu
        355                 360                 365
Glu Glu Gly Gly Cys Glu Leu Arg Val Lys Phe Ser Arg Ser Ala Asp
    370                 375                 380
Ala Pro Ala Tyr Lys Gln Gly Gln Asn Gln Leu Tyr Asn Glu Leu Asn
385                 390                 395                 400
Leu Gly Arg Arg Glu Glu Tyr Asp Val Leu Asp Lys Arg Arg Gly Arg
                405                 410                 415
Asp Pro Glu Met Gly Gly Lys Pro Arg Arg Lys Asn Pro Gln Glu Gly
            420                 425                 430
Leu Tyr Asn Glu Leu Gln Lys Asp Lys Met Ala Glu Ala Tyr Ser Glu

```
            435                 440                 445
Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 120
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
atggccctgc ctgtgacagc cctgctgctg cctctggctc tgctgctgca cgccgctaga      60
cctggatccc aggtgcagct gcagcagcct ggcgctgaac tcgtgcggcc aggcgcttct     120
gtgaagctga gctgtaaagc cagcggctac accttcacca gctactggat gaactgggtc     180
aagcagcggc ccgaccaggg cctggagtgg atcggcagaa tcgaccccta cgacagcgag     240
acacactaca accagaagtt caaggacaag gccatcctga ccgtggacaa gagcagcagc     300
accgcctaca tgcagctgtc cagcctgacc agcgaggaca cgccgtgta ctactgcgcc     360
agggcaact gggacgacta ttggggccag ggcaccaccc tgacagtgtc tagcggaggc     420
ggaggatctg gcggcggagg aagttctggc ggaggctccg acgtgcagat cacccagagc     480
cctagctacc tggccgcctc tcctggcgag acaatcacca tcaactgccg ggccagcaag     540
agcatctcca aggacctggc ctggtatcag gaaaagcccg gcaagaccaa caagctgctg     600
atctacagcg gcagcacccl gcagagcggc atccccagca gattttccgg cagcggctcc     660
ggcaccgact caccctgac catcagctcc ctggaacccg aggactttgc catgtactat     720
tgccagcagc acaacaagta cccttacacc ttcggcggag gcaccaagct ggaaatcaag     780
gccagctccg gaaccacgac gccagcgccg gaccaccaa caccggcgcc caccatcgcg     840
tcgcagcccc tgtccctgcg cccagaggcg tgccggccag cggcgggggg cgcagtgcac     900
acgagggggc tggacttcgc ctgtgatatc tacatctggg cgcccttggc cgggacttgt     960
ggggtccttc tcctgtcact ggttatcacc ctttactgca acggggcag aaagaaactc    1020
ctgtatatat tcaaacaacc atttatgaga ccagtacaaa ctactcaaga ggaagatggc    1080
tgtagctgcc gatttccaga agaagaagaa ggaggatgtg aactgagagt gaagttcagc    1140
aggagcgcag acgcccccgc gtacaagcag ggccagaacc agctctataa cgagctcaat    1200
ctaggacgaa gagaggagta cgatgttttg gacaagagac gtggccggga ccctgagatg    1260
ggggaaagc cgagaaggaa gaaccctcag gaaggcctgt acaatgaact gcagaaagat    1320
aagatggcgg aggcctacag tgagattggg atgaaaggcg agcgccggag gggcaagggg    1380
cacgatggcc tttaccaggg tctcagtaca gccaccaagg acacctacga cgcccttcac    1440
atgcaggccc tgccccctcg c                                              1461

<210> SEQ ID NO 121
<211> LENGTH: 673
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 121

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Pro Gly Ala
            20                  25                  30

Glu Leu Val Arg Pro Gly Ala Ser Val Lys Leu Ser Cys Lys Ala Ser
        35                  40                  45

Gly Tyr Thr Phe Thr Ser Tyr Trp Met Asn Trp Val Lys Gln Arg Pro
50                  55                  60

Asp Gln Gly Leu Glu Trp Ile Gly Arg Ile Asp Pro Tyr Asp Ser Glu
65                  70                  75                  80

Thr His Tyr Asn Gln Lys Phe Lys Asp Lys Ala Ile Leu Thr Val Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Gly Asn Trp Asp Asp Tyr Trp
        115                 120                 125

Gly Gln Gly Thr Thr Leu Thr Val Ser Ser Gly Gly Gly Gly Ser Gly
130                 135                 140

Gly Gly Gly Ser Gly Gly Gly Ser Asp Val Gln Ile Thr Gln Ser
145                 150                 155                 160

Pro Ser Tyr Leu Ala Ala Ser Pro Gly Glu Thr Ile Thr Ile Asn Cys
                165                 170                 175

Arg Ala Ser Lys Ser Ile Ser Lys Asp Leu Ala Trp Tyr Gln Glu Lys
            180                 185                 190

Pro Gly Lys Thr Asn Lys Leu Leu Ile Tyr Ser Gly Ser Thr Leu Gln
        195                 200                 205

Ser Gly Ile Pro Ser Arg Phe Ser Gly Ser Gly Ser Gly Thr Asp Phe
210                 215                 220

Thr Leu Thr Ile Ser Ser Leu Glu Pro Glu Asp Phe Ala Met Tyr Tyr
225                 230                 235                 240

Cys Gln Gln His Asn Lys Tyr Pro Tyr Thr Phe Gly Gly Gly Thr Lys
                245                 250                 255

Leu Glu Ile Lys Ala Ser Ser Gly Glu Ser Lys Tyr Gly Pro Pro Cys
            260                 265                 270

Pro Pro Cys Pro Ala Pro Glu Phe Leu Gly Gly Pro Ser Val Phe Leu
        275                 280                 285

Phe Pro Pro Lys Pro Lys Asp Thr Leu Met Ile Ser Arg Thr Pro Glu
290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400
```

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

His Tyr Thr Gln Lys Ser Leu Ser Leu Ser Leu Gly Lys Met Asp Ile
                485                 490                 495

Tyr Ile Trp Ala Pro Leu Ala Gly Thr Cys Gly Val Leu Leu Leu Ser
            500                 505                 510

Leu Val Ile Thr Leu Tyr Cys Lys Arg Gly Arg Lys Lys Leu Leu Tyr
        515                 520                 525

Ile Phe Lys Gln Pro Phe Met Arg Pro Val Gln Thr Thr Gln Glu Glu
530                 535                 540

Asp Gly Cys Ser Cys Arg Phe Pro Glu Glu Glu Glu Gly Gly Cys Glu
545                 550                 555                 560

Leu Arg Val Lys Phe Ser Arg Ser Ala Asp Ala Pro Ala Tyr Lys Gln
                565                 570                 575

Gly Gln Asn Gln Leu Tyr Asn Glu Leu Asn Leu Gly Arg Arg Glu Glu
            580                 585                 590

Tyr Asp Val Leu Asp Lys Arg Arg Gly Arg Asp Pro Glu Met Gly Gly
        595                 600                 605

Lys Pro Arg Arg Lys Asn Pro Gln Glu Gly Leu Tyr Asn Glu Leu Gln
610                 615                 620

Lys Asp Lys Met Ala Glu Ala Tyr Ser Glu Ile Gly Met Lys Gly Glu
625                 630                 635                 640

Arg Arg Arg Gly Lys Gly His Asp Gly Leu Tyr Gln Gly Leu Ser Thr
                645                 650                 655

Ala Thr Lys Asp Thr Tyr Asp Ala Leu His Met Gln Ala Leu Pro Pro
            660                 665                 670

Arg

<210> SEQ ID NO 122
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 123
<211> LENGTH: 847
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
aggtggcccg aaagtcccaa ggcccaggca tctagtgttc ctactgcaca gccccaggca    60
gaaggcagcc tagccaaagc tactactgca cctgccacta cgcgcaatac tggccgtggc   120
ggggaggaga agaaaaagga gaaagagaaa gaagaacagg aagagaggga gaccaagacc   180
cctgaatgtc catcccatac ccagccgctg ggcgtctatc tcttgactcc cgcagtacag   240
gacttgtggc ttagagataa ggccaccttt acatgtttcg tcgtgggctc tgacctgaag   300
gatgcccatt tgacttggga ggttgccgga aaggtaccca ggggggggt tgaggaaggg   360 ttgctggagc gccattccaa tggctctcag agccagcact caagactcac ccttccgaga   420
tccctgtgga acgccgggac ctctgtcaca tgtactctaa atcatcctag cctgccccca   480
cagcgtctga tggcccttag agagccagcc gcccaggcac agttaagct tagcctgaat   540 ctgctcgcca gtagtgatcc cccagaggcc gccagctggc tcttatgcga agtgtccggc   600
tttagccccg ccaacatctt gctcatgtgg ctggaggacc agcgagaagt gaacaccagc   660
ggcttcgctc cagcccggcc cccaccccag ccgggttcta ccacattctg ggcctggagt   720
gtcttaaggg tcccagcacc acctagcccc cagccagcca catacacctg tgttgtgtcc   780
catgaagata gcaggaccct gctaaatgct tctaggagtc tggaggtttc ctacgtgact   840
gaccatt                                                            847

```
<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Gly Gly Ser Gly Gly Gly Gly Ser
1               5                   10

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ggtggcggag gttctggagg tggaggttcc                                      30

<210> SEQ ID NO 126
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1, 2, 3, 4, 5, or 6
      "Gly Gly Gly Gly Ser" repeating units

<400> SEQUENCE: 126

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 127
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 128

His His His His His His
```

```
<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Gly Ser
1

<210> SEQ ID NO 130
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Gly Gly Ser Gly Gly Gly Gly Ser Gly Gly Gly Gly Ser Gly
1               5                   10                  15

Gly Gly Gly Ser
            20

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gly Gly Gly Ser Gly Gly Gly Gly Ser Gly Gly Gly Gly Ser
1               5                   10                  15

<210> SEQ ID NO 132
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass between 50 and
      5,000 nucleotides

<400> SEQUENCE: 132
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
```

```
aaaaaaaaaa aaaaaaaaaa aaaaaaaaaa aaaaaaaaaa aaaaaaaaaa aaaaaaaaaa    540
aaaaaaaaaa aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaaa aaaaaaaaaa aaaaaaaaaa    660
aaaaaaaaaa aaaaaaaaaa aaaaaaaaaa aaaaaaaaaa aaaaaaaaaa aaaaaaaaaa    720
aaaaaaaaaa aaaaaaaaaa aaaaaaaaaa aaaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaaaaaaaa aaaaaaaaaa   1200
aaaaaaaaaa aaaaaaaaaa aaaaaaaaaa aaaaaaaaaa aaaaaaaaaa aaaaaaaaaa   1260
aaaaaaaaaa aaaaaaaaaa aaaaaaaaaa aaaaaaaaaa aaaaaaaaaa aaaaaaaaaa   1320
aaaaaaaaaa aaaaaaaaaa aaaaaaaaaa aaaaaaaaaa aaaaaaaaaa aaaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aaaaaaaaaa aaaaaaaaaa   1500
aaaaaaaaaa aaaaaaaaaa aaaaaaaaaa aaaaaaaaaa aaaaaaaaaa aaaaaaaaaa   1560
aaaaaaaaaa aaaaaaaaaa aaaaaaaaaa aaaaaaaaaa aaaaaaaaaa aaaaaaaaaa   1620
aaaaaaaaaa aaaaaaaaaa aaaaaaaaaa aaaaaaaaaa aaaaaaaaaa aaaaaaaaaa   1680
aaaaaaaaaa aaaaaaaaaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaaaaa aaaaaaaaaa   1800
aaaaaaaaaa aaaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aaaaaaaaaa aaaaaaaaaa   1980
aaaaaaaaaa aaaaaaaaaa aaaaaaaaaa aaaaaaaaaa aaaaaaaaaa aaaaaaaaaa   2040
aaaaaaaaaa aaaaaaaaaa aaaaaaaaaa aaaaaaaaaa aaaaaaaaaa aaaaaaaaaa   2100
aaaaaaaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaaaaaa aaaaaaaaaa aaaaaaaaaa aaaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa aaaaaaaaaa aaaaaaaaaa aaaaaaaaaa aaaaaaaaaa   2400
aaaaaaaaaa aaaaaaaaaa aaaaaaaaaa aaaaaaaaaa aaaaaaaaaa aaaaaaaaaa   2460
aaaaaaaaaa aaaaaaaaaa aaaaaaaaaa aaaaaaaaaa aaaaaaaaaa aaaaaaaaaa   2520
aaaaaaaaaa aaaaaaaaaa aaaaaaaaaa aaaaaaaaaa aaaaaaaaaa aaaaaaaaaa   2580
aaaaaaaaaa aaaaaaaaaa aaaaaaaaaa aaaaaaaaaa aaaaaaaaaa aaaaaaaaaa   2640
aaaaaaaaaa aaaaaaaaaa aaaaaaaaaa aaaaaaaaaa aaaaaaaaaa aaaaaaaaaa   2700
aaaaaaaaaa aaaaaaaaaa aaaaaaaaaa aaaaaaaaaa aaaaaaaaaa aaaaaaaaaa   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
```

| | |
|---|---|
| aaaaaaaaaa aaaaaaaaaa aaaaaaaaaa aaaaaaaaaa aaaaaaaaaa aaaaaaaaaa | 2940 |
| aaaaaaaaaa aaaaaaaaaa aaaaaaaaaa aaaaaaaaaa aaaaaaaaaa aaaaaaaaaa | 3000 |
| aaaaaaaaaa aaaaaaaaaa aaaaaaaaaa aaaaaaaaaa aaaaaaaaaa aaaaaaaaaa | 3060 |
| aaaaaaaaaa aaaaaaaaaa aaaaaaaaaa aaaaaaaaaa aaaaaaaaaa aaaaaaaaaa | 3120 |
| aaaaaaaaaa aaaaaaaaaa aaaaaaaaaa aaaaaaaaaa aaaaaaaaaa aaaaaaaaaa | 3180 |
| aaaaaaaaaa aaaaaaaaaa aaaaaaaaaa aaaaaaaaaa aaaaaaaaaa aaaaaaaaaa | 3240 |
| aaaaaaaaaa aaaaaaaaaa aaaaaaaaaa aaaaaaaaaa aaaaaaaaaa aaaaaaaaaa | 3300 |
| aaaaaaaaaa aaaaaaaaaa aaaaaaaaaa aaaaaaaaaa aaaaaaaaaa aaaaaaaaaa | 3360 |
| aaaaaaaaaa aaaaaaaaaa aaaaaaaaaa aaaaaaaaaa aaaaaaaaaa aaaaaaaaaa | 3420 |
| aaaaaaaaaa aaaaaaaaaa aaaaaaaaaa aaaaaaaaaa aaaaaaaaaa aaaaaaaaaa | 3480 |
| aaaaaaaaaa aaaaaaaaaa aaaaaaaaaa aaaaaaaaaa aaaaaaaaaa aaaaaaaaaa | 3540 |
| aaaaaaaaaa aaaaaaaaaa aaaaaaaaaa aaaaaaaaaa aaaaaaaaaa aaaaaaaaaa | 3600 |
| aaaaaaaaaa aaaaaaaaaa aaaaaaaaaa aaaaaaaaaa aaaaaaaaaa aaaaaaaaaa | 3660 |
| aaaaaaaaaa aaaaaaaaaa aaaaaaaaaa aaaaaaaaaa aaaaaaaaaa aaaaaaaaaa | 3720 |
| aaaaaaaaaa aaaaaaaaaa aaaaaaaaaa aaaaaaaaaa aaaaaaaaaa aaaaaaaaaa | 3780 |
| aaaaaaaaaa aaaaaaaaaa aaaaaaaaaa aaaaaaaaaa aaaaaaaaaa aaaaaaaaaa | 3840 |
| aaaaaaaaaa aaaaaaaaaa aaaaaaaaaa aaaaaaaaaa aaaaaaaaaa aaaaaaaaaa | 3900 |
| aaaaaaaaaa aaaaaaaaaa aaaaaaaaaa aaaaaaaaaa aaaaaaaaaa aaaaaaaaaa | 3960 |
| aaaaaaaaaa aaaaaaaaaa aaaaaaaaaa aaaaaaaaaa aaaaaaaaaa aaaaaaaaaa | 4020 |
| aaaaaaaaaa aaaaaaaaaa aaaaaaaaaa aaaaaaaaaa aaaaaaaaaa aaaaaaaaaa | 4080 |
| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

<210> SEQ ID NO 133
<211> LENGTH: 2000
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<221> NAME/KEY: misc_feature
<222> LOCATION: (1)..(2000)
<223> OTHER INFORMATION: This sequence may encompass between 50 and
      2,000 nucleotides

<400> SEQUENCE: 133
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaaa aaaaaaaaaa aaaaaaaaaa    1260
aaaaaaaaaa aaaaaaaaaa aaaaaaaaaa aaaaaaaaaa aaaaaaaaaa aaaaaaaaaa    1320
aaaaaaaaaa aaaaaaaaaa aaaaaaaaaa aaaaaaaaaa aaaaaaaaaa aaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa aaaaaaaaaa aaaaaaaaaa aaaaaaaaaa aaaaaaaaaa aaaaaaaaaa    1560
aaaaaaaaaa aaaaaaaaaa aaaaaaaaaa aaaaaaaaaa aaaaaaaaaa aaaaaaaaaa    1620
aaaaaaaaaa aaaaaaaaaa aaaaaaaaaa aaaaaaaaaa aaaaaaaaaa aaaaaaaaaa    1680
aaaaaaaaaa aaaaaaaaaa aaaaaaaaaa aaaaaaaaaa aaaaaaaaaa aaaaaaaaaa    1740
aaaaaaaaaa aaaaaaaaaa aaaaaaaaaa aaaaaaaaaa aaaaaaaaaa aaaaaaaaaa    1800
aaaaaaaaaa aaaaaaaaaa aaaaaaaaaa aaaaaaaaaa aaaaaaaaaa aaaaaaaaaa    1860
aaaaaaaaaa aaaaaaaaaa aaaaaaaaaa aaaaaaaaaa aaaaaaaaaa aaaaaaaaaa    1920
aaaaaaaaaa aaaaaaaaaa aaaaaaaaaa aaaaaaaaaa aaaaaaaaaa aaaaaaaaaa    1980
aaaaaaaaaa aaaaaaaaaa                                                2000

```
<210> SEQ ID NO 134
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
tttttttttt tttttttttt tttttttttt tttttttttt tttttttttt tttttttttt      60
tttttttttt tttttttttt tttttttttt tttttttttt                           100

<210> SEQ ID NO 135
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass between 50 and
      5,000 nucleotides

<400> SEQUENCE: 135
tttttttttt tttttttttt tttttttttt tttttttttt tttttttttt tttttttttt      60
tttttttttt tttttttttt tttttttttt tttttttttt tttttttttt tttttttttt     120
tttttttttt tttttttttt tttttttttt tttttttttt tttttttttt tttttttttt     180
tttttttttt tttttttttt tttttttttt tttttttttt tttttttttt tttttttttt     240
tttttttttt tttttttttt tttttttttt tttttttttt tttttttttt tttttttttt     300
tttttttttt tttttttttt tttttttttt tttttttttt tttttttttt tttttttttt     360
tttttttttt tttttttttt tttttttttt tttttttttt tttttttttt tttttttttt     420
tttttttttt tttttttttt tttttttttt tttttttttt tttttttttt tttttttttt     480
tttttttttt tttttttttt tttttttttt tttttttttt tttttttttt tttttttttt     540
tttttttttt tttttttttt tttttttttt tttttttttt tttttttttt tttttttttt     600
tttttttttt tttttttttt tttttttttt tttttttttt tttttttttt tttttttttt     660
tttttttttt tttttttttt tttttttttt tttttttttt tttttttttt tttttttttt     720
tttttttttt tttttttttt tttttttttt tttttttttt tttttttttt tttttttttt     780
tttttttttt tttttttttt tttttttttt tttttttttt tttttttttt tttttttttt     840
tttttttttt tttttttttt tttttttttt tttttttttt tttttttttt tttttttttt     900
tttttttttt tttttttttt tttttttttt tttttttttt tttttttttt tttttttttt     960
tttttttttt tttttttttt tttttttttt tttttttttt tttttttttt tttttttttt    1020
tttttttttt tttttttttt tttttttttt tttttttttt tttttttttt tttttttttt    1080
tttttttttt tttttttttt tttttttttt tttttttttt tttttttttt tttttttttt    1140
tttttttttt tttttttttt tttttttttt tttttttttt tttttttttt tttttttttt    1200
tttttttttt tttttttttt tttttttttt tttttttttt tttttttttt tttttttttt    1260
tttttttttt tttttttttt tttttttttt tttttttttt tttttttttt tttttttttt    1320
tttttttttt tttttttttt tttttttttt tttttttttt tttttttttt tttttttttt    1380
tttttttttt tttttttttt tttttttttt tttttttttt tttttttttt tttttttttt    1440
tttttttttt tttttttttt tttttttttt tttttttttt tttttttttt tttttttttt    1500
```

-continued

| | | | | | | |
|---|---|---|---|---|---|---|
| tttttttttt | tttttttttt | tttttttttt | tttttttttt | tttttttttt | tttttttttt | 1560 |
| tttttttttt | tttttttttt | tttttttttt | tttttttttt | tttttttttt | tttttttttt | 1620 |
| tttttttttt | tttttttttt | tttttttttt | tttttttttt | tttttttttt | tttttttttt | 1680 |
| tttttttttt | tttttttttt | tttttttttt | tttttttttt | tttttttttt | tttttttttt | 1740 |
| tttttttttt | tttttttttt | tttttttttt | tttttttttt | tttttttttt | tttttttttt | 1800 |
| tttttttttt | tttttttttt | tttttttttt | tttttttttt | tttttttttt | tttttttttt | 1860 |
| tttttttttt | tttttttttt | tttttttttt | tttttttttt | tttttttttt | tttttttttt | 1920 |
| tttttttttt | tttttttttt | tttttttttt | tttttttttt | tttttttttt | tttttttttt | 1980 |
| tttttttttt | tttttttttt | tttttttttt | tttttttttt | tttttttttt | tttttttttt | 2040 |
| tttttttttt | tttttttttt | tttttttttt | tttttttttt | tttttttttt | tttttttttt | 2100 |
| tttttttttt | tttttttttt | tttttttttt | tttttttttt | tttttttttt | tttttttttt | 2160 |
| tttttttttt | tttttttttt | tttttttttt | tttttttttt | tttttttttt | tttttttttt | 2220 |
| tttttttttt | tttttttttt | tttttttttt | tttttttttt | tttttttttt | tttttttttt | 2280 |
| tttttttttt | tttttttttt | tttttttttt | tttttttttt | tttttttttt | tttttttttt | 2340 |
| tttttttttt | tttttttttt | tttttttttt | tttttttttt | tttttttttt | tttttttttt | 2400 |
| tttttttttt | tttttttttt | tttttttttt | tttttttttt | tttttttttt | tttttttttt | 2460 |
| tttttttttt | tttttttttt | tttttttttt | tttttttttt | tttttttttt | tttttttttt | 2520 |
| tttttttttt | tttttttttt | tttttttttt | tttttttttt | tttttttttt | tttttttttt | 2580 |
| tttttttttt | tttttttttt | tttttttttt | tttttttttt | tttttttttt | tttttttttt | 2640 |
| tttttttttt | tttttttttt | tttttttttt | tttttttttt | tttttttttt | tttttttttt | 2700 |
| tttttttttt | tttttttttt | tttttttttt | tttttttttt | tttttttttt | tttttttttt | 2760 |
| tttttttttt | tttttttttt | tttttttttt | tttttttttt | tttttttttt | tttttttttt | 2820 |
| tttttttttt | tttttttttt | tttttttttt | tttttttttt | tttttttttt | tttttttttt | 2880 |
| tttttttttt | tttttttttt | tttttttttt | tttttttttt | tttttttttt | tttttttttt | 2940 |
| tttttttttt | tttttttttt | tttttttttt | tttttttttt | tttttttttt | tttttttttt | 3000 |
| tttttttttt | tttttttttt | tttttttttt | tttttttttt | tttttttttt | tttttttttt | 3060 |
| tttttttttt | tttttttttt | tttttttttt | tttttttttt | tttttttttt | tttttttttt | 3120 |
| tttttttttt | tttttttttt | tttttttttt | tttttttttt | tttttttttt | tttttttttt | 3180 |
| tttttttttt | tttttttttt | tttttttttt | tttttttttt | tttttttttt | tttttttttt | 3240 |
| tttttttttt | tttttttttt | tttttttttt | tttttttttt | tttttttttt | tttttttttt | 3300 |
| tttttttttt | tttttttttt | tttttttttt | tttttttttt | tttttttttt | tttttttttt | 3360 |
| tttttttttt | tttttttttt | tttttttttt | tttttttttt | tttttttttt | tttttttttt | 3420 |
| tttttttttt | tttttttttt | tttttttttt | tttttttttt | tttttttttt | tttttttttt | 3480 |
| tttttttttt | tttttttttt | tttttttttt | tttttttttt | tttttttttt | tttttttttt | 3540 |
| tttttttttt | tttttttttt | tttttttttt | tttttttttt | tttttttttt | tttttttttt | 3600 |
| tttttttttt | tttttttttt | tttttttttt | tttttttttt | tttttttttt | tttttttttt | 3660 |
| tttttttttt | tttttttttt | tttttttttt | tttttttttt | tttttttttt | tttttttttt | 3720 |
| tttttttttt | tttttttttt | tttttttttt | tttttttttt | tttttttttt | tttttttttt | 3780 |
| tttttttttt | tttttttttt | tttttttttt | tttttttttt | tttttttttt | tttttttttt | 3840 |

-continued

| | |
|---|---|
| tttttttttt tttttttttt tttttttttt tttttttttt tttttttttt tttttttttt | 3900 |
| tttttttttt tttttttttt tttttttttt tttttttttt tttttttttt tttttttttt | 3960 |
| tttttttttt tttttttttt tttttttttt tttttttttt tttttttttt tttttttttt | 4020 |
| tttttttttt tttttttttt tttttttttt tttttttttt tttttttttt tttttttttt | 4080 |
| tttttttttt tttttttttt tttttttttt tttttttttt tttttttttt tttttttttt | 4140 |
| tttttttttt tttttttttt tttttttttt tttttttttt tttttttttt tttttttttt | 4200 |
| tttttttttt tttttttttt tttttttttt tttttttttt tttttttttt tttttttttt | 4260 |
| tttttttttt tttttttttt tttttttttt tttttttttt tttttttttt tttttttttt | 4320 |
| tttttttttt tttttttttt tttttttttt tttttttttt tttttttttt tttttttttt | 4380 |
| tttttttttt tttttttttt tttttttttt tttttttttt tttttttttt tttttttttt | 4440 |
| tttttttttt tttttttttt tttttttttt tttttttttt tttttttttt tttttttttt | 4500 |
| tttttttttt tttttttttt tttttttttt tttttttttt tttttttttt tttttttttt | 4560 |
| tttttttttt tttttttttt tttttttttt tttttttttt tttttttttt tttttttttt | 4620 |
| tttttttttt tttttttttt tttttttttt tttttttttt tttttttttt tttttttttt | 4680 |
| tttttttttt tttttttttt tttttttttt tttttttttt tttttttttt tttttttttt | 4740 |
| tttttttttt tttttttttt tttttttttt tttttttttt tttttttttt tttttttttt | 4800 |
| tttttttttt tttttttttt tttttttttt tttttttttt tttttttttt tttttttttt | 4860 |
| tttttttttt tttttttttt tttttttttt tttttttttt tttttttttt tttttttttt | 4920 |
| tttttttttt tttttttttt tttttttttt tttttttttt tttttttttt tttttttttt | 4980 |
| tttttttttt tttttttttt | 5000 |

<210> SEQ ID NO 136
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass between 100 and
      5,000 nucleotides

<400> SEQUENCE: 136

| | |
|---|---|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |
| aaaaaaaaaa aaaaaaaaaa aaaaaaaaaa aaaaaaaaaa aaaaaaaaaa aaaaaaaaaa | 300 |
| aaaaaaaaaa aaaaaaaaaa aaaaaaaaaa aaaaaaaaaa aaaaaaaaaa aaaaaaaaaa | 360 |
| aaaaaaaaaa aaaaaaaaaa aaaaaaaaaa aaaaaaaaaa aaaaaaaaaa aaaaaaaaaa | 420 |
| aaaaaaaaaa aaaaaaaaaa aaaaaaaaaa aaaaaaaaaa aaaaaaaaaa aaaaaaaaaa | 480 |
| aaaaaaaaaa aaaaaaaaaa aaaaaaaaaa aaaaaaaaaa aaaaaaaaaa aaaaaaaaaa | 540 |
| aaaaaaaaaa aaaaaaaaaa aaaaaaaaaa aaaaaaaaaa aaaaaaaaaa aaaaaaaaaa | 600 |
| aaaaaaaaaa aaaaaaaaaa aaaaaaaaaa aaaaaaaaaa aaaaaaaaaa aaaaaaaaaa | 660 |
| aaaaaaaaaa aaaaaaaaaa aaaaaaaaaa aaaaaaaaaa aaaaaaaaaa aaaaaaaaaa | 720 |

-continued

| | |
|---|---|
| aaaaaaaaaa aaaaaaaaaa aaaaaaaaaa aaaaaaaaaa aaaaaaaaaa aaaaaaaaaa | 780 |
| aaaaaaaaaa aaaaaaaaaa aaaaaaaaaa aaaaaaaaaa aaaaaaaaaa aaaaaaaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaaa aaaaaaaaaa aaaaaaaaaa | 1140 |
| aaaaaaaaaa aaaaaaaaaa aaaaaaaaaa aaaaaaaaaa aaaaaaaaaa aaaaaaaaaa | 1200 |
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa aaaaaaaaaa aaaaaaaaaa aaaaaaaaaa aaaaaaaaaa | 2040 |
| aaaaaaaaaa aaaaaaaaaa aaaaaaaaaa aaaaaaaaaa aaaaaaaaaa aaaaaaaaaa | 2100 |
| aaaaaaaaaa aaaaaaaaaa aaaaaaaaaa aaaaaaaaaa aaaaaaaaaa aaaaaaaaaa | 2160 |
| aaaaaaaaaa aaaaaaaaaa aaaaaaaaaa aaaaaaaaaa aaaaaaaaaa aaaaaaaaaa | 2220 |
| aaaaaaaaaa aaaaaaaaaa aaaaaaaaaa aaaaaaaaaa aaaaaaaaaa aaaaaaaaaa | 2280 |
| aaaaaaaaaa aaaaaaaaaa aaaaaaaaaa aaaaaaaaaa aaaaaaaaaa aaaaaaaaaa | 2340 |
| aaaaaaaaaa aaaaaaaaaa aaaaaaaaaa aaaaaaaaaa aaaaaaaaaa aaaaaaaaaa | 2400 |
| aaaaaaaaaa aaaaaaaaaa aaaaaaaaaa aaaaaaaaaa aaaaaaaaaa aaaaaaaaaa | 2460 |
| aaaaaaaaaa aaaaaaaaaa aaaaaaaaaa aaaaaaaaaa aaaaaaaaaa aaaaaaaaaa | 2520 |
| aaaaaaaaaa aaaaaaaaaa aaaaaaaaaa aaaaaaaaaa aaaaaaaaaa aaaaaaaaaa | 2580 |
| aaaaaaaaaa aaaaaaaaaa aaaaaaaaaa aaaaaaaaaa aaaaaaaaaa aaaaaaaaaa | 2640 |
| aaaaaaaaaa aaaaaaaaaa aaaaaaaaaa aaaaaaaaaa aaaaaaaaaa aaaaaaaaaa | 2700 |
| aaaaaaaaaa aaaaaaaaaa aaaaaaaaaa aaaaaaaaaa aaaaaaaaaa aaaaaaaaaa | 2760 |
| aaaaaaaaaa aaaaaaaaaa aaaaaaaaaa aaaaaaaaaa aaaaaaaaaa aaaaaaaaaa | 2820 |
| aaaaaaaaaa aaaaaaaaaa aaaaaaaaaa aaaaaaaaaa aaaaaaaaaa aaaaaaaaaa | 2880 |
| aaaaaaaaaa aaaaaaaaaa aaaaaaaaaa aaaaaaaaaa aaaaaaaaaa aaaaaaaaaa | 2940 |
| aaaaaaaaaa aaaaaaaaaa aaaaaaaaaa aaaaaaaaaa aaaaaaaaaa aaaaaaaaaa | 3000 |
| aaaaaaaaaa aaaaaaaaaa aaaaaaaaaa aaaaaaaaaa aaaaaaaaaa aaaaaaaaaa | 3060 |

```
aaaaaaaaaa aaaaaaaaaa aaaaaaaaaa aaaaaaaaaa aaaaaaaaaa aaaaaaaaaa    3120
aaaaaaaaaa aaaaaaaaaa aaaaaaaaaa aaaaaaaaaa aaaaaaaaaa aaaaaaaaaa    3180
aaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aaaaaaaaaa aaaaaaaaaa aaaaaaaaaa    3360
aaaaaaaaaa aaaaaaaaaa aaaaaaaaaa aaaaaaaaaa aaaaaaaaaa aaaaaaaaaa    3420
aaaaaaaaaa aaaaaaaaaa aaaaaaaaaa aaaaaaaaaa aaaaaaaaaa aaaaaaaaaa    3480
aaaaaaaaaa aaaaaaaaaa aaaaaaaaaa aaaaaaaaaa aaaaaaaaaa aaaaaaaaaa    3540
aaaaaaaaaa aaaaaaaaaa aaaaaaaaaa aaaaaaaaaa aaaaaaaaaa aaaaaaaaaa    3600
aaaaaaaaaa aaaaaaaaaa aaaaaaaaaa aaaaaaaaaa aaaaaaaaaa aaaaaaaaaa    3660
aaaaaaaaaa aaaaaaaaaa aaaaaaaaaa aaaaaaaaaa aaaaaaaaaa aaaaaaaaaa    3720
aaaaaaaaaa aaaaaaaaaa aaaaaaaaaa aaaaaaaaaa aaaaaaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aaaaaaaaaa aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaaaaaaa aaaaaaaaaa aaaaaaaaaa aaaaaaaaaa    4020
aaaaaaaaaa aaaaaaaaaa aaaaaaaaaa aaaaaaaaaa aaaaaaaaaa aaaaaaaaaa    4080
aaaaaaaaaa aaaaaaaaaa aaaaaaaaaa aaaaaaaaaa aaaaaaaaaa aaaaaaaaaa    4140
aaaaaaaaaa aaaaaaaaaa aaaaaaaaaa aaaaaaaaaa aaaaaaaaaa aaaaaaaaaa    4200
aaaaaaaaaa aaaaaaaaaa aaaaaaaaaa aaaaaaaaaa aaaaaaaaaa aaaaaaaaaa    4260
aaaaaaaaaa aaaaaaaaaa aaaaaaaaaa aaaaaaaaaa aaaaaaaaaa aaaaaaaaaa    4320
aaaaaaaaaa aaaaaaaaaa aaaaaaaaaa aaaaaaaaaa aaaaaaaaaa aaaaaaaaaa    4380
aaaaaaaaaa aaaaaaaaaa aaaaaaaaaa aaaaaaaaaa aaaaaaaaaa aaaaaaaaaa    4440
aaaaaaaaaa aaaaaaaaaa aaaaaaaaaa aaaaaaaaaa aaaaaaaaaa aaaaaaaaaa    4500
aaaaaaaaaa aaaaaaaaaa aaaaaaaaaa aaaaaaaaaa aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa aaaaaaaaaa    4680
aaaaaaaaaa aaaaaaaaaa aaaaaaaaaa aaaaaaaaaa aaaaaaaaaa aaaaaaaaaa    4740
aaaaaaaaaa aaaaaaaaaa aaaaaaaaaa aaaaaaaaaa aaaaaaaaaa aaaaaaaaaa    4800
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000
```

EFFECTIVE TARGETING OF PRIMARY HUMAN LEUKEMIA USING ANTI-CD123 CHIMERIC ANTIGEN RECEPTOR ENGINEERED T CELLS

This application is a divisional of U.S. Ser. No. 14/184,895, filed Feb. 20, 2014, allowed, which claims priority to U.S. Ser. No. 61/865,856, filed Aug. 14, 2013 and U.S. Ser. No. 61/767,058, filed Feb. 20, 2013, and the entire contents of each of these applications is incorporated herein by reference.

SEQUENCE LISTING

The instant application contains a Sequence Listing which has been submitted electronically in ASCII format and is hereby incorporated by reference in its entirety. Said ASCII copy, created on Feb. 14, 2014, is named N2067-700110 Sequence Listing.txt and is 266,240 bytes in size.

FIELD OF THE INVENTION

The present invention relates generally to T cells engineered to express a Chimeric Antigen Receptor (CAR) and their use, e.g., to treat a disease or condition associated expression of interleukin 3 receptor alpha chain (IL-3Rα, CD123).

BACKGROUND OF THE INVENTION

Most patients with acute myeloid leukemia (AML) are incurable using standard therapy (Mrozek et al, 2012, J Clin Oncol, 30:4515-23) and those with relapsed or refractory AML (RR-AML) have a particularly poor prognosis (Kern et al, 2003, Blood 2003, 101:64-70; Wheatley et al, 1999, Br J Haematol, 107:69-79). Genetic engineering can impart to T cells specificity toward a target of choice. T cells can be transduced with genetic material encoding a single chain variable fragment (scFv) of an antibody, in conjunction with a signaling molecule, thereby using the complementarity determining region (CDR) to recognize a cell surface antigen in a non-MHC restricted manner. These cells are termed chimeric antigen receptor (CAR) T cells. Preclinical and clinical attempts to target at least 20 different surface molecules in a variety of malignancies have shown some activity yet were often limited by poor persistence of the infused CAR T cell product (Sadelain et al, 2009, Curr Opin Immunol 2009, 21:215-23). Recent success with anti-CD19 redirected T cells in patients with advanced CLL and ALL (Porter et al, 2011, N Engl J Med, 365:725-33; Kalos et al, 2011, Science Transl Med, 3:95ra73; Grupp and Kalos, 2013, N Engl J Med, 368:1509-18) demonstrated that these cells can eradicate massive tumor burden after a single infusion with remission lasting up to 3 years to date, underscoring the dramatic potential of CAR T cell therapy. There have been few preclinical attempts to target AML in animal models (Marin et al, 2010, Haematologica, 95:2144-52; Tettamanti et al, 2013, Br J Haematol, 161:389-401) although a recently published small clinical trial demonstrated that it is feasible to produce and infuse T cells to patients with an aggressive malignancy (Ritchie et al, 2013, Mol Ther, epub ahead of print PMID 23831595).

SUMMARY OF THE INVENTION

The invention provides, among other things, compositions comprising at least one chimeric antigen receptor (CAR) specific to CD123 (referred as CAR123, or CD123 CAR), vectors comprising the same, and recombinant T cells comprising a CD123 CAR. The invention also includes methods of making a genetically modified T cell expressing a CAR (CART) wherein the expressed CAR comprises an anti-CD123 binding domain.

The present invention also relates generally to the use of T cells engineered to express a CAR to treat a disease associated with expression of interleukin 3 receptor alpha chain (IL-3Ra, CD123). In one aspect, the disease is a cancer that associated with expression of CD123. In one aspect, the cancer is a hematologic cancer.

A CAR of the invention can also be used in a method whereby a engineered CART123 cell is used to eradicate CD123-expressing normal cells.

Accordingly, in one aspect, the invention pertains to an isolated nucleic acid molecule encoding a chimeric antigen receptor (CAR), wherein the CAR comprises an antibody or antibody fragment which includes an anti-CD123 binding domain (e.g., a humanized antibody or antibody fragment that specifically binds to CD123), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-CD123 binding domain described herein (e.g., a humanized antibody or antibody fragment that specifically binds to CD123 as described herein), a transmembrane domain described herein, and an intracellular signaling domain described herein (e.g., an intracellular signaling domain comprising a costimulatory domain and/or a primary signaling domain).

In one embodiment, the encoded anti-CD123 binding domain comprises one or more (e.g., all three) light chain complementary determining region 1 (LC CDR1), light chain complementary determining region 2 (LC CDR2), and light chain complementary determining region 3 (LC CDR3) of an anti-CD123 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD123 binding domain described herein, e.g., a humanized anti-CD123 binding domain comprising one or more, e.g., all three, LC CDRs and one or more, e.g., all three, HC CDRs. In one embodiment, the encoded anti-CD123 binding domain comprises a light chain variable region described herein (e.g., in Table 1 or SEQ ID NO:2 or SEQ ID NO:101) and/or a heavy chain variable region described herein (e.g., in Table 1 or SEQ ID NO:2 or SEQ ID NO:101). In one embodiment, the encoded anti-CD123 binding domain is a scFv comprising a light chain and a heavy chain of an amino acid sequence of Table 1 or SEQ ID NO:2 or SEQ ID NO:101. In an embodiment, the anti-CD123 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 1 or SEQ ID NO:2 or SEQ ID NO:101, or a sequence with 95-99% identity with an amino acid sequence of Table 1 or SEQ ID NO:2 or SEQ ID NO:101; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 1 or SEQ ID NO:2 or SEQ ID NO:101, or a sequence with 95-99% identity to an amino acid sequence of Table 1 or SEQ ID NO:2 or SEQ ID NO:101. In one embodiment, the anti-CD123 binding domain comprises a sequence selected from a group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, or a sequence with 95-99% identify thereof. In one embodiment, the nucleic acid sequence encoding the anti-CD123 binding domain comprises a sequence selected from a group consisting of SEQ ID NO:37, SEQ ID NO:43, SEQ ID NO:49, SEQ ID NO:55, SEQ ID NO:61, SEQ ID NO:67, SEQ ID NO:73, and SEQ ID NO:79, or a sequence with 95-99% identify thereof. In one embodiment, the encoded anti-CD123 binding domain is a scFv, and a light chain variable region comprising an amino acid sequence described herein, e.g., in Table 1 or SEQ ID NO:2 or SEQ ID NO:101, is attached to a heavy chain variable region comprising an amino acid sequence described herein, e.g., in Table 1 or SEQ ID NO:2 or SEQ ID NO:101, via a linker, e.g., a linker described herein. In one embodiment, the encoded anti-CD123 binding domain includes a (Gly$_4$-Ser)n linker, wherein n is 1, 2, 3, 4, 5, or 6, preferably 4 (SEQ ID NO:126). The light chain variable region and heavy chain variable region of a scFv can be, e.g., in any of the following orientations: light chain variable region-linker-heavy chain variable region or heavy chain variable region-linker-light chain variable region.

In one embodiment, the encoded CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the encoded transmembrane domain comprises a sequence of SEQ ID NO: 5. In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO:5, or a sequence with 95-99% identity to an amino acid sequence of SEQ ID NO:5. In one embodiment, the nucleic acid sequence encoding the transmembrane domain comprises a sequence of SEQ ID NO:12, or a sequence with 95-99% identify thereof.

In one embodiment, the encoded anti-CD123 binding domain is connected to the transmembrane domain by a hinge region, e.g., a hinge region described herein. In one embodiment, the encoded hinge region comprises SEQ ID NO:4 or SEQ ID NO:104 or SEQ ID NO:122 or SEQ ID NO:124, or a sequence with 95-99% identify thereof. In one embodiment, the nucleic acid sequence encoding the hinge region comprises a sequence of SEQ ID NO:11 or SEQ ID NO:105 or SEQ ID NO:123 or SEQ ID NO:125, or a sequence with 95-99% identify thereof.

In one embodiment, the isolated nucleic acid molecule further comprises a sequence encoding a costimulatory domain, e.g., a costimulatory domain described herein. In one embodiment, the encoded costimulatory domain comprises a functional signaling domain of a protein selected from the group consisting of OX40, CD2, CD27, CD28, CD5, ICAM-1, LFA-1 (CD11a/CD18), ICOS (CD278), and 4-1BB (CD137). In one embodiment, the encoded costimulatory domain comprises a sequence of SEQ ID NO:6 or SEQ ID NO:23. In one embodiment, the encoded costimulatory domain comprises an amino acid sequence having at least one, two or three modifications (e.g., substitutions) but not more than 20, 10 or 5 modifications (e.g., substitutions) of an amino acid sequence of SEQ ID NO:6 or SEQ ID NO:23, or a sequence with 95-99% identity to an amino acid sequence of SEQ ID NO:6 or SEQ ID NO:23. In one embodiment, the nucleic acid sequence encoding the costimulatory domain comprises a sequence of SEQ ID NO:13 or SEQ ID NO:27, or a sequence with 95-99% identify thereof.

In one embodiment, the isolated nucleic acid molecule further comprises a sequence encoding an intracellular signaling domain, e.g., an intracellular signaling domain described herein. In one embodiment, the encoded intracellular signaling domain comprises a functional signaling domain of 4-1BB and/or a functional signaling domain of CD3 zeta. In one embodiment, the encoded intracellular signaling domain comprises a functional signaling domain of CD27 and/or a functional signaling domain of CD3 zeta. In one embodiment, the encoded intracellular signaling domain comprises the sequence of SEQ ID NO: 6 or SEQ ID NO:23 and/or the sequence of SEQ ID NO:7 or SEQ ID NO:98. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:6 or SEQ ID NO:23 and/or an amino acid sequence of SEQ ID NO:7 or SEQ ID NO:98, or a sequence with 95-99% identity to an amino acid sequence of SEQ ID NO:6 or SEQ ID NO:23 and/or an amino acid sequence of SEQ ID NO:7 or SEQ ID NO:98. In one embodiment, the encoded intracellular signaling domain comprises the sequence of SEQ ID NO:6 or SEQ ID NO:23 and the sequence of SEQ ID NO:7 or SEQ ID NO:98, wherein the sequences comprising the intracellular signaling domain are expressed in the same frame and as a single polypeptide chain. In one embodiment, the nucleic acid sequence encoding the intracellular signaling domain comprises a sequence of SEQ ID NO:13 or SEQ ID NO:27, or a sequence with 95-99% identify thereof, and/or a sequence of SEQ ID NO:14 or SEQ ID NO:99, or a sequence with 95-99% identify thereof.

In another aspect, the invention pertains to an isolated nucleic acid molecule encoding a CAR construct comprising a leader sequence, e.g., a leader sequence described herein, e.g., of SEQ ID NO:3; an anti-CD123 binding domain described herein, e.g., an anti-CD123 binding domain comprising a LC CDR1, a LC CDR2, a LC CDR3, a HC CDR1, a HC CDR2 and a HC CDR3 described herein, e.g., an anti-CD123 binding domain described in Table 1 or SEQ ID NO:2, or a sequence with 95-99% identify thereof; a hinge region described herein, e.g., of SEQ ID NO:4 or SEQ ID NO:104 or SEQ ID NO:122 or SEQ ID NO:124; a transmembrane domain described herein, e.g., having a sequence of SEQ ID NO:5; and an intracellular signaling domain, e.g., an intracellular signaling domain described herein. In one embodiment, the encoded intracellular signaling domain comprises a costimulatory domain, e.g., a costimulatory domain described herein, e.g., a 4-1BB costimulatory domain having a sequence of SEQ ID NO:6, and/or a primary signaling domain, e.g., a primary signaling domain described herein, e.g., a CD3 zeta stimulatory domain having a sequence of SEQ ID NO:7 or SEQ ID NO:98. In one embodiment, the encoded intracellular signaling domain comprises a costimulatory domain, e.g., a costimulatory domain described herein, e.g., a CD27 costimulatory domain having a sequence of SEQ ID NO:23, and/or a primary signaling domain, e.g., a primary signaling domain described herein, e.g., a CD3 zeta stimulatory domain having a sequence of SEQ ID NO:7 or SEQ ID NO:98. In one embodiment, the isolated nucleic acid molecule encoding the CAR construct includes a leader sequence encoded by the nucleic acid sequence of SEQ ID NO:3, or a sequence with 95-99% identity thereto. In one embodiment, the isolated nucleic acid molecule encoding the CAR construct includes an anti-CD123 binding domain sequence encoded by the nucleic acid sequence of SEQ ID NO:37, SEQ ID NO:43, SEQ ID NO:49, SEQ ID NO:55, SEQ ID NO:61, SEQ ID NO:67, SEQ ID NO:73, and SEQ ID NO:79, or a sequence with 95-99% identity thereto. In one embodiment, the isolated nucleic acid molecule encoding the CAR construct includes a transmembrane sequence encoded by the nucleic acid sequence of SEQ ID NO:12, or a sequence with 95-99% identity thereto. In one embodiment, the isolated nucleic acid molecule encoding the CAR construct includes an intracellular signaling domain sequence encoded by the nucleic acid sequence of SEQ ID NO:13 or SEQ ID NO:27, or a sequence with 95-99% identity thereto and/or a nucleic acid sequence of SEQ ID NO:14 or SEQ ID NO:99, or a sequence with 95-99% identity thereto.

In one embodiment, the isolated nucleic acid molecule comprises (e.g., consists of) a nucleic acid encoding a CAR amino acid sequence of SEQ ID NO:41, SEQ ID NO:47, SEQ ID NO:53, SEQ ID NO:59, SEQ ID NO:65, SEQ ID NO:71, SEQ ID NO:77, or SEQ ID NO:83, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:41, SEQ ID NO:47, SEQ ID NO:53, SEQ ID NO:59, SEQ ID NO:65, SEQ ID NO:71, SEQ ID NO:77, or SEQ ID NO:83, or an amino acid sequence having 85%, 90%, 95%, 96%, 97%, 98% or 99% identity to an amino acid sequence of SEQ ID NO:41, SEQ ID NO:47, SEQ ID NO:53, SEQ ID NO:59, SEQ ID NO:65, SEQ ID NO:71, SEQ ID NO:77, or SEQ ID NO:83. In one embodiment, the isolated nucleic acid molecule comprises (e.g., consists of) a nucleic acid encoding a CAR amino acid sequence of SEQ ID NO:1, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:1, or an amino acid sequence having 85%, 90%, 95%, 96%, 97%, 98% or 99% identity to an amino acid sequence of SEQ ID NO:1.

In one embodiment, the isolated nucleic acid molecule comprises (e.g., consists of) a nucleic acid sequence of SEQ ID NO:40, SEQ ID NO:46, SEQ ID NO:52, SEQ ID NO:58, SEQ ID NO:64, SEQ ID NO:70, SEQ ID NO:76, or SEQ ID NO:80 or a nucleic acid sequence having 85%, 90%, 95%, 96%, 97%, 98% or 99% identity to a nucleic acid sequence of of SEQ ID NO:40, SEQ ID NO:46, SEQ ID NO:52, SEQ ID NO:58, SEQ ID NO:64, SEQ ID NO:70, SEQ ID NO:76, or SEQ ID NO:80. In one embodiment, the isolated nucleic acid molecule comprises (e.g., consists of) a nucleic acid sequence of SEQ ID NO:8, or a nucleic acid sequence having 85%, 90%, 95%, 96%, 97%, 98% or 99% identity to a nucleic acid sequence of SEQ ID NO:8.

In one aspect, the invention pertains to an isolated nucleic acid molecule encoding an anti-CD123 binding domain, wherein the anti-CD123 binding domain comprises one or more (e.g., all three) light chain complementary determining region 1 (LC CDR1), light chain complementary determining region 2 (LC CDR2), and light chain complementary determining region 3 (LC CDR3) of an anti-CD123 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD123 binding domain described herein, e.g., a humanized anti-CD123 binding domain comprising one or more, e.g., all three, LC CDRs and one or more, e.g., all three, HC CDRs. In one embodiment, the encoded anti-CD123 binding domain comprises a light chain variable region described herein (e.g., in SEQ ID NO:36, 42, 48, 54, 60, 66, 72 or 78) and/or a heavy chain variable region described herein (e.g., in SEQ ID NO:36, 42, 48, 54, 60, 66, 72 or 78). In one embodiment, the encoded anti-CD123 binding domain is a scFv comprising a light chain and a heavy chain of an amino acid sequence of in SEQ ID NO:36, 42, 48, 54, 60, 66, 72 or 78. In an embodiment, the anti-CD123 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in SEQ ID NO:36, 42, 48, 54, 60, 66, 72 or 78, or a sequence with 95-99% identity with an amino acid sequence of SEQ ID NO:36, 42, 48, 54, 60, 66, 72 or 78; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided SEQ ID NO:36, 42, 48, 54, 60, 66, 72 or 78, or a sequence with 95-99% identity to an amino acid sequence SEQ ID NO:36, 42, 48, 54, 60, 66, 72 or 78. In one embodiment, the anti-CD123 binding domain comprises a sequence selected from a group consisting of SEQ ID NO:36, 42, 48, 54, 60, 66, 72 or 78, or a sequence with 95-99% identify thereof. In one embodiment, the nucleic acid sequence encoding the anti-CD123 binding domain comprises a sequence selected from a group consisting of SEQ ID NO:37, SEQ ID NO:43, SEQ ID NO:49, SEQ ID NO:55, SEQ ID NO:61, SEQ ID NO:67, SEQ ID NO:73, and SEQ ID NO:79, or a sequence with 95-99% identify thereof.

In another aspect, the invention pertains to an isolated polypeptide molecule encoded by the nucleic acid molecule. In one embodiment, the isolated polypeptide molecule comprises a sequence selected from the group consisting of SEQ ID NO:41, SEQ ID NO:47, SEQ ID NO:53, SEQ ID NO:59, SEQ ID NO:65, SEQ ID NO:71, SEQ ID NO:77, and SEQ ID NO:83, or a sequence with 95-99% identify thereof.

In another aspect, the invention pertains to an isolated chimeric antigen receptor (CAR) molecule comprising an anti-CD123 binding domain (e.g., a humanized antibody or antibody fragment that specifically binds to CD123), a transmembrane domain, and an intracellular signaling domain (e.g., an intracellular signaling domain comprising a costimulatory domain and/or a primary signaling domain). In one embodiment, the CAR comprises an antibody or antibody fragment which includes an anti-CD123 binding domain described herein (e.g., a humanized antibody or antibody fragment that specifically binds to CD123 as described herein), a transmembrane domain described herein, and an intracellular signaling domain described herein (e.g., an intracellular signaling domain comprising a costimulatory domain and/or a primary signaling domain described herein).

In one embodiment, the anti-CD123 binding domain comprises one or more (e.g., all three) light chain complementary determining region 1 (LC CDR1), light chain complementary determining region 2 (LC CDR2), and light chain complementary determining region 3 (LC CDR3) of an anti-CD123 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD123 binding domain described herein, e.g., a humanized anti-CD123 binding domain comprising one or more, e.g., all three, LC CDRs and one or more, e.g., all three, HC CDRs. In one embodiment, the anti-CD123 binding domain comprises a light chain variable region described herein (e.g., in Table 1 or SEQ ID NO:2 or SEQ ID NO:101) and/or a heavy chain variable region described herein (e.g., in Table 1 or SEQ ID NO:2 or SEQ ID NO:101). In one embodiment, the anti-CD123 binding domain is a scFv comprising a light chain and a heavy chain of an amino acid sequence of Table 1 or SEQ ID NO:2 or SEQ ID NO:101. In an embodiment, the anti-CD123 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided in Table 1 or SEQ ID NO:2 or SEQ ID NO:101, or a sequence with 95-99% identity with an amino acid sequence of Table 1 or SEQ ID NO:2 or SEQ ID NO:101; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided in Table 1 or SEQ ID NO:2 or SEQ ID NO:101, or a sequence with 95-99% identity to an amino acid sequence of Table 1 or SEQ ID NO:2 or SEQ ID NO:101. In one embodiment, the anti-CD123 binding domain comprises a sequence selected from a group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, or a sequence with 95-99% identify thereof. In one embodiment, the anti-CD123 binding domain is a scFv, and a light chain variable region comprising an amino acid sequence described herein, e.g., in Table 1 or SEQ ID NO:2 or SEQ ID NO:101, is attached to a heavy chain variable region comprising an amino acid sequence described herein, e.g., in Table 1 or SEQ ID NO:2 or SEQ ID NO:101, via a linker, e.g., a linker described herein. In one embodiment, the anti-CD123 binding domain includes a (Gly₄-Ser)n linker, wherein n is 1, 2, 3, 4, 5, or 6, preferably 4 (SEQ ID NO:126). The light chain variable region and heavy chain variable region of a scFv can be, e.g., in any of the following orientations: light chain variable region-linker-heavy chain variable region or heavy chain variable region-linker-light chain variable region.

In one embodiment, the isolated CAR molecule comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 5. In one embodiment, the transmembrane domain comprises an amino acid sequence having at least one, two or three modifications (e.g., substitutions) but not more than 20, 10 or 5 modifications (e.g., substitutions) of an amino acid sequence of SEQ ID NO: 5, or a sequence with 95-99% identity to an amino acid sequence of SEQ ID NO: 5.

In one embodiment, the anti-CD123 binding domain is connected to the transmembrane domain by a hinge region, e.g., a hinge region described herein. In one embodiment, the encoded hinge region comprises SEQ ID NO:4 or SEQ ID NO:104 or SEQ ID NO:122 or SEQ ID NO:124, or a sequence with 95-99% identity thereof.

In one embodiment, the isolated CAR molecule further comprises a sequence encoding a costimulatory domain, e.g., a costimulatory domain described herein. In one embodiment, the costimulatory domain comprises a functional signaling domain of a protein selected from the group consisting of OX40, CD2, CD27, CD28, CD5, ICAM-1, LFA-1 (CD11a/CD18) and 4-1BB (CD137). In one embodiment, the costimulatory domain comprises a sequence of SEQ ID NO: 6. In one embodiment, the costimulatory domain comprises a sequence of SEQ ID NO:23. In one embodiment, the costimulatory domain comprises an amino acid sequence having at least one, two or three modifications (e.g., substitutions) but not more than 20, 10 or 5 modifications (e.g., substitutions) of an amino acid sequence of SEQ ID NO: 6 or SEQ ID NO:23, or a sequence with 95-99% identity to an amino acid sequence of SEQ ID NO: 6 or SEQ ID NO:23.

In one embodiment, the isolated CAR molecule further comprises a sequence encoding an intracellular signaling domain, e.g., an intracellular signaling domain described herein. In one embodiment, the intracellular signaling domain comprises a functional signaling domain of 4-1BB and/or a functional signaling domain of CD3 zeta. In one embodiment, the intracellular signaling domain comprises the sequence of SEQ ID NO: 6 and/or the sequence of SEQ ID NO:7. In one embodiment, the intracellular signaling domain comprises the sequence of SEQ ID NO:6 and/or the sequence of SEQ ID NO:98. In one embodiment, the intracellular signaling domain comprises a functional signaling domain of CD27 and/or a functional signaling domain of CD3 zeta. In one embodiment, the intracellular signaling domain comprises the sequence of SEQ ID NO:23 and/or the sequence of SEQ ID NO:7. In one embodiment, the intracellular signaling domain comprises the sequence of SEQ ID NO:23 and/or the sequence of SEQ ID NO:98. In one embodiment, the intracellular signaling domain comprises an amino acid sequence having at least one, two or three modifications (e.g., substitutions) but not more than 20, 10 or 5 modifications (e.g., substitutions) of an amino acid sequence of SEQ ID NO:6 or SEQ ID NO:23 and/or an amino acid sequence of SEQ ID NO:7 or SEQ ID NO:98, or a sequence with 95-99% identity to an amino acid sequence of SEQ ID NO:6 or SEQ ID NO:23 and/or an amino acid sequence of SEQ ID NO:7 or SEQ ID NO:98. In one embodiment, the intracellular signaling domain comprises the sequence of SEQ ID NO:6 or SEQ ID NO:23 and the sequence of SEQ ID NO: 7 or SEQ ID NO:98, wherein the sequences comprising the intracellular signaling domain are expressed in the same frame and as a single polypeptide chain.

In one embodiment, the isolated CAR molecule further comprises a leader sequence, e.g., a leader sequence described herein. In one embodiment, the leader sequence comprises an amino acid sequence of SEQ ID NO: 3, or a sequence with 95-99% identity to an amino acid sequence of SEQ ID NO:3.

In another aspect, the invention pertains to an isolated CAR molecule comprising a leader sequence, e.g., a leader sequence described herein, e.g., a leader sequence of SEQ ID NO: 3, or having 95-99% identity thereof; an anti-CD123 binding domain described herein, e.g., an anti-CD123 binding domain comprising a LC CDR1, a LC CDR2, a LC CDR3, a HC CDR1, a HC CDR2 and a HC CDR3 described herein, e.g., an anti-CD123 binding domain described in Table 1 or SEQ ID NO:2 or SEQ ID NO:101, or a sequence with 95-99% identify thereof; a hinge region, e.g., a hinge region described herein, e.g., a hinge region of SEQ ID NO:4 or having 95-99% identity thereof; a transmembrane domain, e.g., a transmembrane domain described herein, e.g., a transmembrane domain having a sequence of SEQ ID NO:5 or a sequence having 95-99% identity thereof; an intracellular signaling domain, e.g., an intracellular signaling domain described herein (e.g., an intracellular signaling domain comprising a costimulatory domain and/or a primary signaling domain). In one embodiment, the intracellular signaling domain comprises a costimulatory domain, e.g., a costimulatory domain described herein, e.g., a 4-1BB costimulatory domain having a sequence of SEQ ID NO:6, or a CD27 costimulatory domain having a sequence of SEQ ID NO:23 or having 95-99% identity thereof, and/or a primary signaling domain, e.g., a primary signaling domain described herein, e.g., a CD3 zeta stimulatory domain having a sequence of SEQ ID NO:7 or SEQ ID NO:98, or having 95-99% identity thereof. In one embodiment, the intracellular signaling domain comprises a costimulatory domain, e.g., a costimulatory domain described herein, e.g., a 4-1BB costimulatory domain having a sequence of SEQ ID NO:6 or a CD27 costimulatory domain having a sequence of SEQ ID NO:23, and/a primary signaling domain, e.g., a primary signaling domain described herein, e.g., a CD3 zeta stimulatory domain having a sequence of SEQ ID NO:7 or SEQ ID NO:98.

In one embodiment, the isolated CAR molecule comprises (e.g., consists of) an amino acid sequence of SEQ ID NO:41, SEQ ID NO:47, SEQ ID NO:53, SEQ ID NO:59, SEQ ID NO:65, SEQ ID NO:71, SEQ ID NO:77, or SEQ ID NO:83, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:41, SEQ ID NO:47, SEQ ID NO:53, SEQ ID NO:59, SEQ ID NO:65, SEQ ID NO:71, SEQ ID NO:77, or SEQ ID NO:83, or an amino acid sequence having 85%, 90%, 95%, 96%, 97%, 98% or 99% identity to an amino acid sequence SEQ ID NO:41, SEQ ID NO:47, SEQ ID NO:53, SEQ ID NO:59, SEQ ID NO:65, SEQ ID NO:71, SEQ ID NO:77, or SEQ ID NO:83. In one embodiment, the isolated CAR molecule comprises (e.g., consists of) an amino acid sequence of SEQ ID NO:1 or SEQ ID NO:107, SEQ ID NO:109, SEQ ID NO:111, SEQ ID NO:113, SEQ ID NO:115, SEQ ID NO:117, SEQ ID NO:119, or SEQ ID NO:121, or an amino acid sequence having at least one, two, three, four, five, 10, 15, 20 or 30 modifications (e.g., substitutions) but not more than 60, 50 or 40 modifications (e.g., substitutions) of an amino acid sequence of SEQ ID NO:1 or SEQ ID NO:107, SEQ ID NO:109, SEQ ID NO:111, SEQ ID NO:113, SEQ ID NO:115, SEQ ID NO:117, SEQ ID NO:119, or SEQ ID NO:121, or an amino acid sequence having 85%, 90%, 95%, 96%, 97%, 98% or 99% identity to an amino acid sequence of SEQ ID NO:1 or SEQ ID NO:107, SEQ ID NO:109, SEQ ID NO:111, SEQ ID NO:113, SEQ ID NO:115, SEQ ID NO:117, SEQ ID NO:119, or SEQ ID NO:121.

In one aspect, the invention pertains to an anti-CD123 binding domain comprising one or more (e.g., all three) light chain complementary determining region 1 (LC CDR1), light chain complementary determining region 2 (LC CDR2), and light chain complementary determining region 3 (LC CDR3) of an anti-CD123 binding domain described herein, and one or more (e.g., all three) heavy chain complementary determining region 1 (HC CDR1), heavy chain complementary determining region 2 (HC CDR2), and heavy chain complementary determining region 3 (HC CDR3) of an anti-CD123 binding domain described herein, e.g., a humanized anti-CD123 binding domain comprising one or more, e.g., all three, LC CDRs and one or more, e.g., all three, HC CDRs. In one embodiment, the anti-CD123 binding domain comprises a light chain variable region described herein (e.g., in SEQ ID NO:36, SEQ ID NO:42, SEQ ID NO:48, SEQ ID NO:54, SEQ ID NO:60, SEQ ID NO:66, SEQ ID NO:72, and SEQ ID NO:78) and/or a heavy chain variable region described herein (e.g. in SEQ ID NO:36, SEQ ID NO:42, SEQ ID NO:48, SEQ ID NO:54, SEQ ID NO:60, SEQ ID NO:66, SEQ ID NO:72, or SEQ ID NO:78). In one embodiment, the anti-CD123 binding domain is a scFv comprising a light chain and a heavy chain of an amino acid sequence of in SEQ ID NO:36, SEQ ID NO:42, SEQ ID NO:48, SEQ ID NO:54, SEQ ID NO:60, SEQ ID NO:66, SEQ ID NO:72, or SEQ ID NO:78. In an embodiment, the anti-CD123 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided, in SEQ ID NO:36, SEQ ID NO:42, SEQ ID NO:48, SEQ ID NO:54, SEQ ID NO:60, SEQ ID NO:66, SEQ ID NO:72, or SEQ ID NO:78 or a sequence with 95-99% identity with an amino acid sequence in SEQ ID NO:36, SEQ ID NO:42, SEQ ID NO:48, SEQ ID NO:54, SEQ ID NO:60, SEQ ID NO:66, SEQ ID NO:72, or SEQ ID NO:78; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided SEQ ID NO:36, SEQ ID NO:42, SEQ ID NO:48, SEQ ID NO:54, SEQ ID NO:60, SEQ ID NO:66, SEQ ID NO:72, or SEQ ID NO:78, or a sequence with 95-99% identity to an amino acid sequence in SEQ ID NO:36, SEQ ID NO:42, SEQ ID NO:48, SEQ ID NO:54, SEQ ID NO:60, SEQ ID NO:66, SEQ ID NO:72, or SEQ ID NO:78. In one embodiment, the anti-CD123 binding domain comprises a sequence selected from a group consisting of SEQ ID NO:36, SEQ ID NO:42, SEQ ID NO:48, SEQ ID NO:54, SEQ ID NO:60, SEQ ID NO:66, SEQ ID NO:72, or SEQ ID NO:78, or a sequence with 95-99% identify thereof.

In another aspect, the invention pertains to a vector comprising a nucleic acid molecule described herein, e.g., a nucleic acid molecule encoding a CAR described herein. In one embodiment, the vector is selected from the group consisting of a DNA, a RNA, a plasmid, a lentivirus vector, adenoviral vector, or a retrovirus vector.

In one embodiment, the vector is a lentivirus vector. In one embodiment, the vector further comprises a promoter. In one embodiment, the promoter is an EF-1 promoter. In one embodiment, the EF-1 promoter comprises a sequence of the promoter sequence of SEQ ID NO:106.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases (SEQ ID NO:127). In one embodiment, the nucleic acid sequence in the vector further comprises a 3'UTR, e.g., a 3' UTR described herein, e.g., comprising at least one repeat of a 3'UTR derived from human beta-globulin, e.g., a 3' UTR present in SEQ ID NO:94. In one embodiment, the nucleic acid sequence in the vector further comprises promoter, e.g., a T2A promoter, e.g., a T2A promoter present in SEQ ID NO:94.

In another aspect, the invention pertains to a cell comprising a vector described herein. In one embodiment, the cell is a cell described herein, e.g., a human T cell, e.g., a human T cell described herein. In one embodiment, the human T cell is a CD8+ T cell.

In another aspect, the invention pertains to a method of making a cell comprising transducing a cell described herein, e.g., a T cell described herein, with a vector of comprising a nucleic acid encoding a CAR, e.g., a CAR described herein.

The present invention also provides a method of generating a population of RNA-engineered cells, e.g., cells described herein, e.g., T cells, transiently expressing exogenous RNA. The method comprises introducing an in vitro transcribed RNA or synthetic RNA into a cell, where the RNA comprises a nucleic acid encoding a CAR molecule described herein.

In another aspect, the invention pertains to a method of providing an anti-tumor immunity in a mammal comprising administering to the mammal an effective amount of a cell expressing a CAR molecule, e.g., a cell expressing a CAR molecule described herein. In one embodiment, the cell is an autologous T cell. In one embodiment, the cell is an allogeneic T cell. In one embodiment, the mammal is a human.

In another aspect, the invention pertains to a method of treating a mammal having a disease or disorder associated with expression of CD123 (e.g., a proliferative disease, a precancerous condition, and a noncancer related indication associated with the expression of CD123) comprising administering to the mammal an effective amount of the cells expressing a CAR molecule, e.g., a CAR molecule described herein.

In one embodiment, the cells expressing a CAR molecule, e.g., a CAR molecule described herein, are administered in combination with an agent that increases the efficacy of a cell expressing a CAR molecule, e.g., an agent described herein.

In one embodiment, the cells expressing a CAR molecule, e.g., a CAR molecule described herein, are administered in combination with an agent that ameliorates one or more side effect associated with administration of a cell expressing a CAR molecule, e.g., an agent described herein.

In one embodiment, the cells expressing a CAR molecule, e.g., a CAR molecule described herein, are administered in combination with an agent that treats the disease associated with CD123, e.g., an agent described herein.

In one embodiment, the cells expressing a CAR molecule, e.g., a CAR molecule described herein, are administered at a dose and/or dosing schedule described herein.

In one embodiment, the cells expressing a CAR molecule, e.g., a CAR molecule described herein, are administered as a first line treatment for the disease, e.g., the cancer, e.g., the cancer described herein. In another embodiment, the cells expressing a CAR molecule, e.g., a CAR molecule described herein, are administered as a second, third, fourth line treatment for the disease, e.g., the cancer, e.g., the cancer described herein.

In one embodiment, the mammal, e.g., human subject, has previously received treatment with an anti-CD19 therapy, e.g., a CD19 CART therapy. In an embodiment, the mammal, e.g., human subject, experienced a relapse with the anti-CD19 therapy In one embodiment, a population of cells described herein is administered.

In another aspect, the invention pertains to a method of eradicating CD123-expressing normal cells, the method comprising administering a cell expressing a CAR molecule described herein. In one aspect, the eradication is in a subject to whom the a CD123-CAR molecule expressing cell has been administered, such that the method is applicable for use as a cellular conditioning therapy prior to cell transplantation. In one embodiment, the CD123-expressing normal cell is a CD123-expressing stem cell and the cell transplantation comprises a stem cell transplantation. For example, in one embodiment, the cell expressing a CD123 CAR molecule, e.g., described herein, is used for bone marrow ablation to eliminate at least a portion of existing bone marrow from a subject. Bone marrow ablation, using a cell expressing a CD123 CAR molecule, may be performed, for example, in a subject in need of a bone marrow transplant. For example, in one embodiment, a cell expressing a CD123 CAR molecule, e.g., a CART123, is used in a cellular conditioning regimen prior to bone marrow or stem cell transplantation. In one embodiment, a cell expressing a CD123 CAR molecule is used for bone marrow ablation in at least part of a treatment for a disease including, but not limited to a hematological cancer, a solid tumor, a hematologic disease, a metabolic disorder, HIV, HTLV, a lysosomal storage disorder, and an immunodeficiency.

In another aspect, the invention pertains to the isolated nucleic acid molecule encoding a CAR of the invention, the isolated polypeptide molecule of a CAR of the invention, the vector comprising a CAR of the invention, and the cell comprising a CAR of the invention for use as a medicament, e.g., as described herein.

In another aspect, the invention pertains to a the isolated nucleic acid molecule encoding a CAR of the invention, the isolated polypeptide molecule of a CAR of the invention, the vector comprising a CAR of the invention, and the cell comprising a CAR of the invention for use in the treatment of a disease expressing CD123, e.g., a disease expressing CD123 as described herein.

In one aspect, the CD123 CAR of the invention is used for therapy against a disease, disorder or condition associated with CD123 expression. In one aspect, the disease, disorder or condition is cancer associated with CD123 expression, including but is not limited to AML, myelodysplastic syndrome, acute lymphoblastic leukemia (ALL), hairy cell leukemia, Prolymphocytic leukemia, Chronic myeloid leukemia, Hodgkin lymphoma, Blastic plasmacytoid dendritic cell neoplasm, and the like.

In one aspect, a cell expressing a CD123 CAR is used for cancer therapy against cancers which express CD123. In one embodiment, the cancer is a hematologic cancer such as, e.g., acute myeloid leukemia (AML).

The present invention also relates generally to the treatment of a patient having a cancer associated with expression of CD123, or at risk of having a cancer associated with expression of CD123, using cellular infusion. In one embodiment, the cellular infusion comprises at least one CD123 CAR-expressing cell. An example of a cancer associated with expression of CD123 includes, but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like.

In one embodiment, lymphocyte infusion, for example allogeneic lymphocyte infusion, is used in the treatment of the cancer, wherein the lymphocyte infusion comprises at least one CD123 CAR-expressing cell. In one embodiment, autologous lymphocyte infusion is used in the treatment of the cancer, wherein the autologous lymphocyte infusion comprises at least one CD123-expressing cell. In another embodiment, a CD123 CAR-expressing cell of the invention can be used to eradicate CD123-expressing normal cells, thereby being applicable for use as a cellular conditioning therapy prior to cell transplantation. In one embodiment, the CD123-expressing normal cell is a CD123-expressing stem cell and the cell transplantation comprises a stem cell transplantation.

In one aspect, the invention relates to a method of bone marrow ablation in a subject that comprises using a CD123 CAR-expressing cell, e.g., described herein, to eliminate at least a portion of native bone marrow in a subject in need of a bone marrow transplant. In one embodiment, the invention includes a method of treating a subject having a disease or disorder where bone marrow transplantation may be beneficial that comprises administering a CD123 Car-expressing cell, e.g., described herein, to a subject in need of a bone marrow transplant. Exemplary diseases in which the present method of using a CD123 CAR-expressing cell for bone marrow ablation may be used as at least a part of a treatment include, but are not limited to a hematological cancer, a solid tumor, a hematologic disease, a metabolic disorder, HIV, HTLV, a lysosomal storage disorder, and an immunodeficiency.

In one embodiment, the CD123 CAR is introduced into T cells, e.g., using in vitro transcription, and the subject (e.g., human) receives an initial administration of cells comprising a CD123 CAR molecule, and one or more subsequent administrations of cells comprising a CD123 CAR molecule, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of cells comprising a CD123 CAR molecule are administered to the subject (e.g., human) per week, e.g., 2, 3, or 4 administrations of cells comprising a CD123 CAR molecule are administered per week. In one embodiment, the subject (e.g., human subject) receives more than one administration of cells comprising a CD123 CAR molecule per week (e.g., 2, 3 or 4 administrations per week) (also referred to herein as a cycle), followed by a week of no administration of cells comprising a CD123 CAR molecule, and then one or more additional administration of cells comprising a CD123 CAR molecule (e.g., more than one administration of the cells comprising a CD123 CAR molecule per week) is administered to the subject. In another embodiment, the subject (e.g., human subject) receives more than one cycle of cells comprising a CD123 CAR molecule, and the time between each cycle is less than 10, 9, 8, 7, 6, 5, 4, or 3 days. In one embodiment, the cells comprising a CD123 CAR molecule are administered every other day for 3 administrations per week. In one embodiment, the cells comprising a CD123 CAR molecule are administered for at least two, three, four, five, six, seven, eight or more weeks.

In one aspect, the invention includes a population of autologous cells that are transfected or transduced with a vector comprising a nucleic acid molecule encoding a CD123-CAR molecule, e.g., as described herein. In one embodiment, the vector is a retroviral vector. In one embodiment, the vector is a self-inactivating lentiviral vector as described elsewhere herein. In one embodiment, the vector is delivered (e.g., by transfecting or electroporating) to a cell, e.g., a T cell, wherein the vector comprises a nucleic acid molecule encoding a CD123 CAR molecule as described herein, which is transcribed as an mRNA molecule, and the CD123 CAR molecule is translated from the RNA molecule and expressed on the surface of the cell.

In one embodiment, the nucleic acid molecule encoding a CD123 CAR molecule, e.g., as described herein, is expressed as an mRNA molecule. In one embodiment, the genetically modified CD123 CAR-expressing cells, e.g., T cells, can be generated by transfecting or electroporating an RNA molecule encoding the desired CARs (e.g., without a vector sequence) into the cell. In one embodiment, a CD123 CAR molecule is translated from the RNA molecule once it is incorporated and expressed on the surface of the recombinant cell.

BRIEF DESCRIPTION OF THE DRAWINGS

FIGS. 1A-1H depicts the results of the following experiments: (FIG. 1A) Primary patient AML samples are frequently $CD123^+$. Blasts were gated using standard side $scatter^{low}$ $CD45^{dim}$ characteristics. (FIG. 1B) The expression of CD123 within different primary samples is heterogeneous but always present, as revealed by gating on blasts and using residual normal lymphocytes or isotype-matched controls to determine the correct gating for CD123. (FIG. 1C) $CD123^{bright}$ and $CD123^{dim}$ sub populations were flow-sorted from primary AML specimens, and the expression of CD123 RNA was quantified using Taqman RTqPCR. A melanoma cell line (A375) was employed as negative control. (FIG. 1D) Results of the degranulation and cytokine production assays. (FIG. 1E) CART123 cells, but not CART19 cells, produce cytokines in response to MOLM14 (a $CD123^+$ AML cell line) or primary AML. CAR staining was accomplished using anti-idiotype anti-mouseCAR19 or with goat anti-mouse Fab (for CD123 CAR). Intracellular cytokines were IFNγ, MIP1β, and TNFα. (FIG. 1F) CART123, CART19, or untransduced T cells were labeled with CFSE and exposed to primary AML cells for 96 hours. Proliferation and enrichment of the CART123 cell population is shown. (FIG. 1G) An overnight fluorocytometric based killing assay demonstrated killing of primary AML blasts by CART123, but not by CART19 cells. (FIG. 1H) Elaboration of the indicated cytokines after a 24 hour incubation of CART123 (black) or CART19 (white) with MOLM14 AML.

(FIG. 2A) Schematic of xenograft model, IV: intravenous injection; BLI: Bioluminescent imaging. Quantification of BLI radiance was used as a surrogate measurement of AML burden. (FIG. 2B) Eradication of MOLM14 occurred only in xenografted mice treated with CART123 cells, as measured by BLI radiance and displayed colorimetrically. (FIG. 2C) Summary BLI data from three MOLM14 xenograft experiments. (FIG. 2D) Survival analysis of MOLM14-bearing xenograft mice demonstrates significant survival of CART123-treated mice in comparison to vehicle- and CART19-treated mice. (FIG. 2E) Schematic of re-challenge model. (FIG. 2F) Summary of BLI of control mice (not depicted in FIG. 2E, these mice received $1\times10^6$ $gfp/luciferase^+$ MOLM14 without prior CART123), primary challenge mice (top row in FIG. 2E) or secondary challenge mice that had previously cleared MOLM14 (bottom row in FIG. 2E). The dotted line indicates the baseline BLI in mice with no luciferase disease. (FIG. 2G) Mice experiencing re-challenge (secondary challenge) with MOLM14 demonstrate more robust increase in peripheral CART123 cells than mice undergoing a primary MOLM14 challenge. (FIG. 2H) Representative mouse showing that initial successful engraftment of MOLM14 is associated with low PB CART123 number, and that late rejection is accompanied by elevation in CART123 cells.

(FIG. 3A) Schematic of Primary AML xenograft model (FIG. 3B) Peripheral blood 15 days after receiving T cells (experiment D29) showing eradication or marked reduction of circulating blasts. (FIG. 3C) Composite survival of mice from three independent experiments. T cells were injected on D15. (FIG. 3D) Blasts up-regulate CD123 in vivo. Ungated representation of a primary AML (UPN34) showing low level expression of CD123 and high level expression of CD33. Upon injection into NSGS mice treated with control un-transduced T cells, UPN34 up-regulated CD123 expression as shown using a comparison before T cells (D13, left) and after T cells (D27, right). All mice receiving control T cells subsequently died of disease, and all mice receiving CART123 cells exhibited long-term survival. (FIG. 3E) CD123 expression level inversely correlates with proliferation and the majority of AML blast proliferation occurs in the BM. Blood, BM, and spleen isolated from moribund mice was stained for intracellular expression of the proliferation marker Ki67 after surface staining for CD123 in CD45$^{dim}$ blasts.

FIGS. 4A-4G depicts the results of the following experiments: (FIG. 4A) Healthy bone marrow progenitor populations exhibit moderate to bright expression of CD123. FMO: fluorescence-minus-one. (FIG. 4B) CD123$^{dim/neg}$ BM progenitors differentiate to CD123$^+$ in semisolid culture. (FIG. 4C) CART123 cells markedly impair hematopoietic function. (FIG. 4D) Cycling BM cells upregulate CD123. (FIG. 4E) Xenograft model for myeloablative potential of CART123 cells. (FIG. 4F) Progressive decline in circulating human B-cells (left) is seen in CART123 mice, and is accompanied by an increase in T cells (right). (FIG. 4G) Myeloablation of human BM in CART123 mice.

FIGS. 7A-7B depicts a schematic representation of the different CD123 CAR constructs (FIG. 7A) and vector map of one CD123 CAR molecule (FIG. 7B).

Figure 26B:
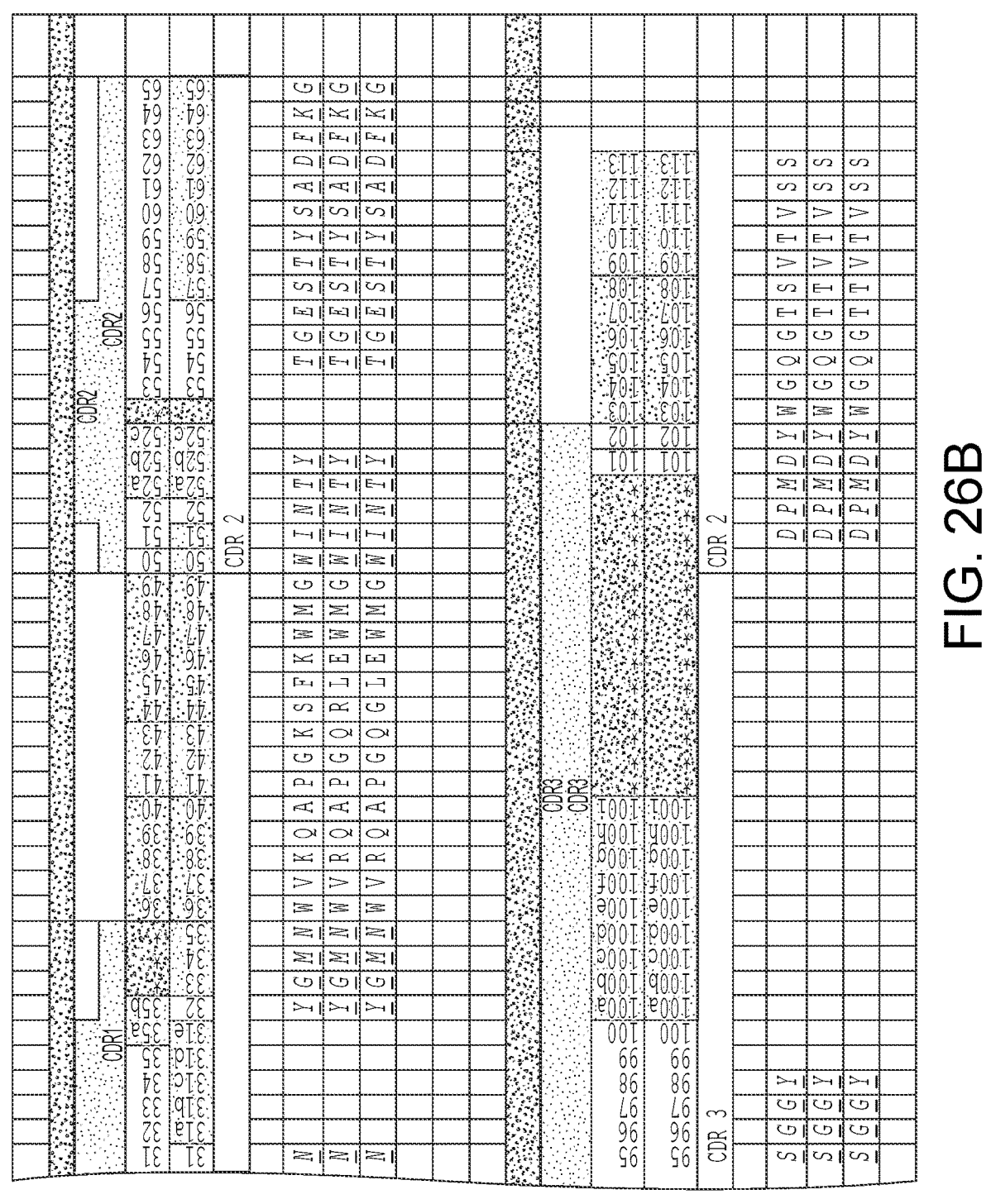

FIGS. 26A-26B is a table showing the VH sequences of humanized anti-CD123 (SEQ ID NOS 93 and 33-34, respectively, in order of appearance).

Figure 27A:
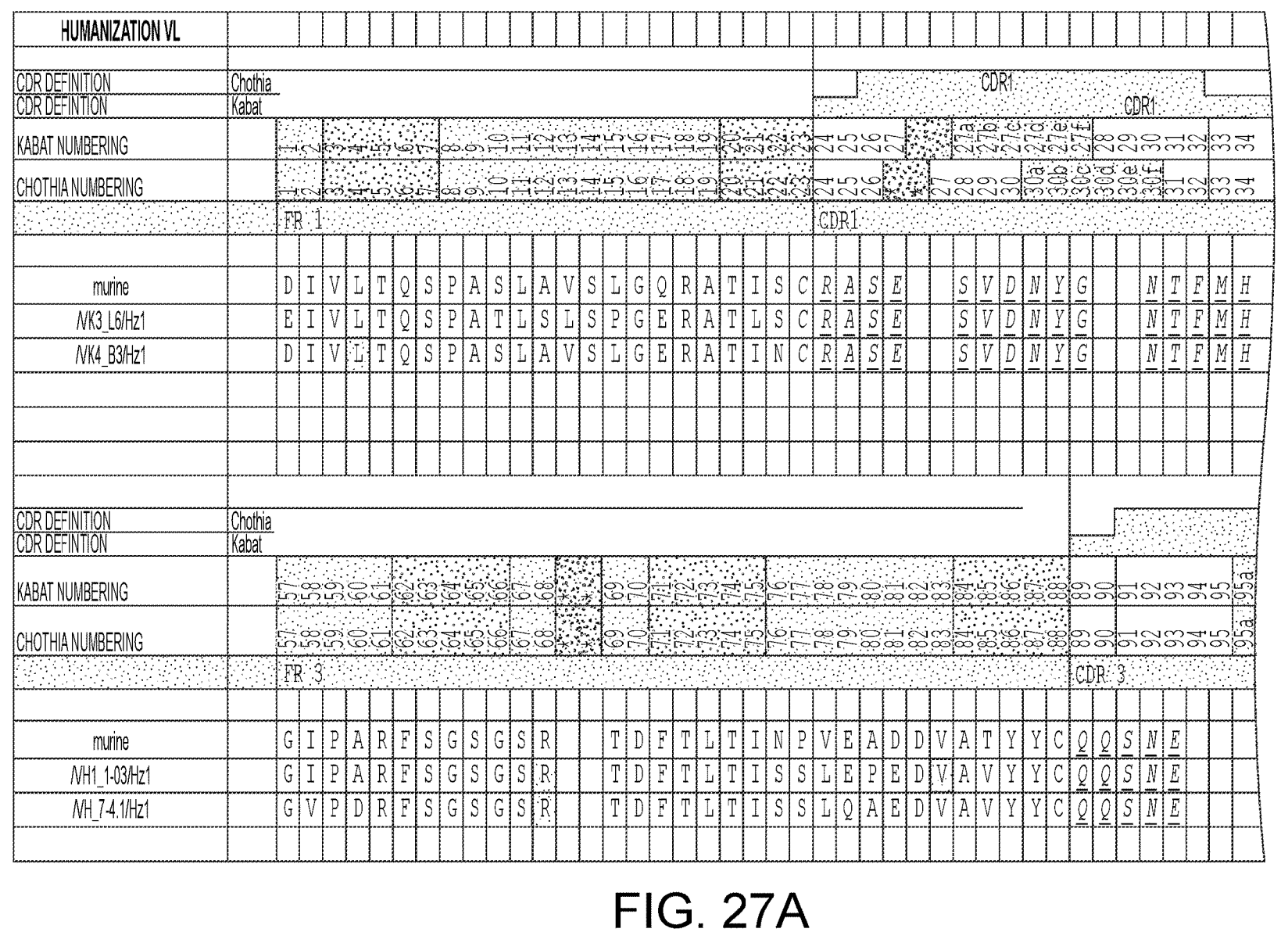

FIGS. 27A-27B is a table showing the VL sequences of humanized anti-CD123 (SEQ ID NOS 92 and 31-32, respectively, in order of appearance).

FIG. 32 is an image showing surface CAR expression in transduced T cells on day 10 of expansion.

DETAILED DESCRIPTION

Definitions

Figure 1E:
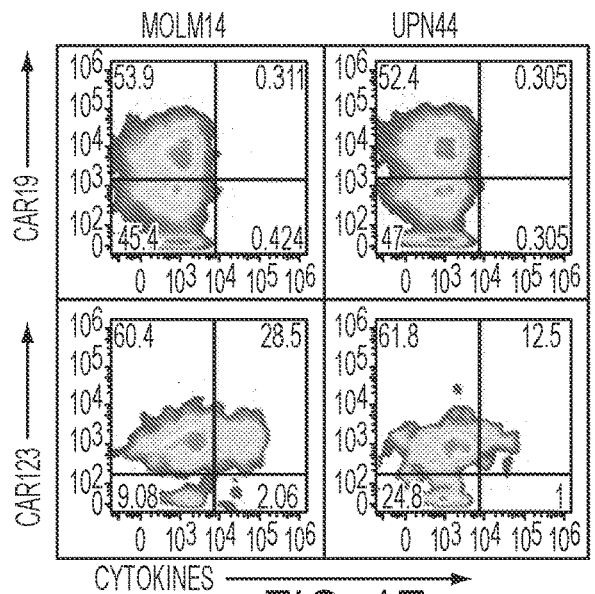
Figure 1G:
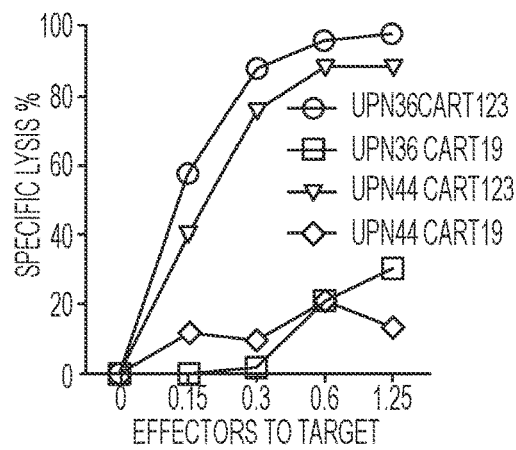
Figure 1F:
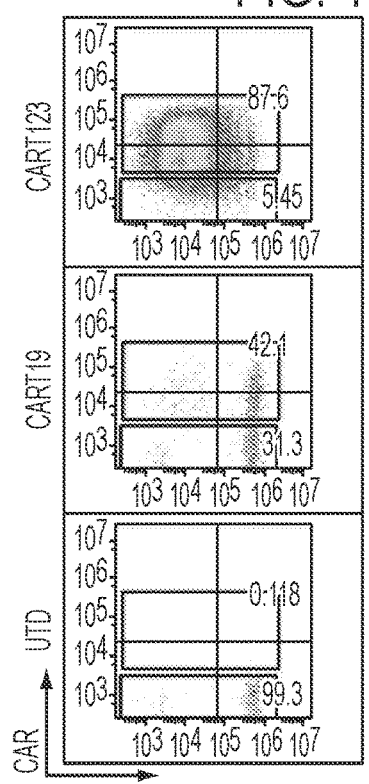

Unless defined otherwise, all technical and scientific terms used herein have the same meaning as commonly understood by one of ordinary skill in the art to which the invention pertains.

The terms "a" and "an" are used herein to refer to one or to more than one (i.e., to at least one) of the grammatical object of the article. By way of example, "an element" means one element or more than one element.

The term "about" as used herein when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

As used herein, the terms "alpha subunit of the IL-3 receptor," "IL3Rα," "CD123," "IL3Rα chain" and "IL3Rα subunit" refer interchangeably to an antigenic determinant known to be detectable on leukemia precursor cells. The human and murine amino acid and nucleic acid sequences can be found in a public database, such as GenBank, UniProt and Swiss-Prot. For example, the amino acid sequence of human IL3Rα can be found at Accession No. NP 002174 and the nucleotide sequence encoding of the human IL3Rα can be found at Accession No. NM 005191. In one aspect the antigen-binding portion of the CAR recognizes and binds an antigen within the extracellular domain of the CD123 protein. In one aspect, the CD123 protein is expressed on a cancer cell.

As used herein, the term "Chimeric Antigen Receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined herein. In one aspect, the stimulatory molecule is the zeta chain associated with the T cell receptor complex. In one aspect, the intracellular signaling domain further comprises one or more functional signaling domains derived from at least one costimulatory molecule as defined below. In one aspect, the costimulatory molecule is chosen from 4-1BB (i.e., CD137), CD27, and/or CD28. In one aspect, the CAR comprises a chimeric fusion protein comprising an extracellular antigen recognition domain, a transmembrane domain and a cytoplasmic signaling domain comprising a functional signaling domain derived from a stimulatory molecule. In one aspect, the CAR comprises a chimeric fusion protein comprising an extracellular antigen recognition domain, a transmembrane domain and a cytoplasmic signaling domain comprising a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain comprising two functional signaling domains derived from one or more co-stimulatory molecule(s) and a functional signaling domain derived from a stimulatory molecule. In one aspect, the CAR comprises a chimeric fusion protein comprising an extracellular antigen recognition domain, a transmembrane domain and an intracellular signaling domain comprising at least two functional signaling domains derived from one or more co-stimulatory molecule(s) and a functional signaling domain derived from a stimulatory molecule. In one aspect the CAR comprises an optional leader sequence at the amino-terminus (N-ter) of the CAR fusion protein. In one aspect, the CAR further comprises a leader sequence at the N-terminus of the extracellular antigen recognition domain, wherein the leader sequence is optionally cleaved from the antigen recognition domain, e.g., a scFv) during cellular processing and localization of the CAR to the cellular membrane. As used herein, the terms intracellular and cytoplasmic are used interchangeably.

The term "signaling domain" refers to the functional portion of a protein which acts by transmitting information within the cell to regulate cellular activity via defined signaling pathways by generating second messengers or functioning as effectors by responding to such messengers.

The term "antibody," as used herein, refers to a protein, or polypeptide sequence derived from an immunoglobulin molecule which specifically binds with an antigen, e.g., non-covalently, reversibly, and in a specific manner. An antibody can be polyclonal or monoclonal, multiple or single chain, or an intact immunoglobulin, and may be derived from natural sources or from recombinant sources. An antibody can be a tetramer of immunoglobulin molecule. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" includes, but is not limited to, monoclonal antibodies, human antibodies, humanized antibodies, camelid antibodies, and chimeric antibodies. The antibodies can be of any isotype/class (e.g., IgG, IgE, IgM, IgD, IgA and IgY), or subclass (e.g., IgG1, IgG2, IgG3, IgG4, IgA1 and IgA2).

The term "antibody fragment" refers to at least one portion of an intact antibody, or recombinant variants thereof, and refers to the antigen binding domain, e.g., an antigenic determining variable regions of an intact antibody that is sufficient to confer recognition and specific binding of the antibody fragment to a target, such as an antigen. Examples of antibody fragments include, but are not limited to, Fab, Fab', F(ab')2, and Fv fragments, single chain or "scFv" antibody fragments, linear antibodies, single domain antibodies such as sdAb (either $V_L$ or $V_H$), camelid $V_{HH}$ domains, and multi-specific antibodies formed from antibody fragments. The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single chain polypeptide, and wherein the scFv retains the specificity of the intact antibody from which it is derived. Unless specified, as used herein an scFv may have the $V_L$ and $V_H$ variable regions in either order, e.g., with respect to the N-terminal and C-terminal ends of the polypeptide, the scFv may comprise $V_L$-linker-$V_H$ or may comprise $V_H$-linker-$V_L$.

The portion of the CAR composition of the invention comprising an antibody or antibody fragment thereof may exist in a variety of forms where the antigen binding domain is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). In one aspect, the antigen binding domain of a CAR composition of the invention comprises an antibody fragment. In a further aspect, the CAR comprises an antibody fragment that comprises a scFv.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant or synthetic DNA or amino acid sequence technology which is available and well known in the art.

The term "antibody heavy chain" refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

The term "recombinant antibody" refers to an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized or can be derived from a biological sample, or it can be a macromolecule that is not necessarily a polypeptide. Such a biological sample can include, but is not limited to a tissue sample, a tumor sample, a cell or a fluid with other biological components.

The term "anti-tumor effect" as used herein, refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

As used herein, the term "autologous" is meant to refer to any material derived from the same individual to whom it is later to be re-introduced into the individual.

"Allogeneic" refers to any material derived from a different animal of the same species as the individual to whom the material is introduced. Two or more individuals are said to be allogeneic to one another when the genes at one or more loci are not identical.

In some aspects, allogeneic material from individuals of the same species may be sufficiently unlike genetically to interact antigenically.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of CD123" as used herein includes but is not limited to, a disease associated with expression of CD123 or condition associated with cells which express CD123 including, e.g., a proliferative disease such as a cancer or malignancy or a precancerous condition such as a myelodysplasia, a myelodysplastic syndrome or a preleukemia; or a noncancer related indication associated with cells which express CD123. In one aspect, a cancer associated with expression of CD123 is a hematological cancer. In one aspect, a hematological cancer includes but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like. Further disease associated with expression of CD123 expression include, but are not limited to, e.g., atypical and/or non-classical cancers, malignancies, precancerous conditions or proliferative diseases associated with expression of CD123. Non-cancer related indications associated with expression of CD123 may also be included.

As used herein, the term "conservative sequence modifications" is intended to refer to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a CAR of the invention can be replaced with other amino acid residues from the same side chain family and the altered CAR can be tested for the ability to bind CD123 using the functional assays described herein.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule expressed by a T cell that provides the primary cytoplasmic signaling sequence(s) that regulate primary activation of the TCR complex in a stimulatory way for at least some aspect of the T cell signaling pathway. In one aspect, the primary signal is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITEM. Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d. In a specific CAR molecule of the invention, the intracellular signaling domain in any one or more CAR molecules of the invention comprises an intracellular signaling sequence, e.g., a primary signaling sequence of CD3-zeta. In a specific CAR of the invention, the primary signaling sequence of CD3-zeta is the human sequence (SEQ ID NO:98), or the equivalent residues from a non-human species, e.g., mouse, rodent, monkey, ape and the like.

An "antigen presenting cell" or "APC" as used herein, means an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the CAR containing cell, e.g., a CART cell. Examples of immune effector function, e.g., in a CART cell, include cytolytic activity and helper activity, including the secretion of cytokines.

In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CART, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

As used herein "zeta" or alternatively "zeta chain", "CD3-zeta" or "TCR-zeta" is defined as the protein provided as GenBan Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplamic domain of the zeta chain that are sufficient to functionally transmit an initial signal necessary for T cell activation. In one aspect the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof. In one aspect, the "zeta stimulatory domain" or a "CD3-zeta stimulatory domain" is the sequence provided as SEQ ID NO:7 and SEQ ID NO:98. A "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Costimulatory molecules include, but are not limited to, an MHC class I molecule, BTLA and a Toll ligand receptor, as well as OX40, CD27, CD28, CD5, ICAM-1, LFA-1 (CD11a/CD18) and 4-1BB (CD137).

A costimulatory intracellular signaling domain can be derived from the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like.

The intracellular signaling domain can comprise the entire intracellular portion, or the entire native intracellular signaling domain, of the molecule from which it is derived, or a functional fragment thereof.

As used herein "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or the equivalent residues from a non-human species, e.g., mouse, rodent, monkey, ape and the like. In one aspect, the "4-1BB costimulatory domain" is the human sequence or the equivalent residues from a non-human species, e.g., mouse, rodent, monkey, ape and the like. In one aspect, the "4-1BB costimulatory domain" is the sequence provided as SEQ ID NO:6 or the equivalent residues from a non-human species, e.g., mouse, rodent, monkey, ape and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA encodes a protein if transcription and translation of mRNA corresponding to that gene, cDNA, or RNA produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins or a RNA may also include introns to the extent that the nucleotide sequence encoding the protein may in some version contain an intron(s).

"Effective amount" or "therapeutically effective amount" are used interchangeably herein, and refer to an amount of a compound, formulation, material, or composition, as described herein effective to achieve a particular biological result.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a regulatory sequence, e.g., a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, a liposome, and the like. Examples of viral transfer vectors include, but are not limited to, adenoviral vectors, adeno-associated virus vectors, retroviral vectors, lentiviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" or "identity" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies and antibody fragments thereof are human immunoglobulins (recipient antibody or antibody fragments) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody or antibody fragment can comprise residues which are found neither in the recipient antibody or antibody fragment nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

The term "human" antibody refers to fully human antibodies as well as effectively human antibodies. "Fully human" refers to an immunoglobulin, such as an antibody or fragment, where the whole molecule is of human origin or consists of an amino acid sequence identical to a human form of the antibody or immunoglobulin. An "effectively human" antibody is an antibody that includes a sufficient number of human amino acid positions such that the antibody does not elicit an immunogenic response in a normal human.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

A "lentiviral vector" is a vector derived from at least a portion of a lentivirus genome, including especially a self-inactivating lentiviral vector as provided in Milone et al., Mol. Ther. 17(8): 1453-1464 (2009). Other Examples or lentivirus vectors that may be used in the clinic include but are not limited to, e.g., the LENTIVECTOR® gene delivery technology from Oxford BioMedica, the LENTIMAX™ vector system from Lentigen and the like. Nonclinical types of lentiviral vectors are also available and would be known to one skilled in the art.

The term "operably linked" or alternatively "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

"Parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, a synthetic peptide, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "flexible polypeptide linker" as used in the context of an scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$ (SEQ ID NO: 129), where n is a positive integer equal to or greater than 1. For example, n=1, n=2, n=3. n=4, n=5 and n=6, n=7, n=8, n=9 and n=10. In one embodiment, the flexible polypeptide linkers include, but are not limited to, (Gly$_4$ Ser)$_4$ (SEQ ID NO: 130) or (Gly$_4$ Ser)$_3$ (SEQ ID NO: 131). In another embodiment, the linkers include multiple repeats of (Gly$_2$Ser), (GlySer) or (Gly$_3$Ser) (SEQ ID NO: 129). Also included within the scope of the invention are linkers described in WO2012/138475, incorporated herein by reference in its entirety).

As used herein, a 5' cap (also termed an RNA cap, an RNA 7-methylguanosine cap or an RNA m$^7$G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 132), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site. A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals including human).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

By the term "synthetic" as it refers to a nucleic acid or polypeptide, including an antibody, is meant a nucleic acid, polypeptide, including an antibody, which has been generated by a mechanism not found naturally within a cell. In some instances, the term "synthetic" may include and therefore overlap with the term "recombinant" and in other instances, the term "synthetic" means that the nucleic acid, polypeptide, including an antibody, has been generated by purely chemical or other means.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell. The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

By the term "specifically binds," as used herein, is meant an antibody or antigen binding fragment thereof, or a ligand, which recognizes and binds with a cognate binding partner (e.g., a stimulatory and/or costimulatory molecule present on a T cell) protein present in a sample, but which antibody, antigen binding fragment thereof or ligand does not substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

Description

Provided herein are compositions and methods of use for the treatment of a disease such as a cancer using an anti-CD123 chimeric antigen receptor (CAR) and T cells comprising a CD123 CAR molecule.

In one aspect, the invention provides CD123 CAR constructs comprising an antibody or antibody fragment that specifically binds to a CD123 protein expressed on a cell surface. In one aspect, the invention provides a cell (e.g., T cell) engineered to express a CAR, wherein the CAR T cell ("CART") exhibits an antitumor property. In one aspect a cell is transformed with the CAR and the CAR is expressed on the cell surface. In some embodiments, the cell (e.g., T cell) is transduced with a viral vector encoding a CAR. In some embodiments, the viral vector is a retroviral vector. In some embodiments, the viral vector is a lentiviral vector. In some such embodiments, the cell may stably express the CAR. In another embodiment, the cell (e.g., T cell) is transfected with a nucleic acid, e.g., mRNA, cDNA, DNA, encoding a CAR. In some such embodiments, the cell may transiently express the CAR.

In one aspect, the anti-CD123 protein binding portion of the CD123 CAR is a scFv antibody fragment. In one aspect such antibody fragments are functional in that they retain the equivalent binding affinity, e.g., they bind the same antigen with comparable efficacy, as the IgG antibody from which it is derived. In one aspect such antibody fragments are functional in that they provide a biological response that can include, but is not limited to, activation of an immune response, inhibition of signal-transduction origination from its target antigen, inhibition of kinase activity, and the like, as will be understood by a skilled artisan.

In one aspect, the CD123 antigen binding domain of the CAR is a murine scFv antibody fragment. In another aspect, the CD128 antigen binding domain of the CAR is a scFv antibody fragment that is humanized compared to the murine sequence of the scFv from which it is derived. In one aspect, the scFv for the murine sequence comprises SEQ ID NO:2 or SEQ ID NO:101. Humanization of this mouse scFv may be desired for the clinical setting, where the mouse-specific residues may induce a human-anti-mouse antigen (HAMA) response in patients who receive CD123 treatment, e.g., treatment with T cells transduced with the CD123 construct.

In one aspect, the anti-CD123 binding domain portion of a CAR is encoded by a transgene whose sequence has been codon optimized for expression in a mammalian cell. In one aspect, entire CAR construct of the invention is encoded by a transgene whose entire sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences. A variety of codon optimization methods is known in the art, and include, e.g., methods disclosed in at least U.S. Pat. Nos. 5,786,464 and 6,114,148.

In one aspect, the anti-CD123 binding domain of a CAR is a humanized anti-CD123 binding domain. For example, in one embodiment, the anti-CD123 binding domain comprises the scFv portion provided in SEQ ID NO:36. In one aspect, the humanized anti-CD123 binding domain comprises the scFv portion provided in SEQ ID NO:42. In one aspect, the humanized anti-CD123 binding domain comprises the scFv portion provided in SEQ ID NO:48. In one aspect, the humanized anti-CD123 binding domain comprises the scFv portion provided in SEQ ID NO:54. In one aspect, the humanized anti-CD123 binding domain comprises the scFv portion provided in SEQ ID NO:60. In one aspect, the humanized anti-CD123 binding domain comprises the scFv portion provided in SEQ ID NO:66. In one aspect, the humanized anti-CD123 binding domain comprises the scFv portion provided in SEQ ID NO:72. In one aspect, the humanized anti-CD123 binding domain comprises the scFv portion provided in SEQ ID NO:80.

In one aspect, a CAR disclosed herein includes an antigen binding domain of a specific antibody with an intracellular signaling domain. For example, in some aspects, the intracellular signaling domain includes, but is not limited to, CD3-zeta chain, 4-1BB, CD27 and CD28 signaling modules and combinations thereof. In one aspect, the antigen binding domain binds to CD123. In one aspect, the CAR comprises the polypeptide sequence shown in SEQ ID NO:1. In one aspect, the CAR comprises the polypeptide sequence shown in SEQ ID NO:41. In one aspect, the CAR comprises the polypeptide sequence shown in SEQ ID NO:47. In one aspect, the CAR comprises the polypeptide sequence shown in SEQ ID NO:53. In one aspect, the CAR comprises the polypeptide sequence shown in SEQ ID NO:59. In one aspect, the CAR comprises the polypeptide sequence shown in SEQ ID NO:65. In one aspect, the CAR comprises the polypeptide sequence shown in SEQ ID NO:71. In one aspect, the CAR comprises the polypeptide sequence shown in SEQ ID NO:77. In one aspect, the CAR comprises the polypeptide sequence shown in SEQ ID NO:83.

Furthermore, the present invention provides anti-CD123 CAR compositions and their use in recombinantly engineered T cells (also referred to herein as "CART123 cells") for use in methods for treating, among other diseases, cancer or any malignancy or autoimmune disease involving cells or tissues in which CD123 is expressed.

In another aspect, the CART123 cells comprising a CAR of the invention can be used to eradicate CD123-expressing normal cells, and may be applicable for use as a cellular conditioning therapy prior to cell transplantation. In one aspect, the CD123-expressing normal cell is a CD123-expressing normal stem cell and the cell transplantation is a stem cell transplantation. For example, in one aspect, a CAR of the invention is used for bone marrow ablation, e.g., to eliminate at least a portion of existing bone marrow from a subject. Bone marrow ablation, using a CAR of the invention, may be performed, for example, in a subject in need of a bone marrow transplant. For example, in certain instances, treatment of hematologic malignancies, such as AML, would benefit from a combined therapy comprising an anti-cancer therapy and a bone marrow transplant or reconditioning therapy. However, the present invention is not limited to bone marrow ablation for treating cancer. Rather, a CAR of the invention may be used as a cellular conditioning regimen for ablating existing bone marrow prior to bone marrow or stem cell transplant for the treatment for any disease, disorder, or condition in which bone marrow transplantation would be beneficial. In one aspect, a CAR of the invention is used for bone marrow ablation as at least part of a treatment for a disease including, but not limited to, a hematological cancer, a solid tumor, a hematologic disease, a metabolic disorder, HIV, HTLV, a lysosomal storage disorder, and an immunodeficiency.

In one aspect, the invention provides a cell (e.g., T cell) engineered to express a chimeric antigen receptor (CAR), wherein the CAR T cell exhibits an antitumor property. A preferred antigen is CD123. In one aspect, the antigen recognition domain of the CAR comprises a fully human anti-CD123 antibody or antibody fragment. Accordingly, the invention provides a fully human anti-CD123-CAR engineered into a T cell and methods of their use for adoptive therapy.

In one aspect, the anti-CD123-CAR comprises at least one intracellular domain selected from the group of a CD137 (4-1BB) signaling domain, a CD28 signaling domain, a CD3zeta signal domain, a CD27 signaling domain, and any combination thereof. In one aspect, the anti-CD123-CAR comprises at least one intracellular signaling domain is from one or more co-stimulatory molecule(s) other than a CD137 (4-1BB) or CD28, a CD3zeta signal domain, and any combination thereof.

Chimeric Antigen Receptor (CAR)

The present invention encompasses a recombinant DNA construct comprising polynucleotide sequences encoding a CAR, wherein the CAR comprises an antibody fragment that binds specifically to CD123, e.g., a human antibody fragment that specifically binds to CD123. In one aspect, CD123 is human CD123, and the nucleic acid sequence encoding the antibody fragment is contiguous with and in the same reading frame as a nucleic acid sequence encoding an intracellular signaling domain. The intracellular signaling domain can comprise, a costimulatory signaling domain and/or a primary signaling domain, e.g., a zeta chain portion. The costimulatory signaling domain refers to a portion of the CAR comprising at least a portion of the intracellular domain of a costimulatory molecule.

In one aspect, the present invention encompasses an isolated chimeric nucleic acid construct comprising sequences of a CAR, wherein the sequence comprises the nucleic acid sequence of an anti-CD123 binding domain operably linked to the nucleic acid sequence of an intracellular domain. An exemplary intracellular domain that can be used in the CAR includes but is not limited to the intracellular domain of CD3-zeta, CD28, 4-1BB, and the like. In some instances, the CAR can comprise any combination of CD3-zeta, CD28, 4-1BB, and the like.

In specific aspects, a CAR construct of the invention comprises a scFv domain selected from the group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, wherein the scFv may be preceded by an optional leader sequence such as provided in SEQ ID NO:3, and followed by an optional hinge sequence such as provided in SEQ ID NO:4, a transmembrane region such as provided in SEQ ID NO:5, an intracellular signalling domain that includes SEQ ID NO:6 and a CD3 zeta sequence that includes SEQ ID NO:7 or SEQ ID NO:98, wherein the domains are contiguous with and in the same reading frame to form a single fusion protein. Also included in the invention is a nucleotide sequence that encodes the polypeptide of each of the scFv fragments selected from the group consisting of of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, and each of the domains of SEQ ID NOS:3-7. Also included in the invention is a nucleotide sequence that encodes the polypeptide of each of the scFv fragments selected from the group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, and each of the domains of SEQ ID NOS: 3-6 and SEQ ID NO:98. In one aspect, the CD123 CAR construct comprises an optional leader sequence, an extracellular antigen binding domain that specifically binds CD123, a hinge, a transmembrane domain, and an intracellular stimulatory domain. In one aspect, the CD123 CAR construct comprises an optional leader sequence, an extracellular antigen binding domain that specifically binds CD123, a hinge, a transmembrane domain, an intracellular signaling domain that includes a costimulatory domain and a primary stimulatory domain. Specific CD123CAR constructs containing a humanized scFv domain are provided in SEQ ID NO:41, SEQ ID NO:47, SEQ ID NO:53, SEQ ID NO:59, SEQ ID NO:65, SEQ ID NO:71, SEQ ID NO:77, and SEQ ID NO:83. Specific CD123 CAR constructs containing a murine scFv domain is provided in SEQ ID NO:1 and SEQ ID NO:107, SEQ ID NO:109, SEQ ID NO:111, SEQ ID NO:113, SEQ ID NO:115, SEQ ID NO:117, SEQ ID NO:119, and SEQ ID NO:121.

An exemplary leader sequence is provided as SEQ ID NO: 3. An exemplary hinge/spacer sequence is provided as SEQ ID NO:4. An exemplary transmembrane domain sequence is provided as SEQ ID NO:5. An exemplary sequence of a costimulatory domain of the 4-1BB protein is provided as SEQ ID NO:6. An exemplary sequence of a costimulatory domain of the CD27 protein is provided as SEQ ID NO:23. An exemplary primary signaling domain of a CD3zeta domain sequence is provided as SEQ ID NO:7. Another exemplary primary signaling domain of a CD3zeta domain sequence is provided as SEQ ID NO:98.

In one aspect, the present invention encompasses a recombinant nucleic acid construct comprising a nucleic acid molecule encoding a CAR, wherein the nucleic acid molecule comprises the nucleic acid sequence encoding an anti-CD123 binding domain, e.g., described herein, that is contiguous with, and in the same reading frame as a nucleic acid sequence encoding an intracellular signaling domain. In one aspect, the anti-CD123 binding domain is selected from one or more of SEQ ID NO:36, SEQ ID NO:42, SEQ ID NO:48, SEQ ID NO:54, SEQ ID NO:60, SEQ ID NO:66, SEQ ID NO:72, and SEQ ID NO:78. In one aspect, the anti-CD123 binding domain is encoded by a nucleotide sequence provided in a sequence selected from the group consisting of SEQ ID NO: 37, SEQ ID NO: 43, SEQ ID NO: 49, SEQ ID NO:55, SEQ ID NO: 61, SEQ ID NO: 67, SEQ ID NO:73, and SEQ ID NO:79. In one aspect, the anti-CD123 binding domain is encoded by SEQ ID NO: 37. In one aspect, the anti-CD123 binding domain is encoded by SEQ ID NO: 43. In one aspect, the anti-CD123 binding domain is encoded by SEQ ID NO: 49. In one aspect, the anti-CD123 binding domain is encoded by SEQ ID NO: 55. In one aspect, the anti-CD123 binding domain is encoded by SEQ ID NO: 61. In one aspect, the anti-CD123 binding domain is encoded by SEQ ID NO: 67. In one aspect, the anti-CD123 binding domain is encoded by SEQ ID NO: 73. In one aspect, the anti-CD123 binding domain is encoded by SEQ ID NO: 80.

In one aspect, the present invention encompasses a recombinant nucleic acid construct comprising a nucleic acid molecule encoding a CAR, wherein the nucleic acid molecule comprises a nucleic acid sequence encoding an anti-CD123 binding domain selected from the group consisting of SEQ ID NO:40, SEQ ID NO:46, SEQ ID NO:52, SEQ ID NO:58, SEQ ID NO:64, SEQ ID NO:70, SEQ ID NO:76, and SEQ ID NO:82 wherein the sequence is contiguous with and in the same reading frame as the nucleic acid sequence encoding an intracellular signaling domain. An exemplary intracellular signaling domain that can be used in the CAR includes, but is not limited to, one or more intracellular signaling domains of, e.g., CD3-zeta, CD28, 4-1BB, and the like. In some instances, the CAR can comprise any combination of intracellular signaling domains of CD3-zeta, CD28, 4-1BB, and the like. In one aspect the nucleic acid construct comprises SEQ ID NO: 40. In one aspect the nucleic acid sequence of a CAR construct is SEQ ID NO:46. In one aspect the nucleic acid construct comprises SEQ ID NO:52. In one aspect the nucleic acid construct comprises SEQ ID NO:58. In one aspect the nucleic acid construct comprises SEQ ID NO:64. In one aspect the nucleic acid construct comprises SEQ ID NO:70. In one aspect the nucleic acid construct comprises SEQ ID NO:76. In one aspect the nucleic acid construct comprises SEQ ID NO:82.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the nucleic acid of interest can be produced synthetically, rather than cloned.

The present invention includes retroviral and lentiviral vector constructs expressing a CAR that can be directly transduced into a cell.

The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 133). RNA so produced can efficiently transfect different kinds of cells. In one aspect, the template includes sequences for the CAR. In an embodiment, an RNA CAR vector is transduced into a T cell by elecroporation.

Antigen Binding Domain

In one aspect, a CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in a CAR of the invention include those associated with viral, bacterial and parasitic infections, autoimmune disease and cancer cells.

In one aspect, the CAR-mediated T-cell response can be directed to an antigen of interest by way of engineering an antigen binding domain that specifically binds a desired antigen into the CAR. In the context of the present invention, "tumor antigen" or "hyperproliferative disorder antigen" or "antigen associated with a hyperproliferative disorder" refers to an antigen that is common to a specific hyperproliferative disorder. In certain aspects, a hyperproliferative disorder antigen is derived from a cancer, including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinoma such as breast cancer, prostate cancer, ovarian cancer, pancreatic cancer, and the like.

In one aspect, the tumor antigen of the present invention comprises one or more antigenic cancer epitopes immunologically recognized by tumor infiltrating lymphocytes (TIL) derived from a cancer tumor of a mammal.

In one aspect, the antigen binding moiety portion of a CAR comprises an antigen binding domain that targets CD123, including but not limited to human CD123. An exemplary human CD123 mRNA sequence is provided as GenBank Accession No. M74782. An exemplary CD123 protein sequence is available as UniProtKB Accession No. P26951. In some embodiments, an antigen binding domain targets an epitope found in the CD123 extracellular domain, e.g., an epitope within human CD123 extracellular domain; e.g., an epitope comprising one or more amino acid residues 19-305 of UniProtKB Accession No. P26951.

The antigen binding domain can be any domain that binds to the antigen including, but not limited to, a monoclonal antibody, a polyclonal antibody, a recombinant antibody, a synthetic antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof. Thus, in one aspect, the antigen binding domain comprises a human antibody or an antibody fragment. In another aspect, the antigen binding domain comprises a humanized antibody or antibody fragment. In one embodiment, the anti-CD123 binding domain comprises one or more (e.g., one, two, or all three) light chain complementary determining region 1 (LC CDR1), light chain complementary determining region 2 (LC CDR2), and light chain complementary determining region 3 (LC CDR3) of an anti-CD123 binding domain described herein, and one or more (e.g., one, two, or all three) heavy chain complementary determining region 1 (HC CDR1), heavy chain complementary determining region 2 (HC CDR2), and heavy chain complementary determining region 3 (HC CDR3) of an anti-CD123 binding domain described herein. In one embodiment, the anti-CD123 binding domain comprises a light chain variable region described herein and/or a heavy chain variable region described herein. In one embodiment, the anti-CD123 binding domain is a scFv comprising a light chain variable region and a heavy chain variable region of an amino acid sequence, e.g., a light chain variable region and heavy chain variable region described herein. In an embodiment, the anti-CD123 binding domain (e.g., an scFv) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 85-99% (e.g., 90-99%, or 95-99%) identity to an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 85-99% (e.g., 90-99%, or 95-99%) identity to an amino acid sequence provided herein. In one aspect, the antigen binding domain comprises one or more sequence selected from the group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78. In one aspect the humanized CAR is selected from one or more sequence selected from the group consisting of SEQ ID NO:41, SEQ ID NO:47, SEQ ID NO:53, SEQ ID NO:59, SEQ ID NO:65, SEQ ID NO:71, SEQ ID NO:77, and SEQ ID NO:83.

In some aspects, a non-human antibody or fragment thereof is humanized, where specific sequences or regions of the antibody or fragment thereof are modified to increase similarity to an antibody naturally produced in a human. In one aspect, the antigen binding domain portion is humanized.

A humanized antibody or fragment thereof can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or fragment thereof has one or more amino acid residues introduced into it from a source which is nonhuman. These nonhuman amino acid residues are often referred to as "import" residues, which are typically taken from an "import" variable domain. As provided herein, a humanized antibody or antibody fragment comprises one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530, 101; 5,585,089; 6,548,640, the contents of which are incorporated herein by reference herein in their entirety). In such humanized antibodies, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

In some aspects, an antibody or antibody fragment is humanized with retention of high affinity for the target antigen and other favorable biological properties. According to one aspect of the invention, humanized antibodies or antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody or fragment thereof may retain a similar antigenic specificity as the original antibody, e.g., in the present invention, the ability to bind human CD123. However, using certain methods of humanization, the affinity and/or specificity of binding of the antibody or fragment thereof for human CD123 may be increased using methods of "directed evolution," as described by Wu et al., J. Mol. Biol., 294:151 (1999), the contents of which are incorporated herein by reference herein in their entirety.

In one aspect, an antigen binding moiety is characterized by particular functional features or properties of an antibody. For example, the antigen binding moiety binds specifically to CD123, including but is not limited to human CD123. In one aspect, the invention relates to an antigen binding moiety comprising an antibody or functional (e.g., antigen binding) fragment thereof, wherein the antibody or functional fragment thereof specifically binds to a CD123 protein or fragment thereof, wherein the antibody or functional fragment thereof is encoded by an amino acid sequence comprising SEQ ID NO: 2. In another aspect, the antigen binding moiety comprises an amino acid sequence encoded by a nucleic acid sequence of SEQ ID NO: 9.

In one aspect, an anti-CD123 binding domain is a single chain variable fragment (scFv). In another aspect, an anti-CD123 binding domain is, for example, a Fv, a Fab, and or a (Fab')$_2$, or a bi-functional (e.g. bi-specific) hybrid antibody (e.g., Lanzavecchia et al., Eur. J. Immunol. 17, 105 (1987)). In one aspect, an antibody or antibody fragment of the invention binds a CD123 protein with wild-type or enhanced affinity. In some instances, scFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise a linker (e.g., a Ser-Gly linker) with an optimized length and/or amino acid composition. The linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

An scFv can comprise a linker of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The linker sequence may comprise any naturally occurring amino acid. In some embodiments, the linker sequence comprises amino acids glycine and serine. In another embodiment, the linker sequence comprises sets of glycine and serine repeats such as (Gly$_4$Ser)n (SEQ ID NO: 35), where n is a positive integer equal to or greater than 1. In one embodiment, the linker can be (Gly$_4$Ser)$_4$ (SEQ ID NO: 130) or (Gly$_4$Ser)$_3$ (SEQ ID NO: 131). Variation in the linker length may retain or enhance activity, giving rise to superior efficacy in activity studies.

In one aspect, a portion of a CAR composition of the invention comprising an antibody or antibody fragment further comprises heavy and light chain variable regions comprising amino acid sequences that are homologous to the amino acid sequences of the anti-CD123 antibodies described herein, and wherein the anti-CD123 binding portion retains the desired functional properties of the anti-CD123 antibodies.

In some aspects, the CD123 CAR composition of the invention further comprises one or more altered residues compared to the $V_H$ and/or $V_L$ sequences disclosed herein, e.g., sequences which can be used as starting material to engineer a modified antibody fragment portion, which modified anti-CD123 binding portion may have altered properties as compared to the starting antibody. In various aspects, the portion comprising an antibody or antibody fragment of the CAR composition of the invention is engineered by modifying one or more amino acids within one or both variable regions (e.g., $V_H$ and/or $V_L$), for example within one or more CDR regions and/or within one or more framework regions. In one specific aspect, the CAR composition of the invention comprises an antibody fragment. In a further aspect, that antibody fragment comprises an scFv.

Stability and Mutations

The stability of an anti-CD123 binding domain, e.g., scFv molecules (e.g., soluble scFv), can be evaluated in reference to the biophysical properties (e.g., thermal stability) of a conventional control scFv molecule or a full length antibody. In one embodiment, the humanized scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule) in the described assays.

The improved thermal stability of the anti-CD123 binding domain, e.g., scFv, is subsequently conferred to the entire CD123 CAR construct, leading to improved therapeutic properties of the CD123 CAR construct. The thermal stability of the anti-CD123 binding domain, e.g., scFv, can be improved by at least about 2° C. or 3° C. as compared to a conventional antibody. In one embodiment, the anti-CD123 binding domain, e.g., scFv, has a 1° C. improved thermal stability as compared to a conventional antibody. In another embodiment, the anti-CD123 binding domain, e.g., scFv, has a 2° C. improved thermal stability as compared to a conventional antibody. In another embodiment, the anti-CD123 binding domain, e.g., scFv, has a 4, 5, 6, 7, 8, 9, 10, 11, 12, 13, 14, 15° C. improved thermal stability as compared to a conventional antibody. Comparisons can be made, for example, between the scFv molecules disclosed herein and scFv molecules or Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

Mutations in scFv (arising through humanization or direct mutagenesis of the soluble scFv) alter the stability of the scFv and improve the overall stability of the scFv and the CD123 CAR construct. Stability of the humanized scFv is compared against the murine scFv using measurements such as Tm, temperature denaturation and temperature aggregation. The binding capacity of the mutant scFvs can be determined using assays described in the Examples.

In one embodiment, the anti-CD123 binding domain, e.g., scFv, comprises at least one mutation arising from the humanization process such that the mutated scFv confers improved stability to the CD123 construct. In another embodiment, the anti-CD123 binding domain, e.g., scFv, comprises at least 1, 2, 3, 4, 5, 6, 7, 8, 9, 10 mutations arising from the humanization process such that the mutated scFv confers improved stability to the CD123 construct.

Methods of Evaluating Protein Stability

The stability of an antigen binding domain may be assessed using, e.g., the methods described below. Such methods allow for the determination of multiple thermal unfolding transitions where the least stable domain either unfolds first or limits the overall stability threshold of a multidomain unit that unfolds cooperatively (e.g. a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J. Mol. Biol. 393: 672-692). Once the least stable domain is identified, the sequence encoding this domain (or a portion thereof) may be employed as a test sequence in the methods.

a) Thermal Stability

The thermal stability of the compositions may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition can be measured biochemically. An exemplary biochemical method for assessing thermal stability is a thermal challenge assay. In a "thermal challenge assay", a composition is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide) the binding activity of the binding protein may be determined by a functional or quantitative ELISA.

Such an assay may be done in a high-throughput format and those disclosed in the Examples using E. coli and high throughput screening. A library of anti-CD123 binding domain, e.g., scFv, variants may be created using methods known in the art. Anti-CD123 binding domain, e.g., scFv, expression may be induced and the anti-CD123 binding domain, e.g., scFv, may be subjected to thermal challenge. The challenged test samples may be assayed for binding and those anti-CD123 binding domains, e.g., scFvs, which are stable may be scaled up and further characterized.

Thermal stability is evaluated by measuring the melting temperature (Tm) of a composition using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for an anti-CD123 binding domain, e.g., scFv, are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81°

C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition using an analytical calorimetric technique (e.g. DSC). The specific heat of a composition is the energy (e.g. in kcal/mol) is required to rise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (AG), enthalpy of unfolding (ΔH), or entropy of unfolding (ΔS). One or more of the above biochemical assays (e.g. a thermal challenge assay) are used to determine the temperature (e.g. the $T_C$ value) at which 50% of the composition retains its activity (e.g. binding activity).

In addition, mutations to the anti-CD123 binding domain, e.g., scFv, alter the thermal stability of the anti-CD123 binding domain, e.g., scFv, compared with the unmutated anti-CD123 binding domain, e.g., scFv. When the humanized anti-CD123 binding domain, e.g., scFv, is incorporated into an anti-CD123 CAR construct, the anti-CD123 binding domain, e.g., humanized scFv confers thermal stability to the overall anti-CD123 CAR construct. In one embodiment, the anti-CD123 binding domain, e.g., scFv, comprises a single mutation that confers thermal stability to the anti-CD123 binding domain, e.g., scFv. In another embodiment, the anti-CD123 binding domain, e.g., scFv, comprises multiple mutations that confer thermal stability to the anti-CD123 binding domain, e.g., scFv. In one embodiment, the multiple mutations in the anti-CD123 binding domain, e.g., scFv, have an additive effect on thermal stability of the anti-CD123 binding domain, e.g., scFv.

b) % Aggregation

The stability of a composition can be determined by measuring its propensity to aggregate. Aggregation can be measured by a number of non-limiting biochemical or biophysical techniques. For example, the aggregation of a composition may be evaluated using chromatography, e.g. Size-Exclusion Chromatography (SEC). SEC separates molecules on the basis of size. A column is filled with semi-solid beads of a polymeric gel that will admit ions and small molecules into their interior but not large ones. When a protein composition is applied to the top of the column, the compact folded proteins (e.g. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

In one aspect, the antigen binding domain of the CAR comprises an amino acid sequence that is homologous to an antigen binding domain amino acid sequence described herein, and the antigen binding domain retains the desired functional properties of the anti-CD123 antibody fragments described herein. In one specific aspect, the CAR composition of the invention comprises an antibody fragment. In a further aspect, that antibody fragment comprises an scFv.

In various aspects, the antigen binding domain of the CAR is engineered by modifying one or more amino acids within one or both variable regions (e.g., VH and/or VL), for example within one or more CDR regions and/or within one or more framework regions. In one specific aspect, the CAR composition of the invention comprises an antibody fragment. In a further aspect, that antibody fragment comprises an scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences, refers to two or more sequences that are the same. Two sequences are "substantially identical" if two sequences have a specified percentage of amino acid residues or nucleotides that are the same (e.g., 60% identity, optionally 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

In one aspect, the present invention contemplates modifications of the starting antibody or fragment (e.g., scFv) amino acid sequence that generate functionally equivalent molecules. For example, the VH or VL of an anti-CD123 binding domain, e.g., scFv, comprised in the CAR can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting VH or VL framework region of the anti-CD123 binding domain, e.g., scFv. The present invention contemplates modifications of the entire CAR construct, e.g., modifications in one or more amino acid sequences of the various domains of the CAR construct in order to generate functionally equivalent molecules. The CAR construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting CAR construct.

Transmembrane Domain

With respect to the transmembrane domain, in various embodiments, a CAR can be designed to comprise a transmembrane domain that is attached to the extracellular domain of the CAR. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 up to 15 amino acids of the intracellular region). In one aspect, the transmembrane domain is one that is associated with one of the other domains of the CAR is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another CAR on the CART cell surface. In a different aspect, the amino acid sequence of the transmembrane domain may be modified or substituted so as to minimize interactions with the binding domains of the native binding partner present in the same CART.

The transmembrane domain may be derived either from a natural or from a recombinant source. Where the source is natural, the domain may be derived from any membrane-bound or transmembrane protein. A transmembrane region of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, the transmembrane domain can be attached to the extracellular region of the CAR, e.g., the antigen binding domain of the CAR, via a hinge, e.g., a hinge from a human protein. For example, in one embodiment, the hinge can be a human Ig (immunoglobulin) hinge, e.g., an IgG4 hinge, or a CD8a hinge. In one embodiment, the hinge or spacer comprises (e.g., consists of) the amino acid sequence of SEQ ID NO:4. In one aspect, the transmembrane domain comprises (e.g., consists of) a transmembrane domain of SEQ ID NO: 5 or 12.

In one aspect, the hinge or spacer comprises an IgG4 hinge. For example, in one embodiment, the hinge or spacer comprises a hinge of the amino acid sequence ESKYGPPCPPCPAPEFLGGPSVFLFPPKPKDTLMISRTPEVTCVVVDVSQEDPEVQ FNWYVDGVEVHNAKTKPREEQFN-STYRVVSVLTVLHQDWLNGKEYKCKVSNK GLPSSIEKTISKAKGQPREPQVYTLPPSQEEMT-KNQVSLTCLVKGFYPSDIAVEWE SNGQPEN-NYKTTPPVLDSDGSFFLY-SRLTVDKSRWQEGNVFSCSVMHEALHNHY TQKSLSLSLGKM (SEQ ID NO:104). In some embodiments, the hinge or spacer comprises a hinge encoded by a nucleotide sequence of (SEQ ID NO: 105)
GAGAGCAAGTACGGCCCTCCCTGCCCCCCTTGCCCTGCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG.

In one aspect, the hinge or spacer comprises an IgD hinge. For example, in one embodiment, the hinge or spacer comprises a hinge of the amino acid sequence RWPESPKAQASSVPTAQPQAEGSLAKATTAPATTRNTGRGGEEKKKEKEKEEQE ERETKTPECPSHTQPLGVYLLTPAVQDLWLRDKATFTCFVVGSDLKDAHLTWEV AGKVPTGGVEEGLLERHSNGSQSQHSRLTLPRSLWNAGTSVTCTLNHPSLPPQRL MALREPAAQAPVKLSLNLLASSDPPEAASWLLCEVSGFSPPNILLMWLEDQREV NTSGFAPARPPPQPGSTTFWAWSVLRVPAPPSPQPATYTCVVSHEDSRTLLNASR SLEVSYVTDH (SEQ ID NO:122). In some embodiments, the hinge or spacer comprises a hinge encoded by a nucleotide sequence of (SEQ ID NO: 123)
AGGTGGCCCGAAAGTCCCAAGGCCCAGGCATCTAGTGTTCCTACTGCACA

GCCCCAGGCAGAAGGCAGCCTAGCCAAAGCTACTACTGCACCTGCCACTA

CGCGCAATACTGGCCGTGGCGGGGAGGAGAAGAAAAAGGAGAAAGAGAAA

GAAGAACAGGAAGAGAGGGAGACCAAGACCCCTGAATGTCCATCCCATAC

CCAGCCGCTGGGCGTCTATCTCTTGACTCCCGCAGTACAGGACTTGTGGC

TTAGAGATAAGGCCACCTTTACATGTTTCGTCGTGGGCTCTGACCTGAAG

GATGCCCATTTGACTTGGGAGGTTGCCGGAAAGGTACCCACAGGGGGGT

TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT.

In one aspect, the transmembrane domain may be recombinant, in which case it will comprise predominantly hydrophobic residues such as leucine and valine. In one aspect, a triplet of phenylalanine, tryptophan and valine may be found at each end of a recombinant transmembrane domain.

Optionally, a short oligo- or polypeptide linker, e.g., between 2 and 10 amino acids in length may form the linkage between the transmembrane domain and the cytoplasmic region of the CAR. A glycine-serine is an example of a suitable linker. For example, in one aspect, the linker comprises the amino acid sequence of GGGGSGGGGS (SEQ ID NO:124). In some embodiments, the linker is encoded by a nucleotide sequence of GGTGGCGGAGGTTCTGGAGGTGGAGGTTCC (SEQ ID NO:125).

Cytoplasmic Domain

The cytoplasmic domain or region of the CAR includes an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" or alternatively "cytoplasmic signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary intracellular signaling domain) and those that act in an antigen-independent manner to provide a secondary or co-stimulatory signal (secondary cytoplasmic signaling domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs.

Examples of ITAM containing primary intracellular signaling domains that are of particular use in the invention include those of TCR zeta, FcR gamma, FcR beta, CD3 gamma, CD3 delta, CD3 epsilon, CD5, CD22, CD79a, CD79b, and CD66d. In one embodiment, a CAR of the invention, e.g., a CAR selected from the group consisting of SEQ ID NO:41, SEQ ID NO:47, SEQ ID NO:53, SEQ ID NO:59, SEQ ID NO:65, SEQ ID NO:71, SEQ ID NO:77, and SEQ ID NO:83, comprises an intracellular signaling domain, e.g., a primary signaling domain, of CD3-zeta. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the CAR can comprise the CD3-zeta signaling domain by itself or it can be combined with any other desired intracellular signaling domain(s) useful in the context of a CAR of the invention. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119(3):696-706).

The intracellular signaling sequences within the cytoplasmic portion of a CAR of the invention may be linked to each other in a random or specified order. Optionally, a short oligo- or polypeptide linker, for example, between 2 and 10 amino acids (e.g., 2, 3, 4, 5, 6, 7, 8, 9 or 10 amino acids) in length may form the linkage between intracellular signaling sequences. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue.

In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB. In one aspect, the signaling domain of CD3-zeta is a signaling domain of SEQ ID NO: 7 or 14. In one aspect, the signaling domain of 4-1BB is a signaling domain of SEQ ID NO: 6 or 13.

In one aspect, the intracellular signaling domain is designed to comprise the signaling domain of CD3-zeta and the signaling domain of CD27. In one aspect, the signaling domain of CD27 comprises an amino acid sequence of QRRKYRSNKGESPVEPAEPCRYSCPREEEGSTIP-IQEDYRKPEPACSP (SEQ ID NO:23). In one aspect, the signalling domain of CD27 is encoded by a nucleic acid sequence of

```
                                        (SEQ ID NO: 27)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC.
```

In one aspect, a CAR-expressing cell described herein can further comprise a second CAR, e.g., a second CAR that includes a different antigen binding domain, e.g., to the same target (CD123) or a different target, e.g., CD19.

In another aspect, the present invention provides a population of CAR-expressing cells, e.g., CART cells. In some embodiments, the population of CAR-expressing cells comprises a mixture of cells expressing different CARs. For example, in one embodiment, the population of CART cells can include a first cell expressing a CAR having an anti-CD123 binding domain described herein, and a second cell expressing a CAR having a different anti-CD123 binding domain, e.g., an anti-CD123 binding domain described herein that differs from the anti-CD123 binding domain in the CAR expressed by the first cell. As another example, the population of CAR-expressing cells can include a first cell expressing a CAR that includes an anti-CD123 binding domain, e.g., as described herein, and a second cell expressing a CAR that includes an antigen binding domain to a target other than CD123, e.g., an antigen binding domain to a target expressed on a cancer cell or a target expressed on normal tissue. In one embodiment, the population of CAR-expressing cells includes, e.g., a first cell expressing a CAR that includes a primary intracellular signaling domain, and a second cell expressing a CAR that includes a secondary signaling domain.

In another aspect, the present invention provides a population of cells wherein at least one cell in the population expresses a CAR having an anti-CD123 binding domain described herein, and a second cell expressing another agent, e.g., an agent which enhances the activity of a CAR-expressing cell. For example, in one embodiment, the agent is an agent which inhibits an inhibitory molecule. Inhibitory molecules, e.g., PD1, can, in some embodiments, decrease the ability of a CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. The agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., the polypeptide that is associated with a positive signal is CD28, ICOS, and fragments thereof, e.g., an intracellular signaling domain of CD28 and/or ICOS. In one embodiment, the fusion protein is expressed by the same cell that expressed the CAR. In another embodiment, the fusion protein is expressed by a cell, e.g., a T cell that does not express an anti-CD123 CAR.

RNA Transfection

Disclosed herein are methods for producing an in vitro transcribed RNA CAR. The present invention also includes a CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length (SEQ ID NO: 133). RNA so produced can efficiently transfect different kinds of cells. In one aspect, the template includes sequences for the CAR.

In one aspect the CD123 CAR is encoded by a messenger RNA (mRNA). In one aspect the mRNA encoding the CD123 CAR is introduced into a T cell for production of a CART cell.

In one embodiment, the in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired temple for in vitro transcription is a CAR of the present invention. For example, the template for the RNA CAR comprises an extracellular region comprising a single chain variable domain of an anti-tumor antibody; a hinge region, a transmembrane domain (e.g., a transmembrane domain of CD8a); and a cytoplasmic region that includes an intracellular signaling domain, e.g., comprising the signaling domain of CD3-zeta and the signaling domain of 4-1BB.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

In one embodiment, the nucleic acid sequence in the vector further comprises a 3'UTR, e.g., a 3' UTR described herein, e.g., comprising at least one repeat of a 3'UTR derived from human beta-globulin, e.g., a 3' UTR present in SEQ ID NO:94. In one embodiment, the nucleic acid sequence in the vector further comprises a cleavable peptide, e.g., a T2A self-cleavable peptide, e.g., a T2A self-cleavable peptide present in SEQ ID NO:94.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 134) (size can be 50-5000 T (SEQ ID NO: 135)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 136).

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides (SEQ ID NO: 90) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a CAR

The present invention provides nucleic acid molecules encoding one or more CAR constructs described herein. In one aspect, the nucleic acid molecule is provided as a messenger RNA transcript. In one aspect, the nucleic acid molecule is provided as a DNA construct.

Accordingly, in one aspect, the invention pertains to an isolated nucleic acid molecule encoding a chimeric antigen receptor (CAR), wherein the CAR comprises a anti-CD123 binding domain (e.g., a humanized anti-CD123 binding domain), a transmembrane domain, and an intracellular signaling domain comprising a stimulatory domain, e.g., a costimulatory signaling domain and/or a primary signaling domain, e.g., zeta chain. In one embodiment, the anti-CD123 binding domain is an anti-CD123 binding domain described herein, e.g., an anti-CD123 binding domain which comprises a sequence selected from a group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, or a sequence with 95-99% identify thereof. In one embodiment, the isolated nucleic acid molecule further comprises a sequence encoding a costimulatory domain. In one embodiment, the costimulatory domain is a functional signaling domain of a protein selected from the group consisting of OX40, CD27, CD28, CD5, ICAM-1, LFA-1 (CD11a/CD18), ICOS (CD278), and 4-1BB (CD137). In one embodiment, the costimulatory domain comprises a sequence of SEQ ID NO: 6 or SEQ ID NO:23, or a sequence with 95-99% identity thereof. In one embodiment, the transmembrane domain is transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO: 5, or a sequence with 95-99% identity thereof. In one embodiment, the intracellular signaling domain comprises a functional signaling domain of 4-1BB and a functional signaling domain of CD3 zeta. In one embodiment, the intracellular signaling domain comprises a functional signaling domain of CD27 and a functional signaling domain of CD3 zeta. In one embodiment, the intracellular signaling domain comprises the sequence of SEQ ID NO:6 or SEQ ID NO:23, or a sequence with 95-99% identity thereof, and the sequence of SEQ ID NO: 7 or SEQ ID NO:98, or a sequence with 95-99% identity thereof, wherein the sequences comprising the intracellular signaling domain are expressed in the same frame and as a single polypeptide chain. In one embodiment, the anti-CD123 binding domain is connected to the transmembrane domain by a hinge region, e.g., a hinge described herein. In one embodiment, the hinge region comprises SEQ ID NO:4, or a sequence with 95-99% identity thereof. In one embodiment, the hinge region comprises SEQ ID NO:104 or SEQ ID NO:122 or SEQ ID NO:124, or a sequence with 95-99% identity thereof.

In another aspect, the invention pertains to an isolated nucleic acid molecule encoding a CAR construct comprising a leader sequence of SEQ ID NO:3, a scFv domain having a sequence selected from the group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78 (or a sequence with 95-99% identify thereof), a hinge region of SEQ ID NO:4 (or a sequence with 95-99% identity thereof), a transmembrane domain having a sequence of SEQ ID NO:5 (or a sequence with 95-99% identity thereof), a 4-1BB costimulatory domain having a sequence of SEQ ID NO:6 (or a sequence with 95-99% identity thereof) or a CD27 costimulatory domain having a sequence of SEQ ID NO:23 (or a sequence with 95-99% identity thereof), and a CD3 zeta stimulatory domain having a sequence of SEQ ID NO:7 or SEQ ID NO:98 (or a sequence with 95-99% identity thereof).

In another aspect, the invention pertains to an isolated polypeptide molecule encoded by the nucleic acid molecule. In one embodiment, the isolated polypeptide molecule comprises a sequence selected from the group consisting of SEQ ID NO:41, SEQ ID NO:47, SEQ ID NO:53, SEQ ID NO:59, SEQ ID NO:65, SEQ ID NO:71, SEQ ID NO:77, and SEQ ID NO:83 or a sequence with 95-99% identify thereof.

In another aspect, the invention pertains to a nucleic acid molecule encoding a chimeric antigen receptor (CAR) molecule that comprises an anti-CD123 binding domain, a transmembrane domain, and an intracellular signaling domain comprising a stimulatory domain, and wherein said anti-CD123 binding domain comprises a sequence selected from the group consisting of SEQ ID NO:36, SEQ ID NO:42, SEQ ID NO:48, SEQ ID NO:54, SEQ ID NO:60, SEQ ID NO:66, SEQ ID NO:72, and SEQ ID NO:78, or a sequence with 95-99% identify thereof.

In one embodiment, the encoded CAR molecule further comprises a sequence encoding a costimulatory domain. In one embodiment, the costimulatory domain is a functional signaling domain of a protein selected from the group consisting of OX40, CD27, CD28, CD5, ICAM-1, LFA-1 (CD11a/CD18) and 4-1BB (CD137). In one embodiment, the costimulatory domain comprises a sequence of SEQ ID NO:6. In one embodiment, the costimulatory domain comprises a sequence of SEQ ID NO:23. In one embodiment, the transmembrane domain is a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment, the transmembrane domain comprises a sequence of SEQ ID NO:5. In one embodiment, the intracellular signaling domain comprises a functional signaling domain of 4-1BB and a functional signaling domain of zeta.

In one embodiment, the intracellular signaling domain comprises the sequence of SEQ ID NO:6 and the sequence of SEQ ID NO:7, wherein the sequences comprising the intracellular signaling domain are expressed in the same frame and as a single polypeptide chain. In one embodiment, the intracellular signaling domain comprises a functional signaling domain of CD27 and a functional signaling domain of zeta. In one embodiment, the intracellular signaling domain comprises the sequence of SEQ ID NO:23 and the sequence of SEQ ID NO:7, wherein the sequences comprising the intracellular signaling domain are expressed in the same frame and as a single polypeptide chain. In one embodiment, the anti-CD123 binding domain is connected to the transmembrane domain by a hinge region. In one embodiment, the hinge region comprises SEQ ID NO:4. In one embodiment, the hinge region comprises SEQ ID NO:104 or SEQ ID NO:122 or SEQ ID NO:124.

In another aspect, the invention pertains to an encoded CAR molecule comprising a leader sequence of SEQ ID NO:3, a scFv domain having a sequence selected from the group consisting SEQ ID NO:36, SEQ ID NO:42, SEQ ID NO:48, SEQ ID NO:54, SEQ ID NO:60, SEQ ID NO:66, SEQ ID NO:72, and SEQ ID NO:78, or a sequence with 95-99% identify thereof, a hinge region of SEQ ID NO:4 or SEQ ID NO:104 or SEQ ID NO:122 or SEQ ID NO:124, a transmembrane domain having a sequence of SEQ ID NO:5, a 4-1BB costimulatory domain having a sequence of SEQ ID NO:6 or a CD27 costimulatory domain having a sequence of SEQ ID NO:23, and a CD3 zeta stimulatory domain having a sequence of SEQ ID NO:7 or SEQ ID NO:98. In one embodiment, the encoded CAR molecule comprises a sequence selected from a group consisting of SEQ ID NO:41, SEQ ID NO:47, SEQ ID NO:53, SEQ ID NO:59, SEQ ID NO:65, SEQ ID NO:71, SEQ ID NO:77, and SEQ ID NO:83, or a sequence with 95-99% identify thereof.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a nucleic acid, e.g., DNA, of the present invention is inserted. Vectors derived from retroviruses, such as the lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of low immunogenicity.

In brief summary, the expression of nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

An expression construct of the present invention may also be used for nucleic acid immunization and gene therapy, using standard gene delivery protocols. Methods for gene delivery are known in the art. See, e.g., U.S. Pat. Nos.

5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1a promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In one aspect, the vector comprises a suicide gene, where expression of the gene results in the death of the cell comprising the vector. For example, in some instances, prolonged expression of the CAR of the invention is not desirable. In one aspect, inclusion of a suicide gene in the vector allows for finer control over CAR expression in a subject. In one aspect, expression of the suicide gene is inducible, for example with the use of an inducible promoter regulating suicide gene expression.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY). In some embodiments, a method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a nanoparticle, e.g., a liposome or other suitable sub-micron sized delivery system. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a CAR encoding nucleic acid molecule. In one aspect, a CAR vector can be directly transduced into a cell, e.g., a T cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the CAR construct in mammalian T cells. In one aspect, the mammalian T cell is a human T cell.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T cell lines available in the art, may be used. In certain aspects of the present invention, T cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another aspect, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one aspect, T cells are isolated by incubation with anti-CD3/anti-CD28 (e.g., 3×28)-conjugated beads, such as DYNABEADS® M-450 CD3/CD28 T, for a time period sufficient for positive selection of the desired T cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another aspect, the time period is 10 to 24 hours. In one aspect, the incubation time period is 24 hours. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain aspects, it may be desirable to enrich for or positively select for regulatory T cells which typically express $CD4^+$, $CD25^+$, $CD62L^{hi}$, $GITR^+$, and $FoxP3^+$. Alternatively, in certain aspects, T regulatory cells are depleted by anti-C25 conjugated beads or other similar method of selection.

In one embodiment, a T cell population can be selected that expresses one or more of IFN-γ, TNFα, IL-17A, IL-2, IL-3, IL-4, GM-CSF, IL-10, IL-13, granzyme B, and perforin. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/ml is used. In one aspect, a concentration of 1 billion cells/ml is used. In a further aspect, greater than 100 million cells/ml is used. In a further aspect, a concentration of cells of 10, 15, 20, 25, 30, 35, 40, 45, or 50 million cells/ml is used. In yet another aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (e.g., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related aspect, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one aspect, the concentration of cells used is $5×10^6$/ml. In other aspects, the concentration used can be from about $1×10^5$/ml to $1×10^6$/ml, and any integer value in between.

In other aspects, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells or CD8$^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain aspects, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one aspect, the agent providing the co-stimulatory signal is bound to a cell surface and the agent providing the primary activation signal is in solution or coupled to a surface. In certain aspects, both agents can be in solution. In another aspect, the agents may be in soluble form, and then crosslinked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one aspect, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one aspect, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one aspect an increase of from about 1 to about 3 fold is observed as compared to the expansion observed using a ratio of 1:1. In one aspect, the ratio of CD3:CD28 antibody bound to the beads ranges from 100:1 to 1:100 and all integer values therebetween. In one aspect of the present invention, more anti-CD28 antibody is bound to the particles than anti-CD3 antibody, e.g., the ratio of CD3:CD28 is less than one. In certain aspects of the invention, the ratio of anti CD28 antibody to anti CD3 antibody bound to the beads is greater than 2:1. In one particular aspect, a 1:100 CD3:CD28 ratio of antibody bound to beads is used. In another aspect, a 1:75 CD3:CD28 ratio of antibody bound to beads is used. In a further aspect, a 1:50 CD3:CD28 ratio of antibody bound to beads is used. In another aspect, a 1:30 CD3:CD28 ratio of antibody bound to beads is used. In one aspect, a 1:10 CD3:CD28 ratio of antibody bound to beads is used. In another aspect, a 1:3 CD3:CD28 ratio of antibody bound to the beads is used. In yet another aspect, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain aspects the ratio of cells to particles ranges from 1:100 to 100:1 and any integer values in-between and in further aspects the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one aspect, a ratio of particles to cells of 1:1 or less is used. In one particular aspect, an advantageous particle to cell ratio is 1:5. In further aspects, the ratio of particles to cells can be varied depending on the day of stimulation. For example, in one aspect, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular aspect, the ratio of particles to cells is 1:1 on the first day of stimulation and adjusted to 1:5 on the third and fifth days of stimulation. In another aspect, particles are added on a daily or every other day basis to a final ratio of 1:1 on the first day, and 1:5 on the third and fifth days of stimulation. In another aspect, the ratio of particles to cells is 2:1 on the first day of stimulation and adjusted to 1:10 on the third and fifth days of stimulation. In another aspect, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type. In one aspect, the most typical ratios for use are about 1:1, 2:1 or 3:1 on the first day.

In further aspects of the present invention, the cells, such as T cells, are combined with agent-coated beads, the beads and the cells are subsequently separated, and then the cells are cultured. In an alternative aspect, prior to culture, the agent-coated beads and cells are not separated but are cultured together. In a further aspect, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one aspect the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain aspects, it may be desirable to significantly decrease the volume in which particles and cells are mixed together (e.g., increase the concentration of cells), to ensure maximum contact of cells and particles. For example, in one aspect, a concentration of about 2 billion cells/ml is used. In another aspect, greater than 100 million cells/ml is used. In a further aspect, a concentration of cells of 10, 15, 20, 25, 30, 35, 40, 45, or 50 million cells/ml is used. In yet another aspect, a concentration of cells from 75, 80, 85, 90, 95, or 100 million cells/ml is used. In further aspects, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain aspects. For example, using high concentration of cells allows more efficient selection of CD8+ T cells that normally have weaker CD28 expression.

In one aspect of the present invention, the mixture may be cultured for several hours (about 3 hours) to about 14 days or any hourly integer value in between. In another aspect, the mixture may be cultured for 21 days. In one aspect of the invention the beads and the T cells are cultured together for about eight days. In another aspect, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree. Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Once an anti-CD123 CAR is constructed, various assays can be used to evaluate the activity of the molecule, such as but not limited to, the ability to expand T cells following antigen stimulation, sustain T cell expansion in the absence of re-stimulation, and anti-cancer activities in appropriate animal models. Assays to evaluate the effects of a CD123 CAR are described in further detail below:

Therapeutic Application for Diseases and Disorders

Hematological cancer conditions are the types of cancer such as leukemia and malignant lymphoproliferative conditions that affect blood, bone marrow and the lymphatic system.

Leukemia can be classified as acute leukemia and chronic leukemia. Acute leukemia can be further classified as acute myelogenous leukemia (AML) and acute lymphoid leukemia (ALL). Chronic leukemia includes chronic myelogenous leukemia (CML) and chronic lymphoid leukemia (CLL). Other related conditions include myelodysplastic syndromes (MDS, formerly known as "preleukemia") which are a diverse collection of hematological conditions united by ineffective production (or dysplasia) of myeloid blood cells and risk of transformation to AML.

In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Existing treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15; 17), t(8;21), and inv16 (p13;q22). Negative factors include increasing age, a preceding myelodysplastic phase, secondary leukemia, high WBC count, and absence of Auer rods.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

The present invention provides, among other things, compositions and methods for treating cancer. In one aspect, the cancer is a hematologic cancer including but is not limited to leukemia (such as acute myelogenous leukemia, chronic myelogenous leukemia, acute lymphoid leukemia, chronic lymphoid leukemia and myelodysplastic syndrome) and malignant lymphoproliferative conditions, including lymphoma (such as multiple myeloma, non-Hodgkin's lymphoma, Burkitt's lymphoma, and small cell- and large cell-follicular lymphoma).

The present invention also provides compositions and methods for inhibiting the proliferation or reducing a CD123-expressing cell population. An exemplary method includes contacting a population of cells comprising a CD123-expressing cell with a CD123 CART cell of the invention that binds to the CD123-expressing cell. In a specific aspect, the present invention provides methods for inhibiting the proliferation or reducing the population of cancer cells expressing CD123, the methods comprising contacting the CD123-expressing cancer cell population with a CD123 CART cell of the invention that binds to the CD123-expressing cell. In another aspect, the present invention provides methods for inhibiting the proliferation or reducing the population of cancer cells expressing CD123, the methods comprising contacting the CD123-expressing cancer cell population with a CD123 CART cell of the invention that binds to the CD123-expressing cell. In certain aspects, the CD123 CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for myeloid leukemia or another cancer associated with CD123-expressing cells relative to a negative control. In one aspect, the subject is a human.

The present invention also provides methods for preventing, treating and/or managing a disorder associated with CD123-expressing cells (e.g., a hematologic cancer), the methods comprising administering to a subject in need a CD123 CART cell of the invention that binds to the CD123-expressing cell. In one aspect, the subject is a human. Non-limiting examples of disorders associated with CD123-expressing cells include autoimmune disorders (such as lupus), inflammatory disorders (such as allergies and asthma) and cancers (such as hematological cancers).

The present invention also provides methods for preventing, treating and/or managing a disease associated with CD123-expressing cells, the methods comprising administering to a subject in need a CD123 CART cell of the invention that binds to the CD123-expressing cell. In one aspect, the subject is a human. Non-limiting examples of diseases associated with CD123-expressing cells include Acute Myeloid Leukemia (AML), myelodysplasia, B-cell Acute Lymphoid Leukemia, T-cell Acute Lymphoid Leukemia, hairy cell leukemia, blastic plasmacytoid dendritic cell neoplasm, chronic myeloid leukemia, hodgkin lymphoma, and the like.

The present invention provides methods for preventing relapse of cancer associated with CD123-expressing cells, the methods comprising administering to a subject in need thereof a CD123 CART cell of the invention that binds to the CD123-expressing cell. In another aspect, the methods comprise administering to the subject in need thereof an effective amount of a CD123 CART cell of the invention that binds to the CD123-expressing cell in combination with an effective amount of another therapy.

In one aspect, CD123 is considered to be a "cancer stem cell" marker in AML. Therefore, a CD123 CART cell of the invention can prevent relapse of AML, or even treat AML that is mostly CD123-negative but with a "stem" population of CD123-expressing cells.

In one aspect, the invention provides compositions and methods for treating a disease or disorder that is negative for CD19 and positive for CD123. In another aspect, the invention provides compositions and methods for treating a disease or disorder wherein part of the tumor is negative for CD19 and positive for CD123. For example, a CART123 cell comprising a CAR of the invention may be useful for treating subjects that have undergone treatment for a disease or disorder associated with elevated expression levels of CD19, wherein the subject that has undergone treatment for elevated levels of CD19 exhibits a disease or disorder associated with elevated levels of CD123.

In one aspect, B-cell acute lymphoid leukemia (ALL) is an example of serial targeting using CART cells comprising a CAR. For example, treatment with CART19 can sometimes result in CD19-negative relapse, which can be treated with CART123 cells of the invention. Alternatively, the present invention includes dual targeting of B-ALL using CART cells comprising an anti-CD19 CAR and an anti-CD123 CAR.

Bone Marrow Ablation

In one aspect, the present invention provides compositions and methods for bone marrow ablation. For example, in one aspect, the invention provides compositions and methods for eradication of at least a portion of existing bone marrow in a subject. It is described herein that, in certain instances, the CART123 cells comprising a CD123 CAR of the present invention eradicates CD123 positive bone marrow myeloid progenitor cells.

In one aspect, the invention provides a method of bone marrow ablation comprising administering a CD123 CAR T cell of the invention to a subject in need of bone marrow ablation. For example, the present method may be used to eradicate some or all of the existing bone marrow of a subject having a disease or disorder in which bone marrow transplantation or bone marrow reconditioning is a beneficial treatment strategy. In one aspect, the bone marrow ablation method of the invention, comprising the administration of a CD123 CAR T cell described elsewhere herein, is performed in a subject prior to bone marrow transplantation. Thus, in one aspect, the method of the invention provides a cellular conditioning regimen prior to bone marrow or stem cell transplantation. In one aspect, bone marrow transplantation comprises transplantation of a stem cell. The bone marrow transplantation may comprise transplantation of autologous or allogeneic cells.

The present invention provides a method of treating a disease or disorder comprising administering a CD123 CAR T cell of the invention to eradicate at least a portion of existing bone marrow. The method may be used as at least a portion of a treatment regimen for treating any disease or disorder where bone marrow transplantation is beneficial. That is, the present method may be used in any subject in need of a bone marrow transplant. In one aspect, bone marrow ablation comprising administration of a CD123 CAR T cell is useful in the treatment of AML. In certain aspects, bone marrow ablation by way of the present method is useful in treating a hematological cancer, a solid tumor, a hematologic disease, a metabolic disorder, HIV, HTLV, a lysosomal storage disorder, and an immunodeficiency.

Compositions and methods disclosed herein may be used to eradicate at least a portion of existing bone marrow to treat hematological cancers including, but not limited to, leukemia, lymphoma, myeloma, ALL, AML, CLL, CML, Hodgkin's disease, Non-Hodgkin's lymphoma, and multiple myeloma.

Compositions and methods disclosed herein may be used to treat hematologic diseases including, but not limited to myelodysplasia, anemia, paroxysmal nocturnal hemoglobinuria, aplastic anemia, acquired pure red cell anemia, Diamon-Blackfan anemia, Fanconi anemia, cytopenia, amegakaryotic thrombocytopenia, myeloproliferative disorders, polycythemia vera, essential thrombocytosis, myelofibrosis, hemoglobinopathies, sickle cell disease, β thalassemia major, among others.

Compositions and methods disclosed herein may be used to treat lysosomal storage disorders including, but not limited to lipidoses, sphigolipodeses, leukodystrophies, mucopolysaccharidoses, glycoproteinoses, infantile neuronal ceroid lipofuscinosis, Jansky-Bielschowsky disease, Niemann-Pick disease, Gaucher disease, adrenoleukodystrophy, metachromatic leukodystrophy, Krabbe disease, Hurler syndrome, Scheie syndrome, Hurler-Scheie syndrome, hunter syndrome, Sanfilippo syndrome, Morquio syndrome, Maroteaux-Lamy syndrome, Sly syndrome, mucolipidosis, fucolipidosis, aspartylglucosaminuria, alpha-mannosidoses, and Wolman disease.

Compositions and methods disclosed herein may be used to treat immunodeficiencies including, but not limited to, T-cell deficiencies, combined T-cell and B-cell deficiencies, phagocyte disorders, immune dysregulation diseases, innate immune deficiencies, ataxia telangiectasia, DiGeorge syndrome, severe combined immunodeficiency (SCID), Wiskott-Aldrich syndrome, Kostmann syndrome, Shwachman-Diamond syndrome, Griscelli syndrome, and NF-Kappa-B Essential Modulator (NEMO) deficiency.

In one aspect, the present invention provides a method of treating cancer comprising bone marrow conditioning, where at least a portion of bone marrow of the subject is eradicated by the CD123 CAR T cell of the invention. For example, in certain instances, the bone marrow of the subject comprises a malignant precursor cell that can be targeted and eliminated by the activity of the CD123 CAR T cell. In one aspect, a bone marrow conditioning therapy comprises administering a bone marrow or stem cell transplant to the subject following the eradication of native bone marrow. In one aspect, the bone marrow reconditioning therapy is combined with one or more other anti-cancer therapies, including, but not limited to anti-tumor CAR therapies, chemotherapy, radiation, and the like.

In one aspect, eradication of the administered CD123 CART cells may be required prior to infusion of bone marrow or stem cell transplant. Eradication of the CD123 CAR T cells may be accomplished using any suitable strategy or treatment, including, but not limited to, use of a suicide gene, limited CAR persistence using RNA encoded CARs, or anti-T cell modalities including antibodies or chemotherapy.

Therapeutic Application

In one aspect, the invention pertains to a vector comprising a CD123 CAR operably linked to promoter for expression in mammalian T cells. In one aspect, the invention provides a recombinant T cell expressing the CD123 CAR for use in treating CD123-expressing tumors, wherein the recombinant T cell expressing the CD123 CAR is termed a CD123 CART. In one aspect, the CD123 CART of the invention is capable of contacting a tumor cell with at least one CD123 CAR of the invention expressed on its surface such that the CD123 CART is activated in response to the antigen and the CART targets the tumor cell and growth of the tumor is inhibited.

In one aspect, the invention pertains to a method of inhibiting growth of a CD123-expressing tumor cell, comprising contacting the tumor cell with an anti-CD123 CAR T cell described herein such that the CART is activated in response to the antigen and targets the cancer cell, wherein the growth of the tumor is inhibited.

In another aspect, the invention pertains to a method of treating cancer in a subject. The method comprises administering to the subject an anti-CD123 CAR T cell of the present invention such that the cancer is treated in the subject. An example of a cancer that is treatable by the anti-CD123 CAR T cell of the invention includes but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like.

The present invention includes a type of cellular therapy where T cells are genetically modified to express a chimeric antigen receptor (CAR) and the CAR T cell is infused to a recipient in need thereof. The infused cell is able to kill tumor cells in the recipient. In some embodiments, the CAR-modified T cells are able to replicate in vivo resulting in long-term persistence that can lead to sustained tumor control. In various aspects, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

The invention also includes a type of cellular therapy where T cells are modified, e.g., by in vitro transcribed RNA, to transiently express a chimeric antigen receptor (CAR) and the CAR T cell is infused to a recipient in need thereof. The infused cell is able to kill tumor cells in the recipient. Thus, in various aspects, the T cells administered to the patient, is present for less than one month, e.g., three weeks, two weeks, one week, after administration of the T cell to the patient.

Without wishing to be bound by any particular theory, the anti-tumor immunity response elicited by the CAR-modified T cells may be an active or a passive immune response. In another aspect, the CAR transduced T cells exhibit specific proinflammatory cytokine secretion and potent cytolytic activity in response to human cancer cells expressing the CD123, resist soluble CD123 inhibition, mediate bystander killing and mediate regression of an established human tumor. For example, antigen-less tumor cells within a heterogeneous field of CD123-expressing tumor may be susceptible to indirect destruction by CD123-redirected T cells that has previously reacted against adjacent antigen-positive cancer cells.

In one aspect, the method of the invention provides for eradication of at least a portion of existing bone marrow of a subject. As described herein, in certain instances, the CD123 CAR T cell of the invention eradicates the CD123 expressing bone marrow myeloid progenitor cells. Thus, the present invention may be used as a cellular conditioning regimen for the ablation of at least a portion of existing bone marrow prior to bone marrow transplantation. The method can be used to treat any disease or disorder where bone marrow transplantation is beneficial or necessary, including, but not limited a hematological cancer, a solid tumor, a hematologic disease, a metabolic disorder, HIV, HTLV, a lysosomal storage disorder, and an immunodeficiency.

In one aspect, the fully-human CAR-modified T cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (e.g., a human) and genetically modified (e.g., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with expression of CD123. In certain aspects, the cells of the invention are used in the treatment of patients at risk for developing diseases, disorders and conditions associated with expression of CD123. Thus, the present invention provides methods for the treatment or prevention of diseases, disorders and conditions associated with expression of CD123 comprising administering to a subject in need thereof, a therapeutically effective amount of the CAR-modified T cells of the invention. An example of a diseases, disorders and conditions associated with expression of CD123 includes but is not limited to AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, and the like.

A CAR-modified T cell of the present invention may be administered either alone, or as a pharmaceutical composition in combination with diluents and/or with other components such as IL-2 or other cytokines or cell populations.

The present invention also provides methods for inhibiting the proliferation or reducing a CD123-expressing cell population, the methods comprising contacting a population of cells comprising an CD123-expressing cell with an CD123CART cell described herein that binds to the CD123-expressing cell. In a specific aspect, the present invention provides methods for inhibiting the proliferation or reducing the population of cancer cells expressing CD123, the methods comprising contacting the CD123-expressing cancer cell population with an CD123CART cell described herein that binds to the CD123-expressing cell. In one aspect, the present invention provides methods for inhibiting the proliferation or reducing the population of cancer cells expressing CD123, the methods comprising contacting the CD123-expressing cancer cell population with an CD123CART cell described herein that binds to the CD123-expressing cell. In certain aspects, the CD123CART cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for a cancer associated with CD123-expressing cells relative to a negative control. In one aspect, the subject is a human.

The present invention also provides methods for preventing, treating and/or managing a disease associated with CD123-expressing cells (e.g., AML, myelodysplastic syndrome, ALL, hairy cell leukemia, Prolymphocytic leukemia, Chronic myeloid leukemia, Hodgkin lymphoma, Blastic plasmacytoid dendritic cell neoplasm, among others), the methods comprising administering to a subject in need a CD123CART cell described herein that binds to the CD123-expressing cell. In one aspect, the subject is a human.

The present invention provides methods for preventing relapse of cancer associated with CD123-expressing cells, the methods comprising administering to a subject in need thereof an CD123CART cell described herein that binds to the CD123-expressing cell. In one aspect, the methods comprise administering to the subject in need thereof an effective amount of an CD123CART cell described herein that binds to the CD123-expressing cell in combination with an effective amount of another therapy. In one aspect, the subject suffers from or is susceptible to relapse after CD19 therapy, e.g., therapy with a CD19 CART.

Combination Therapies

A CAR-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A CAR-expressing cell described herein and the at least one additional therapeutic agent can be administered simultaneously, in the same or in separate compositions, or sequentially. For sequential administration, the CAR-expressing cell described herein can be administered first, and the additional agent can be administered second, or the order of administration can be reversed.

In further aspects, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation.

In one embodiment, a CAR-expressing cell described herein can be used in combination with a chemotherapeutic agent. General Chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary chemotherapeutic agents include an anthracycline, an antimetabolite and targeted antibodies, e.g., an anti-CD33 antibody such as gemtuzumab.

Exemplary antimetabolites include, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®) and gemcitabine (Gemzar®). Preferred antimetabolites include, e.g., 5-fluorouracil (Adrucil®, Efudex®, Fluoroplex®), floxuridine (FUDF®), capecitabine (Xeloda®), pemetrexed (Alimta®), raltitrexed (Tomudex®) and gemcitabine (Gemzar®).

Exemplary anthracyclines include, without limitation, daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®). Preferred anthracyclines include daunorubicin (Cerubidine®, Rubidomycin®) and doxorubicin (Adriamycin®).

Drugs that inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993) can also be used. In a further aspect, the cell compositions of the present invention may be administered to a patient in conjunction with (e.g., before, simultaneously or following) bone marrow transplantation, T cell ablative therapy using chemotherapy agents such as, fludarabine, external-beam radiation therapy (XRT), cyclophosphamide, and/or antibodies such as OKT3 or CAMPATH. In one aspect, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

In one embodiment, the subject can be administered an agent which reduces or ameliorates a side effect associated with the administration of a CAR-expressing cell. Side effects associated with the administration of a CAR-expressing cell include, but are not limited to CRS, and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a CAR-expressing cell described herein to a subject and further administering an agent to manage elevated levels of a soluble factor resulting from treatment with a CAR-expressing cell. In one embodiment, the soluble factor elevated in the subject is one or more of IFN-γ, TNFα, IL-2 and IL-6. Therefore, an agent administered to treat this side effect can be an agent which neutralizes one or more of these soluble factors. Such agents include, but are not limited to a steroid, an inhibitor of TNFα, and an inhibitor of IL-6. An example of a TNFα inhibitor is entanercept. An example of an IL-6 inhibitor is Tocilizumab (toc).

In one embodiment, the subject can be administered an agent which enhances the activity of a CAR-expressing cell. For example, in one embodiment, the agent can be an agent which inhibits an inhibitory molecule. Inhibitory molecules, e.g., Programmed Death 1 (PD1), can, in some embodiments, decrease the ability of a CAR-expressing cell to mount an immune effector response. Examples of inhibitory molecules include PD1, PD-L1, CTLA4, TIM3, LAGS, VISTA, BTLA, TIGIT, LAIR1, CD160, 2B4 and TGFR beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the CAR-expressing cell. In an embodiment the inhibitor is an shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, CAS No. 477202-00-9 and marketed as Yervoy®; Bristol-Myers Squibb; Tremelimumab (IgG2 monoclonal antibody available from Pfizer, formerly known as ticilimumab, CP-675,206).

PD1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD1, PD-L1 and PD-L2 have been shown to downregulate T cell activation upon binding to PD1 (Freeman et a. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1. Antibodies, antibody fragments, and other inhibitors of PD1, PD-L1 and PD-L2 are available in the art and may be used combination with a CD123 CAR described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pidilizumab (CT-011; Cure Tech) is a humanized IgG1k monoclonal antibody that binds to PD-1Pidilizumab and other humanized anti-PD1 monoclonal antibodies are disclosed in WO2009/101611. Lambrolizumab (also referred to as MK03475; Merck) is a humanized IgG4 monoclonal antibody that binds to PD1. Lambrolizumab and other humanized anti-PD1 antibodies are disclosed in U.S. Pat. No. 8,354,509 and WO2009/114335. MDPL3280A (Genentech/Roche) is a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906. Other anti-PD-L1 binding agents include YW243.55.570 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD1 and B7-H1. Other anti-PD1 antibodies include AMP 514 (Amplimmune), among others, e.g., anti-PD1 antibodies disclosed in U.S. Pat. No. 8,609,089, US 2010028330, and/or US 20120114649. The agent which enhances the activity of a CAR-expressing cell can be, e.g., a fusion protein comprising a first domain and a second domain, wherein the first domain is an inhibitory molecule, or fragment thereof, and the second domain is a polypeptide that is associated with a positive signal, e.g., the polypeptide that is associated with a positive signal is CD28, ICOS, and fragments thereof, e.g., an intracellular signaling domain of CD28 and/or ICOS. In one embodiment, the fusion protein is expressed by the same cell that expressed the CAR. In another embodiment, the fusion protein is expressed by a cell, e.g., a T cell that does not express an anti-CD123CD123 CAR.

Pharmaceutical Compositions and Treatments

Pharmaceutical compositions of the present invention may comprise a CAR-expressing cell, e.g., a plurality of CAR-expressing cells, as described herein, in combination with one or more pharmaceutically or physiologically acceptable carriers, diluents or excipients. Such compositions may comprise a buffer such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain aspects, T cells can be activated from blood draws of from 10 cc to 400 cc. In certain aspects, T cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection. In another aspect, the T cell compositions of the present invention are administered by i.v. injection. The compositions of T cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T cells. These T cell isolates may be expanded by methods known in the art and treated such that one or more CAR constructs of the invention may be introduced, thereby creating a CAR T cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded CAR T cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Anti-CD123 Chimeric Antigen Receptor Engineered T Cells for AML

Most patients with acute myeloid leukemia (AML) are incurable with standard therapy. Without wishing to be bound by any particular theory, it is believed that successful CART cell therapy relies on a suitable cell-surface molecule. To date however, no AML-specific surface antigen has been found as many antigens are shared between immature myeloid cells and AML blasts.

CD123, the transmembrane alpha chain of the IL-3 receptor, is expressed on the majority of primary AML specimens (Jordan, 2010, Science Translational Medicine, 2:31ps21; Jin et al, 2009, Cell Stem Cell, 5:31-42; Munoz et al, 2001, Haematologica, 86:1261-1269), and high CD123 expression is associated with a poor prognosis (Testa et al, 2002, Blood, 100:2980-8). Furthermore, AML stem cells can be eliminated in immunodeficient mice by treatment with anti-CD123 antibody (Yalcintepe et al, 2006, Blood, 108:3530-7; Jin et al, 2009, Cell Stem Cell, 5:31-42). These observations implicate CD123 as a possible target for CAR T cell therapy. However, CD123 is also expressed on myeloid progenitors, plasmacytoid dendritic cells, mast cells, basophils, megakaryocytes and some B cells.

It is demonstrated herein that human CD123-redirected T cells (CART123) eradicate both primary AML and normal bone marrow in humanized immune system mice. Without wishing to be bound by a particular theory, as human AML is likely preceded by clonal evolution in normal or "pre-leukemic" hematopoietic stem cells (Weissman, 2005, JAMA, 294:1359-66; Miyamoto et al., 2000, PNAS, 97:7521-6; Hong et al, 2008, Science, 319:336-9; Nilsson et al, 2002, Blood, 100:259-67; Welch et al, 2012, Cell, 150: 264-78; Walter et al, 2012, N Engl J Med, 366:1090-8), the data presented herein support CART123 as a viable strategy for the treatment of AML and as a novel cellular conditioning regimen prior to bone marrow transplantation.

Materials and Methods

T Cell Transduction

Normal donor T cells were positively selected from leukapheresis packs, expanded in vitro with anti-CD3/CD28 beads (Invitrogen) and IL-2 (Chiron) and transduced with lentiviral supernatant from 293T cells transfected with pELNS anti-CD123-41BB-CD3zeta plasmid DNA.

Cells

MOLM14 cell lines were obtained from the ATCC and maintained in RPMI media supplemented with 10% fetal calf serum, penicillin and streptomycin (R10). To produce a bioluminescent model, MOLM14 cells were transduced with a luc2-gfp-luciferase lentiviral construct and sorted twice to high purity.

Primary AML cells were obtained from the Stem Cell and Xenograft Core facility at the University of Pennsylvania, or directly from patient blood under an IRB-approved protocol. Cells were frozen in 90% fetal calf serum and 10% DMSO until required for use. For all functional studies, AML cells were thawed at least 12 hours before analysis and rested overnight at $1\times10^6$/ml in R10. For all xenograft studies, primary cells were thawed, washed once in PBS, and injected directly into mice.

Flow Cytometry

Anti-human antibodies were purchased from Biolegend, Ebioscience, or Becton Dickinson. Cells were isolated from in vitro culture or from animals, washed once in PBS supplemented with 2% fetal calf serum, and stained on ice after blockade of Fc receptors. For quantitation, Invitrogen Countbright beads were used according to the manufacturer's instructions. In all analyses, the population of interest was gated based on forward vs side scatter characteristics, followed by singlet gating, and live cells were gated using Live Dead Aqua (Invitrogen). CD107a degranulation assays and intracellular cytokine production assays were performed as previously described (Betts and Koup, 2004, Methods Cell Bio, 75:497-512) Flow cytometry was performed on a four laser Fortessa (Becton-Dickinson).

Proliferation

T cells were washed and resuspended at up to $1\times10^7$/ml in 100 µl of PBS, and were stained with 100 µl of CFSE 2.5 uM (Life Sciences) for a final concentration of 1.250 µM for 5 minutes at 37 degrees. The reaction was quenched with cold R10 and the cells washed thrice. T cells were incubated at a 1:1 ratio with target cells.

Killing Assay

Killing assays were performed as previously described (Cao et al, 2010, Cytometry A, 77:534-45) In brief, CFSE-labelled targets were incubated at the indicated ratios with effector T cells for 16 hours. Cells were then harvested, Countbright beads and 7-AAD added, and analysed on an Accuri C6 (Becton-Dickinson).

Cytokine Secretion

Effector and target cells were incubated at a 1:1 ratio in X-Vivo media with 10% human serum for 24 hours. Supernatant was analysed by 30-plex array according the manufacturer's instructions (Invitrogen).

RT-PCR

After cell sorting of primary cells, RNA was extracted (Qiagen), followed by reverse transcription and RTqPCR using primers for IL3RA (Life Sciences).

Mice

NOD-SCID-γ-chain$^{-/-}$ (NSG) mice or NSG-S (NSG mice transgenic for human IL-3, SCF and GM-CSF) were originally obtained from Jackson Labs.

In Vivo Models

Details of particular in vivo experiments are described elsewhere herein. The MOLM14 AML cell line was injected in 200 µl of PBS at a concentration of $5\times10^6$/ml into the tail vein, followed by bioluminescent imaging on a Xenogen Spectra camera as previously described. Primary AML blasts were injected in 200 µl of PBS at a concentration of $25\text{-}50\times10^6$/ml. T cells were injected in 200 µl of PBS at a concentration of $5\times10^6$/ml into the tail vein. Mice were sacrificed according to protocol when moribund or upon the development of early hind limb paralysis.

Humanized immune system (HIS) mice were created by injection of fetal liver CD34$^+$ cells into newborn NSG mice. Engraftment of human hematopoiesis was confirmed at 5-6 weeks after injection and prior to release of the mice for downstream experiments.

Methylcellulose Colonies

Sorted CD34$^+$ adult human bone marrow or cord blood was re-suspended in Methocult Optimum (Stemcell Technologies) according to the manufacturer's instructions and plated in 6-well plates for 14 days. In some experiments, CD34$^+$ cells were first cultured for four hours with CART123 or control T cells. After 14 days, colonies were read on an inverted microscope (Zeiss, 4×), followed by solubilisation of the colonies in R10 media overnight and harvest of single cell suspensions for flow cytometry.

Results

Human AML Expresses CD123 and can be Targeted with Anti-CD123 Redirected T Cells (CART123)

The initial step in the design of a therapeutic chimeric-antigen receptor T cell (CAR T) was the selection of an appropriate target that is commonly and homogeneously expressed on the cell surface. The expression of the immature myeloid markers CD33 (FIG. 1A, circles), CD123 (FIG. 1A, triangles) and CD34 (FIG. 1A, squares) were compared in a panel of primary AML specimens. Consistent with previous reports, it was found CD123 to be expressed in the majority of AML at high levels and more frequently than CD33 or CD34 (Jordan, 2010, Sci Transl Med, 31:31ps21; Munoz et al, 2001, Haematologica, 86:1261-1269; Testa et al., 2002, Blood, 100:2980-8) (FIG. 1A). The minority of AML samples appeared to be CD123 negative by strictly drawn gates but demonstrated a higher median fluorescence intensity of CD123 than residual normal lymphocytes suggesting the presence of low-level CD123 expression that is poorly detectable by antibodies; this was confirmed by RTqPCR of sorted CD123dim and bright populations (FIG. 1B and FIG. 1C).

Figure 5:
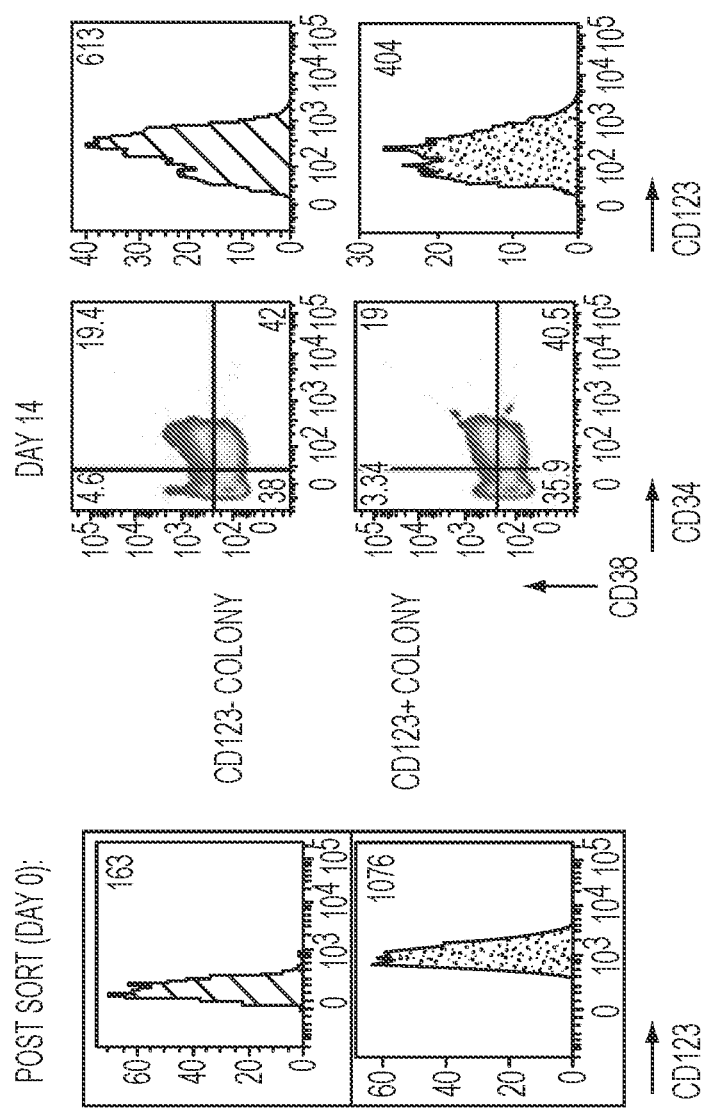
FIG. 5 depicts the results of experiments demonstrating that blasts can grow ex vivo regardless of baseline CD123 expression.
Figure 6:
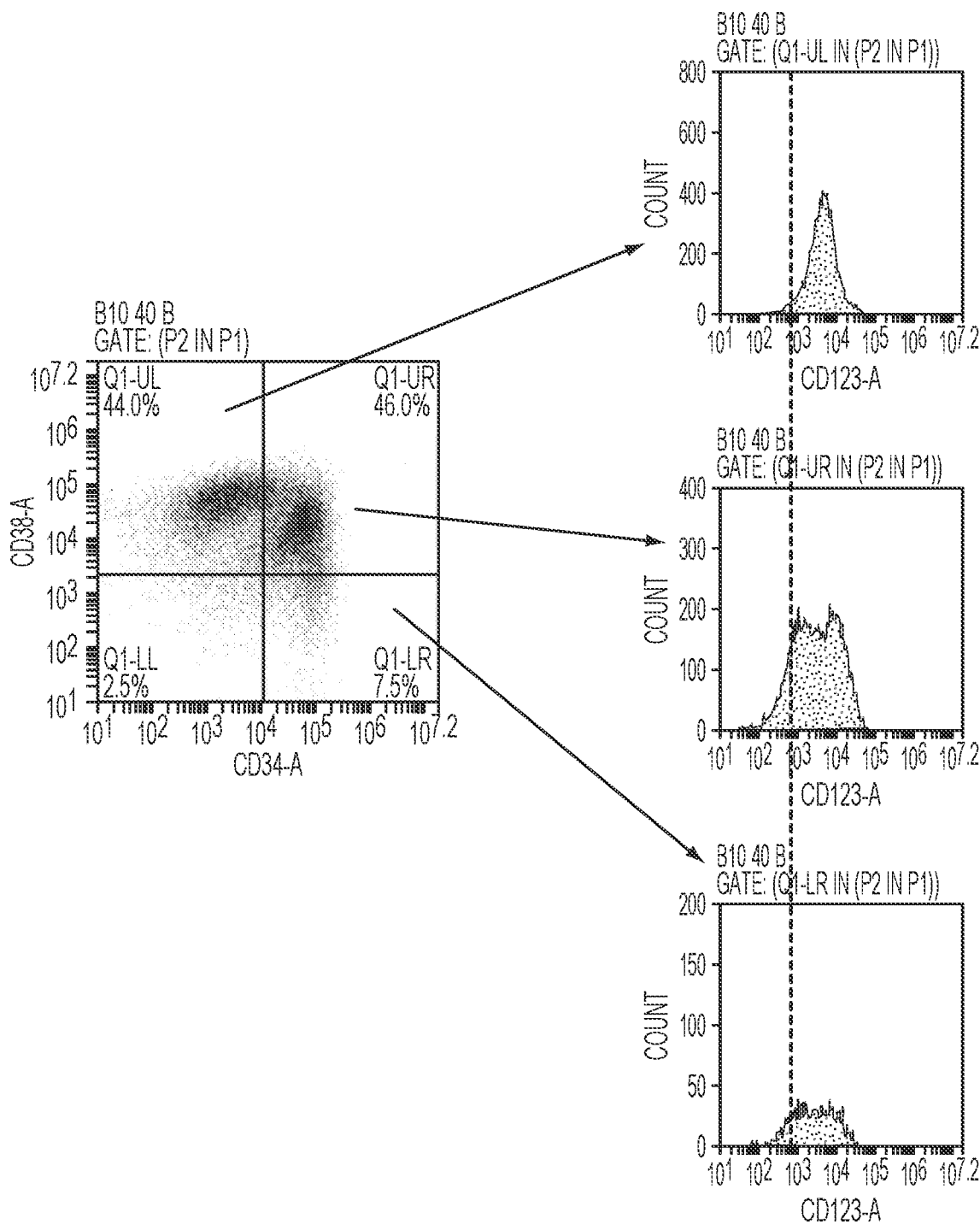
FIG. 6 depicts the results of experiments demonstrating that CD123 is expressed at equivalent levels regardless of leukemia stem cell, progenitor or bulk blast populations as defined CD34//CD38 of primary AML cells.

Furthermore, both CD123$^{dim}$ and CD123$^{bright}$ blasts could form colonies in semisolid media (FIG. 5). Briefly, primary AML blasts were sorted into CD123$^{dim}$ and CD123$^{bright}$ populations and plated in methylcellulose supplemented with human cytokines (Methocult Optimum, Stemcell Technologies). Fourteen days later, colonies derived from sorted cells were solubilized and stained for surface expression of CD45, CD34, CD38 and CD123. Results are shown in FIG. 5. Although there was no selective expression of CD123 on the putative leukemic stem cell population in contrast with prior publications, (FIG. 6), the uniform expression of CD123 on blasts suggested that most AML would be susceptible to CART123.

Figure 7A:
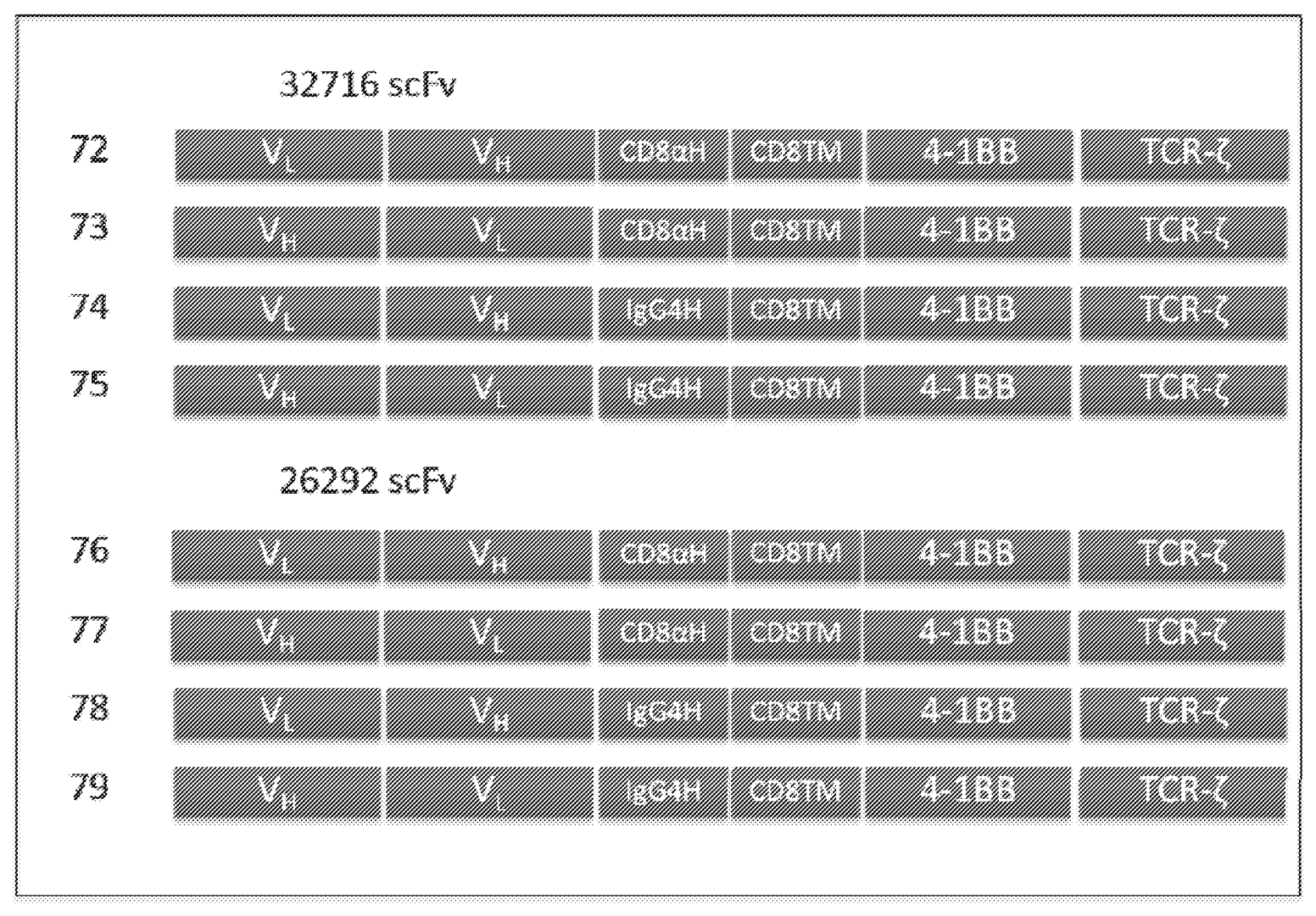
Figure 7B:
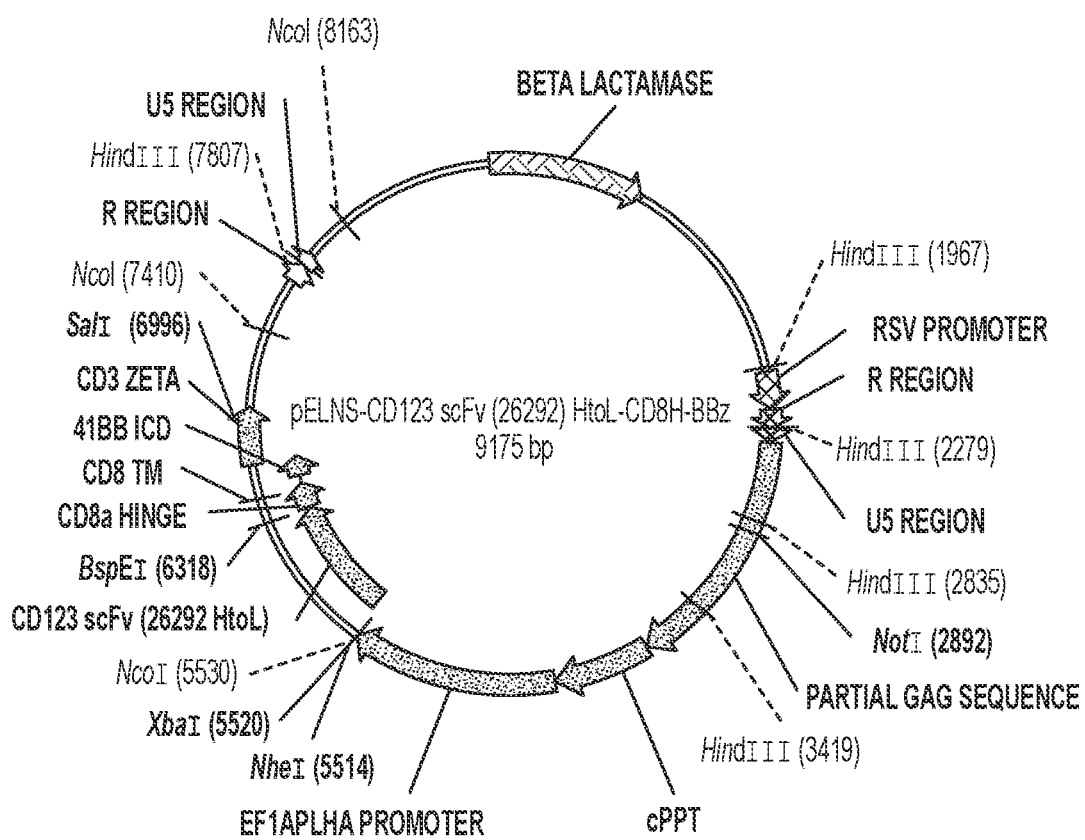
Figure 8:
FIG. 8 depicts the results of experiments demonstrating the selection of the optimal CD123 CAR construct.
Figure 8:
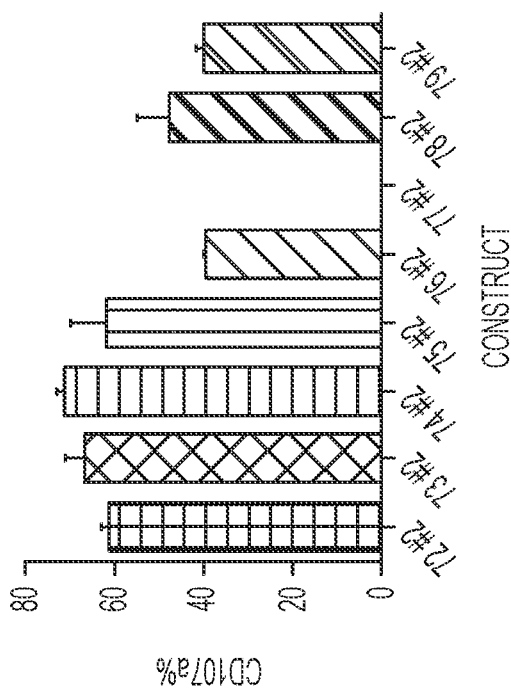

To evaluate the feasibility of targeting CD123 via a CAR technology, single chain variable fragments for an anti-CD123 antibody were cloned into a lentiviral CAR expression vector with the CD3zeta chain and the 4-1BB co-stimulatory molecule in four different configurations and the optimal construct was selected based on the quantity and quality of cytokine production of CD123 CAR transduced T cells (CART123 cells, also referred to as CD123 CART) in response to CD123+ targets. Two different anti-CD123 antibodies (32716 and 26292) are disclosed in SEQ ID NO:2 and SEQ ID NO:101, respectively. In particular, eight different CAR-123 constructs were developed based on the scFv sequence from these two different antibodies cloned into a lentiviral vector with the 4-1BB signalling molecule and the CD3zeta chain as shown in FIGS. 7A-7B. These eight CARs are referred to in FIGS. 7A-7B and throughout as clone 72 (or "1172), clone 73 (or "1173), clone 74 (or "1174"), clone 75 (or "1175"), clone 76 (or "1176"), clone 77 (or "1177"), and clone 78 (or "1178"). Nucleotide and amino acid sequences of the eight different CAR-123 constructs are provided below and in SEQ ID NOs: 107-122. After transduction into primary T cells, the optimal construct was selected based on its ability to target a CD123-expressing AML cell line, MOLM14 (FIG. 8). As shown in FIG. 8, in the left graph, primary human T cells were transduced with the different CD123 CAR constructs and exposed to MOLM14 (a human AML cell line that expresses CD123) in the presence of anti-CD107a. After 2 hours, cells were stained for CD3 and analyzed by flow cytometry for degranulation as a measure of target recognition and cytotoxic potential. In the right graph, primary human T cells transduced with the different CD123 CAR constructs were cultured with irradiated MOLM14 cells for 48 hours, followed by aspiration of the culture supernatant for multiplex cytokine analysis.

Figure 1H:
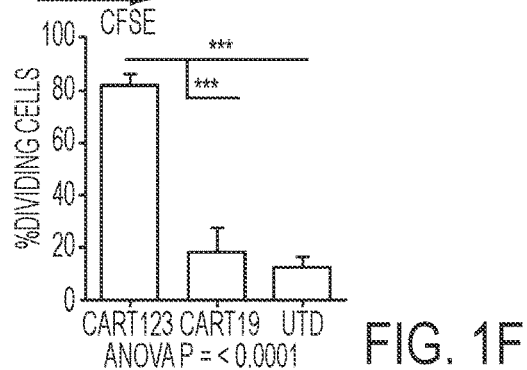

Robust effector functions required for the control of malignancy, including degranulation, cytokine production, proliferation and cytotoxicity were then demonstrated to occur in a CD123-specific fashion, establishing the potential of CART123 as therapeutic agents for AML (FIG. 1D-FIG. 1G). For example, using both degranulation and cytokine production assays, it was demonstrated that the engineered CART123 T cells specifically targeted CD123+ cells. Importantly, CART123 T cells responded much more robustly to primary AML than to normal marrow (FIG. 1D). Exposure of CART123 cells to media, a CD123− cell line, normal bone marrow (NBM), primary AML specimens, or a CD123+ cell line in the presence of anti-CD107a revealed specific degranulation of the CAR+ cells (compared to the CAR− cells, left), with more robust degranulation to AML than to NBM (right). Furthermore, CART123 cells produced a variety of effector and homeostatic cytokines and chemokines, underlining their ability to orchestrate a productive immune response (FIG. 1H).

CART123 Cells Eradicate AML In Vivo and Show a Robust Recall Response

Figure 2A:
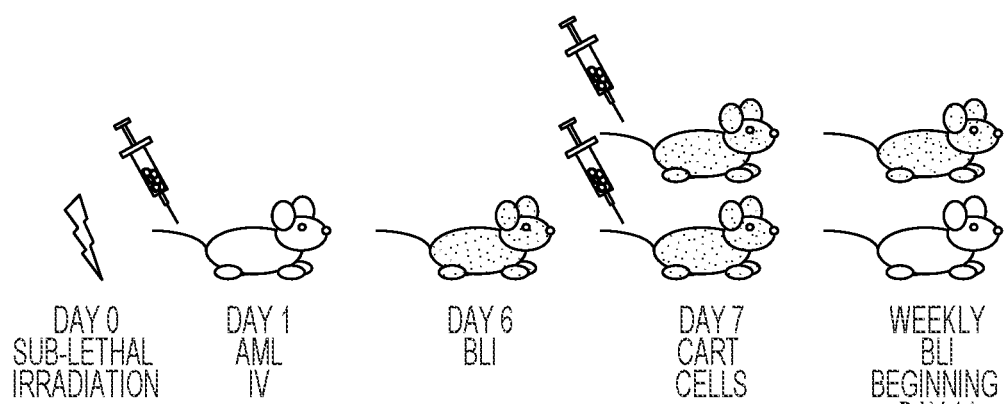
FIGS. 2A-2H depicts the results of experiments demonstrating the preclinical efficacy of CD123 CAR T cells in human AML xenograft models.
Figure 2B:
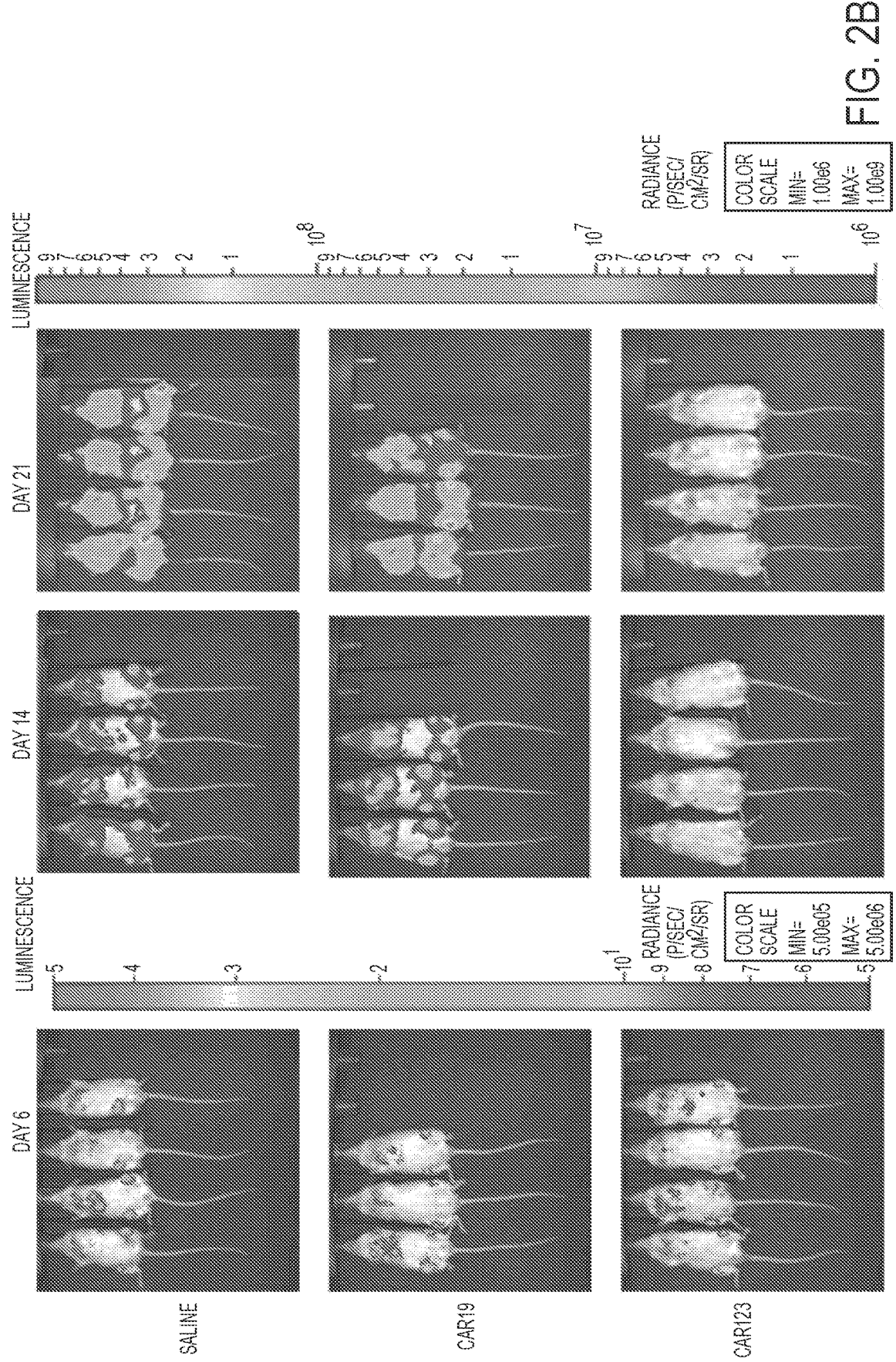
Figure 2C:
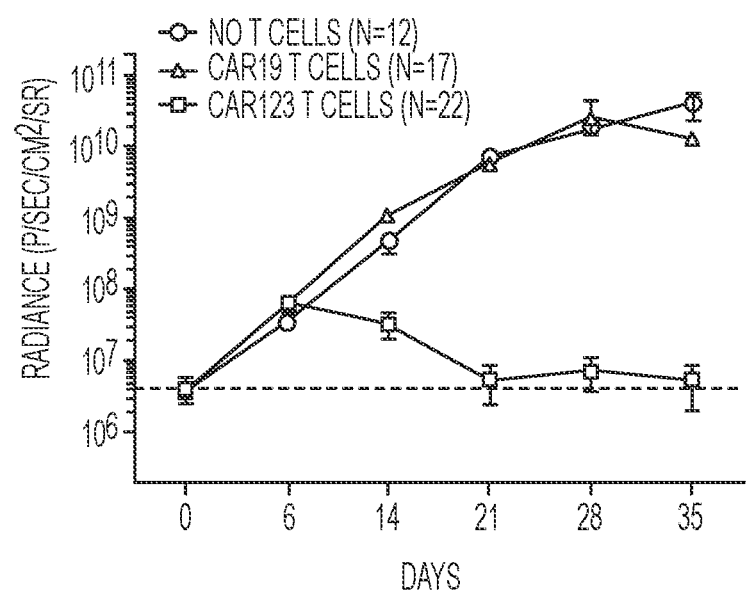
Figure 2D:
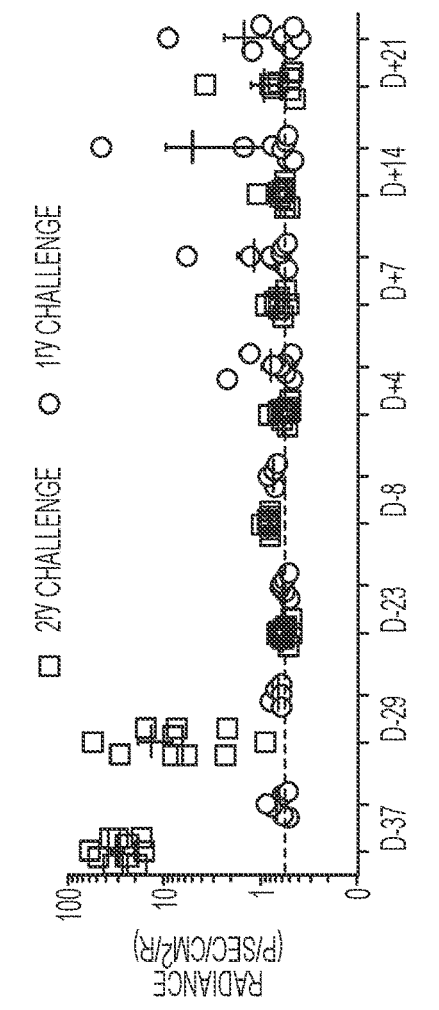

To test the ability of CART123 cells to eradicate AML in vivo, immunodeficient mice engrafted with the CD123+ AML cell line MOLM14 were treated with CART123, control (a T cell expressing an anti-CD19 CAR, termed a CART19) or no T cells. It was observed that CART123 treatment led to long-term survival in this animal model. Briefly, immunodeficient NOD/SCID γchain$^{-/-}$ (NSG) mice were engrafted with MOLM14, followed by one administration of CART123 cells or control CART19 cells (FIG. 2A). Immunodeficient mice were sub-lethally irradiated (200 cGy) on Day 0, then injected via tail vein with $1\times10^6$ GFP/luciferase+ MOLM14 on Day 1. Bioluminescent imaging (BLI) was performed on Day 6 to quantify engraftment and randomize treatment groups. Vehicle, CART19 cells ($1\times10^6$), or CART123 ($1\times10^6$) cells were injected IV on Day 7, and mice were followed with serial BLI. Quantification of BLI radiance was used as a surrogate measurement of AML burden. In comparison with control mice, tumor burden in mice receiving CART123 began to diminish within one week, and was eradicated within two weeks with only rare late relapses (FIG. 2B and FIG. 2C), leading to long-term survival in the majority of mice (FIG. 2D). Briefly, FIG. 2D shows the survival analysis of MOLM14-bearing xenograft mice, which demonstrates significant survival of CART123-treated mice (squares) in comparison to vehicle-treated mice (circles) and CART19-treated mice (triangles). Attrition of CART123 T cell-treated mice was primarily due to BLI-detectable AML progression in facial bones and subsequent anorexia and weight loss. Summary data are from four experiments. Use of luciferase-expressing MOLM14 cells allowed serial bioluminescent assessment of tumor burden, demonstrating the ability of CART123 cells to eradicate tumor with equivalent kinetics, regardless of tumor burden FIG. 2C is summary BLI data from three MOLM14 xenograft experiments, which demonstrate rapid leukemic progression in vehicle-treated (circles) and CART19-treated (triangles) mice, while AML eradication was observed in CART123-treated mice (squares). Mean radiance with standard error of the mean (whiskers) are depicted at each time point.

Figure 2E:
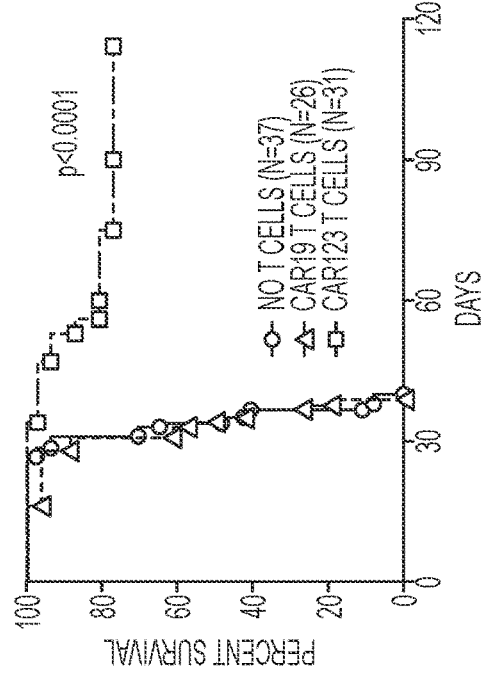

Despite successful initial treatment of leukemia, many patients experience relapse. In order to model this, the ability of mice "cured" of MOLM14 to reject a second infusion of the same leukemia was examined (FIG. 2E). Briefly, immunodeficient mice were sub-lethally irradiated (200 cGy) on Day −8, then injected via tail vein with PBS (top row) or $1\times10^6$ gfp/luciferase+ MOLM14 (bottom row) on Day −7. Bioluminescent imaging (BLI) was performed on Day −1 to quantify engraftment and randomize treatment groups. CART123 cells ($1\times10^6$) were injected IV on Day 0, and mice were followed with serial BLI until AML eradication (this occurred in all mice). Quantification of BLI radiance was used as a surrogate measurement of AML burden. Approximately two weeks after BLI-based assessment of AML eradication, all mice were challenged (top row) or re-challenged (bottom row) with $1\times10^6$ gfp/luciferase+ MOLM14. Mice were then followed with weekly bleeds for T cell numbers and BLI for AML burden.

Figure 2F:
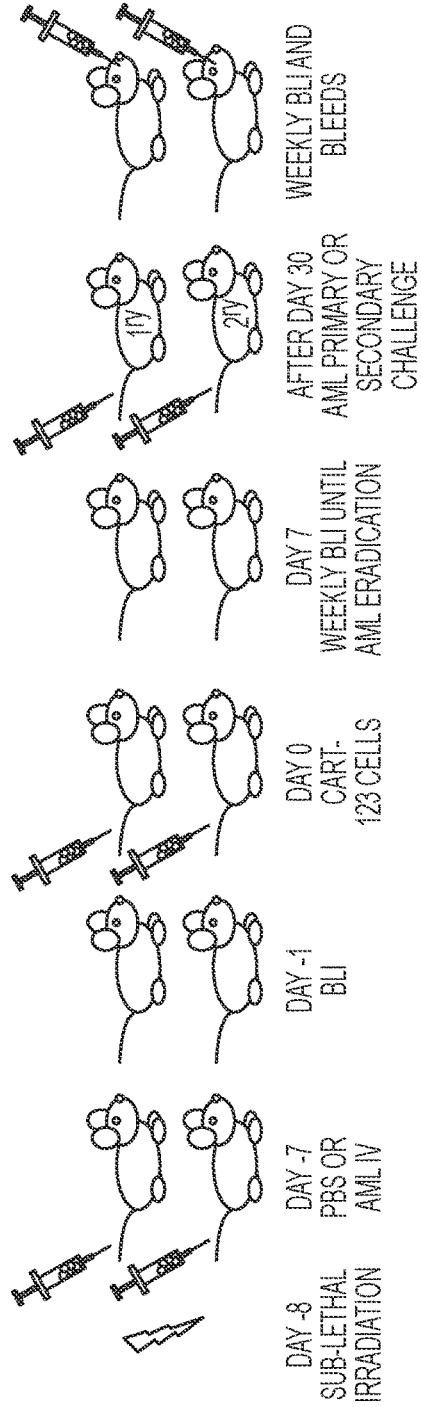
Figure 2G:
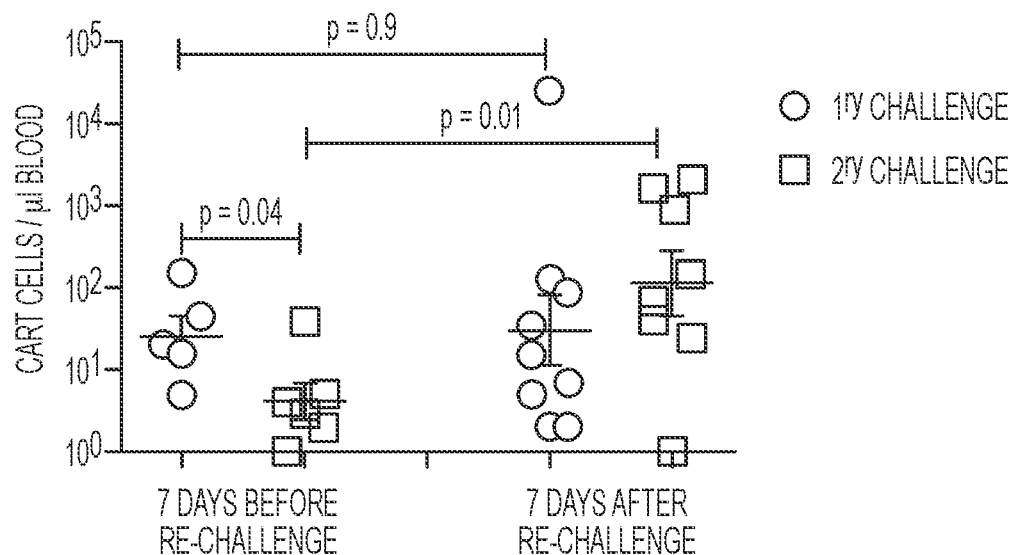
Figure 2H:
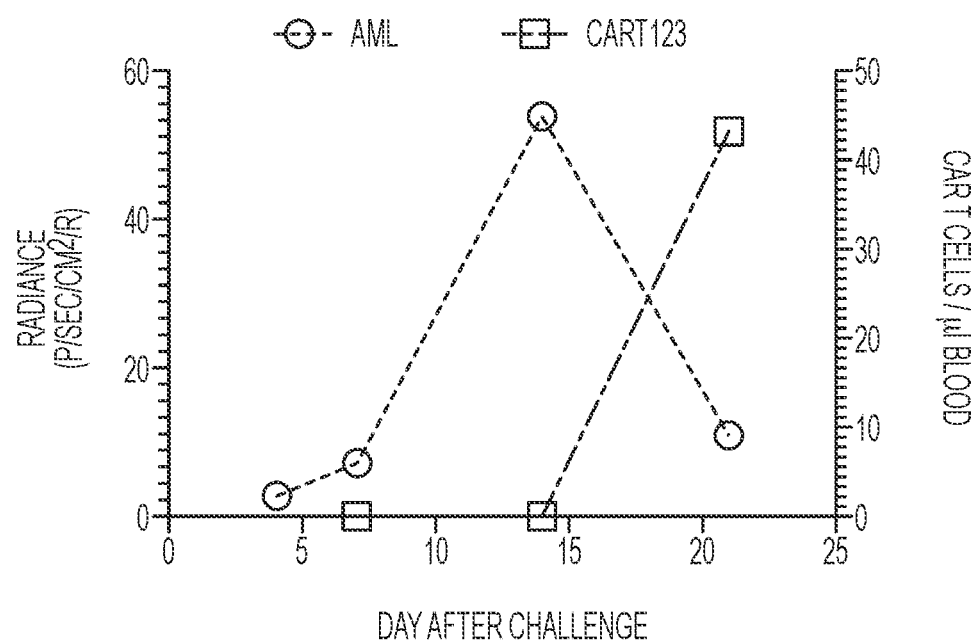
Figure 9:
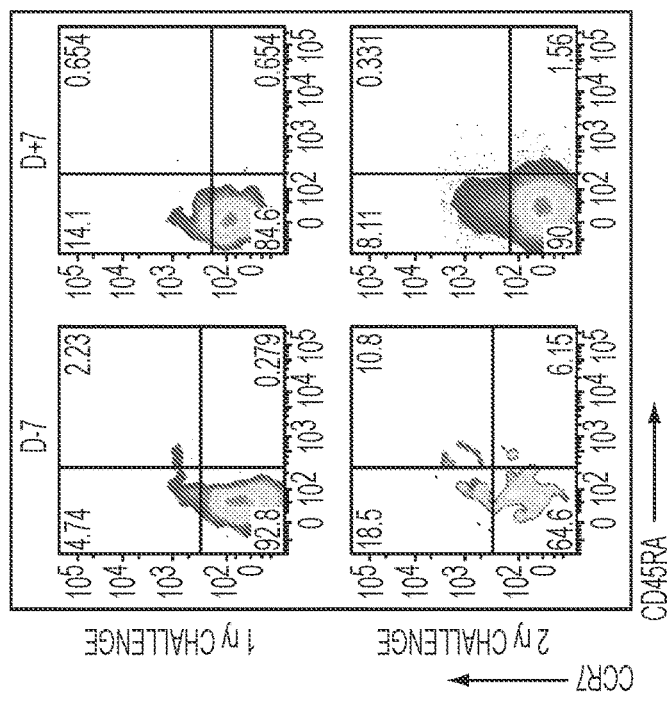
FIG. 9 depicts the results of experiments demonstrating the formation of memory cell populations in CART123 cells after exposure to human leukemia in xenografted mice. Mice previously challenged with AML (2$^{ry}$ challenge group) or not previously challenged (1$^{ry}$ challenge group) were injected with CART123 cells and bled serially for peripheral blood T cell numbers and phenotype.
Figure 9:
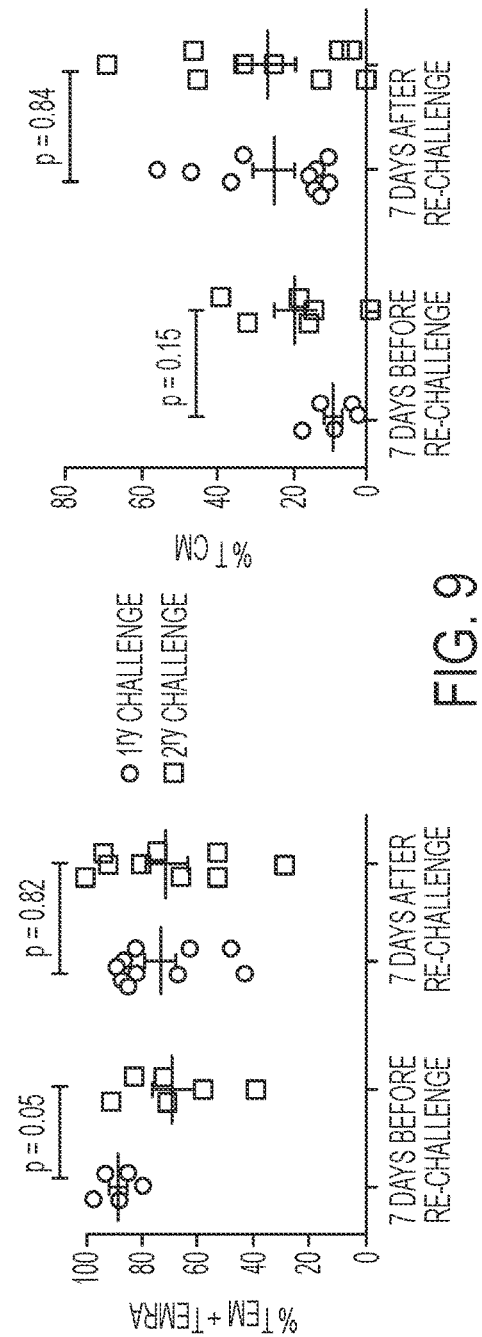

Animals that had previously cleared MOLM14 as well as those that had previously received CART123 cells with no MOLM14 were subsequently able to reject leukemia re-challenge with similar kinetics (FIG. 2F). Mice previously exposed to leukemia showed a trend to higher proportion of central memory T cells and lower proportion of effector memory T cells prior to leukemia re-challenge (FIG. 9). Despite lower baseline circulating CAR+ T cells in the previously leukemia-experienced group compared with the leukemia-naïve group, upon (re)-challenge a more precipitous increase in CAR+ T cells was observed in the former group that was consistent with a recall response (FIG. 2G). Briefly, mice were bled seven days before or after the injection of MOLM14 cells. CART123 cells were live singlet human CD45+ CD3+ CAR+ cells and quantified using counting beads. Importantly, in occasional animals with poor initial CART123 response there was transient tumor escape (FIG. 2F), that was then followed by a delayed increase in CART123 cells and subsequent AML elimination (FIG. 2H).

Primary Patient AML Blasts are Susceptible to CART123 Cells

Figure 3A:
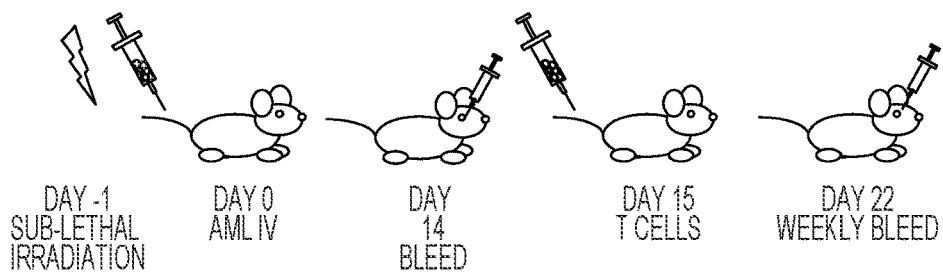
FIGS. 3A-3E depicts the results of the following experiments.

An important disadvantage of tumor cell line models is their inability to recapitulate the true biological heterogeneity of the primary malignancy. AML in particular is a clonally heterogeneous disease (Walter et al, 2012, N Engl J Med, 366:1090-8) and therefore potent CART cell-mediated targeting of a single antigen could lead to an antigen-loss relapse, as has already occurred in a patient with B-cell acute lymphoblastic leukemia treated with CART19 cells (Grupp and Kalos, 2013, N Engl J Med, 368:1509-18). To confirm the effectiveness of CART123 cells in the treatment of primary AML, a recently described model with prompt engraftment of AML was utilized (Wunderlich et al, 2010, Leukemia 1785-8). NOD-SCID-IL2Rγ$^{-/-}$ mice constitutively expressing human stem cell factor, GM-CSF and IL-3 were injected with patient specimens (FIG. 10) and engrafted at approximately 2 weeks. They were then treated with CART123 or control T cells, and followed for eradication of AML and survival (FIG. 3A). Briefly, NSGS mice were sublethally irradiated on D-1, and injected with 5-10× 10$^6$ primary AML blasts via the tail vein on D0. Engraftment was confirmed by the detection of live mouse CD45$^{neg}$ human CD45$^{dim/pos}$ CD123$^{pos}$ cells in the peripheral blood, usually occurring around D14. The following day, mice were injected with thawed CART123 cells or control T cells (CART19 or un-transduced T cells in some experiments). Mice were then bled weekly and analyzed for AML burden.

Figure 3B:
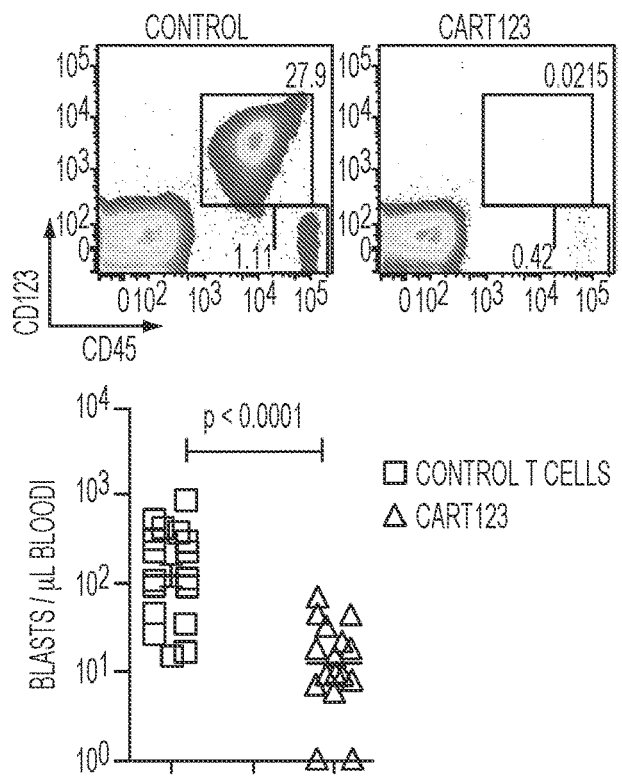
Figure 3C:
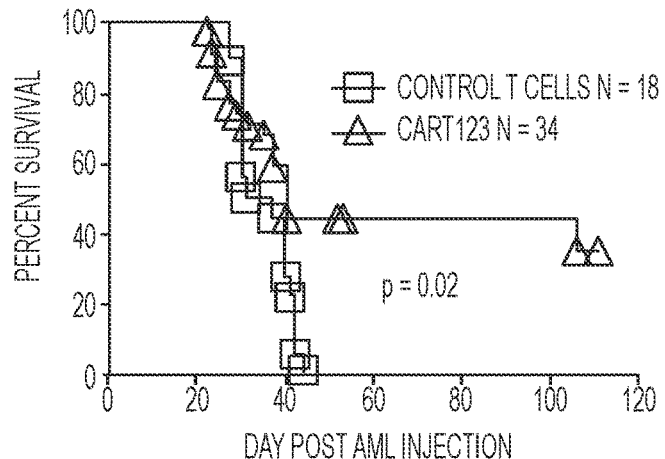
Figures 3D, 3E:
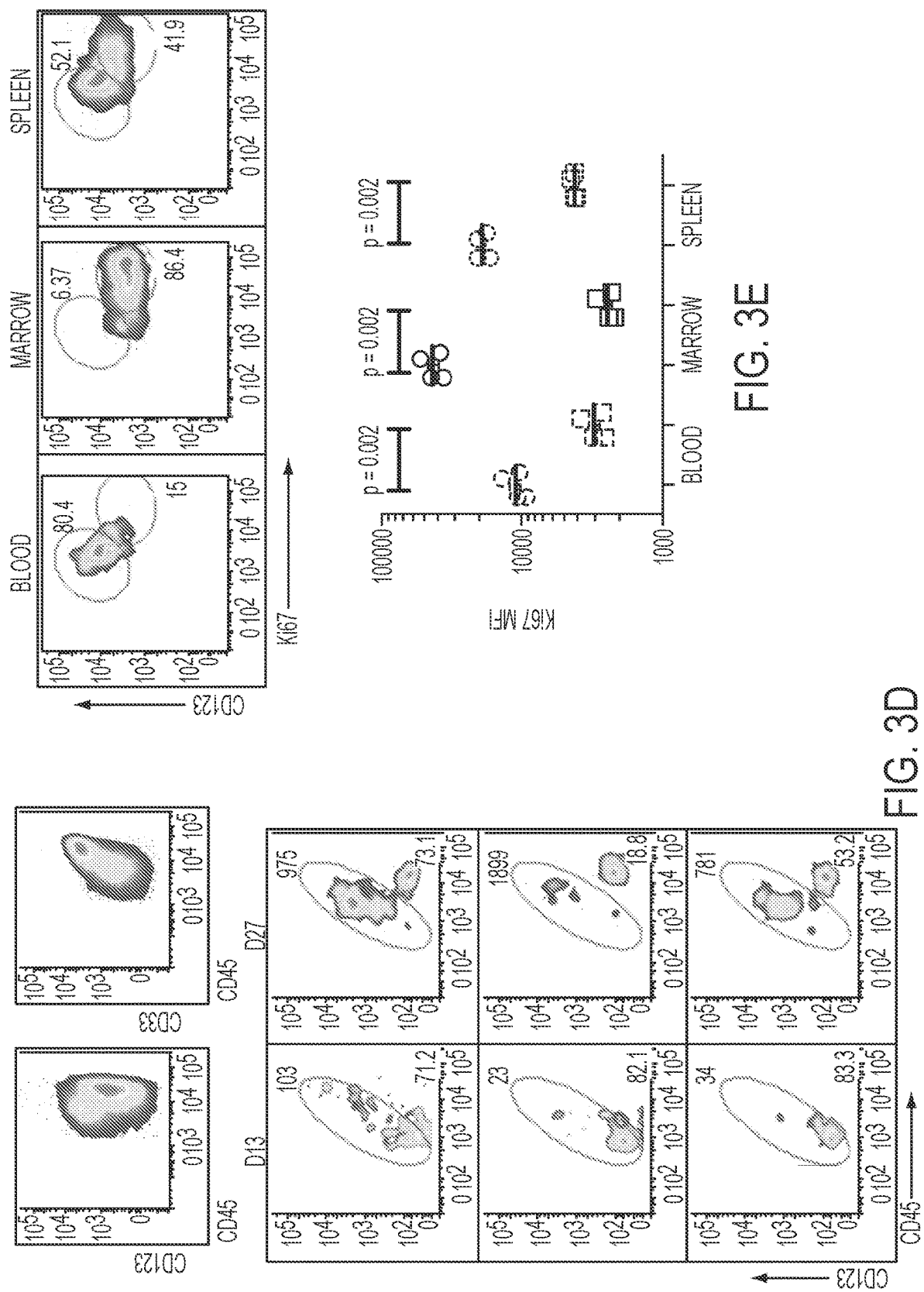

Circulating blasts were eradicated in CART123 recipients but not in controls (FIG. 3B), leading to a survival advantage in the treatment group despite a considerable early attrition rate (FIG. 3C). Note in FIG. 3B that residual CD45$^{bright}$ T cells were poorly detectable in some CART123 mice at this time point, correlating with the observation on the rapid rise and fall of PB T cells upon response to, and clearance of AML (as in FIGS. 2A-2H). Importantly, CART123 cells were effective even against CD123$^{dim}$ leukemia, likely related to up-regulation of CD123 on CD123$^{dim}$ blasts over time (FIG. 3D). Blast CD123 expression level inversely correlated with proliferative capacity as shown by Ki67 staining (FIG. 3E). Taken together with the demonstration that CD123$^{dim}$ blasts up-regulate CD123 in vitro and in vivo, without wishing to be bound by any particular theory, this may indicate that as CD123$^{bright}$ blasts are eliminated, they are replaced by CD123$^{dim}$ blasts which then become a target for CART123 cells.

CART123 Cells Induce Myeloablation

Figure 11:
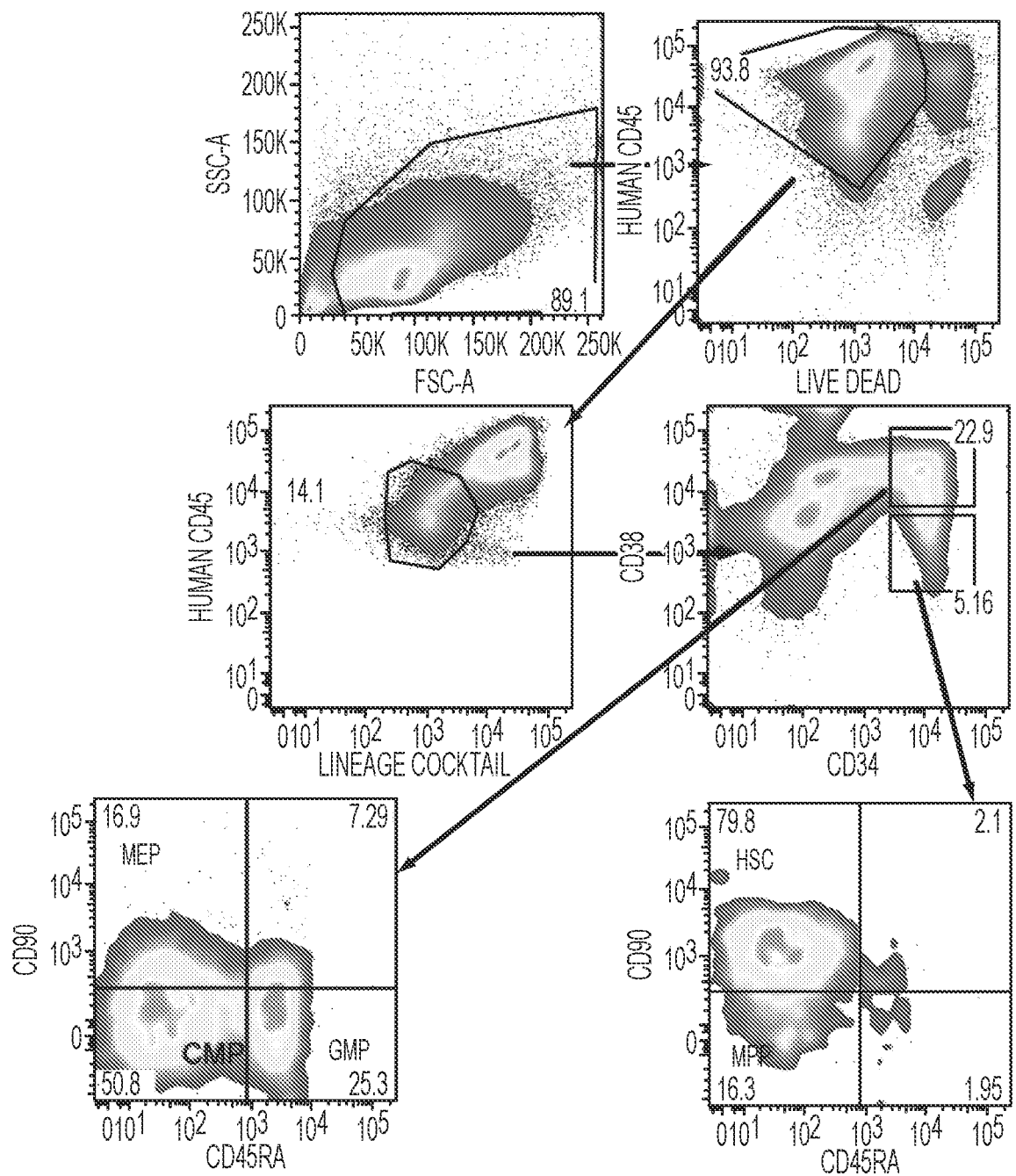
FIG. 11 depicts a gating strategy for normal bone marrow precursors.

Having established that CART123 cells can target and eradicate AML, it was sought to evaluate their effect on normal hematopoiesis. CD123 expression has been noted on some normal hematopoietic cells, including myeloid progenitors, dendritic cells, some B cells and megakaryocytes, and IL-3 signalling plays an important role in myeloid differentiation (Pang et al, 2011, PNAS, 108:20012-20017) First, it was confirmed that CD123 is expressed on the majority of lineage-negative hematopoietic progenitors (FIG. 4A and FIG. 11). Briefly, bone marrow from four normal donors was stained for CD123 after gating on live singlet lineage-negative CD45$^{dim}$ cells, and with the indicated progenitor subpopulations identified using CD34, CD38, CD45RA and CD90 (gating strategy is shown in FIG. 11). CD123 gating was based on normal lymphocytes and confirmed with fluorescence-minus-one (FMO) characteristics. Results are shown in FIG. 4A.

Then, CD123$^-$ and CD123$^+$ were sorted from normal BM precursors and it was found that both populations were capable of producing hematopoietic colonies and that these colonies had equivalent expression of CD123, demonstrating that CD123 expression is a dynamic rather than deterministic process (FIG. 4B). Briefly, CD123$^{dim}$ or CD123$^{moderate}$ CD34$^+$ cells were sorted from normal BM (top panel) and allowed to differentiate during a 14 day culture in methylcellulose. The sorted cultured populations exhibited similar CD123 expression and indistinguishable ability to form myeloid or erythroid colonies.

Furthermore, short-term exposure of cord blood CD34$^+$ cells to CART123 cells led to marked reduction in myeloid colony formation, demonstrating a potent effect of CART123 cells on myeloid progenitor function (FIG. 4C). Briefly, CD34$^+$ cells derived from cord blood were incubated at a 1:10 T:E ratio with CART123 or untransduced T cells for 4 hours, followed by a 14 day culture in methylcellulose medium supplemented with recombinant human cytokines. Hematopoietic function was assessed by manual colony counts or precisely quantified by flow cytometry for the indicated cell populations using Countbright beads.

Figure 4D:
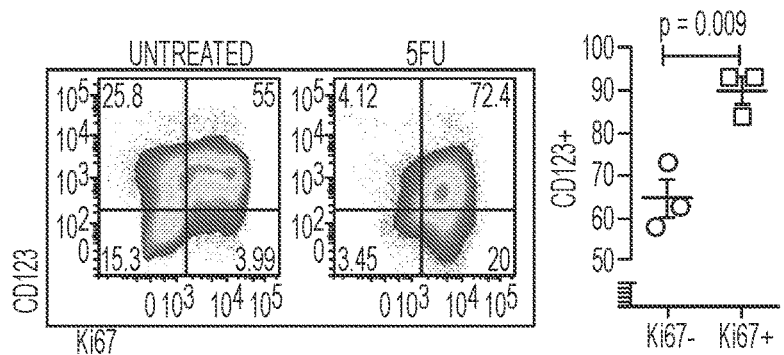

In any potential future clinical trials of CART123 cells for AML, patients would likely have received recent induction chemotherapy. To investigate the effect of post-chemotherapy marrow recovery on CD123 expression in marrow progenitor cells, human bone marrow engrafted mice were treated with 5-fluorouracil. It was found that post-chemotherapy, recovery is associated with an increase in cycling cells as anticipated, and that CD123 expression was higher in cycling cells (FIG. 4D). Briefly, mice previously engrafted with human CD34$^+$ cells were treated with 5-fluorouracil or vehicle. Fourteen days later, BM was harvested from these mice and analyzed for the intracellular proliferation marker Ki67 and CD123, gating on live lineage-negative human cells.

Figure 4E:
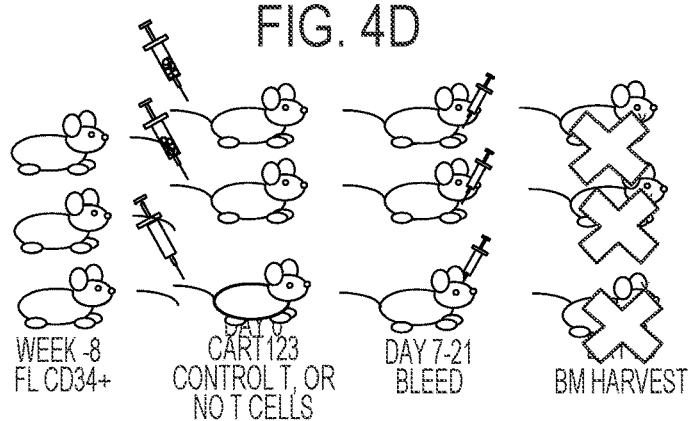
Figure 4F:
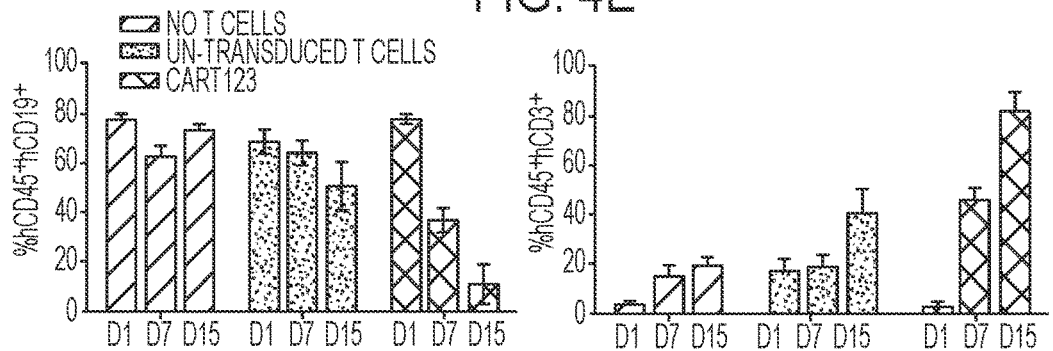
Figure 4G:
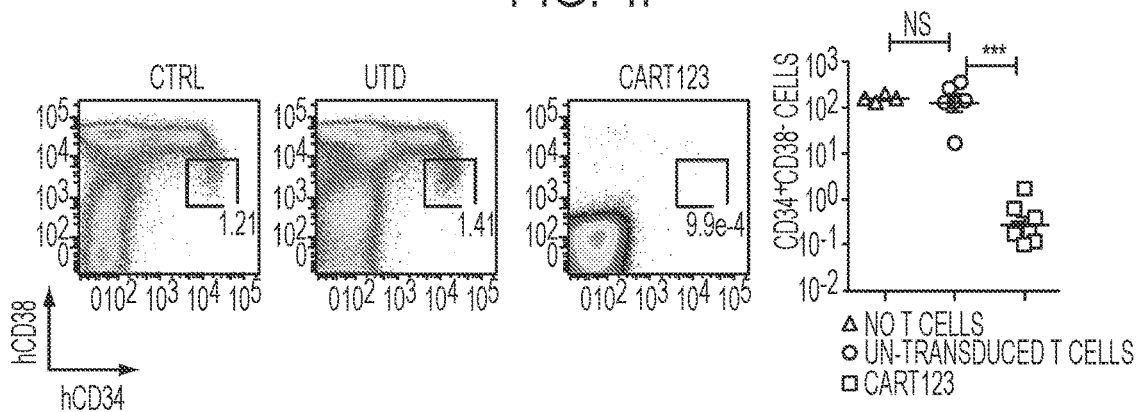
Figure 10:
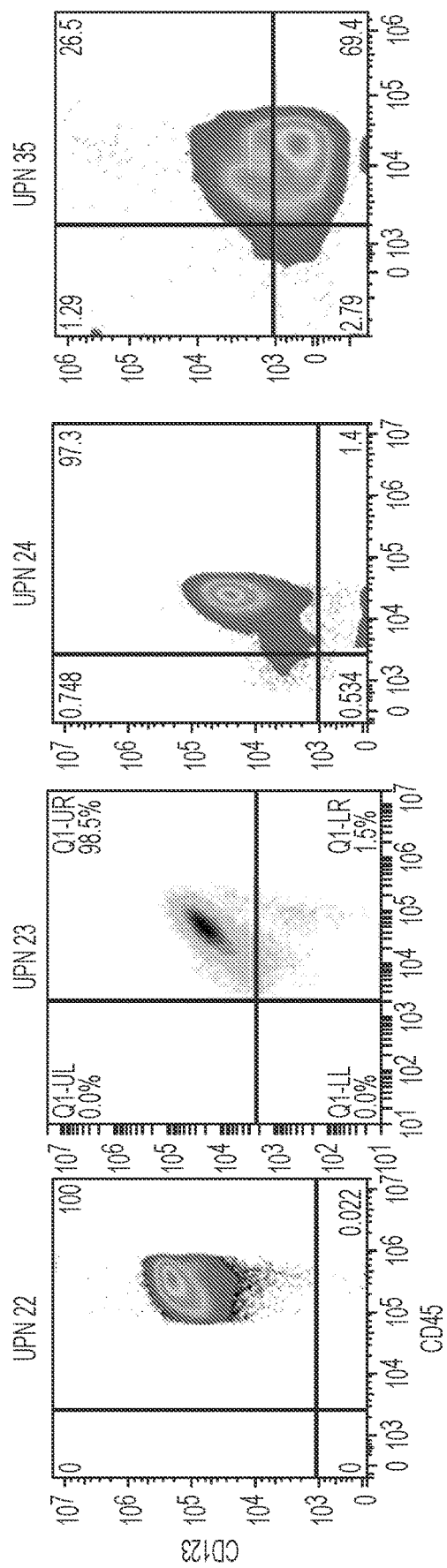
FIG. 10 depicts the results of experiments where four primary AML specimens were injected in different experiments into immunodeficient NSGS mice. Variable levels of CD123 are seen.
Figure 12:
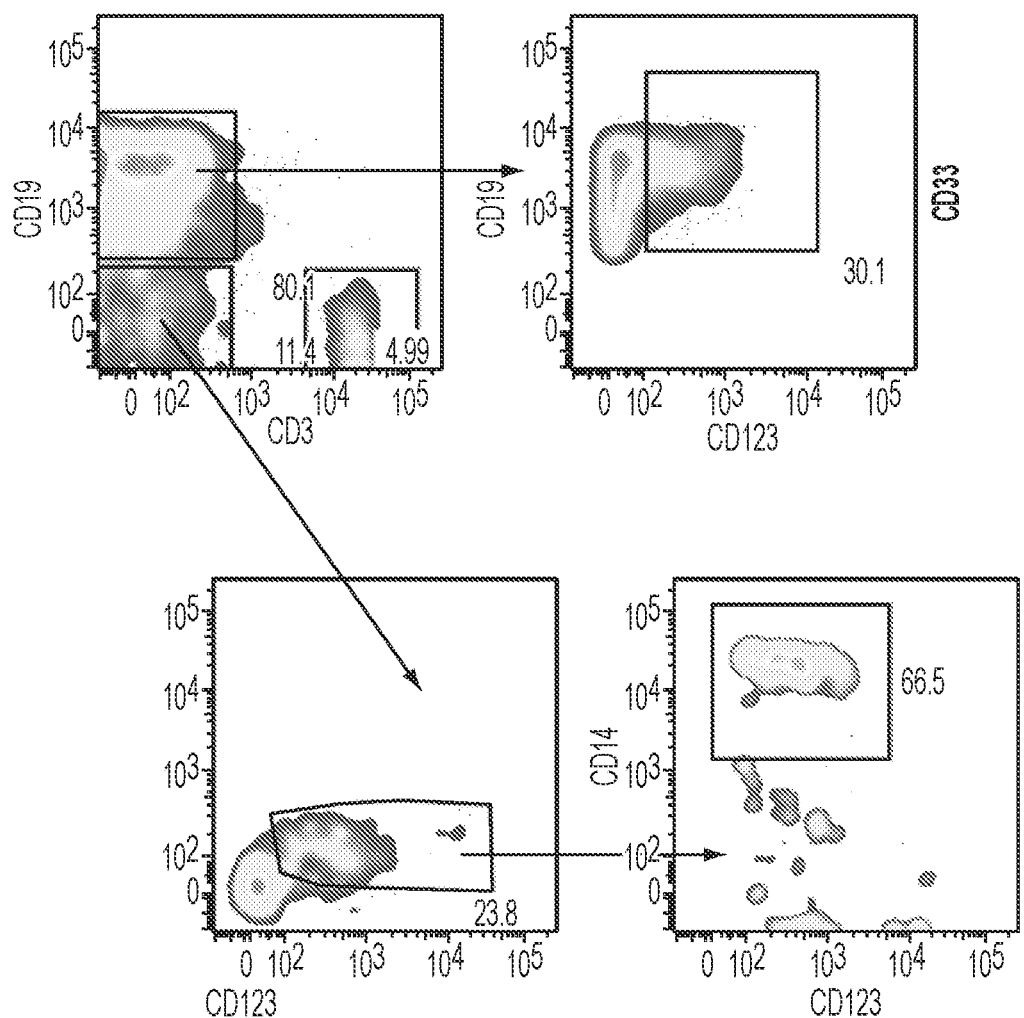
FIG. 12 depicts the results of experiments demonstrating that CD123 is expressed on normal circulating B cells and myelomonocytic cells.
Figure 13:
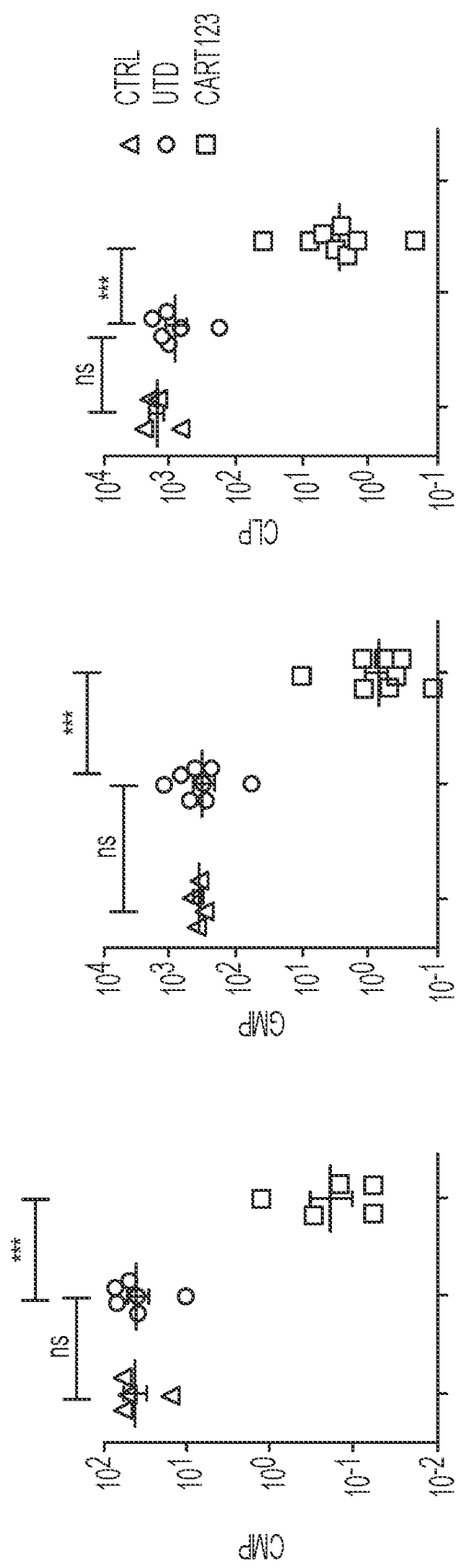
FIG. 13 depicts the results of experiments demonstrating the virtual absence of flow cytometry-defined Common Myeloid Progenitors, Granulocyte-Monocyte Precursors, or Common Lymphoid Progenitors in the marrow 28 days after infusion of CART123 cells into "humanized immune system" mice.

Finally, mice previously engrafted with human CD34$^+$ cells were treated with CART123 cells or control un-transduced T cells (FIG. 4E). Briefly, NSG mice were engrafted with human fetal liver CD34+ cells and bled for confirmation of engraftment after 6-8 weeks. On Day 0, mice received CART123, control un-transduced T cells, or vehicle. Weekly peripheral blood analysis for cell number was followed by harvesting of BM on Day 28 for analysis of residual human hematopoiesis. As anticipated from the baseline level of expression of CD123 on normal circulating B cells and myeloid cells (FIG. 12) a progressive decline in these cells in peripheral blood was observed (FIG. 10). After one month of in vivo exposure, mice receiving CART123 cells had virtually absent human hematopoeisis (FIG. 4G and FIG. 13), demonstrating the potent myeloablative potential of CART123 cells. Briefly, on Day 28 after T cell injection, BM was harvested and analyzed for human progenitor cell populations, gating on live singlet human CD45$^{dim}$ lineage$^-$ cells. Results are shown in FIG. 4G. In another experiment, NSG mice were engrafted with human fetal liver CD34$^+$ cells and treated with CART123, untransduced T cells (UTD) or vehicle (CTRL) after 8 weeks. Four weeks later, bone marrow was harvested and stained for human CD45, human lineage cocktail, CD34, CD38, CD45RA, CD90 and CD123. Absolute cell count was derived using Countbright beads. Results are shown in FIG. 13.

CART 123 Eradicates AML and Bone Marrow

It has been shown herein that CART123 provides a potent means to eradicate AML along with residual normal bone marrow. This approach has human therapeutic applications due to its ability to eradicate malignant cells as well as the pre-malignant marrow precursors that likely exist in AML and in myelodysplastic syndrome (MDS). Furthermore, this approach provides a novel, non-chemotherapy based cellular conditioning regimen prior to bone marrow transplantation. These observations underscore a novel application of CAR-based cellular therapy, with CD123 being a particularly attractive target due to the importance of IL-3 signalling in the developing marrow (Pang et al, 2011, PNAS, 108:

20012-20017) In certain embodiments, this modality provides transient, rather than permanent anti-CD123 pressure, via the use of suicide switches or with "biodegradable" mRNA CAR technology, e.g., as disclosed herein, which has been shown to be practical and effective. In certain embodiments, CART123 may be used for targeting CD123 to treat patients with high-risk AML.

Example 2

Anti-CD123 Chimeric Antigen Receptor Engineered T Cells for B-ALL

Figure 14:
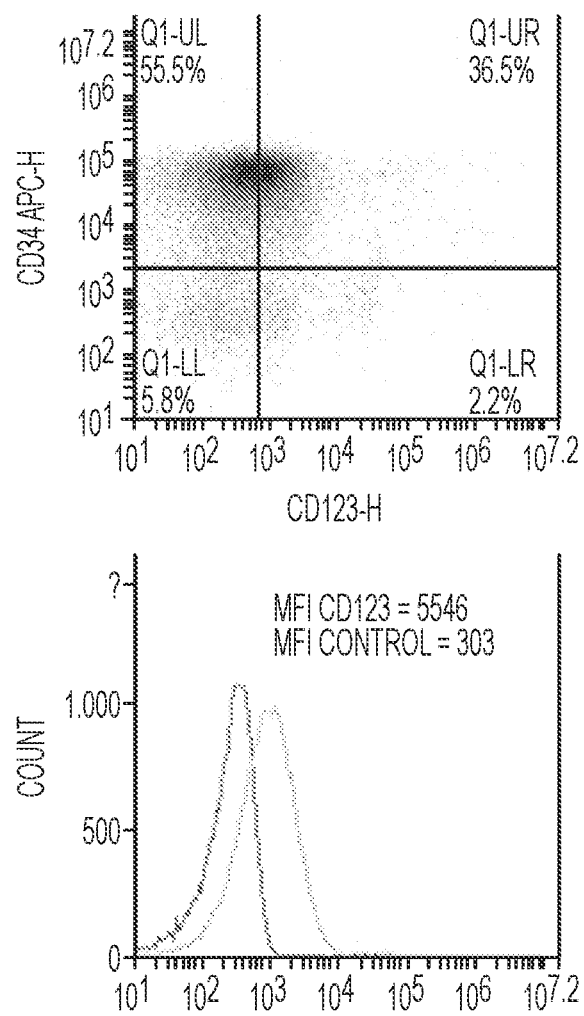
FIG. 14 is an image demonstrating expression of CD123 on the surface of a primary ALL bone marrow sample, which is also positive for the CD34+ marker. Top panel shows a dot plot, bottom panel shows a histogram of expression by the CD34+ cells vs. the CD34-negative population in the same sample.
Figure 15:
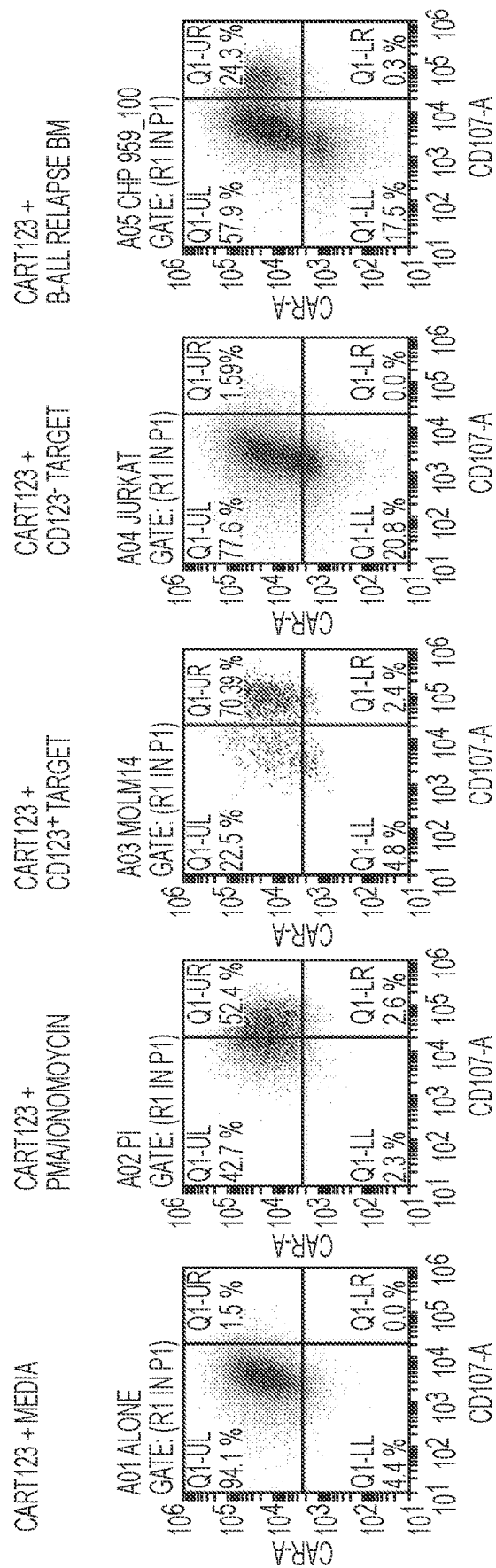
FIG. 15 is an image demonstrating that CART123 cells selectively recognize and are triggered by CD123-positive B-ALL blasts.
Figure 16:
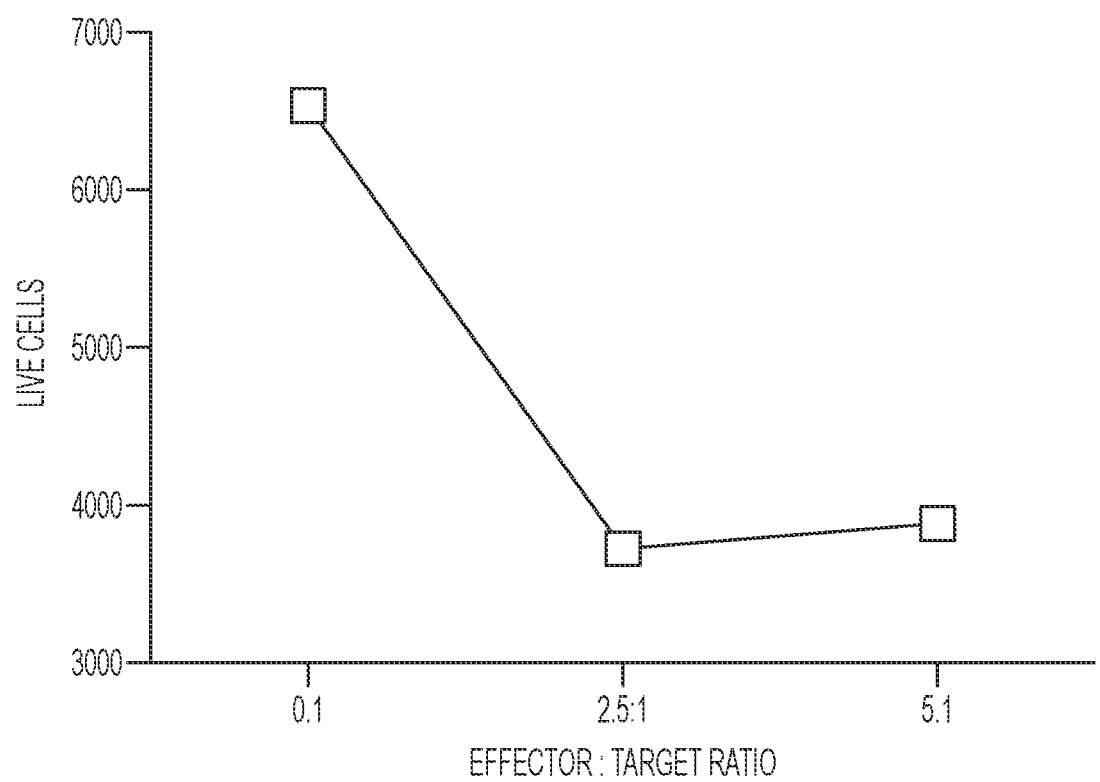
FIG. 16 is an image demonstrating that CART123 cells kill B-ALL blasts.

Experiments were designed to evaluate the ability of CART123 to target B-cell Acute Lymphoblastic Leukemia (B-ALL) cells. It was observed that CART123 cells degranulate in response to or kill B-ALL blasts (FIGS. 15 and 16). CART123 cells selectively recognize B-ALL blasts (FIG. 15). CART123 cells were cultured alone, with PMA/ionomycin as positive control, with known $CD123^+$ tumor cells line, $CD123^-$ cell line, or with the patient's B-ALL blasts and the results are presented in FIG. 14. CART123 selectively responded to B-ALL using the CD107a degranulation assay. In addition., primary B-ALL blasts (targets) were incubated with CART123 cells (effectors) overnight, and the number of remaining live blast cells was evaluated the next day using a FACS-based cytotoxicity assay [REF: PMID: 20229499]. As shown in FIG. 16, increasing the ratio of effectors to targets led to increased killing of the blasts.

Figure 17:
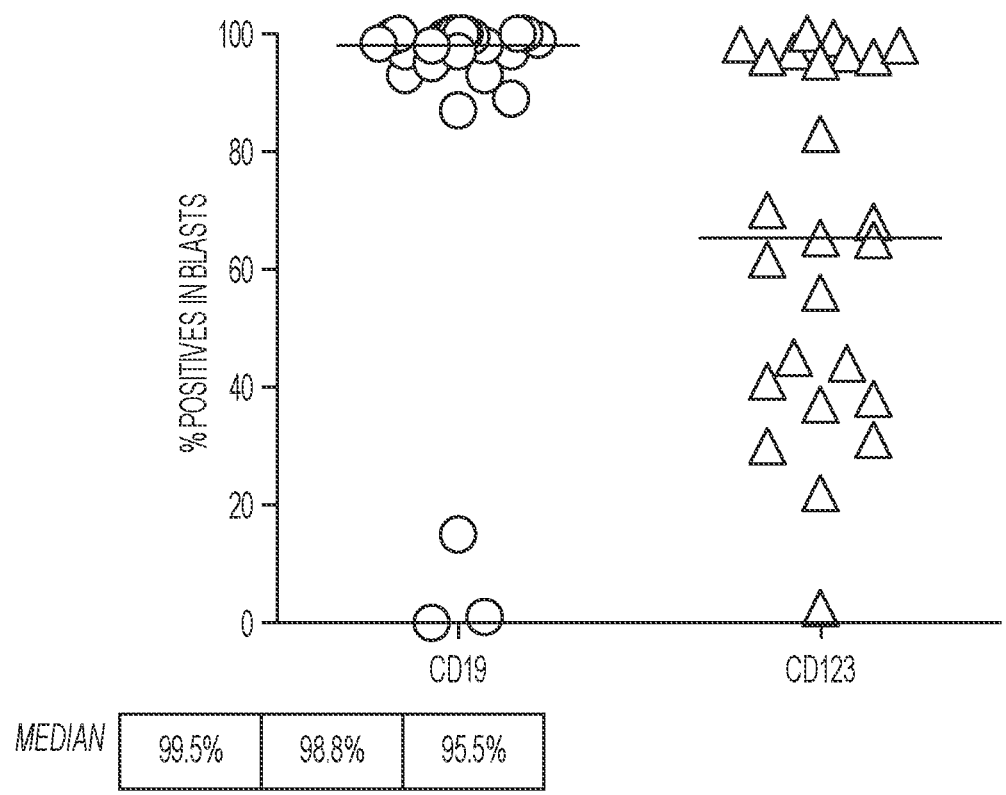
FIG. 17 is a graph showing expression of CD19, CD22, and CD123 in adult and pediatric ALL specimens.
Figure 18:
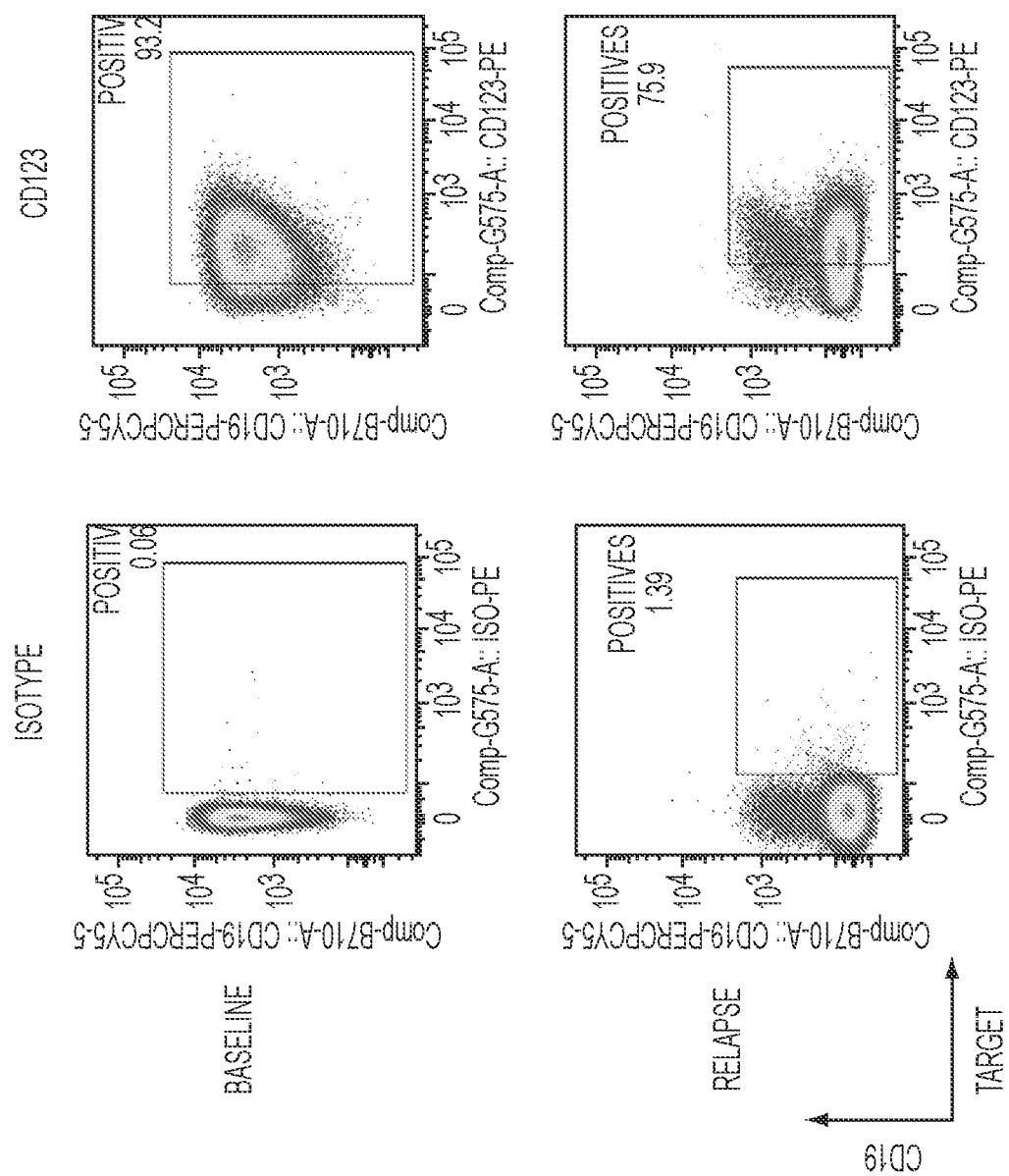
FIG. 18 is a graph showing expression of CD123 in a patient relapsing with CD19-ALL after CART19 therapy.
Figure 19:
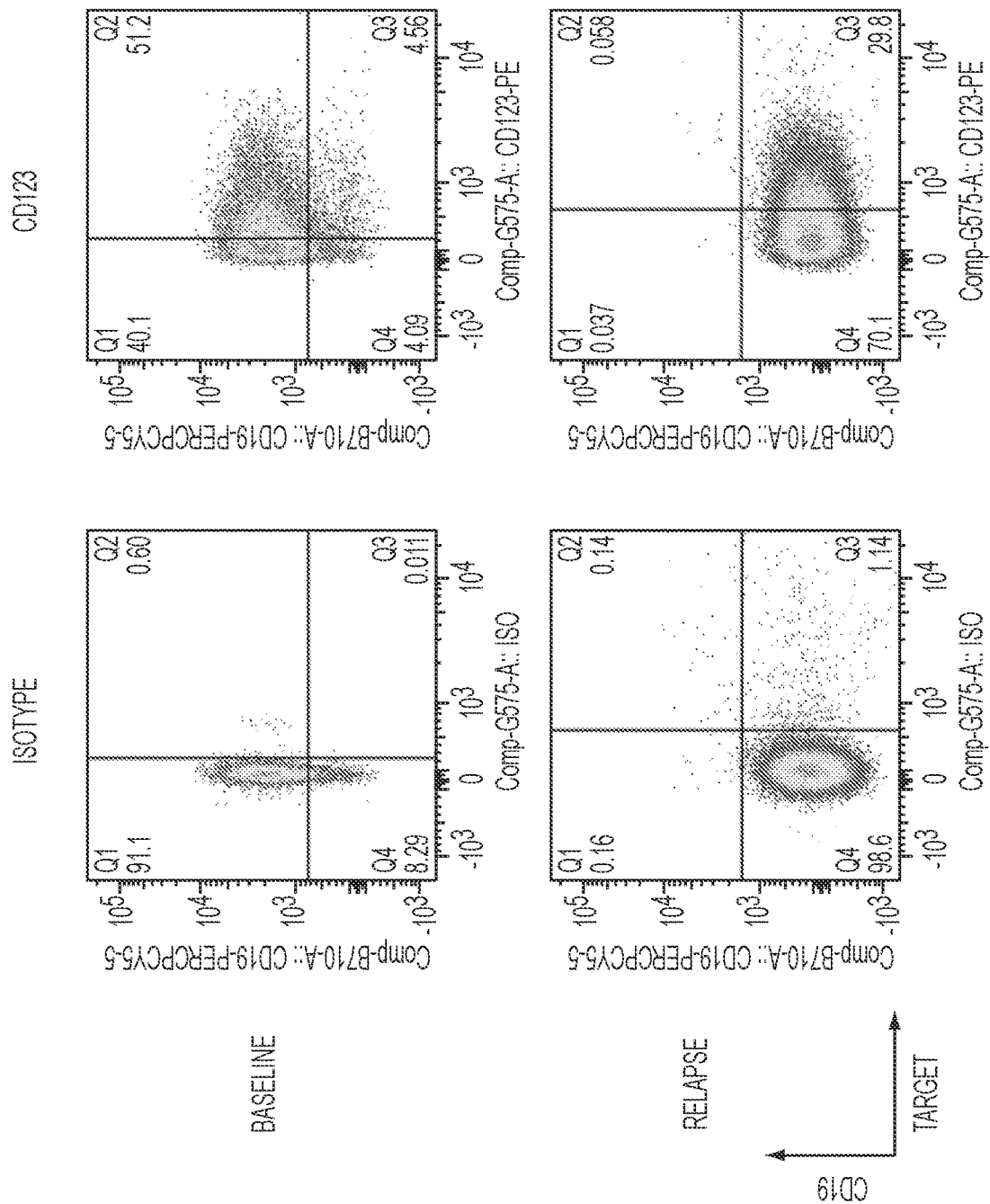
FIG. 19 is a graph showing expression of CD123 in another patient relapsing with CD19-ALL after CART19 therapy.

Furthermore, CD123 expression was demonstrated in ALL. In particular, flow-cytometry screening of a panel of 16 specimens from adults with relapsed or refractory ALL (RR-ALL) showed a high expression level of CD19 (a classical B cell marker), along with expression of CD123 (FIG. 17). Similar findings were found in pediatric specimens (FIG. 17). Expression was shown by flow cytometry of thawed banked patient specimens, gating on $CD45^{dim}$ SSC low blasts. CD123 expression was also demonstrated in CD19-ve ALL relapsing after treatment with CTL019. For example, as shown in FIGS. 18 and 19, patients relapsing with CD19-ALL after CART therapy was shown to retain expression of CD123. These results suggest that CART123 may be used to prevent CD19 relapses resulting from CART19 therapy.

Figure 20:
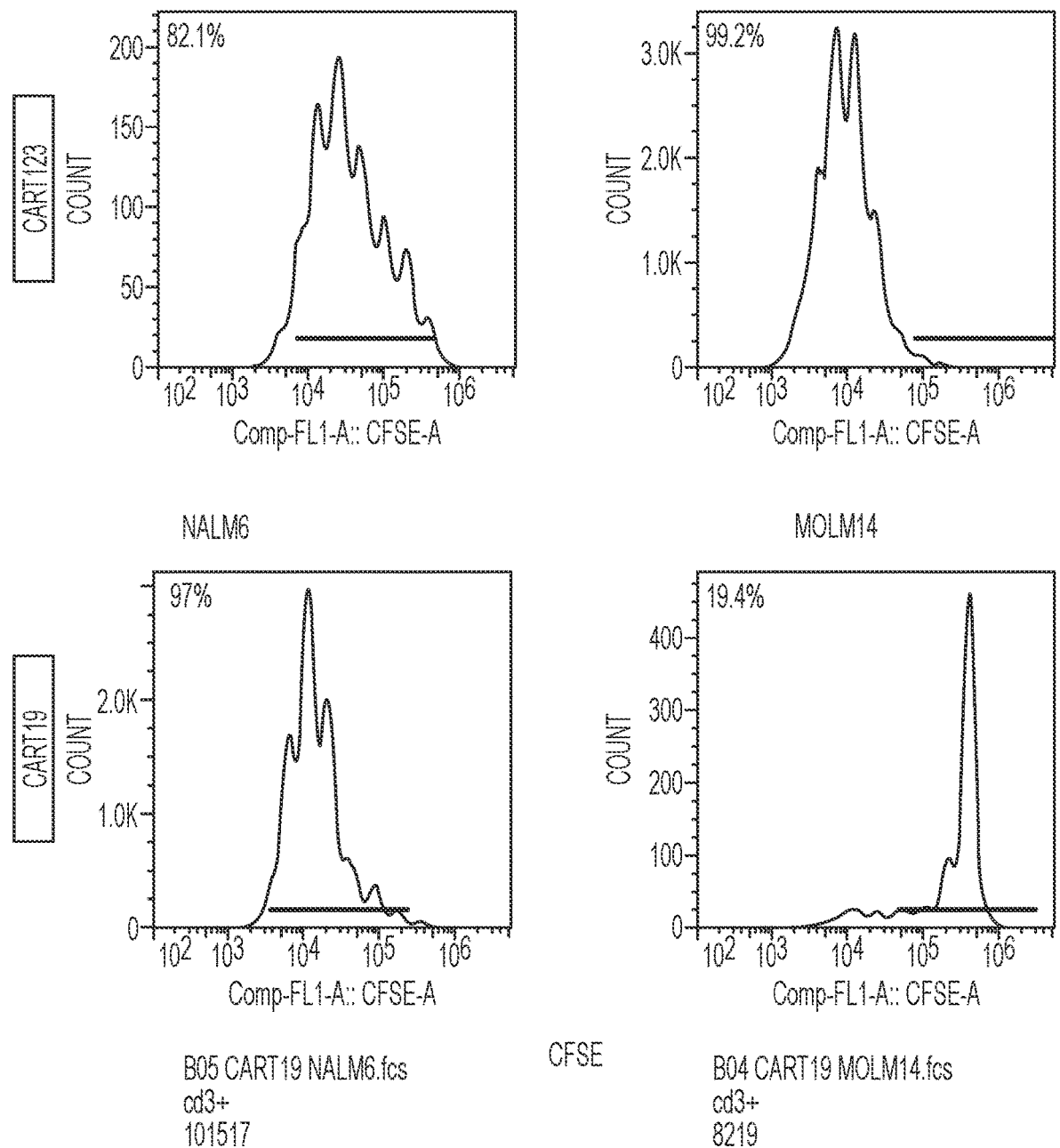
FIG. 20 is a graph showing proliferation in CART19 and CART123 T cells after exposure to the B-ALL cell line.
Figure 21:
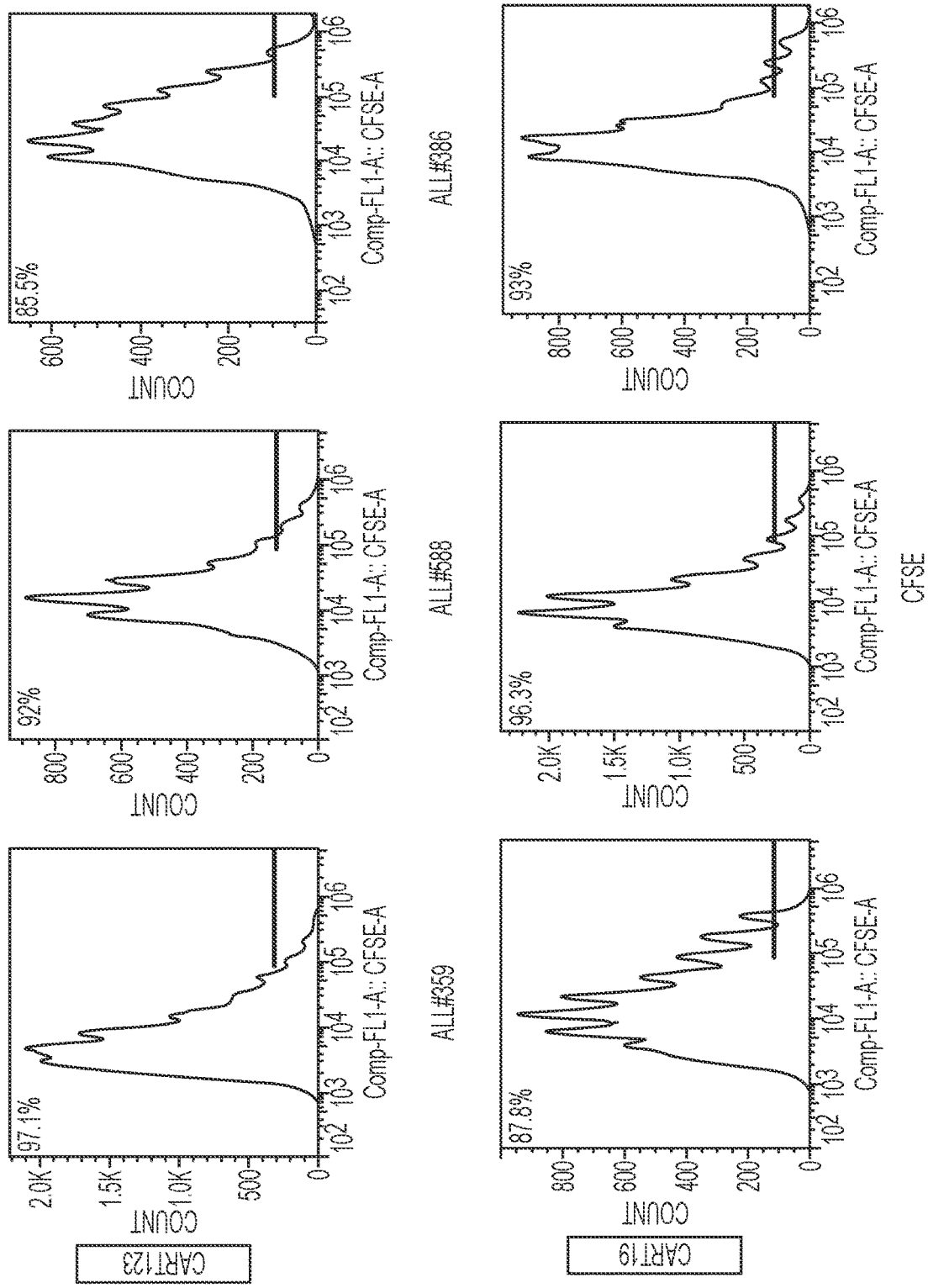
FIG. 21 is a graph showing proliferation in CART19 and CART123 T cells after exposure to primary B-cell ALL samples.
Figure 22:
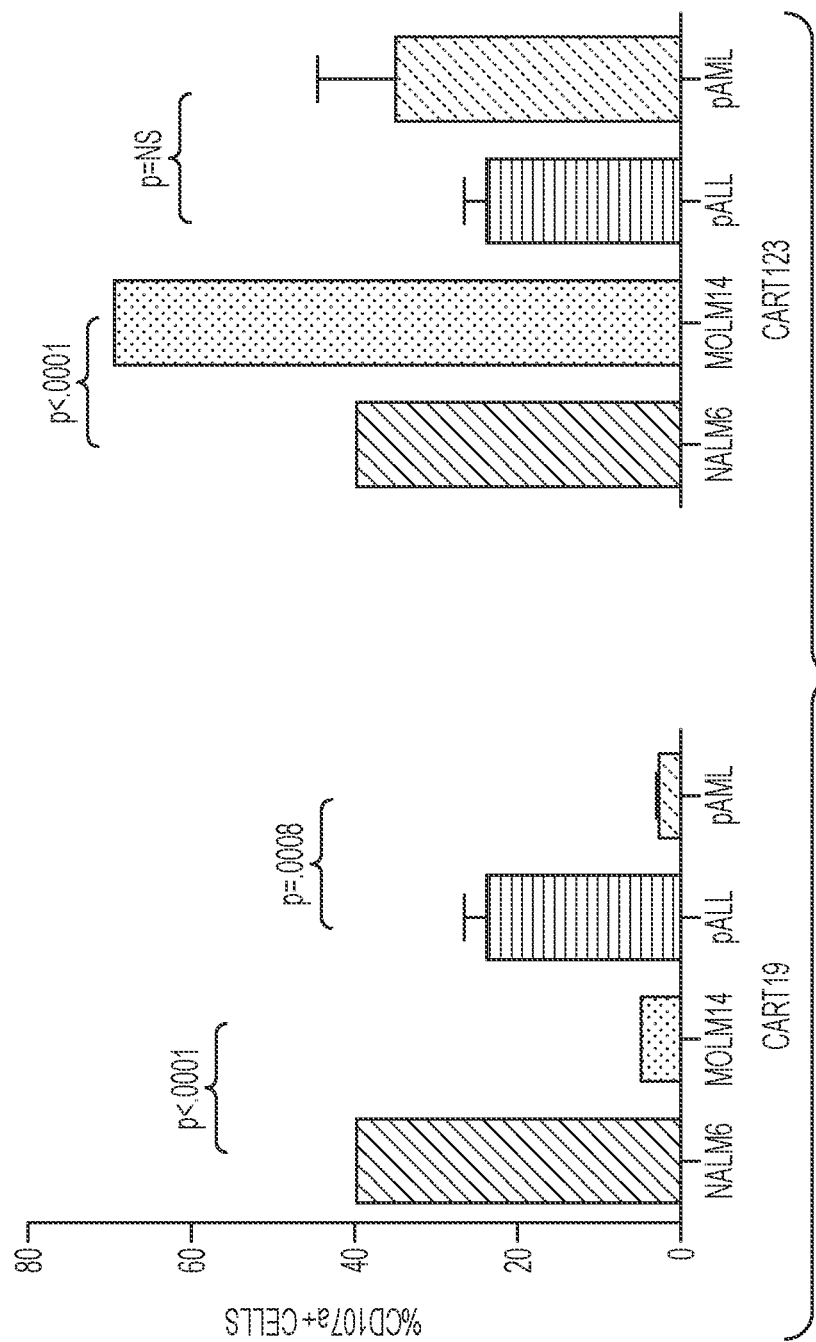
FIG. 22 is a graph showing CD123 cell degranulation in response to NALM6 B-ALL, MOLM14, primary ALL and primary AML.
Figure 23:
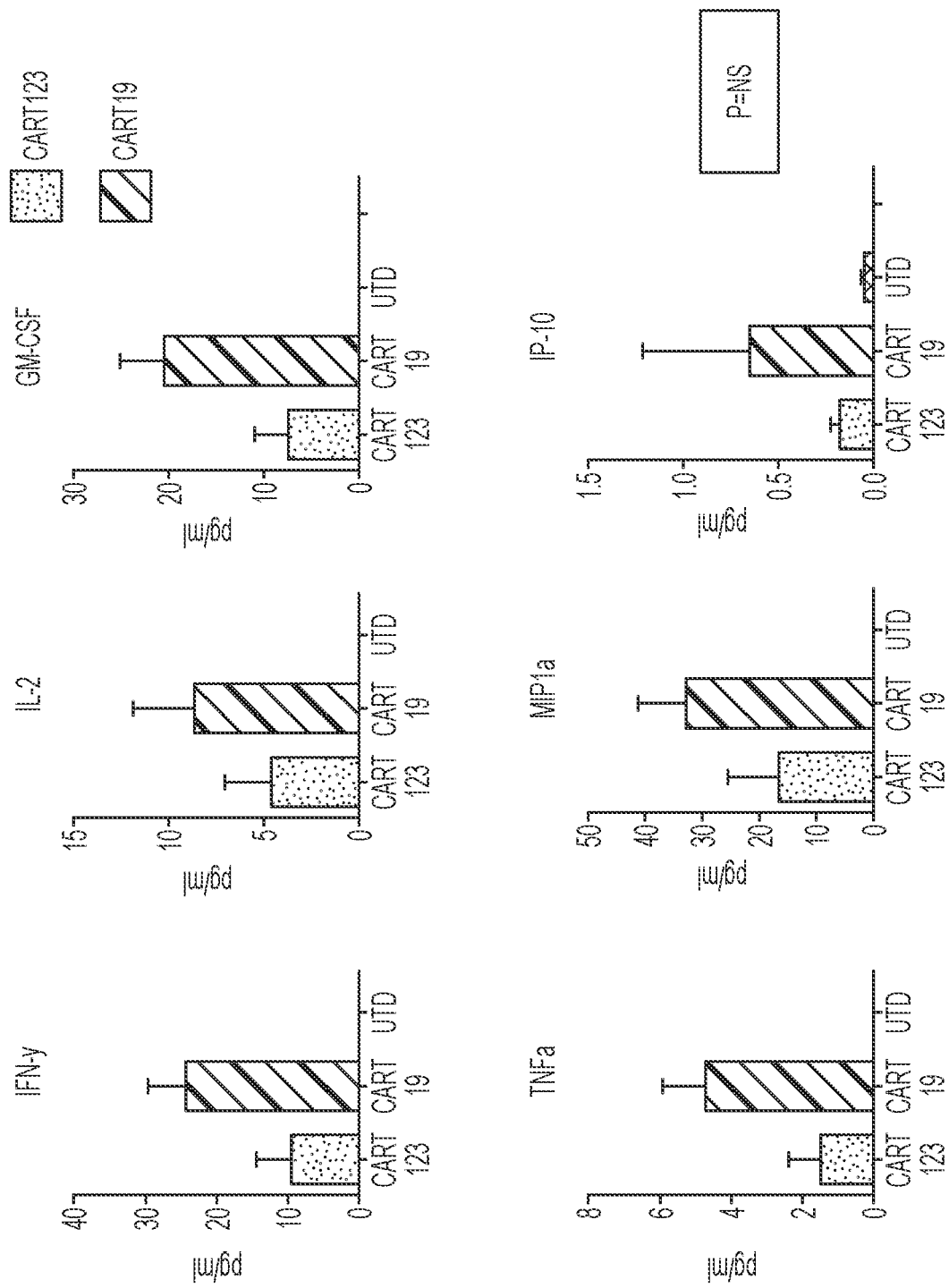
FIG. 23 is a graph showing secretion of soluble cytokines in response to exposure of CART19 and CART123 T cells to primary ALL samples. Co-culture was performed with primary ALL samples.
Figure 24:
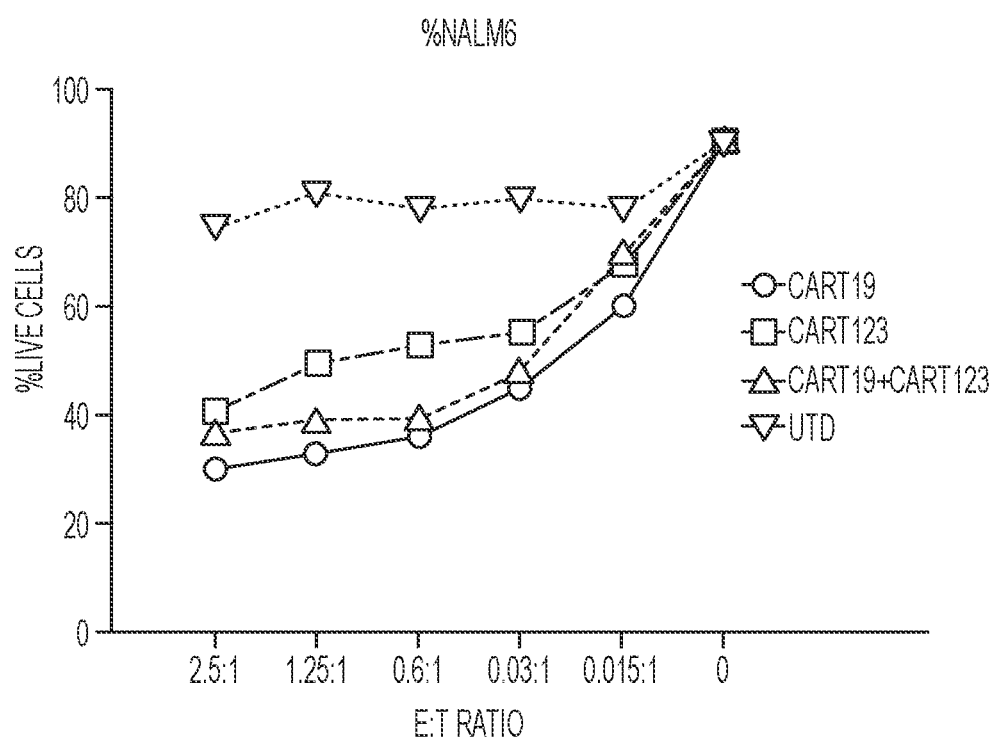
FIG. 24 is a graph showing cytotoxicity at 4 hours. CART123 and CART19 T cells were tested for the ability to kill NALM6 B-ALL cells.

FIGS. 20-24 demonstrate in vitro activity of CART123 1172 against ALL blasts. Exposure to the B-ALL cell line induced robust proliferation in both CART19 and CART123 cells (FIG. 20). CART123 or CART19 cells were stained with CFSE and incubated with the indicated targets for 120 hours, followed by FACS analysis for CFSE dilution. Histograms were gated on live CD3+ T cells. Exposure to primary B-cell ALL samples also induced robust proliferation in both CART19 and CART123 cells (FIG. 21). CART123 cells degranulate robustly in response to NALM6 B-ALL as well as primary ALL, with no difference between primary ALL and AML (FIG. 22). The indicated T cells were incubated with the indicated targets in the presence of anti-CD107a, anti-CD49d, anti-CD28 and monensin for 4 hours, followed by FACS analysis gated on T cells. Exposure to primary ALL samples by coculture of CART123 or CART19 cells with primary ALL samples led to the secretion of multiple effector cytokines at 24 hours (FIG. 23). No difference was noted between CART19 and CART123. Supernatant was collected from a 24 hour co-culture, followed by analysis in a 30-plex kit (selected cytokines are shown). CART123 and CART19 cells showed equivalent ability to kill NALM6 B-ALL cells in cytotoxicity assays at 4 hours (FIG. 24).

Figure 25:
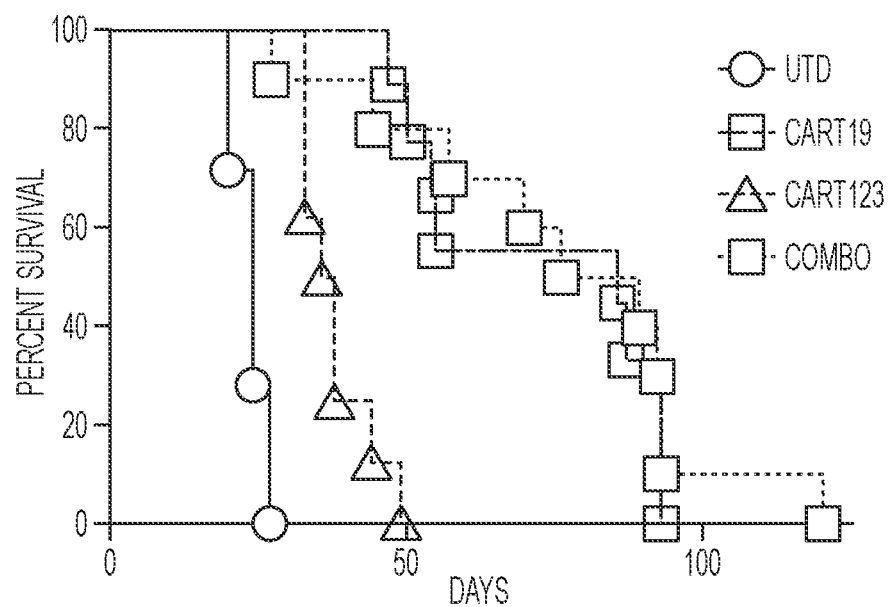
FIG. 25 is a graph showing survival of NSG mice that were injected with 1×10$^6$ Nalm6 click beetle green luciferase cells on D0. On D7, the mice were injected with UTD T cells, CART19 cells, CART123 cells, or a 50:50 mixed population of CART19 and CART123 to a total cell dose of 1×10$^6$ (combo group).
Figure 27B:
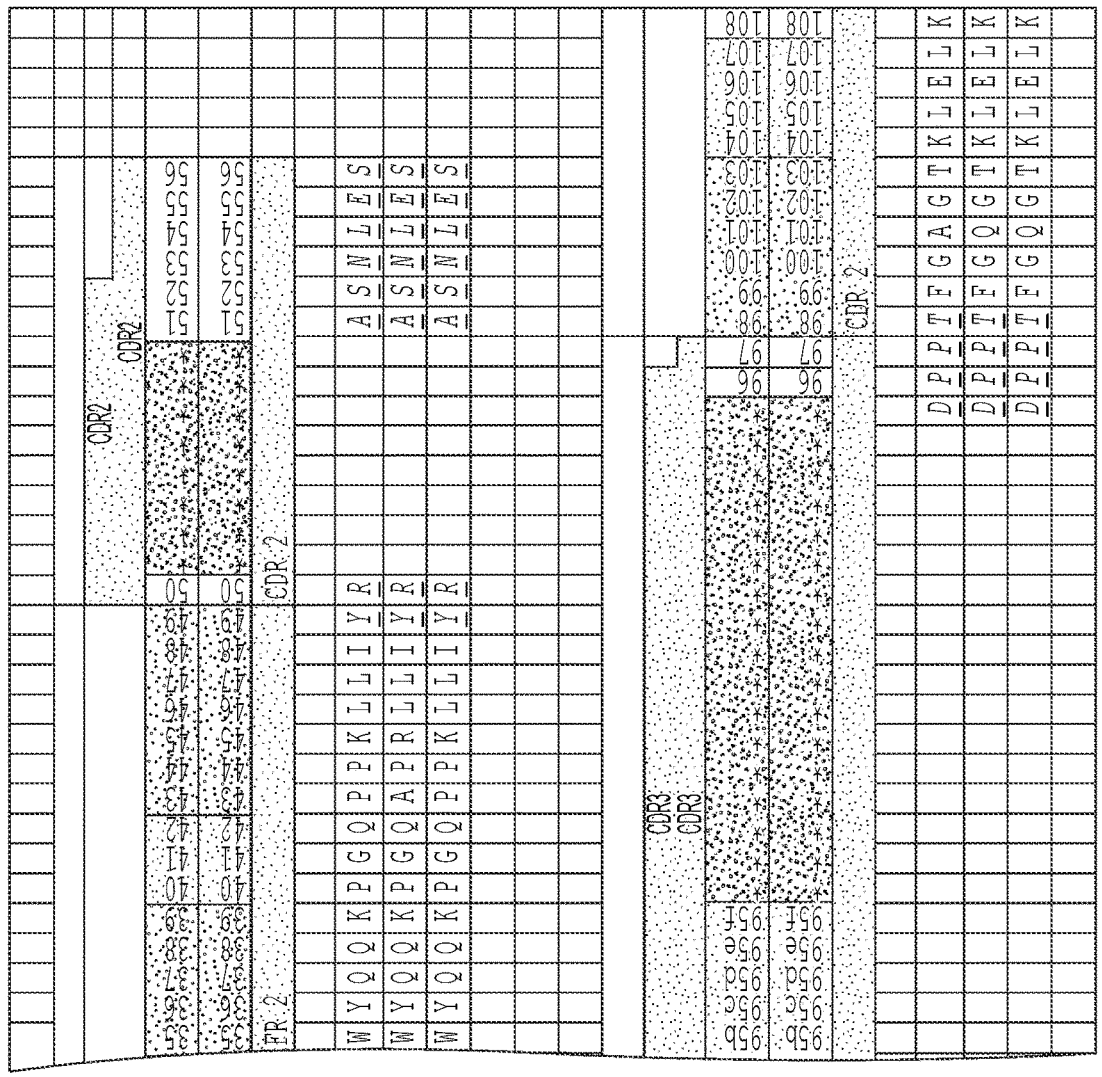

FIG. 25 demonstrates in vivo activity of CART123 in an ALL murine model. In particular, NSG mice were injected with $1 \times 10^6$ Nalm6 click beetle green luciferase cells on D0. On D7, the mice were injected with UTD T cells, CART19 cells, CART123 cells, or a 50:50 mixed population of CART19 and CART123 to a total cell dose of $1 \times 10^6$ (combo group). Mice were followed for survival. As shown in FIG. 25, CART123 monotherapy was clearly superior to untransduced T cells (UTD) but not as effective as CART19 monotherapy at enhancing animal survival. The combination of CART123 and CART19 did not enhance survival compared with CART19 monotherapy. Nonetheless, combo CART19+CART123 therapy could prevent the occurrence of antigen-loss relapses as has already been noted to occur in patients, as illustrated in FIG. 18 and FIG. 19.

The results presented herein reconfirm the successful engineering of anti-CD123 redirected T cells (CART123) and demonstrate potent and specific preclinical activity. These results demonstrate the feasibility of using CART123 for targeting CD123 to treat patients with high-risk ALL. Furthermore, these results demonstrate that CD123 is expressed at high levels in primary ALL specimens and that ALL patients relapsing with CD19-disease retain expression of CD123. CART123 show equivalent in vitro activity against primary ALL, compared with CART19. Combined infusion of CART123 and CART19 could be used to prevent antigen loss relapses by broadening the number of antigens through which immune pressure is exerted on malignancy.

Example 3

CAR Sequences

The scFvs used in the CAR constructs were independently synthesized based on a published sequence (Du et al, 2007 Journal of Immunotherapy 30:607). The original antibodies in Du et al. were from hybridomas that Du et al. obtained from Stemline Therapeutics, NY, N.Y. The scFv sequences were derived from the heavy and light chain variable regions from these antibodies: 26292 and 32716 (FIG. 7A). Each was cloned in a light-to-heavy chain or heavy-to-light chain direction, with a flexible linker connecting the VL and VH domains, into a vector backbone containing the CD8 or IgG4 hinge region along with the 4-1BB molecule and the CD3zeta molecule (FIGS. 7A and 7B).

The polypeptide sequence on the clone entitled CD123 4-1BBCD3z-CAR is provided as the 496 aa polypeptide of SEQ ID NO:1. The leader sequence comprises amino acid residues 1 to 25 of SEQ ID NO:1, and is provided separately as SEQ ID NO:3. The scFv domain is provided separately as SEQ ID NO:2 and comprises a $V_L$ domain comprising amino acid resides 26 to 136 of SEQ ID NO:1, the linker sequence comprising amino acid resides 137 to 151 of SEQ ID NO:1, and the $V_H$ domain sequence comprising amino acid residues 152 to 269 of SEQ ID NO:1. The hinge region comprise amino acid residues 270 to 318 of SEQ ID NO:1, and is provided separately as SEQ ID NO:4. The transmembrane domain comprises amino acid residues 319 to 342 of SEQ ID NO:1, and is provided separately as SEQ ID NO:5 The 4-1BB intracellular domain comprises amino acid residues 343 to 384 of SEQ ID NO:1, and is provided separately as SEQ ID NO:6. The CD3 zeta domain comprises amino acid residues 385 to 496 of SEQ ID NO:1, is provided separately as SEQ ID NO:7.

The nucleotide encoding the polypeptide of SEQ ID NO:1 is provided as SEQ ID NO:8. The nucleotide encoding the polypeptide of SEQ ID NO:2 is provided as SEQ ID NO:9.

The nucleotide encoding the polypeptide of SEQ ID NO:3 is provided as SEQ ID NO:10. The nucleotide encoding the polypeptide of SEQ ID NO:4 is provided as SEQ ID NO:11. The nucleotide encoding the polypeptide of SEQ ID NO:5 is provided as SEQ ID NO:12. The nucleotide encoding the polypeptide of SEQ ID NO:6 is provided as SEQ ID NO:13. The nucleotide encoding the polypeptide of SEQ ID NO:7 is provided as SEQ ID NO:14. The nucleotide encoding the polypeptide of SEQ ID NO:98 is provided as SEQ ID NO:99.

The nucleotide encoding the polypeptide of SEQ ID NO:11 is provided as SEQ ID

```
CD123 4-1BBCD3z-CAR (amino acid sequence)
(corresponding to 1172 in FIG. 7A)
                                       (SEQ ID NO: 1)
MALPVTALLLPLALLLHAARPGSDIVLTQSPASLAVSLGQRATISCRASE
SVDNYGNTFMHWYQQKPGQPPKLLIYRASNLESGIPARFSGSGSRTDFTL
TINPVEADDVATYYCQQSNEDPPTFGAGTKLELKGGGGSGGGGSGGGGSQ
IQLVQSGPELKKPGETVKISCKASGYIFTNYGMNWVKQAPGKSFKWMGWI
NTYTGESTYSADFKGRFAFSLETSASTAYLHINDLKNEDTATYFCARSGG
YDPMDYWGQGTSVTVSSASSGTTTPAPRPPTPAPTIASQPLSLRPEACRP
AAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKMA
EAYSEIGMKGERRRGKGHDGLYQGLSTATKDTYDALHMQALPPR CD123 scFv (amino acid sequence)
                                       (SEQ ID NO: 2)
DIVLTQSPASLAVSLGQRATISCRASESVDNYGNTFMHWYQQKPGQPPKL
LIYRASNLESGIPARFSGSGSRTDFTLTINPVEADDVATYYCQQSNEDPP
TFGAGTKLELKGGGGSGGGGSGGGGSQIQLVQSGPELKKPGETVKISCKA
SGYIFTNYGMNWVKQAPGKSFKWMGWINTYTGESTYSADFKGRFAFSLET
SASTAYLHINDLKNEDTATYFCARSGGYDPMDYWGQGTSVTVSS CD8 leader (amino acid sequence)
                                       (SEQ ID NO: 3)
MALPVTALLLPLALLLHAARP CD8 hinge (amino acid sequence)
                                       (SEQ ID NO: 4)
TTTPAPRPPTPAPTIASQPLSLRPEACRPAAGGAVHTRGLDFACD CD8 transmembrane (amino acid sequence)
                                       (SEQ ID NO: 5)
IYIWAPLAGTCGVLLLSLVITLYC 4-1BB Intracellular domain (amino acid sequence)
                                       (SEQ ID NO: 6)
KRGRKKLLYIFKQPFMRPVQTTQEEDGCSCRFPEEEEGGCEL CD3 zeta (amino acid sequence)
                                       (SEQ ID NO: 7)
RVKFSRSADAPAYKQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR CD3 zeta domain (amino acid sequence; NCBI
Reference Sequence NM_000734.3)
                                       (SEQ ID NO: 98)
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR CD123 4-1BBCD3z-CAR (nucleic acid sequence)
                                       (SEQ ID NO: 8)
ATGGCCCTGCCTGTGACAGCCCTGCTGCTGCCTCTGGCTCTGCTGCTGCA

TGCCGCTAGACCCGGATCCGACATCGTGCTGACACAGAGCCCTGCTTCCC

TGGCCGTGTCCCTGGGACAGAGAGCCACAATCAGCTGCAGGGCCAGCGAG

AGCGTGGACAACTACGGCAACACCTTCATGCACTGGTATCAGCAGAAGCC

CGGCCAGCCCCCCAAGCTGCTGATCTACAGAGCCAGCAACCTGGAAAGCG

GCATCCCCGCCAGATTTTCCGGCAGCGGCAGCAGAACCGACTTCACCCTG

ACCATCAACCCCGTGGAAGCCGACGACGTGGCCACCTACTACTGCCAGCA

GAGCAACGAGGACCCCCCCACATTTGGAGCCGGCACCAAGCTGGAACTGA

AGGGCGGAGGCGGATCTGGCGGCGGAGGATCTTCTGGGGGAGGCTCTCAG

ATTCAGCTGGTGCAGAGCGGCCCAGAGCTGAAGAAACCCGGCGAGACAGT

GAAGATCTCCTGCAAGGCCTCCGGCTACATCTTCACCAATTACGGCATGA

ACTGGGTCAAGCAGGCCCCTGGCAAGAGCTTCAAGTGGATGGGCTGGATC

AACACCTACACCGGCGAGAGCACCTACAGCGCCGACTTCAAGGGCAGATT

CGCCTTCAGCCTGGAAACCAGCGCCAGCACCGCCTACCTGCACATCAACG

ACCTGAAGAACGAGGACACCGCCACCTATTTCTGCGCCAGAAGCGGCGGC

TACGACCCCATGGATTATTGGGGCCAGGGCACCAGCGTGACCGTGTCCTC

TGCTAGCTCCGGAACCACGACGCCAGCGCCGCGACCACCAACACCGGCGC

CCACCATCGCGTCGCAGCCCCTGTCCCTGCGCCCAGAGGCGTGCCGGCCA

GCGGCGGGGGGCGCAGTGCACACGAGGGGGCTGGACTTCGCCTGTGATAT

CTACATCTGGGCGCCCTTGGCCGGGACTTGTGGGGTCCTTCTCCTGTCAC

TGGTTATCACCCTTTACTGCAAACGGGGCAGAAAGAAACTCCTGTATATA

TTCAAACAACCATTTATGAGACCAGTACAAACTACTCAAGAGGAAGATGG

CTGTAGCTGCCGATTTCCAGAAGAAGAAGAAGGAGGATGTGAACTGAGAG

TGAAGTTCAGCAGGAGCGCAGACGCCCCCGCGTACAAGCAGGGCCAGAAC

CAGCTCTATAACGAGCTCAATCTAGGACGAAGAGAGGAGTACGATGTTTT

GGACAAGAGACGTGGCCGGGACCCTGAGATGGGGGGAAAGCCGAGAAGGA

AGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGG

GCACGATGGCCTTTACCAGGGTCTCAGTACAGCCACCAAGGACACCTACG

ACGCCCTTCACATGCAGGCCCTGCCCCCTCGC

CD123 scFv (nucleic acid sequence)
                                       (SEQ ID NO: 9)
GACATCGTGCTGACACAGAGCCCTGCTTCCCTGGCCGTGTCCCTGGGACA

GAGAGCCACAATCAGCTGCAGGGCCAGCGAGAGCGTGGACAACTACGGCA

ACACCTTCATGCACTGGTATCAGCAGAAGCCCGGCCAGCCCCCCAAGCTG

CTGATCTACAGAGCCAGCAACCTGGAAAGCGGCATCCCCGCCAGATTTTC

CGGCAGCGGCAGCAGAACCGACTTCACCCTGACCATCAACCCCGTGGAAG

CCGACGACGTGGCCACCTACTACTGCCAGCAGAGCAACGAGGACCCCCCC

ACATTTGGAGCCGGCACCAAGCTGGAACTGAAGGGCGGAGGCGGATCTGG
```

-continued

CGGCGGAGGATCTTCTGGGGGAGGCTCTCAGATTCAGCTGGTGCAGAGCG

GCCCAGAGCTGAAGAAACCCGGCGAGACAGTGAAGATCTCCTGCAAGGCC

TCCGGCTACATCTTCACCAATTACGGCATGAACTGGGTCAAGCAGGCCCC

TGGCAAGAGCTTCAAGTGGATGGGCTGGATCAACACCTACACCGGCGAGA

GCACCTACAGCGCCGACTTCAAGGGCAGATTCGCCTTCAGCCTGGAAACC

AGCGCCAGCACCGCCTACCTGCACATCAACGACCTGAAGAACGAGGACAC

CGCCACCTATTTCTGCGCCAGAAGCGGCGGCTACGACCCCATGGATTATT

GGGGCCAGGGCACCAGCGTGACCGTGTCCTCT leader (nucleic acid sequence)
(SEQ ID NO: 10)
ATGGCCCTGCCTGTGACAGCCCTGCTGCTGCCTCTGGCTCTGCTGCTGCA

TGCCGCTAGACCC hinge (nucleic acid sequence)
(SEQ ID NO: 11)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGCG

CAGTGCACACGAGGGGGCTGGACTTCGCCTGTGAT transmembrane (nucleic acid sequence)
(SEQ ID NO: 12)
ATCTACATCTGGGCGCCCTTGGCCGGGACTTGTGGGGTCCTTCTCCTGTC

ACTGGTTATCACCCTTTACTGC 4-1BB Intracellular domain (nucleic acid sequence)
(SEQ ID NO: 13)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG

CD3 zeta (nucleic acid sequence)
(SEQ ID NO: 14)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD3 zeta (nucleic acid sequence; NCBI Reference
Sequence NM_000734.3);
(SEQ ID NO: 99)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

CD123 4-1BBCD3z-CAR (26292) (1176) (amino acid
sequence)
(SEQ ID NO: 100)
MALPVTALLLPLALLLHAARPGSDVQITQSPSYLAASPGETITINCRASK

SISKDLAWYQEKPGKTNKLLIYSGSTLQSGIPSRFSGSGSGTDFTLTISS

LEPEDFAMYYCQQHNKYPYTFGGGTKLEIKGGGGSGGGGSSGGGSQVQLQ

QPGAELVRPGASVKLSCKASGYTFTSYWMNWVKQRPDQGLEWIGRIDPYD

SETHYNQKFKDKAILTVDKSSSTAYMQLSSLTSEDSAVYYCARGNWDDYW

GQGTTLTVSSASSGTTTPAPRPPTPAPTIASQPLSLRPEACRPAAGGAVH

TRGLDFACDIYIWAPLAGTCGVLLLSLVITLYCKRGRKKLLYIFKQPFMR

PVQTTQEEDGCSCRFPEEEEGGCELRVKFSRSADAPAYKQGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR

CD123 scFv (26292) (1176) (amino acid sequence)
(SEQ ID NO: 101)
DVQITQSPSYLAASPGETITINCRASKSISKDLAWYQEKPGKTNKLLIYS

GSTLQSGIPSRFSGSGSGTDFTLTISSLEPEDFAMYYCQQHNKYPYTFGG

GTKLEIKGGGGSGGGGSSGGGSQVQLQQPGAELVRPGASVKLSCKASGYT

FTSYWMNWVKQRPDQGLEWIGRIDPYDSETHYNQKFKDKAILTVDKSSST

AYMQLSSLTSEDSAVYYCARGNWDDYWGQGTTLTVSS

CD123 4-1BBCD3z-CAR (26292) (1176) (nucleotide
sequence)
(SEQ ID NO: 102)
ATGGCCCTGCCTGTGACAGCCCTGCTGCTGCCTCTGGCTCTGCTGCTGCA

CGCCGCTAGACCCGGATCCGACGTGCAGATCACACAGAGCCCTAGCTACC

TGGCCGCCAGCCCTGGCGAGACAATCACCATCAACTGCCGGGCCAGCAAG

AGCATCAGCAAGGACCTGGCCTGGTATCAGGAAAAGCCCGGCAAGACCAA

CAAGCTGCTGATCTACAGCGGCAGCACCCTGCAGAGCGGCATCCCCAGCA

GATTTTCCGGCAGCGGCTCCGGCACCGACTTCACCCTGACAATCAGCAGC

CTGGAACCCGAGGACTTCGCCATGTACTACTGCCAGCAGCACAACAAGTA

CCCCTACACCTTCGGCGGAGGCACCAAGCTGGAAATCAAGGGCGGAGGCG

GATCTGGCGGCGGAGGAAGTTCTGGCGGAGGATCTCAGGTGCAGCTGCAG

CAGCCAGGCGCTGAACTCGTGCGCCCTGGCGCTTCTGTGAAGCTGAGCTG

TAAAGCCAGCGGCTACACCTTTACCAGCTACTGGATGAACTGGGTCAAGC

AGCGGCCCGACCAGGGCCTGGAGTGGATCGGCAGAATCGACCCCTACGAC

AGCGAGACACACTACAACCAGAAGTTCAAGGACAAGGCCATCCTGACCGT

GGACAAGAGCAGCTCCACCGCCTACATGCAGCTGTCCAGCCTGACCAGCG

AGGACAGCGCCGTGTACTATTGCGCCAGGGGCAACTGGGACGACTACTGG

GGCCAGGGCACAACCCTGACAGTGTCCTCTGCTAGCTCCGGAACCACGAC

GCCAGCGCCGCGACCACCAACACCGGCGCCCACCATCGCGTCGCAGCCCC

TGTCCCTGCGCCCAGAGGCGTGCCGGCCAGCGGCGGGGGCGCAGTGCAC

ACGAGGGGGCTGGACTTCGCCTGTGATATCTACATCTGGGCGCCCTTGGC

CGGGACTTGTGGGGTCCTTCTCCTGTCACTGGTTATCACCCTTTACTGCA

AACGGGGCAGAAAGAAACTCCTGTATATATTCAAACAACCATTTATGAGA

CCAGTACAAACTACTCAAGAGGAAGATGGCTGTAGCTGCCGATTTCCAGA

-continued

AGAAGAAGAAGGAGGATGTGAACTGAGAGTGAAGTTCAGCAGGAGCGCAG

ACGCCCCCGCGTACAAGCAGGGCCAGAACCAGCTCTATAACGAGCTCAAT

CTAGGACGAAGAGAGGAGTACGATGTTTTGGACAAGAGACGTGGCCGGGA

CCCTGAGATGGGGGAAAGCCGAGAAGGAAGAACCCTCAGGAAGGCCTGT

ACAATGAACTGCAGAAAGATAAGATGGCGGAGGCCTACAGTGAGATTGGG

ATGAAAGGCGAGCGCCGGAGGGGCAAGGGGCACGATGGCCTTTACCAGGG

TCTCAGTACAGCCACCAAGGACACCTACGACGCCCTTCACATGCAGGCCC

TGCCCCCTCGC

CD123 scFv (26292) (1176) (nucleotide sequence)
(SEQ ID NO: 103)
GACGTGCAGATCACACAGAGCCCTAGCTACCTGGCCGCCAGCCCTGGCGA

GACAATCACCATCAACTGCCGGGCCAGCAAGAGCATCAGCAAGGACCTGG

CCTGGTATCAGGAAAAGCCCGGCAAGACCAACAAGCTGCTGATCTACAGC

GGCAGCACCCTGCAGAGCGGCATCCCCAGCAGATTTTCCGGCAGCGGCTC

CGGCACCGACTTCACCCTGACAATCAGCAGCCTGGAACCCGAGGACTTCG

CCATGTACTACTGCCAGCAGCACAACAAGTACCCCTACACCTTCGGCGGA

GGCACCAAGCTGGAAATCAAGGGCGGAGGCGGATCTGGCGGCGGAGGAAG

TTCTGGCGGAGGATCTCAGGTGCAGCTGCAGCAGCCAGGCGCTGAACTCG

TGCGGCCTGGCGCTTCTGTGAAGCTGAGCTGTAAAGCCAGCGGCTACACC

TTTACCAGCTACTGGATGAACTGGGTCAAGCAGCGGCCCGACCAGGGCCT

GGAGTGGATCGGCAGAATCGACCCCTACGACAGCGAGACACACTACAACC

AGAAGTTCAAGGACAAGGCCATCCTGACCGTGGACAAGAGCAGCTCCACC

GCCTACATGCAGCTGTCCAGCCTGACCAGCGAGGACAGCGCCGTGTACTA

TTGCGCCAGGGGCAACTGGGACGACTACTGGGGCCAGGGCACAACCCTGA

CAGTGTCCTCT

IgG4 Hinge (amino acid sequence)
(SEQ ID NO: 104)
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGKM

IgG4 Hinge (nucleotide sequence)
(SEQ ID NO: 105)
GAGAGCAAGTACGGCCCTCCCTGCCCCCCTTGCCCTGCCCCCGAGTTCCT

GGGCGGACCCAGCGTGTTCCTGTTCCCCCCCAAGCCCAAGGACACCCTGA

TGATCAGCCGGACCCCCGAGGTGACCTGTGTGGTGGTGGACGTGTCCCAG

GAGGACCCCGAGGTCCAGTTCAACTGGTACGTGGACGGCGTGGAGGTGCA

CAACGCCAAGACCAAGCCCCGGGAGGAGCAGTTCAATAGCACCTACCGGG

TGGTGTCCGTGCTGACCGTGCTGCACCAGGACTGGCTGAACGGCAAGGAA

TACAAGTGTAAGGTGTCCAACAAGGGCCTGCCCAGCAGCATCGAGAAAAC

CATCAGCAAGGCCAAGGGCCAGCCTCGGGAGCCCCAGGTGTACACCCTGC

CCCCTAGCCAAGAGGAGATGACCAAGAACCAGGTGTCCCTGACCTGCCTG

GTGAAGGGCTTCTACCCCAGCGACATCGCCGTGGAGTGGGAGAGCAACGG

CCAGCCCGAGAACAACTACAAGACCACCCCCCCTGTGCTGGACAGCGACG

GCAGCTTCTTCCTGTACAGCCGGCTGACCGTGGACAAGAGCCGGTGGCAG

GAGGGCAACGTCTTTAGCTGCTCCGTGATGCACGAGGCCCTGCACAACCA

CTACACCCAGAAGAGCCTGAGCCTGTCCCTGGGCAAGATG

EF1α driving CD123 4-1BBCD3z-CAR (32716) (1172)
(nucleotide sequence)
(SEQ ID NO: 106)
EF1αpromoter italicized
*CGTGAGGCTCCGGTGCCCGTCAGTGGGCAGAGCGCACATCGCCCACAGTC*

*CCCGAGAAGTTGGGGGGAGGGGTCGGCAATTGAACCGGTGCCTAGAGAAG*

*GTGGCGCGGGGTAAACTGGGAAAGTGATGTCGTGTACTGGCTCCGCCTTT*

*TCCCGAGGGTGGGGGAGAACCGTATATAAGTGCAGTAGTCGCCGTGAAC*

*GTTCTTTTTCGCAACGGGTTTGCCGCCAGAACACAGGTAAGTGCCGTGTG*

*TGGTTCCCGCGGGCCTGGCCTCTTTACGGGTTATGGCCCTTGCGTGCCTT*

*GAATTACTTCCACCTGGCTGCAGTACGTGATTCTTGATCCCGAGCTTCGG*

*GTTGGAAGTGGGTGGGAGAGTTCGAGGCCTTGCGCTTAAGGAGCCCCTTC*

*GCCTCGTGCTTGAGTTGAGGCCTGGCCTGGGCGCTGGGGCCGCCGCGTGC*

*GAATCTGGTGGCACCTTCGCGCCTGTCTCGCTGCTTTCGATAAGTCTCTA*

*GCCATTTAAAATTTTTGATGACCTGCTGCGACGCTTTTTTTCTGGCAAGA*

*TAGTCTTGTAAATGCGGGCCAAGATCTGCACACTGGTATTTCGGTTTTTG*

*GGGCCGCGGGCGGCGACGGGCCCGTGCGTCCCAGCGCACATGTTCGGCG*

*AGGCGGGGCCTGCGAGCGCGGCCACCGAGAATCGGACGGGGGTAGTCTCA*

*AGCTGGCCGGCCTGCTCTGGTGCCTGGCCTCGCGCCGCCGTGTATCGCCC*

*CGCCCTGGGCGGCAAGGCTGGCCCGGTCGGCACCAGTTGCGTGAGCGGAA*

*AGATGGCCGCTTCCCGGCCCTGCTGCAGGGAGCTCAAAATGGAGGACGCG*

*GCGCTCGGGAGAGCGGGCGGGTGAGTCACCCACACAAAGGAAAAGGGCCT*

*TTCCGTCCTCAGCCGTCGCTTCATGTGACTCCACTGAGTACCGGGCGCCG*

*TCCAGGCACCTCGATTAGTTCTCGTGCTTTTGGAGTACGTCGTCTTTAGG*

*TTGGGGGGAGGGGTTTTATGCGATGGAGTTTCCCCACACTGAGTGGGTGG*

*AGACTGAAGTTAGGCCAGCTTGGCACTTGATGTAATTCTCCTTGGAATTT*

*GCCCTTTTTGAGTTTGGATCTTGGTTCATTCTCAAGCCTCAGACAGTGGT*

*TCAAAGTTTTTTTCTTCCATTTCAGGTGTCGTGAGCTAGCTCTAGAGCCA*

CCATGGCCCTGCCTGTGACAGCCCTGCTGCTGCCTCTGGCTCTGCTGCTG

CATGCCGCTAGACCCGGATCCGACATCGTGCTGACACAGAGCCCTGCTTC

CCTGGCCGTGTCCCTGGGACAGAGAGCCACAATCAGCTGCAGGGCCAGCG

AGAGCGTGGACAACTACGGCAACACCTTCATGCACTGGTATCAGCAGAAG

CCCGGCCAGCCCCCCAAGCTGCTGATCTACAGAGCCAGCAACCTGGAAAG

CGGCATCCCCGCCAGATTTTCCGGCAGCGGCAGCAGAACCGACTTCACCC

TGACCATCAACCCCGTGGAAGCCGACGACGTGGCCACCTACTACTGCCAG

CAGAGCAACGAGGACCCCCCCACATTTGGAGCCGGCACCAAGCTGGAACT

GAAGGGCGGAGGCGGATCTGGCGGCGGAGGATCTTCTGGGGGAGGCTCTC

AGATTCAGCTGGTGCAGAGCGGCCCCGAGCTGAAGAAACCCGGCGAGACA

GTGAAGATCTCCTGCAAGGCCTCCGGCTACATCTTCACCAATTACGGCAT

GAACTGGGTCAAGCAGGCCCCTGGCAAGAGCTTCAAGTGGATGGGCTGGA

TCAACACCTACACCGGCGAGAGCACCTACAGCGCCGACTTCAAGGGCAGA

TTCGCCTTCAGCCTGGAAACCAGCGCCAGCACCGCCTACCTGCACATCAA

CGACCTGAAGAACGAGGACACCGCCACCTATTTCTGCGCCAGAAGCGGCG

GCTACGACCCCATGGATTATTGGGGCCAGGGCACCAGCGTGACCGTGTCC

TCTGCTAGCTCCGGAACCACGACGCCAGCGCCGCGACCACCAACACCGGC

GCCCACCATCGCGTCGCAGCCCCTGTCCCTGCGCCCAGAGGCGTGCCGGC

CAGCGGCGGGGGCGCAGTGCACACGAGGGGGCTGGACTTCGCCTGTGAT

ATCTACATCTGGGCGCCCTTGGCCGGGACTTGTGGGGTCCTTCTCCTGTC

ACTGGTTATCACCCTTTACTGCAAACGGGGCAGAAAGAAACTCCTGTATA

TATTCAAACAACCATTTATGAGACCAGTACAAACTACTCAAGAGGAAGAT

GGCTGTAGCTGCCGATTTCCAGAAGAAGAAGAAGGAGGATGTGAACTGAG

AGTGAAGTTCAGCAGGAGCGCAGACGCCCCCGCGTACAAGCAGGGCCAGA

ACCAGCTCTATAACGAGCTCAATCTAGGACGAAGAGAGGAGTACGATGTT

TTGGACAAGAGACGTGGCCGGGACCCTGAGATGGGGGGAAAGCCGAGAAG

GAAGAACCCTCAGGAAGGCCTGTACAATGAACTGCAGAAAGATAAGATGG

CGGAGGCCTACAGTGAGATTGGGATGAAAGGCGAGCGCCGGAGGGGCAAG

GGGCACGATGGCCTTTACCAGGGTCTCAGTACAGCCACCAAGGACACCTA

CGACGCCCTTCACATGCAGGCCCTGCCCCCTCGC

CD123 CAR 1172 (amino acid sequence)
                              (SEQ ID NO: 107)
MALPVTALLLPLALLLHAARPGSDIVLTQSPASLAVSLGQRATISCRASE

SVDNYGNTFMHWYQQKPGQPPKLLIYRASNLESGIPARFSGSGSRTDFTL

TINPVEADDVATYYCQQSNEDPPTFGAGTKLELKGGGGSGGGGSSGGGSQ

IQLVQSGPELKKPGETVKISCKASGYIFTNYGMNWVKQAPGKSFKWMGWI

NTYTGESTYSADFKGRFAFSLETSASTAYLHINDLKNEDTATYFCARSGG

YDPMDYWGQGTSVTVSSASSGTTTPAPRPPTPAPTIASQPLSLRPEACRP

AAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYKQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR

CD123 CAR 1172 (nucleotide sequence)
                              (SEQ ID NO: 108)
ATGGCCCTGCCTGTGACAGCCCTGCTGCTGCCTCTGGCTCTGCTGCTGCA

TGCCGCTAGACCCGGATCCGACATCGTGCTGACACAGAGCCCTGCTTCCC

TGGCCGTGTCCCTGGGACAGAGAGCCACAATCAGCTGCAGGGCCAGCGAG

AGCGTGGACAACTACGGCAACACCTTCATGCACTGGTATCAGCAGAAGCC

CGGCCAGCCCCCAAGCTGCTGATCTACAGAGCCAGCAACCTGGAAAGCG

GCATCCCCGCCAGATTTTCCGGCAGCGGCAGCAGAACCGACTTCACCCTG

ACCATCAACCCCGTGGAAGCCGACGACGTGGCCACCTACTACTGCCAGCA

GAGCAACGAGGACCCCCCCACATTTGGAGCCGGCACCAAGCTGGAACTGA

AGGGCGGAGGCGGATCTGGCGGCGGAGGATCTTCTGGGGGAGGCTCTCAG

ATTCAGCTGGTGCAGAGCGGCCCAGAGCTGAAGAAACCCGGCGAGACAGT

GAAGATCTCCTGCAAGGCCTCCGGCTACATCTTCACCAATTACGGCATGA

ACTGGGTCAAGCAGGCCCCTGGCAAGAGCTTCAAGTGGATGGGCTGGATC

AACACCTACACCGGCGAGAGCACCTACAGCGCCGACTTCAAGGGCAGATT

CGCCTTCAGCCTGGAAACCAGCGCCAGCACCGCCTACCTGCACATCAACG

ACCTGAAGAACGAGGACACCGCCACCTATTTCTGCGCCAGAAGCGGCGGC

TACGACCCCATGGATTATTGGGGCCAGGGCACCAGCGTGACCGTGTCCTC

TGCTAGCTCCGGAACCACGACGCCAGCGCCGCGACCACCAACACCGGCGC

CCACCATCGCGTCGCAGCCCCTGTCCCTGCGCCCAGAGGCGTGCCGGCCA

GCGGCGGGGGCGCAGTGCACACGAGGGGGCTGGACTTCGCCTGTGATAT

CTACATCTGGGCGCCCTTGGCCGGGACTTGTGGGGTCCTTCTCCTGTCAC

TGGTTATCACCCTTTACTGCAAACGGGGCAGAAAGAAACTCCTGTATATA

TTCAAACAACCATTTATGAGACCAGTACAAACTACTCAAGAGGAAGATGG

CTGTAGCTGCCGATTTCCAGAAGAAGAAGAAGGAGGATGTGAACTGAGAG

TGAAGTTCAGCAGGAGCGCAGACGCCCCCGCGTACAAGCAGGGCCAGAAC

CAGCTCTATAACGAGCTCAATCTAGGACGAAGAGAGGAGTACGATGTTTT

GGACAAGAGACGTGGCCGGGACCCTGAGATGGGGGGAAAGCCGAGAAGGA

AGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGG

GCACGATGGCCTTTACCAGGGTCTCAGTACAGCCACCAAGGACACCTACG

ACGCCCTTCACATGCAGGCCCTGCCCCCTCGC

CD123 CAR 1173 (amino acid sequence)
                              (SEQ ID NO: 109)
MALPVTALLLPLALLLHAARPGSDIVLTQSPASLAVSLGQRATISCRASE

SVDNYGNTFMHWYQQKPGQPPKLLIYRASNLESGIPARFSGSGSRTDFTL

TINPVEADDVATYYCQQSNEDPPTFGAGTKLELKGGGGSGGGGSSGGGSQ

IQLVQSGPELKKPGETVKISCKASGYIFTNYGMNWVKQAPGKSFKWMGWI

NTYTGESTYSADFKGRFAFSLETSASTAYLHINDLKNEDTATYFCARSGG

YDPMDYWGQGTSVTVSSASSGESKYGPPCPPCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

MDIYIWAPLAGTCGVLLLSLVITLYCKRGRKKLLYIFKQPFMRPVQTTQE

EDGCSCRFPEEEEGGCELRVKFSRSADAPAYKQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPR

CD123 CAR 1173 (nucleotide sequence)
                              (SEQ ID NO: 110)
ATGGCCCTGCCTGTGACAGCCCTGCTGCTGCCTCTGGCTCTGCTGCTGCA

TGCCGCTAGACCCGGATCCGACATCGTGCTGACACAGAGCCCTGCTTCCC

TGGCCGTGTCCCTGGGACAGAGAGCCACAATCAGCTGCAGGGCCAGCGAG

AGCGTGGACAACTACGGCAACACCTTCATGCACTGGTATCAGCAGAAGCC

CGGCCAGCCCCCAAGCTGCTGATCTACAGAGCCAGCAACCTGGAAAGCG

```
GCATCCCCGCCAGATTTTCCGGCAGCGGCAGCAGAACCGACTTCACCCTG
ACCATCAACCCCGTGGAAGCCGACGACGTGGCCACCTACTACTGCCAGCA
GAGCAACGAGGACCCCCCCACATTTGGAGCCGGCACCAAGCTGGAACTGA
AGGGCGGAGGCGGATCTGGCGGCGAGGATCTTCTGGGGGAGGCTCTCAG
ATTCAGCTGGTGCAGAGCGGCCCAGAGCTGAAGAAACCCGGCGAGACAGT
GAAGATCTCCTGCAAGGCCTCCGGCTACATCTTCACCAATTACGGCATGA
ACTGGGTCAAGCAGGCCCCTGGCAAGAGCTTCAAGTGGATGGGCTGGATC
AACACCTACACCGGCGAGAGCACCTACAGCGCCGACTTCAAGGGCAGATT
CGCCTTCAGCCTGGAAACCAGCGCCAGCACCGCCTACCTGCACATCAACG
ACCTGAAGAACGAGGACACCGCCACCTATTTCTGCGCCAGAAGCGGCGGC
TACGACCCCATGGATTATTGGGGCCAGGGCACCAGCGTGACCGTGTCCTC
TGCTAGCTCCGGAGAGAGCAAGTACGCCCTCCCTGCCCCCCTTGCCCTG
CCCCCGAGTTCCTGGGCGGACCCAGCGTGTTCCTGTTCCCCCCCAAGCCC
AAGGACACCCTGATGATCAGCCGGACCCCCGAGGTGACCTGTGTGGTGGT
GGACGTGTCCCAGGAGGACCCCGAGGTCCAGTTCAACTGGTACGTGGACG
GCGTGGAGGTGCACAACGCCAAGACCAAGCCCCGGGAGGAGCAGTTCAAT
AGCACCTACCGGGTGGTGTCCGTGCTGACCGTGCTGCACCAGGACTGGCT
GAACGGCAAGGAATACAAGTGTAAGGTGTCCAACAAGGGCCTGCCCAGCA
GCATCGAGAAAACCATCAGCAAGGCCAAGGGCCAGCCTCGGGAGCCCCAG
GTGTACACCCTGCCCCCTAGCCAAGAGGAGATGACCAAGAACCAGGTGTC
CCTGACCTGCCTGGTGAAGGGCTTCTACCCCAGCGACATCGCCGTGGAGT
GGGAGAGCAACGGCCAGCCCGAGAACAACTACAAGACCACCCCCCCTGTG
CTGGACAGCGACGGCAGCTTCTTCCTGTACAGCCGGCTGACCGTGGACAA
GAGCCGGTGGCAGGAGGGCAACGTCTTTAGCTGCTCCGTGATGCACGAGG
CCCTGCACAACCACTACACCCAGAAGAGCCTGAGCCTGTCCCTGGGCAAG
ATGGATATCTACATCTGGGCGCCCTTGGCCGGGACTTGTGGGGTCCTTCT
CCTGTCACTGGTTATCACCCTTTACTGCAAACGGGGCAGAAAGAAACTCC
TGTATATATTCAAACAACCATTTATGAGACCAGTACAAACTACTCAAGAG
GAAGATGGCTGTAGCTGCCGATTTCCAGAAGAAGAAGAAGGAGGATGTGA
ACTGAGAGTGAAGTTCAGCAGGAGCGCAGACGCCCCCGCGTACAAGCAGG
GCCAGAACCAGCTCTATAACGAGCTCAATCTAGGACGAAGAGAGGAGTAC
GATGTTTTGGACAAGAGACGTGGCCGGGACCCTGAGATGGGGGGAAAGCC
GAGAAGGAAGAACCCTCAGGAAGGCCTGTACAATGAACTGCAGAAAGATA
AGATGGCGGAGGCCTACAGTGAGATTGGGATGAAAGGCGAGCGCCGGAGG
GGCAAGGGGCACGATGGCCTTTACCAGGGTCTCAGTACAGCCACCAAGGA
CACCTACGACGCCCTTCACATGCAGGCCCTGCCCCCTCGC

CD123 CAR 1174 (amino acid sequence)
(SEQ ID NO: 111)
MALPVTALLLPLALLLHAARPGSQIQLVQSGPELKKPGETVKISCKASGY
IFTNYGMNWVKQAPGKSFKWMGWINTYTGESTYSADFKGRFAFSLETSAS
TAYLHINDLKNEDTATYFCARSGGYDPMDYWGQGTSVTVSSGGGGSGGGG
SSGGGSDIVLTQSPASLAVSLGQRATISCRASESVDNYGNTFMHWYQQKP
GQPPKLLIYRASNLESGIPARFSGSGSRTDFTLTINPVEADDVATYYCQQ
SNEDPPTFGAGTKLELKASSGTTTPAPRPPTPAPTIASQPLSLRPEACRP
AAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYKQGQN
QLYNELNLGRREEYDVLDKRRGRDPEMGGKPRRKNPQEGLYNELQKDKMA
EAYSEIGMKGERRRGKGHDGLYQGLSTATKDTYDALHMQALPPR CD123 CAR 1175 (nucleotide sequence)
(SEQ ID NO: 112)
ATGGCCCTGCCTGTGACAGCCCTGCTGCTGCCACTGGCTCTGCTGCTGCA
TGCCGCTAGACCCGGATCCCAGATCCAGCTGGTGCAGTCTGGCCCCGAGC
TGAAGAAACCCGGCGAGACAGTGAAGATCAGCTGCAAGGCCAGCGGCTAC
ATCTTCACCAACTACGGCATGAACTGGGTCAAGCAGGCCCCTGGCAAGAG
CTTCAAGTGGATGGGCTGGATCAACACCTACACCGGCGAGAGCACCTACA
GCGCCGACTTCAAGGGCAGATTCGCCTTCAGCCTGGAAACCAGCGCCAGC
ACCGCCTACCTGCACATCAACGACCTGAAGAACGAGGACACCGCCACCTA
CTTTTGCGCCAGAAGCGGCGGCTACGACCCCATGGATTATTGGGGCCAGG
GCACCAGCGTGACCGTGTCTAGCGGAGGCGGAGGATCTGGCGGAGGGGGA
TCTTCTGGCGGCGAAGCGATATCGTGCTGACCCAGTCTCCTGCCAGCCT
GGCCGTGTCTCTGGGACAGAGAGCCACAATCAGCTGCCGGGCCTCTGAGA
GCGTGGACAATTACGGCAACACCTTCATGCACTGGTATCAGCAGAAGCCC
GGCCAGCCCCCCAAGCTGCTGATCTACAGAGCCAGCAACCTGGAAAGCGG
CATCCCCGCCAGATTTTCCGGCAGCGGCAGCAGAACCGACTTCACCCTGA
CCATCAACCCCGTGGAAGCCGACGACGTGGCCACCTATTACTGCCAGCAG
AGCAACGAGGACCCCCCTACCTTTGGAGCCGGCACCAAGCTGGAACTGAA
GGCTAGCTCCGGAACCACGACGCCAGCGCCGACCACCAACACCGGCGC
CCACCATCGCTCGCAGCCCCTGTCCCTGCGCCCAGAGGCGTGCCGGCCA
GCGGCGGGGGCGCAGTGCACACGAGGGGCTGGACTTCGCCTGTGATAT
CTACATCTGGGCGCCCTTGGCCGGGACTTGTGGGGTCCTTCTCCTGTCAC
TGGTTATCACCCTTTACTGCAAACGGGGCAGAAAGAAACTCCTGTATATA
TTCAAACAACCATTTATGAGACCAGTACAAACTACTCAAGAGGAAGATGG
CTGTAGCTGCCGATTTCCAGAAGAAGAAGAAGGAGGATGTGAACTGAGAG
TGAAGTTCAGCAGGAGCGCAGACGCCCCCGCGTACAAGCAGGGCCAGAAC
CAGCTCTATAACGAGCTCAATCTAGGACGAAGAGAGGAGTACGATGTTTT
GGACAAGAGACGTGGCCGGGACCCTGAGATGGGGGGAAAGCCGAGAAGGA
AGAACCCTCAGGAAGGCCTGTACAATGAACTGCAGAAAGATAAGATGGCG
GAGGCCTACAGTGAGATTGGGATGAAAGGCGAGCGCCGGAGGGGCAAGGG
GCACGATGGCCTTTACCAGGGTCTCAGTACAGCCACCAAGGACACCTACG
ACGCCCTTCACATGCAGGCCCTGCCCCCTCGC CD123 CAR 1175 (amino acid sequence)
(SEQ ID NO: 113)
MALPVTALLLPLALLLHAARPGSQIQLVQSGPELKKPGETVKISCKASGY
IFTNYGMNWVKQAPGKSFKWMGWINTYTGESTYSADFKGRFAFSLETSAS
TAYLHINDLKNEDTATYFCARSGGYDPMDYWGQGTSVTVSSGGGGSGGGG
```

SSGGGGSDIVLTQSPASLAVSLGQRATISCRASESVDNYGNTFMHWYQQKP
GQPPKLLIYRASNLESGIPARFSGSGSRTDFTLTINPVEADDVATYYCQQ
SNEDPPTFGAGTKLELKASSGESKYGPPCPPCPAPEFLGGPSVFLFPPKP
KDTLMISRTPEVTCVVVDVSQEDPEVQFNWYVDGVEVHNAKTKPREEQFN
STYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPV
LDSDGSFFLYSRLTVDKSRWQEGNVFSCSVMHEALHNHYTQKSLSLSLGK
MDIYIWAPLAGTCGVLLLSLVITLYCKRGRKKLLYIFKQPFMRPVQTTQE
EDGCSCRFPEEEEGGCELRVKFSRSADAPAYKQGQNQLYNELNLGRREEY
DVLDKRRGRDPEMGGKPRRKNPQEGLYNELQKDKMAEAYSEIGMKGERRR
GKGHDGLYQGLSTATKDTYDALHMQALPPR

CD123 CAR 1175 (nucleotide sequence)
(SEQ ID NO: 114)
ATGGCCCTGCCTGTGACAGCCCTGCTGCTGCCTCTGGCTCTGCTGCTGCA
TGCCGCTAGACCCGGATCCCAGATCCAGCTGGTGCAGTCTGGCCCCGAGC
TGAAGAAACCCGGCGAGACAGTGAAGATCAGCTGCAAGGCCAGCGGCTAC
ATCTTCACCAACTACGGCATGAACTGGGTCAAGCAGGCCCCTGGCAAGAG
CTTCAAGTGGATGGGCTGGATCAACACCTACACCGGCGAGAGCACCTACA
GCGCCGACTTCAAGGGCAGATTCGCCTTCAGCCTGGAAACCAGCGCCAGC
ACCGCCTACCTGCACATCAACGACCTGAAGAACGAGGACACCGCCACCTA
CTTTTGCGCCAGAAGCGGCGGCTACGACCCCATGGATTATTGGGGCCAGG
GCACCAGCGTGACCGTGTCTAGCGGAGGCGGAGGATCTGGCGGAGGGGGA
TCTTCTGGCGGCGGAAGCGATATCGTGCTGACCCAGTCTCCTGCCAGCCT
GGCCGTGTCTCTGGGACAGAGAGCCACAATCAGCTGCCGGGCCTCTGAGA
GCGTGGACAATTACGGCAACACCTTCATGCACTGGTATCAGCAGAAGCCC
GGCCAGCCCCCCAAGCTGCTGATCTACAGAGCCAGCAACCTGGAAAGCGG
CATCCCCGCCAGATTTTCCGGCAGCGGCAGCAGAACCGACTTCACCCTGA
CCATCAACCCCGTGGAAGCCGACGACGTGGCCACCTATTACTGCCAGCAG
AGCAACGAGGACCCCCCTACCTTTGGAGCCGGCACCAAGCTGGAACTGAA
GGCTAGCTCCGGAGAGAGCAAGTACGCCCTCCCTGCCCCCCTTGCCCTG
CCCCCGAGTTCCTGGGCGGACCCAGCGTGTTCCTGTTCCCCCCAAGCCC
AAGGACACCCTGATGATCAGCCGGACCCCCGAGGTGACCTGTGTGGTGGT
GGACGTGTCCCAGGAGGACCCCGAGGTCCAGTTCAACTGGTACGTGGACG
GCGTGGAGGTGCACAACGCCAAGACCAAGCCCCGGGAGGAGCAGTTCAAT
AGCACCTACCGGGTGGTGTCCGTGCTGACCGTGCTGCACCAGGACTGGCT
GAACGGCAAGGAATACAAGTGTAAGGTGTCCAACAAGGGCCTGCCCAGCA
GCATCGAGAAACCATCAGCAAGGCCAAGGGCCAGCCTCGGGAGCCCCAG
GTGTACACCCTGCCCCCTAGCCAAGAGGAGATGACCAAGAACCAGGTGTC
CCTGACCTGCCTGGTGAAGGGCTTCTACCCCAGCGACATCGCCGTGGAGT
GGGAGAGCAACGGCCAGCCCGAGAACAACTACAAGACCACCCCCCCTGTG
CTGGACAGCGACGGCAGCTTCTTCCTGTACAGCCGGCTGACCGTGGACAA
GAGCCGGTGGCAGGAGGGCAACGTCTTTAGCTGCTCCGTGATGCACGAGG CCCTGCACAACCACTACACCCAGAAGAGCCTGAGCCTGTCCCTGGGCAAG
ATGGATATCTACATCTGGGCGCCCTTGGCCGGGACTTGTGGGGTCCTTCT
CCTGTCACTGGTTATCACCCTTTACTGCAAACGGGGCAGAAAGAAACTCC
TGTATATATTCAAACAACCATTTATGAGACCAGTACAAACTACTCAAGAG
GAAGATGGCTGTAGCTGCCGATTTCCAGAAGAAGAAGGAGGATGTGA
ACTGAGAGTGAAGTTCAGCAGGAGCGCAGACGCCCCCGCGTACAAGCAGG
GCCAGAACCAGCTCTATAACGAGCTCAATCTAGGACGAAGAGAGGAGTAC
GATGTTTTGGACAAGAGACGTGGCCGGGACCCTGAGATGGGGGGAAAGCC
GAGAAGGAAGAACCCTCAGGAAGGCCTGTACAATGAACTGCAGAAAGAT
AAGATGGCGGAGGCCTACAGTGAGATTGGGATGAAAGGCGAGCGCCGGAG
GGGCAAGGGGCACGATGGCCTTTACCAGGGTCTCAGTACAGCCACCAAGG
ACACCTACGACGCCCTTCACATGCAGGCCCTGCCCCCTCGC CD123 CAR 1176 (amino acid sequence)
(SEQ ID NO: 115)
MALPVTALLLPLALLLHAARPGSDVQITQSPSYLAASPGETITINCRASK
SISKDLAWYQEKPGKTNKLLIYSGSTLQSGIPSRFSGSGSGTDFTLTISS
LEPEDFAMYYCQQHNKYPYTFGGGTKLEIKGGGGSGGGGSGGGGSQVQLQ
QPGAELVRPGASVKLSCKASGYTFTSYWMNWVKQRPDQGLEWIGRIDPYD
SETHYNQKFKDKAILTVDKSSSTAYMQLSSLTSEDSAVYYCARGNWDDYW
GQGTTLTVSSASSGTTTPAPRPPTPAPTIASQPLSLRPEACRPAAGGAVH
TRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPR CD123 CAR 1176 (nucleotide sequence)
(SEQ ID NO: 116)
ATGGCCCTGCCTGTGACAGCCCTGCTGCTGCCTCTGGCTCTGCTGCTGCA
CGCCGCTAGACCCGGATCCGACGTGCAGATCACACAGAGCCCTAGCTACC
TGGCCGCCAGCCCTGGCGAGACAATCACCATCAACTGCCGGGCCAGCAAG
AGCATCAGCAAGGACCTGGCCTGGTATCAGGAAAAGCCCGGCAAGACCAA
CAAGCTGCTGATCTACAGCGGCAGCACCCTGCAGAGCGGCATCCCCAGCA
GATTTTCCGGCAGCGGCTCCGGCACCGACTTCACCCTGACAATCAGCAGC
CTGGAACCCGAGGACTTCGCCATGTACTACTGCCAGCAGCACAACAAGTA
CCCCTACACCTTCGGCGGAGGCACCAAGCTGGAAATCAAGGGCGGAGGCG
GATCTGGCGGCGGAGGAAGTTCTGGCGGAGGATCTCAGGTGCAGCTGCAG
CAGCCAGGCGCTGAACTCGTGCGGCCTGGCGCTTCTGTGAAGCTGAGCTG
TAAAGCCAGCGGCTACACCTTTACCAGCTACTGGATGAACTGGGTCAAGC
AGCGGCCCGACCAGGGCCTGGAGTGGATCGGCAGAATCGACCCCTACGAC
AGCGAGACACTACAACCAGAAGTTCAAGGACAAGGCCATCCTGACCGT
GGACAAGAGCAGCTCCACCGCCTACATGCAGCTGTCCAGCCTGACCAGCG
AGGACAGCGCCGTGTACTATTGCGCCAGGGGCAACTGGGACGACTACTGG
GGCCAGGGCACAACCCTGACAGTGTCCTCTGCTAGCTCCGGAACCACGAC
GCCAGCGCCGCGACCACCAACACCGGCGCCCACCATCGCGTCGCAGCCCC TGTCCTGCGCCCAGAGGCGTGCCGGCCAGCGGCGGGGGCGCAGTGCAC
ACGAGGGGGCTGGACTTCGCCTGTGATATCTACATCTGGGCGCCCTTGGC
CGGGACTTGTGGGGTCCTTCTCCTGTCACTGGTTATCACCCTTTACTGCA
AACGGGGCAGAAAGAAACTCCTGTATATATTCAAACAACCATTTATGAGA
CCAGTACAAACTACTCAAGAGGAAGATGGCTGTAGCTGCCGATTTCCAGA
AGAAGAAGAAGGAGGATGTGAACTGAGAGTGAAGTTCAGCAGGAGCGCAG
ACGCCCCGCGTACAAGCAGGGCCAGAACCAGCTCTATAACGAGCTCAAT
CTAGGACGAAGAGAGGAGTACGATGTTTTGGACAAGAGACGTGGCCGGGA
CCCTGAGATGGGGGGAAAGCCGAGAAGGAAGAACCCTCAGGAAGGCCTGT
ACAATGAACTGCAGAAAGATAAGATGGCGGAGGCCTACAGTGAGATTGGG
ATGAAAGGCGAGCGCCGGAGGGGCAAGGGGCACGATGGCCTTTACCAGGG
TCTCAGTACAGCCACCAAGGACACCTACGACGCCCTTCACATGCAGGCCC
TGCCCCCTCGC CD123 CAR 1177 (amino acid sequence)
(SEQ ID NO: 117)
MALPVTALLLPLALLLHAARPGSDVQITQSPSYLAASPGETITINCRASK
SISKDLAWYQEKPGKTNKLLIYSGSTLQSGIPSRFSGSGSGTDFTLTISS
LEPEDFAMYYCQQHNKYPYTFGGGTKLEIKGGGGSGGGGSGGGGSQVQLQ
QPGAELVRPGASVKLSCKASGYTFTSYWMNWVKQRPDQGLEWIGRIDPYD
SETHYNQKFKDKAILTVDKSSSTAYMQLSSLTSEDSAVYYCARGNWDDYW
GQGTTLTVSSASSGESKYGPPCPPCPAPEFLGGPSVFLFPPKPKDTLMIS
RTPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPS
QEEMTKNQVSLTCLVKGFYPSDIAVEWESNGQPENNYKTTPPVLDSDGSF
FLYSRLTVDKSRWQEGNVFSCSVMHEALHNHYTQKSLSLSLGKMDIYIWA
PLAGTCGVLLLSLVITLYCKRGRKKLLYIFKQPFMRPVQTTQEEDGCSCR
FPEEEEGGCELRVKFSRSADAPAYKQGQNQLYNELNLGRREEYDVLDKRR
GRDPEMGGKPRRKNPQEGLYNELQKDKMAEAYSEIGMKGERRRGKGHDGL
YQGLSTATKDTYDALHMQALPPR CD123 CAR 1177 (nucleotide sequence)
(SEQ ID NO: 118)
ATGGCCCTGCCTGTGACAGCCCTGCTGCTGCCTCTGGCTCTGCTGCTGCA
CGCCGCTAGACCCGGATCCGACGTGCAGATCACACAGAGCCCTAGCTACC
TGGCCGCCAGCCCTGGCGAGACAATCACCATCAACTGCCGGGCCAGCAAG
AGCATCAGCAAGGACCTGGCCTGGTATCAGGAAAAGCCCGGCAAGACCAA
CAAGCTGCTGATCTACAGCGGCAGCACCCTGCAGAGCGGCATCCCCAGCA
GATTTTCCGGCAGCGGCTCCGGCACCGACTTCACCCTGACAATCAGCAGC
CTGGAACCCGAGGACTTCGCCATGTACTACTGCCAGCAGCACAACAAGTA
CCCCTACACCTTCGGCGGAGGCACCAAGCTGGAAATCAAGGGCGGAGGCG
GATCTGGCGGCGGAGGAAGTTCTGGCGGAGGATCTCAGGTGCAGCTGCAG
CAGCCAGGCGCTGAACTCGTCGGCCTGGCGCTTCTGTGAAGCTGAGCTG
TAAAGCCAGCGGCTACACCTTTACCAGCTACTGGATGAACTGGGTCAAGC
AGCGGCCCGACCAGGGCCTGGAGTGGATCGGCAGAATCGACCCCTACGAC AGCGAGACACACTACAACCAGAAGTTCAAGGACAAGGCCATCCTGACCGT
GGACAAGAGCAGCTCCACCGCCTACATGCAGCTGTCCAGCCTGACCAGCG
AGGACAGCGCCGTGTACTATTGCGCCAGGGGCAACTGGGACGACTACTGG
GGCCAGGGCACAACCCTGACAGTGTCCTCTGCTAGCTCCGGAGAGAGCAA
GTACGGCCCTCCCTGCCCCCCTTGCCCTGCCCCCGAGTTCCTGGGCGGAC
CCAGCGTGTTCCTGTTCCCCCCCAAGCCCAAGGACACCCTGATGATCAGC
CGGACCCCCGAGGTGACCTGTGTGGTGGTGGACGTGTCCCAGGAGGACCC
CGAGGTCCAGTTCAACTGGTACGTGGACGGCGTGGAGGTGCACAACGCCA
AGACCAAGCCCCGGGAGGAGCAGTTCAATAGCACCTACCGGGTGGTGTCC
GTGCTGACCGTGCTGCACCAGGACTGGCTGAACGGCAAGGAATACAAGTG
TAAGGTGTCCAACAAGGGCCTGCCCAGCAGCATCGAGAAAACCATCAGCA
AGGCCAAGGGCCAGCCTCGGGAGCCCCAGGTGTACACCCTGCCCCCTAGC
CAAGAGGAGATGACCAAGAACCAGGTGTCCCTGACCTGCCTGGTGAAGGG
CTTCTACCCCAGCGACATCGCCGTGGAGTGGGAGAGCAACGGCCAGCCCG
AGAACAACTACAAGACCACCCCCCCTGTGCTGGACAGCGACGGCAGCTTC
TTCCTGTACAGCCGGCTGACCGTGGACAAGAGCCGGTGGCAGGAGGGCAA
CGTCTTTAGCTGCTCCGTGATGCACGAGGCCCTGCACAACCACTACACCC
AGAAGAGCCTGAGCCTGTCCCTGGGCAAGATGGATATCTACATCTGGGCG
CCCTTGGCCGGGACTTGTGGGGTCCTTCTCCTGTCACTGGTTATCACCCT
TTACTGCAAACGGGGCAGAAAGAAACTCCTGTATATATTCAAACAACCAT
TTATGAGACCAGTACAAACTACTCAAGAGGAAGATGGCTGTAGCTGCCGA
TTTCCAGAAGAAGAAGAAGGAGGATGTGAACTGAGAGTGAAGTTCAGCAG
GAGCGCAGACGCCCCCGCGTACAAGCAGGGCCAGAACCAGCTCTATAACG
AGCTCAATCTAGGACGAAGAGAGGAGTACGATGTTTTGGACAAGAGACGT
GGCCGGGACCCTGAGATGGGGGGAAAGCCGAGAAGGAAGAACCCTCAGGA
AGGCCTGTACAATGAACTGCAGAAAGATAAGATGGCGGAGGCCTACAGTG
AGATTGGGATGAAAGGCGAGCGCCGGAGGGGCAAGGGGCACGATGGCCTT
TACCAGGGTCTCAGTACAGCCACCAAGGACACCTACGACGCCCTTCACAT
GCAGGCCCTGCCCCCTCGC CD123 CAR 1178 (amino acid sequence)
(SEQ ID NO: 119)
MALPVTALLLPLALLLHAARPGSQVQLQQPGAELVRPGASVKLSCKASGY
TFTSYWMNWVKQRPDQGLEWIGRIDPYDSETHYNQKFKDKAILTVDKSSS
TAYMQLSSLTSEDSAVYYCARGNWDDYWGQGTTLTVSSGGGGSGGGGSSG
GGSDVQITQSPSYLAASPGETITINCRASKSISKDLAWYQEKPGKTNKLL
IYSGSTLQSGIPSRFSGSGSGTDFTLTISSLEPEDFAMYYCQQHNKYPYT
FGGGTKLEIKASSGTTTPAPRPPTPAPTIASQPLSLRPEACRPAAGGAVH
TRGLDFACDIYIWAPLAGTCGVLLLSLVITLYCKRGRKKLLYIFKQPFMR
PVQTTQEEDGCSCRFPEEEEGGCELRVKFSRSADAPAYKQGQNQLYNELN
LGRREEYDVLDKRRGRDPEMGGKPRRKNPQEGLYNELQKDKMAEAYSEIG
MKGERRRGKGHDGLYQGLSTATKDTYDALHMQALPPR CD123 CAR 1178 (nucleotide sequence)
(SEQ ID NO: 120)
ATGGCCCTGCCTGTGACAGCCCTGCTGCTGCCTCTGGCTCTGCTGCTGCA

CGCCGCTAGACCTGGATCCCAGGTGCAGCTGCAGCAGCCTGGCGCTGAAC

TCGTGCGGCCAGGCGCTTCTGTGAAGCTGAGCTGTAAAGCCAGCGGCTAC

ACCTTCACCAGCTACTGGATGAACTGGGTCAAGCAGCGGCCCGACCAGGG

CCTGGAGTGGATCGGCAGAATCGACCCCTACGACAGCGAGACACACTACA

ACCAGAAGTTCAAGGACAAGGCCATCCTGACCGTGGACAAGAGCAGCAGC

ACCGCCTACATGCAGCTGTCCAGCCTGACCAGCGAGGACAGCGCCGTGTA

CTACTGCGCCAGGGGCAACTGGGACGACTATTGGGGCCAGGGCACCACCC

TGACAGTGTCTAGCGGAGGCGGAGGATCTGGCGGCGGAGGAAGTTCTGGC

GGAGGCTCCGACGTGCAGATCACCCAGAGCCCTAGCTACCTGGCCGCCTC

TCCTGGCGAGACAATCACCATCAACTGCCGGGCCAGCAAGAGCATCTCCA

AGGACCTGGCCTGGTATCAGGAAAAGCCCGGCAAGACCAACAAGCTGCTG

ATCTACAGCGGCAGCACCCTGCAGAGCGGCATCCCCAGCAGATTTTCCGG

CAGCGGCTCCGGCACCGACTTCACCCTGACCATCAGCTCCCTGGAACCCG

AGGACTTTGCCATGTACTATTGCCAGCAGCACAACAAGTACCCTTACACC

TTCGGCGGAGGCACCAAGCTGGAAATCAAGGCCAGCTCCGGAACCACGAC

GCCAGCGCCGCGACCACCAACACCGGCGCCCACCATCGCGTCGCAGCCCC

TGTCCCTGCGCCCAGAGGCGTGCCGGCCAGCGGCGGGGGCGCAGTGCAC

ACGAGGGGGCTGGACTTCGCCTGTGATATCTACATCTGGGCGCCCTTGGC

CGGGACTTGTGGGGTCCTTCTCCTGTCACTGGTTATCACCCTTTACTGCA

AACGGGGCAGAAAGAAACTCCTGTATATATTCAAACAACCATTTATGAGA

CCAGTACAAACTACTCAAGAGGAAGATGGCTGTAGCTGCCGATTTCCAGA

AGAAGAAGAAGGAGGATGTGAACTGAGAGTGAAGTTCAGCAGGAGCGCAG

ACGCCCCCGCGTACAAGCAGGGCCAGAACCAGCTCTATAACGAGCTCAAT

CTAGGACGAAGAGAGGAGTACGATGTTTTGGACAAGAGACGTGGCCGGGA

CCCTGAGATGGGGGGAAAGCCGAGAAGGAAGAACCCTCAGGAAGGCCTGT

ACAATGAACTGCAGAAAGATAAGATGGCGGAGGCCTACAGTGAGATTGGG

ATGAAAGGCGAGCGCCGGAGGGGCAAGGGGCACGATGGCCTTTACCAGGG

TCTCAGTACAGCCACCAAGGACACCTACGACGCCCTTCACATGCAGGCCC

TGCCCCCTCGC

CD123 CAR 1179 (amino acid sequence)
(SEQ ID NO: 121)
MALPVTALLLPLALLLHAARPGSQVQLQQPGAELVRPGASVKLSCKASGY

TFTSYWMNWVKQRPDQGLEWIGRIDPYDSETHYNQKFKDKAILTVDKSSS

TAYMQLSSLTSEDSAVYYCARGNWDDYWGQGTTLTVSSGGGGSGGGGSSG

GGSDVQITQSPSYLAASPGETITINCRASKSISKDLAWYQEKPGKTNKLL

IYSGSTLQSGIPSRFSGSGSGTDFTLTISSLEPEDFAMYYCQQHNKYPYT

FGGGTKLEIKASSGESKYGPPCPPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLGKMDIYIWA

PLAGTCGVLLLSLVITLYCKRGRKKLLYIFKQPFMRPVQTTQEEDGCSCR

FPEEEEGGCELRVKFSRSADAPAYKQGQNQLYNELNLGRREEYDVLDKRR

GRDPEMGGKPRRKNPQEGLYNELQKDKMAEAYSEIGMKGERRRGKGHDGL

YQGLSTATKDTYDALHMQALPPR

CD123 CAR 1179 (nucleotide sequence)
(SEQ ID NO: 91)
ATGGCCCTGCCTGTGACAGCCCTGCTGCTGCCTCTGGCTCTGCTGCTGCA

CGCCGCTAGACCTGGATCCCAGGTGCAGCTGCAGCAGCCTGGCGCTGAAC

TCGTGCGGCCAGGCGCTTCTGTGAAGCTGAGCTGTAAAGCCAGCGGCTAC

ACCTTCACCAGCTACTGGATGAACTGGGTCAAGCAGCGGCCCGACCAGGG

CCTGGAGTGGATCGGCAGAATCGACCCCTACGACAGCGAGACACACTACA

ACCAGAAGTTCAAGGACAAGGCCATCCTGACCGTGGACAAGAGCAGCAGC

ACCGCCTACATGCAGCTGTCCAGCCTGACCAGCGAGGACAGCGCCGTGTA

CTACTGCGCCAGGGGCAACTGGGACGACTATTGGGGCCAGGGCACCACCC

TGACAGTGTCTAGCGGAGGCGGAGGATCTGGCGGCGGAGGAAGTTCTGGC

GGAGGCTCCGACGTGCAGATCACCCAGAGCCCTAGCTACCTGGCCGCCTC

TCCTGGCGAGACAATCACCATCAACTGCCGGGCCAGCAAGAGCATCTCCA

AGGACCTGGCCTGGTATCAGGAAAAGCCCGGCAAGACCAACAAGCTGCTG

ATCTACAGCGGCAGCACCCTGCAGAGCGGCATCCCCAGCAGATTTTCCGG

CAGCGGCTCCGGCACCGACTTCACCCTGACCATCAGCTCCCTGGAACCCG

AGGACTTTGCCATGTACTATTGCCAGCAGCACAACAAGTACCCTTACACC

TTCGGCGGAGGCACCAAGCTGGAAATCAAGGCCAGCTCCGGAGAGAGCAA

GTACGGCCCTCCCTGCCCCCCTTGCCCTGCCCCCGAGTTCCTGGGCGGAC

CCAGCGTGTTCCTGTTCCCCCCCAAGCCCAAGGACACCCTGATGATCAGC

CGGACCCCCGAGGTGACCTGTGTGGTGGTGGACGTGTCCCAGGAGGACCC

CGAGGTCCAGTTCAACTGGTACGTGGACGGCGTGGAGGTGCACAACGCCA

AGACCAAGCCCCGGGAGGAGCAGTTCAATAGCACCTACCGGGTGGTGTCC

GTGCTGACCGTGCTGCACCAGGACTGGCTGAACGGCAAGGAATACAAGTG

TAAGGTGTCCAACAAGGGCCTGCCCAGCAGCATCGAGAAAACCATCAGCA

AGGCCAAGGGCCAGCCTCGGGAGCCCCAGGTGTACACCCTGCCCCCTAGC

CAAGAGGAGATGACCAAGAACCAGGTGTCCCTGACCTGCCTGGTGAAGGG

CTTCTACCCCAGCGACATCGCCGTGGAGTGGGAGAGCAACGGCCAGCCCG

AGAACAACTACAAGACCACCCCCCCTGTGCTGGACAGCGACGGCAGCTTC

TTCCTGTACAGCCGGCTGACCGTGGACAAGAGCCGGTGGCAGGAGGGCAA

CGTCTTTAGCTGCTCCGTGATGCACGAGGCCCTGCACAACCACTACACCC

AGAAGAGCCTGAGCCTGTCCCTGGGCAAGATGGATATCTACATCTGGGCG

CCCTTGGCCGGGACTTGTGGGGTCCTTCTCCTGTCACTGGTTATCACCCT

TTACTGCAAACGGGGCAGAAAGAAACTCCTGTATATATTCAAACAACCAT

TTATGAGACCAGTACAAACTACTCAAGAGGAAGATGGCTGTAGCTGCCGA

TTTCCAGAAGAAGAAGAAGGAGGATGTGAACTGAGAGTGAAGTTCAGCAG

GAGCGCAGACGCCCCCGCGTACAAGCAGGGCCAGAACCAGCTCTATAACG

```
-continued
AGCTCAATCTAGGACGAAGAGAGGAGTACGATGTTTTGGACAAGAGACGT

GGCCGGGACCCTGAGATGGGGGGAAAGCCGAGAAGGAAGAACCCTCAGGA

AGGCCTGTACAATGAACTGCAGAAAGATAAGATGGCGGAGGCCTACAGTG

AGATTGGGATGAAAGGCGAGCGCCGGAGGGGCAAGGGGCACGATGGCCTT

TACCAGGGTCTCAGTACAGCCACCAAGGACACCTACGACGCCCTTCACAT

GCAGGCCCTGCCCCCTCGC
```

Example 4

Predicted CDR Designations for the CD123CAR

The predicted CDR designations for the CD123 CAR of SEQ ID NO:1, discussed in Example 3, under Kabat are as follows:

```
VH:
                                          (SEQ ID NO: 15)
QIQLVQSGPELKKPGETVKISCKASGYIFTNYGMNWVKQAPGKSFKWMGW

INTYTGESTYSADFKGRFAFSLETSASTAYLHINDLKNEDTATYFCARSG

GYDPMDYWGQGTSVTVSS;
``` wherein CDR1 is NYGMN (SEQ ID NO: 16), CDR2 is WINTYTGESTYSADFKG (SEQ ID NO: 17), and CDR3 is SGGYDPMDY (SEQ ID NO: 18).

```
VL:
                                          (SEQ ID NO: 19)
DIVLTQSPASLAVSLGQRATISCRASESVDNYGNTFMHWYQQKPGQPPKL

LIYRASNLESGIPARFSGSGSRTDFTLTINPVEADDVATYYCQQSNEDPP

TFGAGTKLELK;
``` wherein CDR1 is RASESVDNYGNTFMH (SEQ ID NO: 20), CDR2 is RASNLES (SEQ ID NO: 21), and CDR3 is QQSNEDPPT (SEQ ID NO: 22).

The predicted CDR designations for the CD123 CAR under Chothia are as follows:

```
VH:
                                          (SEQ ID NO: 15)
QIQLVQSGPELKKPGETVKISCKASGYIFTNYGMNWVKQAPGKSFKWMGW

INTYTGESTYSADFKGRFAFSLETSASTAYLHINDLKNEDTATYFCARSG

GYDPMDYWGQGTSVTVSS;
``` wherein CDR1 is GYIFTNY (SEQ ID NO: 24), CDR2 is NTYTGE (SEQ ID NO: 25), and CDR3 is SGGYDPMDY (SEQ ID NO: 26).

```
VL:
                                          (SEQ ID NO: 19)
DIVLTQSPASLAVSLGQRATISCRASESVDNYGNTFMHWYQQKPGQPPKL

LIYRASNLESGIPARFSGSGSRTDFTLTINPVEADDVATYYCQQSNEDPP

TFGAGTKLELK;
``` wherein CDR1 is SESVDNYGNTF (SEQ ID NO: 28), CDR2 is RAS (SEQ ID NO: 29), and CDR3 is SNEDPP (SEQ ID NO: 30).

The predicted CDR designations for the CD123 CAR of SEQ ID NO:100, disclosed in Example 3, under Kabat are as follows:
- VH CDR1 is SYWMN (SEQ ID NO:84), CDR2 is RIDPYDSETHYNQKFKD (SEQ ID NO:85), and CDR3 is GNWDDY (SEQ ID NO:86).
- VL CDR1 is RASKSISKDLA (SEQ ID NO:87, CDR2 is SGSTLQS (SEQ ID NO:88), and CDR3 is QQHNKYPYT (SEQ ID NO:89).

Example 5

Humanization of Murine Anti-CD123 Antibody

Humanization of murine CD123 antibody may be desired for the clinical setting, where the mouse-specific residues may induce a human-anti-mouse antigen (HAMA) response in patients who receive treatment with T cells transduced with the murine CAR construct. Humanization was accomplished by grafting CDR regions from the murine CD123 antibody of SEQ ID NO:2 onto human germline acceptor frameworks VH1_1-03 or VH7_7-4.1 as well as VK3_L6 or VK4_B3 (vBASE database). In addition to the CDR regions, several framework residues, i.e. VK3 #68, #83, VK4 #4, #68, VH1 #2, #71 and VH7 #2, thought to support the structural integrity of the CDR regions were retained from the murine sequence. Further, the human J elements JH6 and JK2 were used for the heavy and light chain, respectively. The resulting amino acid sequences of the humanized antibody were designated VK3_L6/Hz1 (SEQ ID NO:31) and VK4_B3/Hz1 (SEQ ID NO:32) for the light-chains and VH1_1-03/Hz1 (SEQ ID NO:33), and VH7_4.1/Hz1 (SEQ ID NO:34) for the heavy chains and are shown in FIGS. 26A-26B and 27A-27B. The residue numbering follows Kabat (Kabat E. A. et al, 1991, supra). For CDR definitions, both Kabat as well as Chothia et al, 1987 supra) were used. Frame work residues retained from mouse CD123 are shown shaded. CDR residues are underlined. PTM motif in framework VH7_7-4.1 at position 82a/82b (boxed, original framework sequence was CS) was mutated to NA in the final construct.

Based on the humanized light and heavy chain sequences as shown in FIGS. 26A-26B and 27A-27B, a total of 8 framework combinations were used to generate soluble scFv's for further validation. The order in which the VL and VH domains appear in the scFv was varied (i.e., VL-VH, or VH-VL orientation), and four copies of the "$G_4S$" (SEQ ID NO: 35) subunit, in which each subunit comprises the sequence GGGGS (SEQ ID NO:35) was used to connect the frameworks.

Cloning:

DNA sequences coding for mouse and humanized VL and VH domains were obtained, and the codons for the constructs were optimized for expression in human cells.

Sequences coding for VL and VH domain were subcloned into expression vectors suitable for secretion in mammalian cells. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

TABLE 1

| Name | SEQ ID NO: | Sequence |
|---|---|---|
| | | CAR 1 |
| CAR1 scFv domain | 36 | Divltqspdslavslgeratincrasesvdnygntfmhwyqqkpgqppklliyrasnlesg vpdrfsgsgsrtdftltisslqaedvavyycqqsnedpptfgqgtkleikggggsggggsgg ggsggggsqiqlvqsgselkkpgasvkvsckasgyiftnygmnwvrqapgqglewmg wintytgestysadfkgrfvfsldtsvstaylqinalkaedtavyycarsggydpmdywgq gttvtvss |
| CAR1 scFv domain nt | 37 | gacatcgtgctgacccaatccccggacagcctcgcagtctcactcggagaacgcgccactat caattgtagggcgtcggagtccgtggacaattacggaaacacccttcatgcactggtaccaaca aaaacctggtcagccacctaagctgctgatctaccgcgcctcgaatctggaatcaggagtgcc ggacagattctcggggtccggctcccggacggatttcactttgaccatctcgtcacttcaagct gaggacgtcgccggtgtactactgccagcagagcaacgaagatccacccacgttcggacaag gcaccaagctggagattaaaggaggcggaggctccggtggaggaggatcggaggaggc ggctccggcggaggtggatcgcagattcagctggtgcagtcgggttcagaattgaagaaacc aggagcctcggtgaaggtcagctgcaaggcatcagggtacatcttcactaactacggcatga actgggtgcgccaggctccgggacaggggctggagtggatggggatcaacacttacac cggggagtcaacttactcggctgactttaagggccggtttgtgttctccctcgacactagcgtga gcaccgcctatcttcaaatcaacgccctcaaggcggaagataccgccgtctactactgcgcaa gatccggtgggtacgatccgatggattattggggacagggaaccactgtcaccgtgagcagc |
| CAR1 Soluble scFv - nt | 38 | atggccctccctgtcaccgccctgctgcttccgctggctcttctgctccacgccgctcggcccg acatcgtgctgacccaatccccggacagcctcgcagtctcactcggagaacgcgccactatc aattgtagggcgtcggagtccgtggacaattacggaaacacccttcatgcactggtaccaacaa aaacctggtcagccacctaagctgctgatctaccgcgcctcgaatctggaatcaggagtgccg gacagattctcggggtccggctcccggacggatttcactttgaccatctcgtcacttcaagctga ggacgtcgcggtgtactactgccagcagagcaacgaagatccacccacgttcggacaaggc accaagctggagattaaaggaggcggaggctccggtggaggaggatcggaggaggcgg ctccggcggaggtggatcgcagattcagctggtgcagtcgggttcagaattgaagaaaccag gagcctcggtgaaggtcagctgcaaggcatcagggtacatcttcactaactacggcatgaact gggtgcgccaggctccgggacaggggctggagtggatgggatggatcaacacttacaccg gggagtcaacttactcggctgactttaagggccggtttgtgttctccctcgacactagcgtgagc accgcctatcttcaaatcaacgccctcaaggcggaagataccgccgtctactactgcgcaaga tccggtgggtacgatccgatggattattggggacagggaaccactgtcaccgtgagcagcgg ctcgcaccaccatcaccatcatcatcaccac |
| CAR1 Soluble scFv - aa | 39 | malpvtalllplallllhaarpdivltqspdslayslgeratincrasesvdnygntfmhwyqq kpgqppklliyrasnlesgvpdrfsgsgsrtdftltisslqaedvavyycqqsnedpptfgqg tkleikggggsggggsggggsggggsqiqlvqsgselkkpgasvkvsckasgyiftnyg mnwvrqapgqglewmgwintytgestysadfkgrfvfsldtsvstaylqinalkaedtav yycarsggydpmdywgqgttvtvssgshhhhhhhh |
| CAR 1 - Full - nt lentivirus | 40 | atggccctccctgtcaccgccctgctgcttccgctggctcttctgctccacgccgctcggcccg acatcgtgctgacccaatccccggacagcctcgcagtctcactcggagaacgcgccactatc aattgtagggcgtcggagtccgtggacaattacggaaacacccttcatgcactggtaccaacaa aaacctggtcagccacctaagctgctgatctaccgcgcctcgaatctggaatcaggagtgccg gacagattctcggggtccggctcccggacggatttcactttgaccatctcgtcacttcaagctga ggacgtcgcggtgtactactgccagcagagcaacgaagatccacccacgttcggacaaggc accaagctggagattaaaggaggcggaggctccggtggaggaggatcggaggaggcgg ctccggcggaggtggatcgcagattcagctggtgcagtcgggttcagaattgaagaaaccag gagcctcggtgaaggtcagctgcaaggcatcagggtacatcttcactaactacggcatgaact gggtgcgccaggctccgggacaggggctggagtggatgggatggatcaacacttacaccg gggagtcaacttactcggctgactttaagggccggtttgtgttctccctcgacactagcgtgagc accgcctatcttcaaatcaacgccctcaaggcggaagataccgccgtctactactgcgcaaga tccggtgggtacgatccgatggattattggggacagggaaccactgtcaccgtgagcagcac cactacccccagcaccgaggccacccaccccggctcctaccatcgcctcccagcctctgtccc tgcgtccggaggcatgtagacccgcagctggtggccgtgcatacccggggtcttgacttc gcctgcgatatctacatttgggcccctctggctggtacttgcggggtcctgctgctttcactcgtg atcactctttactgtaagcgcggtcggaagaagcttgctgatactcttaagcaaccccttcatgag gcctgtgcagactactcaagaggaggacggctgttcatgccggttcccagaggaggaggaa ggcggctgcgaactgcgcgtgaaattcagccgcagcgcagatgctcccagcctacaagcagg ggcagaaccagctctacaacgaactcaatcttggtcggagagaggagtacgacgtgctggac aagcggagaggacgggaccagaaatgggcgggaagccgcgcagaaagaaatccccaag agggcctgtacaacgagctccaaaaggataagatggcagaagcctatagcgagattggtatg aaaggggaacgcagaagaggcaaaggccacgacgactgtaccagggactcagcaccgc caccaaggacacctatgacgctcttcatgcaggccctgccgcctcgg |
| CAR 1 - Full - aa | 41 | Malpvtalllplallllhaarpdivltqspdslavslgeratincrasesvdnygntfmhwyq qkpgqppklliyrasnlesgvpdrfsgsgsrtdftltisslqaedvavyycqqsnedpptfg qgtkleikggggsggggsggggsggggsqiqlvqsgselkkpgasvkvsckasgyiftny gmnwvrqapgqglewmgwintytgestysadfkgrfvfsldtsystaylqinalkaedt avyycarsggydpmdywgqgttvtvssttpaprpptpaptiasqplslrpeacrpaagga vhtrgldfacdiyiwaplagtcgvlllslvitlyckrgrkkllyifkqpfmrpvqttqeedgcs crfpeeeeggcelrvkfsrsadapaykqgqnqlynelnlgrreeydvldkrrgrdpemgg kprrknpqeglynelqkdkmaeayseigmkgerrrgkghdglyqglstatkdtydalhm qalppr |

TABLE 1-continued

| Name | SEQ ID NO: | Sequence |
|---|---|---|
| CAR2 | | |
| CAR2 scFv domain | 42 | divltqspdslavslgeratincrasesvdnygntfmhwyqqkpgqppklliyrasnlesgv pdrfsgsgsrtdftltisslqaedvavyycqqsnedpptfgqgtkleikggggsggggsgggg gsggggsqiqlvqsgaevkkpgasvkvsckasgyiftnygmnwvrqapgqrlewmg wintytgestysadfkgrvtitldtsastaymelsslrsedtavyycarsggydpmdywgq gttvtvss |
| CAR2 scFv domain - nt | 43 | gatattgtcctcactcaatcgccggactcactggcggtgtccctcggagagagggcgacgatc aattgccgggcttccgaatccgtcgataactacggaaacacctttatgcactggtaccaacaga agccaggacagccaccaaagctgttgatctaccgcgcttcaaaccttgagtcgggtgtgccg gaccgcttcagcggcagcggttccagaaccgactttacccctcaccatcagctcgctgcaggc cgaagatgtcgccgtctattactgccaacagagcaacgaagatccgcctactttcggacaggg gactaaactggaaatcaagggcggaggaggctcgggtggaggaggatcgggaggaggcg gtccggtggtggcggatcgcaaatccagctggtgcagtccggcgcagaagtgaagaagcc gggagcgtccgtgaaagtgagctgcaaggcctcagggtacatcttcaccaattacggcatga attgggtgcggcaggcaccggacagcgcctggagtggatgggctggatcaacacttacac cggggaaagcacgtactcggccgacttcaaaggacgggtgaccattaccctggatacctcgg cctcaaccgcttacatggagctctcatcacttagatccgaggacactgccgtctactactgtgca aggagcggaggctacgaccctatggactattggggacaaggcactactgtgactgtgtcgtc c |
| CAR2 - Soluble scFv - nt | 44 | atggccctccctgtcaccgccctgctgcttccgctggctcttctgctccacgccgctcggcccg atattgtcctcactcaatcgccggactcactggcggtgtccctcggagagagggcgacgatca attgccgggcttccgaatccgtcgataactacggaaacacctttatgcactggtaccaacagaa gccaggacagccaccaaagctgttgatctaccgcgcttcaaaccttgagtcgggtgtgccgg accgcttcagcggcagcggttccagaaccgactttacccctcaccatcagctcgctgcaggcc gaagatgtcgccgtctattactgccaacagagcaacgaagatccgcctactttcggacagggg actaaactggaaatcaagggcggaggaggctcgggtggaggaggatcgggaggaggcgg tccggtggtggcggatcgcaaatccagctggtgcagtccggcgcagaagtgaagaagccg ggagcgtccgtgaaagtgagctgcaaggcctcagggtacatcttcaccaattacggcatgaat tgggtgcggcaggcaccggacagcgcctggagtggatgggctggatcaacacttacaccg gggaaagcacgtactcggccgacttcaaaggacgggtgaccattaccctggatacctcggcc tcaaccgcttacatggagctctcatcacttagatccgaggacactgccgtctactactgtgcaag gagcggaggctacgaccctatggactattggggacaaggcactactgtgactgtgtcgtccg gctcgcaccaccatcaccatcatcatcaccac |
| CAR2 - Soluble scFv - aa | 45 | malpvtalllplalllhaarpdivltqspdslavslgeratincrasesvdnygntfmhwyqq kpgqppkllyyrasnlesgvpdrfsgsgsrtdftltisslqaedvavyycqqsnedpptfgqg tkleikggggsggggsggggsggggsqiqlvqsgaevkkpgasvkvsckasgyiftnyg mnwvrqapgqrlewmgwintytgestysadfkgrvtitldtsastaymelsslrsedtavy ycarsggydpmdywgqgttvtvssgshhhhhhhh |
| CAR 2 - Full - nt | 46 | atggccctccctgtcaccgccctgctgcttccgctggctcttctgctccacgccgctcggcccg atattgtcctcactcaatcgccggactcactggcggtgtccctcggagagagggcgacgatca attgccgggcttccgaatccgtcgataactacggaaacacctttatgcactggtaccaacagaa gccaggacagccaccaaagctgttgatctaccgcgcttcaaaccttgagtcgggtgtgccgg accgcttcagcggcagcggttccagaaccgactttacccctcaccatcagctcgctgcaggcc gaagatgtcgccgtctattactgccaacagagcaacgaagatccgcctactttcggacagggg actaaactggaaatcaagggcggaggaggctcgggtggaggaggatcgggaggaggcgg tccggtggtggcggatcgcaaatccagctggtgcagtccggcgcagaagtgaagaagccg ggagcgtccgtgaaagtgagctgcaaggcctcagggtacatcttcaccaattacggcatgaat tgggtgcggcaggcaccggacagcgcctggagtggatgggctggatcaacacttacaccg gggaaagcacgtactcggccgacttcaaaggacgggtgaccattaccctggatacctcggcc tcaaccgcttacatggagctctcatcacttagatccgaggacactgccgtctactactgtgcaag gagcggaggctacgaccctatggactattggggacaaggcactactgtgactgtgtcgtccac cactaccccagcaccgaggccacccaccccggctcctaccatcgcctcccagcctctgtccc tgcgtccggaggcatgtagacccgcagctggtggggccgtgcatacccggggtcttgacttc gcctgcgatatctacatttgggcccctctggctggtacttgcggggtcctgctgcttcactcgtg atcactcttactgtaagcgcggtcggaagaagctgctgtacatctttaagcaacccttcatgag gcctgtgcagactactcaagaggaggacggctgttcatgccggttcccagaggaggaa ggcggctgcgaactgcgcgtgaaattcagccgcagcgcagatgctccagcctacaagcagg ggcagaaccagctctacaacgaactcaatcttggtcgagagaggagtacgacgtgctggac aagcggagaggacgggacccagaaatgggcgggaagccgcgcagaaagaatccccaag agggcctgtacaacgagctccaaaaggataagatggcagaagcctatagcgagattggtatg aaagggaacgcagaagaggcaaaggccacgacgactgtaccagggactcagcaccgc caccaaggacacctatgacgctcttcatgcaggccctgccgcctcgg |
| CAR 2 - Full - aa | 47 | Malpvtalllplalllhaarpdivltqspdslavslgeratincrasesvdnygntfmhwyq qkpgqppkllyyrasnlesgvpdrfsgsgsrtdftltisslqaedvavyycqqsnedpptfg qgtkleikggggsggggsggggsggggsqiqlvqsgaevkkpgasvkvsckasgyiftnvgmnwvrqapgqrlewmgwintytgestysadfkgrvtitldtsastaymelsslrsedt avyycarsggydpmdywgqgttvtvsstttpaprppttpaptiasqplslrpeacrpaagga vhtrgldfacdiyiwaplagtcgvlllslvitlyckrgrkklyiifkqpfmrpvqttqeedgcs crfpeeeeggcelrvkfsrsadapaykqgqnqlynelnlgrreeydvldkrrgrdpemgg |

TABLE 1-continued

| Name | SEQ ID NO: | Sequence |
|---|---|---|
| | | kprrknpqeglynelqkdkmaeayseigmkgerrrgkghdglyqglstatkdtydalhmqalppr |

CAR 3

| Name | SEQ ID NO: | Sequence |
|---|---|---|
| CAR3 scFv domain | 48 | Eivltqspatlslspgeratlscrasesvdnygntfmhwyqqkpgqaprlliyrasnlesgiparfsgsgsrtdftltisslepedvavyycqqsnedpptfgqgtkleikggggsggggsggggsqiqlvqsgselkkpgasvkvsckasgyiftnygmnwvrqapgqglewmgwintytgestysadfkgrfvfsldtsvstaylqinalkaedtavyycarsggydpmdywgqgttvtvss |
| CAR3 scFv domain nt | 49 | Gaaattgtgctcacgcaatcacccgccactctgtcgctttccccgggagagcggggccacccctctcctgccgcgcttcggaatcggtcgacaattacggaaatacttttatgcactggtaccaacagaagccagggcaggcgccaaggctgctgatctacagagcctcgaacctcgaaagcggcatccctgcgcggttcagcggtagcggaagccgcaccgatttcaccctgaccatctcatcactggagccggaggatgtggcagtgtactattgtcagcagtcgaacgaggacccgccgactttcgggcaggaaccaagctggaaatcaagggtggaggagggagcggcggaggaggatcggaggagaggcagcggaggcggaggatcgcaaatccaacttgtccagtcgggctccgaactcaaaaagcctggcgcgtccgtgaaggtcagctgcaaagcatcaggatacatcttcactaactacggtatgaattgggtcagacaggctccgggtcagggtctggagtggatgggatggattaacacctacactggggaatcgacttactccgcggacttcaaaggcggttcgtgttttcactggacaccagcgtgtccaccgcttacttgcaaatcaacgccctcaaggccgaggacaccgccgtgtactactgcgcacgctcaggcggatacgatccaatggactactggggacagggcactacggtgactgtgtcctcc |
| CAR 3 - Soluble scFv - nt | 50 | atggccctccctgtcaccgccctgctgcttccgctggctcttctgctccacgccgctcggcccgaaattgtgctcacgcaatcacccgccactctgtcgctttccccgggagagcggggccacccctctcctgccgcgcttcggaatcggtcgacaattacggaaatacttttatgcactggtaccaacagaagccagggcaggcgccaaggctgctgatctacagagcctcgaacctcgaaagcggcatccctgcgcggttcagcggtagcggaagccgcaccgatttcaccctgaccatctcatcactggagccggaggatgtggcagtgtactattgtcagcagtcgaacgaggacccgccgactttcgggcaggaaccaagctggaaatcaagggtggaggagggagcggcggaggaggatcggaggagaggcagcggaggcggaggatcgcaaatccaacttgtccagtcgggctccgaactcaaaaagcctggcgcgtccgtgaaggtcagctgcaaagcatcaggatacatcttcactaactacggtatgaattgggtcagacaggctccgggtcagggtctggagtggatgggatggattaacacctacactggggaatcgacttactccgcggacttcaaaggcggttcgtgttttcactggacaccagcgtgtccaccgcttacttgcaaatcaacgccctcaaggccgaggacaccgccgtgtactactgcgcacgctcaggcggatacgatccaatggactactggggacagggcactacggtgactgtgtcctccggctcgcaccaccatcaccatcatcatcaccac |
| CAR 3 - Soluble scFv - aa | 51 | malpvtalllplalllhaarpeivltqspatlslspgeratlscrasesvdnygntfmhwyqqkpgqaprlliyrasnlesgiparfsgsgsrtdftltisslepedvavyycqqsnedpptfgqgtkleikggggsggggsggggsggggsqiqlvqsgselkkpgasvkvsckasgyiftnygmnwvrqapgqglewmgwintytgestysadfkgrfvfsldtsvstaylqinalkaedtavyycarsggydpmdywgqgttvtvssgshhhhhhhh |
| CAR 3 - Full - nt | 52 | atggccctccctgtcaccgccctgctgcttccgctggctcttctgctccacgccgctcggcccgaaattgtgctcacgcaatcacccgccactctgtcgctttccccgggagagcggggccacccctctcctgccgcgcttcggaatcggtcgacaattacggaaatacttttatgcactggtaccaacagaagccagggcaggcgccaaggctgctgatctacagagcctcgaacctcgaaagcggcatccctgcgcggttcagcggtagcggaagccgcaccgatttcaccctgaccatctcatcactggagccggaggatgtggcagtgtactattgtcagcagtcgaacgaggacccgccgactttcgggcaggaaccaagctggaaatcaagggtggaggagggagcggcggaggaggatcggaggagaggcagcggaggcggaggatcgcaaatccaacttgtccagtcgggctccgaactcaaaaagcctggcgcgtccgtgaaggtcagctgcaaagcatcaggatacatcttcactaactacggtatgaattgggtcagacaggctccgggtcagggtctggagtggatgggatggattaacacctacactggggaatcgacttactccgcggacttcaaaggcggttcgtgttttcactggacaccagcgtgtccaccgcttacttgcaaatcaacgccctcaaggccgaggacaccgccgtgtactactgcgcacgctcaggcggatacgatccaatggactactggggacagggcactacggtgactgtgtcctccaccactacccccagcaccgaggccaccccccggcctctaccatcgctcccagcctctgtccctgcgtccgaggcatgtagacccgcagctggtggggccgtgcatacccggggtcttgacttcgcctgcgatatctacatttgggcccctctggctggtacttgcggggtcctgctgctttcactcgtgatcactctttactgtaagcgcgttcggaagaagctgttcatcttccgggctgctggctgtgttaaccccttcattgaggcctgtgcagactactcaagaggaggacggctgttcatgccggttcccagaggaggaggaagcggctgcgaactgcgcgtgaaattcagccgcagcgcagatgctccagcctacaagcaggggcagaaccagctctacaacgaactcaatcttggtcggagagaggagtacgacgtgctggacaagcgagaggacggacccagaaatgggcgggaagccgcgcagaaagaatcccaagagggcctgtacaacgagctccaaaaggataagatggcagaagcctatagcgagattggtatgaaggggaacgcagaagaggcaaaggccacgacggactgtaccagggactcagcaccgccaccaaggacacctatgacgctcttcacatgcaggccctgccgcctcgg |
| CAR 3 - Full - aa | 53 | Malpvtalllplalllhaarpeivltqspatlslspgeratlscrasesvdnygntfmhwyqqkpgqaprlliyrasnlesgiparfsgsgsrtdftltisslepedvavyycqqsnedpptfgqgtkleikggggsggggsggggsggggsqiqlvqsgselkkpgasvkvsckasgyiftnygmnwvrqapgqglewmgwintytgestysadfkgrfvfsldtsvstaylqinalkaedtavyycarsggydpmdywgqgttvtvssttttpaprpptpaptiasqplslrpeacrpaaggav |

TABLE 1-continued

| Name | SEQ ID NO: | Sequence |
|---|---|---|
| | | htrgldfacdiyiwaplagtcgvllllslvitlyckrgrkkllyifkqpfmrpvqttqeedgcscr fpeeeeggcelrvkfsrsadapaykqgqnqlynelnlgrreeydvldkrrgrdpemggkp rrknpqeglynelqkdkmaeayseigmkgerrrgkghdglyqglstatkdtydalhmqa lppr |

CAR4

| CAR4 scFv domain | 54 | Eivltqspatlslspgeratlscrasesvdnygntfmhwyqqkpgqaprlliyrasnlesgip arfsgsgsrtdftltisslepedvavyycqqsnedpptfgqgtkleikggggsggggsggggs sggggsqiqlvqsgaevkkpgasvkvsckasgyiftnygmnwvrqapgqrlewmgwi ntytgestysadfkgrvtitldtsastaymelsslrsedtavyycarsggydpmdywgqgtt vtvss |
| CAR4 scFv domain nt | 55 | Gagatcgtcttgacgcaatcgccagccaccctgtccctgagcccaggcgagcgcgccaccc tcagctgtcgggcgagcgaaagcgtggacaattacggaaacacctttatgcactggtaccaac agaaaccggggcaggctccgcgcctcctcatctaccgcgcatccaatctggaatcaggaatc ccgcgaggttctccggtagcggatcgcggactgactttactctgaccatctcgtcccttgaac cggaggatgtggctgtgtattactgccagcagtcaaacgaggaccctccaactttcgggcagg gaaccaagctcgaaatcaagggcggtggcggaagcggaggaggaggatcaggcggagg cggctcaggcggtggaggttcacaaattcaactggtgcagtcgggagcggaggtcaagaag ccgggagcctcagtgaaagtgagctgcaaggcttcggttacattttcactaattacggcatga actgggtgaggcaggcccctggccaacggttggaatggatgggatggatcaacacctacac cggggagtcgacttactccgcggacttcaaggggagagtcacgatcaccctggatacgtccg caagcactgcctacatggaactgtcctccctgcgctcggaagataccgcagtctactactgcg ccagatcggcggatatgacccgatggactactggggacagggaactactgtcaccgtgtcc tcg |
| CAR4 - Soluble scFv - nt | 56 | atggccctccctgtcaccgccctgctgcttccgctggctcttctgctccacgccgctcggcccg agatcgtcttgacgcaatcgccagccaccctgtccctgagcccaggcgagcgcgccaccctc agctgtcgggcgagcgaaagcgtggacaattacggaaacacctttatgcactggtaccaaca gaaaccggggcaggctccgcgcctcctcatctaccgcgcatccaatctggaatcaggaatcc ccgcgaggttctccggtagcggatcgcggactgactttactctgaccatctcgtcccttgaacc ggaggatgtggctgtgtattactgccagcagtcaaacgaggaccctccaactttcgggcagg gaaccaagctcgaaatcaagggcggtggcggaagcggaggaggaggatcaggcggagg cggctcaggcggtggaggttcacaaattcaactggtgcagtcgggagcggaggtcaagaag ccgggagcctcagtgaaagtgagctgcaaggcttcggttacattttcactaattacggcatga actgggtgaggcaggcccctggccaacggttggaatggatgggatggatcaacacctacac cggggagtcgacttactccgcggacttcaaggggagagtcacgatcaccctggatacgtccg caagcactgcctacatggaactgtcctccctgcgctcggaagataccgcagtctactactgcg ccagatcggcggatatgacccgatggactactggggacagggaactactgtcaccgtgtcc tcgggctcgcaccaccatcaccatcatcaccac |
| CAR4 - Soluble scFv -aa | 57 | malpvtalllplalllhaarpeivltqspatlslspgeratlscrasesvdnygntfmhwyqqk pgqaprlliyrasnlesgiparfsgsgsrtdftltisslepedvavyycqqsnedpptfgqgtkl eikggggsggggsggggsggggsqiqlvqsgaevkkpgasvkvsckasgyiftnygmn wvrqapgqrlewmgwintytgestysadfkgrvtitldtsastaymelsslrsedtavyyca rsggydpmdywgqgttvtvssgshhhhhhhh |
| CAR 4 - Full - nt | 58 | atggccctccctgtcaccgccctgctgcttccgctggctcttctgctccacgccgctcggcccg agatcgtcttgacgcaatcgccagccaccctgtccctgagcccaggcgagcgcgccaccctc agctgtcgggcgagcgaaagcgtggacaattacggaaacacctttatgcactggtaccaaca gaaaccggggcaggctccgcgcctcctcatctaccgcgcatccaatctggaatcaggaatcc ccgcgaggttctccggtagcggatcgcggactgactttactctgaccatctcgtcccttgaacc ggaggatgtggctgtgtattactgccagcagtcaaacgaggaccctccaactttcgggcagg gaaccaagctcgaaatcaagggcggtggcggaagcggaggaggaggatcaggcggagg cggctcaggcggtggaggttcacaaattcaactggtgcagtcgggagcggaggtcaagaag ccgggagcctcagtgaaagtgagctgcaaggcttcggttacattttcactaattacggcatga actgggtgaggcaggcccctggccaacggttggaatggatgggatggatcaacacctacac cggggagtcgacttactccgcggacttcaaggggagagtcacgatcaccctggatacgtccg caagcactgcctacatggaactgtcctccctgcgctcggaagataccgcagtctactactgcg ccagatcggcggatatgacccgatggactactggggacagggaactactgtcaccgtgtcc tcgaccactaccccagcaccgaggccaccacccccggctcctaccatcgcctcccagcctct gtccctgcgtccggaggcatgtagacccgcagctggtggggccgtgcataccggggtcttg acttcgcctgcgatatctacatttgggcccctctggctggtacttgcggggtcctgctgctttcac tcgtgatcactcttactgtaagcgcggtcggaagaagctgctgtacatctttaagcaacccttca tgaggcctgtgcagactactcaagaggaggacggctgttcatgccggttcccagaggagga ggaaggcggctgcgaactgcgcgtgaaattcagccgcagcgacgcagatgctccagcctacaag cagggcagaaccagctctacaacgaactcaatcttggtcggagagaggagtacgacgtgct ggacaagcgagaggacgggacccagaaatgggcggaagccgcgcagaaagaatccc caagagggcctgtacaacgagctccaaaaggataagatggcagaagcctatagcgagattg gtatgaaaggggaacgcagaagaggcaaaggccacgacggactgtaccagggactcagc accgccaccaaggacacctatgacgctcttcacatgcaggccctgccgcctcgg |
| CAR 4 - Full - aa | 59 | Malpvtalllplalllhaarpeivltqspatlslspgeratlscrasesvdnygntfmhwyqq kpgqaprlliyrasnlesgiparfsgsgsrtdftltisslepedvavyycqqsnedpptfgqg tkleikggggsggggsggggsggggsqiqlvqsgaevkkpgasvkvsckasgyiftnyg |

TABLE 1-continued

| Name | SEQ ID NO: | Sequence |
|---|---|---|
| | | mnwvrqapgqrlewmgwintytgestysadfkgrvtitldtsastaymelsslrsedtav yycarssggydpmdywgqgttvtvsstttpaprppptpaptiasqplslrpeacrpaaggavh trgldfacdiyiwaplagtcgvlllslvitlyckrgrkklllyifkqpfmrpvqttqeedgcscrf peeeeggcelrvkfsrsadapaykqgqnqlynelnlgrreeydvldkrrgrdpemggkpr rknpqeglynelqkdkmaeayseigmkgerrrgkghdglyqglstatkdtydalhmqal ppr |
| CAR 5 | | |
| CAR5 scFv domain | 60 | Qiqlvqsgselkkpgasvkvsckasgyiftnygmnwvrqapgqglewmgwintytge stysadfkgrfvfsldtsvstaylqinalkaedtavyycarsggydpmdywgqgttvtvssg gggsggggsggggsggggsdivltqspdslavslgeratincrasesvdnygntfmhwyq qkpgqppklliyrasnlesgvpdrfsgsgsrtdftltisslqaedvavyycqqsnedpptfgq gtkleik |
| CAR5 scFv domain nt | 61 | Cagatccagttggtccagtcaggctccgaactgaaaaagccgggtgcatccgtcaaggtgtc gtgcaaagcctccggttacatttcaccaactacggcatgaactgggtccgccaggcccctgg gcagggactcgaatggatgggtggatcaacacttacaccggagagtcgacttactcggccg atttcaagggacggttcgtgttttccctggacacttcagtctcgaccgcatatctccaaatcaacg cgcttaaggcggaagatactgctgtctactactgcgccagatcaggaggttacgatccaatgg actactgggacagggcaccactgtgacggtgtcgtcggaggaggaggatcgggcggag gcgggtccggcggtggaggagcggaggaggcggaagcgacatcgtgctgacccagtcg ccagatagcctggcggtgtccttgggtgagagggctaccatcaattgtcgcgcgtcagagtcc gtggacaattacgggaatacctttcatgcactggtaccaacaaaagcccggacaaccgccgaa gctgctgatctacagagcaagcaacctcgaatcaggagtgccggaccgctttagcgggtcag gaagccggactgacttcacccctgactatctcctcgctccaggccgaggacgtggccgtgtatt actgccagcagagcaacgaagatcctccaacgttcggccaaggaaccaaactggagattaa g |
| CAR5 - Soluble scFv - nt | 62 | atggccctccctgtcaccgccctgctgcttccgctggctcttctgctccacgccgctcggcccc agatccagttggtccagtcaggctccgaactgaaaaagccgggtgcatccgtcaaggtgtcgt gcaaagcctccggttacatttcaccaactacggcatgaactgggtccgccaggcccctgggc agggactcgaatggatgggtggatcaacacttacaccggagagtcgacttactcggccgatt tcaagggacggttcgtgttttccctggacacttcagtctcgaccgcatatctccaaatcaacgcg cttaaggcggaagatactgctgtctactactgcgccagatcaggaggttacgatccaatggact actgggacagggcaccactgtgacggtgtcgtcggaggaggaggatcgggcggaggc gggtccggcggtggaggagcggaggaggcggaagcgacatcgtgctgacccagtcgcc agatagcctggcggtgtccttgggtgagagggctaccatcaattgtcgcgcgtcagagtccgt ggacaattacgggaatacctttcatgcactggtaccaacaaaagcccggacaaccgccgaag ctgctgatctacagagcaagcaacctcgaatcaggagtgccggaccgctttagcgggtcagg aagccggactgacttcacccctgactatctcctcgctccaggccgaggacgtggccgtgtatta ctgccagcagagcaacgaagatcctccaacgttcggccaaggaaccaaactggagattaag ggctcgcaccaccatcaccatcatcatcaccac |
| CAR5 - Soluble scFv -aa | 63 | malpvtalllplallllhaarpqiqlvqsgselkkpgasvkvsckasgyiftnygmnwvrqa pgqglewmgwintytgestysadfkgrfvfsldtsvstaylqinalkaedtavyycarsgg ydpmdywgqgttvtvssgggsgggsgggsgggsgggsdivltqspdslavslgeratinc rasesvdnygntfmhwyqqkpgqppklliyrasnlesgvpdrfsgsgsrtdftltisslqae dvavyycqqsnedpptfgqgtkleikgshhhhhhhh |
| CAR 5 - Full - nt | 64 | atggccctccctgtcaccgccctgctgcttccgctggctcttctgctccacgccgctcggcccc agatccagttggtccagtcaggctccgaactgaaaaagccgggtgcatccgtcaaggtgtcgt gcaaagcctccggttacatttcaccaactacggcatgaactgggtccgccaggcccctgggc agggactcgaatggatgggtggatcaacacttacaccggagagtcgacttactcggccgatt tcaagggacggttcgtgttttccctggacacttcagtctcgaccgcatatctccaaatcaacgcg cttaaggcggaagatactgctgtctactactgcgccagatcaggaggttacgatccaatggact actgggacagggcaccactgtgacggtgtcgtcggaggaggaggatcgggcggagcgc gggtccggcggtggaggagcggaggaggcggaagcgacatcgtgctgacccagtcgcc agatagcctggcggtgtccttgggtgagagggctaccatcaattgtcgcgcgtcagagtccgt ggacaattacgggaatacctttcatgcactggtaccaacaaaagcccggacaaccgccgaag ctgctgatctacagagcaagcaacctcgaatcaggagtgccggaccgctttagcgggtcagg aagccggactgacttcacccctgactatctcctcgctccaggccgaggacgtggccgtgtatta ctgccagcagagcaacgaagatcctccaacgttcggccaaggaaccaaactggagattaag accactaccccagcaccgaggccacccaccccggctcctcaactcgcctcccagcctctgtc cctgcgtccggaggcatgtagacccgcagctggtggggccgtgcataccggggtcttgact tcgcctgcgatatctacatttgggcccctctggctggtacttgcggggtcctgctgcttcactcg tgatcactctttactgtaagcgcggtcggaagaagctgctgtacatcttttaagcaacccttcatga ggcctgtgcagactactcaagaggaggacggctgttcatgccggttcccagaggaggaga aggcggctgcgaactgcgcgtgaaattcagccgcagcgacgatgctccagcctacaagcg gggcagaaccagctctacaacgaactcaatcttggtcggagagaggagtacgacgtgctgg acaagcggaggacgggacccagaaatgggcggaagccgcgcagaaagaatcccca agagggcctgtacaacgagctccaaaaggataagatggcagaagcctatagcgagattggta tgaaaggggaaccgcagaagaggcaaaggccacgacgactgtaccagggactcagcacc gccaccaaggacacctatgacgctcttcacatgcaggccctgccgcctcgg |

TABLE 1-continued

| Name | SEQ ID NO: | Sequence |
|---|---|---|
| CAR 5 - Full - aa | 65 | Malpvtalllplalllhaarpqiqlvqsgselkkpgasykysckasgyiftnygmnwvrqa pgqglewmgwintytgestysadfkgrfvfsldtsvstaylqinalkaedtavyycarssgg ydpmdywgqgttvtvssgggsgggsgggsgggsdivltqspdslavslgeratin crasesvdnygntfmhwyqqkpgqppklliyrasnlesgvpdrfsgsgsrtdftltisslq aedvavyycqqsnedpptfgqgtkleiktttpaprpptpaptiasqlslrpeacrpaagga vhtrgldfacdiyiwaplagtcgvlllslvitlyckrgrkkllyifkqpfmrpvqttqeedgcs crfpeeeeggcelrykfsrsadapaykqgqnqlynelnlgrreeydvldkrrgrdpemgg kprrknpqeglynelqkdkmaeayseigmkgerrrgkghdglyqglstatkdtydalhm qalppr |

CAR6

| Name | SEQ ID NO: | Sequence |
|---|---|---|
| CAR6 scFv domain | 66 | Qiqlvqsgselkkpgasykysckasgyiftnygmnwvrqapgqglewmgwintytge stysadfkgrfvfsldtsvstaylqinalkaedtavyycarsggydpmdywgqgttvtvssg gggsgggsgggsgggseivltqspatlslspgeratlscrasesvdnygntfmhwyq qkpgqaprlliyrasnlesgiparfsgsgsrtdftltisslepedvavyycqqsnedpptfgqg tkleik |
| CAR6 scFv domain nt | 67 | cagatccaactggtgcaatcaggatcggagctgaagaagcctggggcttcagtgaaagtcag ctgcaaagcctccggttacatcttcaccaactacggcatgaactgggtgcgccaggcccctgg acagggactcgaatggatggggtggatcaacacctataccgggaatccacgtactcagcag atttcaagggacgcttcgtcttttcgctggatacctccgtgtccactgcgtacctccaaatcaatg ccctcaaagccgaagatactgcggtctactactgcgcacggagcggaggctacgacccgat ggactactggggacagggaaccacggtgaccgtgtccagcggaggaggcggatcgggag gcggtggttcaggcggtggaggcagcggcggaggtggaagcgaaatcgtcttgactcaga gcccagcgactttgtccctgtcgcccggagagcgggcaactctgtcatgccgcgcttcggaat cggtggacaactatggaaacacctttatgcactggtaccaacagaagccgggacaagccccg agacttctgatctaccgggcctcgaatctcgaaagcggcatcccggctagattctcggggtcg ggatcaaggaccgacttcactcttactatttcctcactggagccagaagatgtggcggtgtacta ctgtcagcagtccaatgaggacccgccaactttcgggcagggcaccaagctggagattaag |
| CAR6 - Soluble scFv - nt | 68 | atggccctcctgtcaccgccctgctgcttccgctggctcttctgctccacgccgctcggcccc agatccaactggtgcaatcaggatcggagctgaagaagcctggggcttcagtgaaagtcagc tgcaaagcctccggttacatcttcaccaactacggcatgaactgggtgcgccaggcccctgga cagggactcgaatggatggggtggatcaacacctataccggggaatccacgtactcagcaga tttcaagggacgcttcgtcttttcgctggatacctccgtgtccactgcgtacctccaaatcaatgc cctcaaagccgaagatactgcggtctactactgcgcacggagcggaggctacgacccgatg gactactggggacagggaaccacggtgaccgtgtccagcggaggaggcggatcgggagg cggtggttcaggcggtggaggcagcggcggaggtggaagcgaaatcgtcttgactcagagc ccagcgactttgtccctgtcgcccggagagcgggcaactctgtcatgccgcgcttcggaatcg gtggacaactatggaaacacctttatgcactggtaccaacagaagccgggacaagccccgag acttctgatctaccgggcctcgaatctcgaaagcggcatcccggctagattctcggggtcggg atcaaggaccgacttcactcttactatttcctcactggagccagaagatgtggcggtgtactact gtcagcagtccaatgaggacccgccaactttcgggcagggcaccaagctggagattaaggg ctcgcaccaccatcaccatcatcaccac |
| CAR6 - Soluble scFv - aa | 69 | malpvtalllplalllhaarpqiqlvqsgselkkpgasvkvsckasgyiftnygmnwvrqa pgqglewmgwintytgestysadfkgrfvfsldtsvstaylqinalkaedtavyycarsgg ydpmdywgqgttvtvssgggsgggsgggsgggseivltqspatlslspgeratlscr asesvdnygntfmhwyqqkpgqaprlliyrasnlesgiparfsgsgsrtdftltisslepedv avyycqqsnedpptfgqgtkleikgshhhhhhhh |
| CAR6 - Full - nt | 70 | atggccctcctgtcaccgccctgctgcttccgctggctcttctgctccacgccgctcggcccc agatccaactggtgcaatcaggatcggagctgaagaagcctggggcttcagtgaaagtcagc tgcaaagcctccggttacatcttcaccaactacggcatgaactgggtgcgccaggcccctgga cagggactcgaatggatggggtggatcaacacctataccggggaatccacgtactcagcaga tttcaagggacgcttcgtcttttcgctggatacctccgtgtccactgcgtacctccaaatcaatgc cctcaaagccgaagatactgcggtctactactgcgcacggagcggaggctacgacccgatg gactactggggacagggaaccacggtgaccgtgtccagcggaggaggcggatcgggagg cggtggttcaggcggtggaggcagcggcggaggtggaagcgaaatcgtcttgactcagagc ccagcgactttgtccctgtcgcccggagagcgggcaactctgtcatgccgcgcttcggaatcg gtggacaactatggaaacacctttatgcactggtaccaacagaagccgggacaagccccgag acttctgatctaccgggcctcgaatctcgaaagcggcatcccggctagattctcggggtcggg atcaaggaccgacttcactcttactatttcctcactggagccagaagatgtggcggtgtactact gtcagcagtccaatgaggacccgccaactttcgggcagggcaccaagctggagattaagac cactaccccagcaccgaggccaccaccccggctcctaccatcgcctcccagcctctgtccc tgcgtccggaggcatgtagacccgcagctggtggggccgtgcataccggggtcttgacttc gcctgcgatatctacatttgggcccctctggctggtacttgcggggtcctgctgctttcactcgtg atcactcttttactgtaagcgcggtcggaagaagctgctgtacatctttaagcaacccttcatgag gcctgtgcagactactcaagaggaggacggctgttcatgccggttcccagaggaggaggaa ggcgctgcgaactgcgcgtgaaattcagccgcagcgcagatgctccagcctacaagcagg ggcagaaccagctctacaacgaactcaatcttggtcggagagaggagtacgacgtgctggac aagcggagaggacgggacccagaaatgggcgggaagccgcgcagaaagaatcccaag agggcctgtacaacgagctccaaaaggataagatggcagaagcctatagcgagattggtatg aaaggggaacgcagaagaggcaaaggccacgacggactgtaccagggactcagcaccgc caccaaggacacctatgacgctcttcacatgcaggccctgccgcctcgg |

TABLE 1-continued

| Name | SEQ ID NO: | Sequence |
|---|---|---|
| 109375 CAR6 - Full - aa | 71 | Malpvtalllplalllhaarpqiqlvqsgselkkpgasvkvsckasgyiftnygmnwvrqa pgqglewmgwintytgestysadfkgrfvfsldtsvstaylqinalkaedtavyycarsgg ydpmdywgqgttvtvssggggsggggsggggsggggseivltqspatlslspgeratlsc rasesvdnygntfmhwyqqkpgqaprlliyrasnlesgiparfsgsgsrtdftltisslepe dvavyycqqsnedpptfgqgtkleikttttpaprpptpaptiasqplslrpeacrpaaggav htrgldfacdiyiwaplagtcgvlllslvitlyckrgrkkllyifkqpfmrpvqttqeedgcscr fpeeeeggcelrvkfsrsadapaykqgqnqlynelnlgrreeydvldkrrgrdpemggkp rrknpqeglynelqkdkmaeayseigmkgerrrgkghdglyqglstatkdtydalhmqa lppr |

CAR7

| Name | SEQ ID NO: | Sequence |
|---|---|---|
| CAR7 scFv domain | 72 | Qiqlvqsgaevkkpgasvkvsckasgyiftnygmnwvrqapgqrlewmgwintytge stysadfkgrvtitldtsastaymelsslrsedtavyycarsggydpmdywgqgttvtvssg gggsggggsggggsggggsdivltqspdslayslgeratincrasesvdnygntfmhwyq qkpgqppklliyrasnlesgvpdrfsgsgsrtdftltisslqaedvavyycqqsnedpptfgq gtkleik |
| CAR7 scFv domain nt | 73 | Cagatccagctggtgcagtcgggagctgaagtgaaaaagccgggagcatcggtgaaggtg tcatgcaaagccagcggttacatcttcactaactacggtatgaactgggtgagacaagcgcct ggccagagattggaatggatgggatggatcaataccfacaccggggaatcaacttacagcgc cgacttcaagggacgcgtgaccatcacgctggacacctccgcgtccactgcctacatggagc tctcgtcattgcggagcgaggacaccgccgtctactactgcgcacggtcaggagggtacgat ccgatggactactggggacagggcactaccgtcaccgtgagctccggtggaggcggcagc ggcggtggcggatcaggtggaggaggatcaggaggaggagggtccgatatcgtgcttactc agtcacccgattcgctggcagtctccctcggagaacgcgccaccatcaattgtcgcgcgtccg aatccgtcgacaactacggcaacacctttatgcactggtaccaacagaagcctggacaaccg ccaaaactgctgatctaccgcgctagcaacctcgaatcgggcgtgccagataggttctcggc tcggggagccggacggattttactctgactatttcgtccctccaagcagaggacgtcgccgtgt attactgccagcaatcgaatgaggacccgccaacttcggacaggggaccaagctggagatt aag |
| CAR7 - Soluble scFv - nt | 74 | atggccctccctgtcaccgccctgctgcttccgctggctcttctgctccacgccgctcggcccc agatccagctggtgcagtcgggagctgaagtgaaaaagccgggagcatcggtgaaggtgtc atgcaaagccagcggttacatcttcactaactacggtatgaactgggtgagacaagcgcctgg ccagagattggaatggatgggatggatcaataccfacaccggggaatcaacttacagcgcc gacttcaagggacgcgtgaccatcacgctggacacctccgcgtccactgcctacatggagctct cgtcattgcggagcgaggacaccgccgtctactactgcgcacggtcaggagggtacgatcc gatgactactggggacagggcactaccgtcaccgtgagctccggtggaggcggcagcgg cggtggcggatcaggtggaggaggatcaggaggaggagggtccgatatcgtgcttactcag tcacccgattcgctggcagtctccctcggagaacgcgccaccatcaattgtcgcgcgtccgaa tccgtcgacaactacggcaacacctttatgcactggtaccaacagaagcctggacaaccgcc aaaactgctgatctaccgcgctagcaacctcgaatcgggcgtgccagataggttctcggctc ggggagccggacggattttactctgactatttcgtccctccaagcagaggacgtcgccgtgtat tactgccagcaatcgaatgaggacccgccaacttcggacaggggaccaagctggagattaa gggctcgcaccaccatcaccatcatcatcaccac |
| CAR7 - Soluble scFv - aa | 75 | malpvtalllplalllhaarpqiqlvqsgaevkkpgasvkvsckasgyiftnygmnwvrqa pgqrlewmgwintytgestysadfkgrvtitldtsastaymelsslrsedtavyycarsggy dpmdywgqgttvtvssggggsggggsggggsggggsdivltqspdslavslgeratincr asesvdnygntfmhwyqqkpgqppklliyrasnlesgvpdrfsgsgsrtdftltisslqaed vavyycqqsnedpptfgqgtkleikgshhhhhhhh |
| CAR 7 Full - nt | 76 | atggccctccctgtcaccgccctgctgcttccgctggctcttctgctccacgccgctcggcccc agatccagctggtgcagtcgggagctgaagtgaaaaagccgggagcatcggtgaaggtgtc atgcaaagccagcggttacatcttcactaactacggtatgaactgggtgagacaagcgcctgg ccagagattggaatggatgggatggatcaataccfacaccggggaatcaacttacagcgcc gacttcaagggacgcgtgaccatcacgctggacacctccgcgtccactgcctacatggagctct cgtcattgcggagcgaggacaccgccgtctactactgcgcacggtcaggagggtacgatcc gatgactactggggacagggcactaccgtcaccgtgagctccggtggaggcggcagcgg cggtggcggatcaggtggaggaggatcaggaggaggagggtccgatatcgtgcttactcag tcacccgattcgctggcagtctccctcggagaacgcgccaccatcaattgtcgcgcgtccgaa tccgtcgacaactacggcaacacctttatgcactggtaccaacagaagcctggacaaccgcc aaaactgctgatctaccgcgctagcaacctcgaatcgggcgtgccagataggttctcggctc ggggagccggacggattttactctgactatttcgtccctccaagcagaggacgtcgccgtgtat tactgccagcaatcgaatgaggacccgccaacttcggacaggggaccaagctggagattaa gaccactaccccagcaccgaggccacccacccccggctcctaccatcgcctcccagcctctgt ccctgcgtccggaggcatgtagacccgcagctggtggggccgtgcatacccggggtcttga cttcgcctgcgatatctacatttgggcccctctggctggtacttgcggggtcctgctgctttcact cgtgatcactcttactgtaagcgcggtcggaagaaagcttctgtacatctttaagcaaccttcat gaggcctgtgcagactactcaagaggaggacggctgttcatgccggttcccagaggaggag gaaggcggctgcgaactgcgcgtgaaattcagccgcagcgcagatgctccagcctacaagc aggggcagaaccagctctacaacgaactcaatcttggtcggagagaggagtacgacgtgct ggacaagcggagaggacgggacccagaaatgggcgggaagccgcgcagaaagaatccc caagagggcctgtacaacgagctccaaaaggataagatgcagaagcctatagcgagattg |

TABLE 1-continued

| Name | SEQ ID NO: | Sequence |
|---|---|---|
| | | gtatgaaaggggaacgcagaagaggcaaaggccacgacggactgtaccagggactcagc<br>accgccaccaaggacacctatgacgctcttcacatgcaggccctgccgcctcgg |
| CAR 7<br>Full - aa | 77 | Malpvtalllplalllhaarpqiqlvqsgaevkkpgasykysckasgyiftnygmnwyrq<br>apgqrlewmgwintytgestysadfkgrvtitldtsastaymelsslrsedtavyycarsgg<br>ydpmdywgqgttvtvssgggggsggggsggggsggggsdivltqspdslavslgeratin<br>crasesvdnygntfmhwyqqkpgqppklliyrasnlesgvpdrfsgsgsrtdftltisslq<br>aedvavyycqqsnedpptfgqgtkleikttttpaprpptpaptiasqplslrpeacrpaagga<br>vhtrgldfacdiyiwaplagtcgvllllslvitlyckrgrkkllyifkqpfmrpvqttqeedgcs<br>crfpeeeeggcelrykfsrsadapaykqgqnqlynelnlgrreeydvldkrrgrdpemgg<br>kprrknpqeglynelqkdkmaeayseigmkgerrrgkghdglyqglstatkdtydalhm<br>qalppr |
| | | CAR8 |
| CAR8<br>scFv<br>domain | 78 | Qiqlvqsgaeykkpgasvkvsckasgyiftnygmnwyrqapgqrlewmgwintytge<br>stysadfkgrvtitldtsastaymelsslrsedtavyycarsggydpmdywgqgttvtvssg<br>gggsggggsggggsggggseivltqspatlslspgeratlscrasesvdnygntfmhwyq<br>qkpgqaprlliyrasnlesgiparfsgsgsrtdftltisslepedvavyycqqsnedpptfgqg<br>tkleik |
| CAR8<br>scFv<br>domain nt | 79 | Cagatccagctggtgcaatcgggagctgaagtgaagaagcccggagcttcagtcaaagtca<br>gctgcaaggcgtcgggctatatcttcaccaactacgggatgaactgggtgcggcaggcccct<br>ggacaaagactggaatggatgggatggatcaacacttatactggcgagagcacgtactcagc<br>cgactttaagggacgggtgactatcaccctcgatacctccgcctccactgctacatggaactc<br>tcgtccttgcgctccgaggacactgccgtgtactactgcgccaggtcgggtggctacgatccg<br>atggattactggggtcaaggaaccaccgtcactgtgtcgtccggcggaggcgggagcggag<br>gtggtggttcgggaggaggagggtcaggcggaggaggcagcgaaatcgtgctgacccaaa<br>gcccggcaactctgtcactcagcccaggggagagggcaaccctgtcatgtcgggctagcga<br>atccgtggacaattacggaaacacgtttatgcactggtaccaacagaaaccaggacaggcgc<br>ctagacttctcatctaccgcgcgagcaatttggaatccggcatcccagcccgcttctccgggtc<br>ggggtcacgcaccgatttcactctgaccatttcctccctggaacccgaggacgtggcagtcta<br>ctactgccagcagtcgaatgaggacccgccgaccttcggacagggcaccaagctggagatt<br>aag |
| CAR8 -<br>Soluble<br>scFv - nt | 80 | atggccctccctgtcaccgccctgctgcttccgctggctcttctgctccacgccgctcggcccc<br>agatccagctggtgcaatcgggagctgaagtgaagaagcccggagcttcagtcaaagtcag<br>ctgcaaggcgtcgggctatatcttcaccaactacgggatgaactgggtgcggcaggccccctg<br>gacaaagactggaatggatgggatggatcaacacttatactggcgagagcacgtactcagcc<br>gactttaagggacgggtgactatcaccctcgatacctccgcctccactgctacatggaactct<br>cgtccttgcgctccgaggacactgccgtgtactactgcgccaggtcgggtggctacgatccga<br>tggattactggggtcaaggaaccaccgtcactgtgtcgtccggcggaggcgggagcggagg<br>tggtggttcgggaggaggagggtcaggcggaggaggcagcgaaatcgtgctgacccaaag<br>cccggcaactctgtcactcagcccaggggagagggcaaccctgtcatgtcgggctagcgaat<br>ccgtggacaattacggaaacacgtttatgcactggtaccaacagaaaccaggacaggcgcct<br>agacttctcatctaccgcgcgagcaatttggaatccggcatcccagcccgcttctccgggtcg<br>gggtcacgcaccgatttcactctgaccatttcctccctggaacccgaggacgtggcagtctact<br>actgccagcagtcgaatgaggacccgccgaccttcggacagggcaccaagctggagattaa<br>gggctcgcaccaccatcaccatcatcatccaccac |
| CAR8 -<br>Soluble<br>scFv - aa | 81 | malpvtalllplalllhaarpqiqlvqsgaevkkpgasvkvsckasgyiftnygmnwvrqa<br>pgqrlewmgwintytgestysadfkgrvtitldtsastaymelsslrsedtavyycarsggy<br>dpmdywgqgttvtvssggggsggggsggggsggggseivltqspatlslspgeratlscra<br>sesvdnygntfmhwyqqkpgqaprlliyrasnlesgiparfsgsgsrtdftltisslepedva<br>vyycqqsnedpptfgqgtkleikgshhhhhhhh |
| CAR 8 -<br>Full - nt | 82 | atggccctccctgtcaccgccctgctgcttccgctggctcttctgctccacgccgctcggcccc<br>agatccagctggtgcaatcgggagctgaagtgaagaagcccggagcttcagtcaaagtcag<br>ctgcaaggcgtcgggctatatcttcaccaactacgggatgaactgggtgcggcaggccccctg<br>gacaaagactggaatggatgggatggatcaacacttatactggcgagagcacgtactcagcc<br>gactttaagggacgggtgactatcaccctcgatacctccgcctccactgctacatggaactct<br>cgtccttgcgctccgaggacactgccgtgtactactgcgccaggtcgggtggctacgatccga<br>tggattactggggtcaaggaaccaccgtcactgtgtcgtccggcggaggcgggagcggagg<br>tggtggttcgggaggaggagggtcaggcggaggaggcagcgaaatcgtgctgacccaaag<br>cccggcaactctgtcactcagcccaggggagagggcaaccctgtcatgtcgggctagcgaat<br>ccgtggacaattacggaaacacgtttatgcactggtaccaacagaaaccaggacaggcgcct<br>agacttctcatctaccgcgcgagcaatttggaatccggcatcccagcccgcttctccgggtcg<br>gggtcacgcaccgatttcactctgaccatttcctccctggaacccgaggacgtggcagtctact<br>actgccagcagtcgaatgaggacccgccgaccttcggacagggcaccaagctggagattaa<br>gaccactaccccagcaccgaggccacccacccccggctcctaccatcgcctcccagcctctgt<br>ccctgcgtccggaggcatgtagaacccgctggtggggccgtgcataccccgggtcttga<br>cttcgcctgcgatatctacatttgggcccctctggctggtacttgcgggtcctgctgctttcact<br>cgtgatcactctttactgtaagcgcggtcggaagaagctgctgtacatctttaagcaacccttcat<br>gaggcctgtgcagactactcaagaggaggacggctgttcatgccggttcccagaggaggag<br>gaaggcggctgcgaactgcgcgtgaaattcagccgcagcgcagatgctccagcctacaagc<br>aggggcagaaccagctctacaacgaactcaatcttggtcggagagaggagtacgacgtgct |

TABLE 1-continued

| Name | SEQ ID NO: | Sequence |
|---|---|---|
| | | ggacaagcggagaggacgggacccagaaatgggcgggaagccgcgcagaaagaatccc<br>caagagggcctgtacaacgagctccaaaaggataagatggcagaagcctatagcgagattg<br>gtatgaaaggggaacgcagaagaggcaaaggccacgacggactgtaccagggactcagc<br>accgccaccaaggacacctatgacgctcttcacatgcaggccctgccgcctcgg |
| CAR 8 - Full - aa | 83 | Malpvtallplalllhaarpqiqlvqsgaevkkpgasvkvsckasgyiftnygmnwvrq<br>apgqrlewmgwintytgestysadfkgrvtitltdtsastaymelsslrsedtavyycarsgg<br>ydpmdywgqgttvtvssgggsgggsgggsgggseivltqspatlslspgeratlsc<br>rasesvdnygntfmhwyqqkpgqaprlliyrasnlesgiparfsgsgsrtdftltisslepe<br>dvavyycqqsnedpptfgqgtkleiktttpaprpptpaptiasqplslrpeacrpaaggav<br>htrgldfacdiyiwaplagtcgvlllslvitlyckrgrkkllyifkqpfmrpvqttqeedgcscr<br>fpeeeeggcelrvkfsrsadapaykqgqnqlynelnlgrreeydvldkrrgrdpemggkp<br>rrknpqeglynelqkdkmaeayseigmkgerrrgkghdglyqglstatkdtydalhmqa<br>lppr |

TABLE 2

Exemplary CD123 CAR sequences for in vitro transcription

| Name | SEQ ID | Sequence |
|---|---|---|
| pD-A(xs) dsRED T2A CD123 CAR 1172-nt | 94 | GGCAGCGGAGAGGGCAGAGGAAGTCTTCTAACATGCGGTGACGTGGAGGAGAATCCCGGCcctagagc<br>cacc<u>atggccctgcctgtgacagccctgctgctgcctctggctctgctgctgcatg<br>ccgctagaccgatccgacatcgtgctgacacagagccctgcttccctggccgtg<br>tccctgggacagagagccacaatcagctgcagggccagcgagagcgtgacaacta<br>cggcaacaccttcatgcactggtatcagcagaagcccggccagccccccaagctgc<br>tgatctacagagccagcaacctggaaagcggcatccccgccagattttccggcagc<br>ggcagcagaaccgacttcaccctgaccatcaaccccgtggaagccgacgacgtggc<br>cacctactactgccagcagagcaacgaggacccccccacatttggagcggcacca<br>agctggaactgaagggcggaggcggatctggcggcggaggatcttctggggaggc<br>tctcagattcagctggtgcagagcggcccagagctgaagaaacccggcgagacagt<br>gaagatctcctgcaaggcctccggctacatcttcaccaattacggcatgaactggg<br>tcaagcaggcccctggcaagagcttcaagtggatgggctggatcaacacctacacc<br>ggcgagagcacctacagcgccgacttcaagggcagattcgccttcagcctggaaac<br>cagcgccagcaccgcctacctgcacatcaacgacctgaagaacgaggacaccgcca<br>cctatttctgcgcgcagaagcggcggctacgaccccatggattattgggccagggc<br>accagcgtgaccgtgtcctctgctagctccggaaccacgacgccagcgccgccacc<br>accaacaccggcgcccaccatcgcgtcgcagcccctgtccctgcgcccagaggcgt<br>gccggccagcggcggggggcagtgcacacagggggctggacttcgcctgtgat<br>atctacatctgggcgccctggccgggacttgtggggtccttctcctgtcactggt<br>tatcacccttactgcaaacggggcagaaagaaactcctgtatatattcaaacaac<br>cattatgagaccagtacaaactactcaagaggaagatggctgtagctgccgatt<br>ccagaagaagaagaaggaggatgtgaactgagagtgaagttcagcaggagcgcaga<br>cgcccccgcgtacaagcagggccagaaccagctctataacgagctcaatctaggac<br>gaagagaggagtacgatgttttggacaagagacgtggccgggaccctgagatgggg<br>ggaaagccgagaaggaagaaccctcaggaaggcctgtacaatgaactgcagaaaga<br>taagatggcggaggcctacagtgagattgggatgaaaggcgagcgccggaggggca<br>agggcacgatggcctttaccagggtctcagtacagccaccaaggacacctacgac<br>gcccttcacatgcaggccctgccccctcgct</u>aagtcgac*AGCTCGCTTTCTTGCTG<br>TCCAATTTCTATTAAAGGTTCCTTTGTTCCCTAAGTCCAACTACTAAACTGGGGGA<br>TATTATGAAGGGCCTTGAGCATCTGGATTCTGCCTAATAAAAAACATTTATTTTCA<br>TTGCTGCGTCGAGAGCTCGCTTTCTTGCTGTCCAATTTCTATTAAAGGTTCCTTTG<br>TTCCCTAAGTCCAACTACTAAACTGGGGGATATTATGAAGGGCCTTGAGCATCTGG<br>ATTCTGCCTAATAAAAAACATTTATTTTCATTGCTGCCTCGACG*aattcaaaaaaa<br>aaaaaaaaaaaaaaaaaaaaaaaaaaaaaaaaaaaaaaaaaaaaaaaaaaaaaaaa<br>aaaaaaaaaaaaaaaaaaaaaaaaaaaaaaaaaaaaaaaaaaaaaaaaaaaaaaaa<br>aaaaaaaaaaaaaaaaaaaaaaaaaaa |
| pD-A(xs) dsRED T2A CD123CA R 1172-aa | 95 | Malpvtallplalllhaarpgsdivltqspaslavslgqratiscrasesvdnyg<br>ntfmhwyqqkpgqppklliyrasnlesgiparfsgsgsrtdftltinpveaddvat<br>yycqqsnedpptfgagtklelkggggsggggsggggsqiqlvqsgpelkkpgetvk<br>isckasgyiftnygmnwvkqapgksfkwmgwintytgestysadfkgrfafsletss<br>astaylhindlknedtatyfcarsggydpmdywgqgtsvtvssassgttttpaprpp<br>tpaptiasqpllslrpeacrpaaggavhtrgldfacdiyiwaplagtcgvlllslvi<br>tlyckrgrkkllyifkqpfmrpvqttqeedgcscrfpeeeeggcelrvkfsrsada<br>paykqgqnqlynelnlgrreeydvldkrrgrdpemggkprrknpqeglynelqkdk<br>maeayseigmkgerrrgkghdglyqglstatkdtydalhmqalppr |
| pD-A(xs) CD123 CAR 1176-nt | 96 | atggccctgcctgtgacagccctgctgctgcctctggctctgctgctgcacgccgc<br>tagacctggatcccaggtgcagctgcagcagcctggcgctgaactcgtgcggccag<br>gcgcttctgtgaagctgagctgtaaagccagcggctacaccttcaccagctactgg<br>atgaactggggtcaagcagcggcccgaccagggcctggagtggatcggcagaatcga |

TABLE 2-continued

Exemplary CD123 CAR sequences for in vitro transcription

| Name | SEQ ID | Sequence |
|---|---|---|
| | | cccctacgacagcgagacacactacaaccagaagttcaaggacaaggccatcctga |
| | | ccgtggacaagagcagcagcaccgcctacatgcagctgtccagcctgaccagcgag |
| | | gacagcgccgtgtactactgcgccagggcaactgggacgactattggggccaggg |
| | | caccaccctgacagtgtctagcggaggcggaggatctggcggcggaggaagttctg |
| | | gcggaggctccgacgtgcagatcacccagagcccagctacctggccgcctctcct |
| | | ggcgagacaatcaccatcaactgcggggccagcaagagcatctccaaggacctggc |
| | | ctggtatcaggaaaagcccggcaagaccaacaagctgctgatctacagcggcagca |
| | | ccctgcagagcggcatccccagcagattttccggcagcggctccggcaccgacttc |
| | | accctgaccatcagctccctggaacccgaggactttgccatgtactattgccagca |
| | | gcacaacaagtaccctaccttcggcggaggcaccaagctggaaatcaaggcca |
| | | gctccggagagagcaagtacggccctcctgcccccttgcctgccccgagttc |
| | | ctgggcggaccagcgtgttcctgttccccccaagcccaaggacaccctgatgat |
| | | cagccggacccccgaggtgacctgtgtggtggtggacgtgtcccaggaggaccccg |
| | | aggtccagttcaactggtacgtggacggcgtggaggtgcacaacgccaagaccaag |
| | | ccccgggaggagcagttcaatagcacctacccgggtggtgtccgtgctgaccgtgct |
| | | gcaccaggactggctgaacggcaaggaatacaagtgtaaggtgtccaacaaggcc |
| | | tgcccagcagcatcgagaaaaccatcagcaaggccaaggccagcctcgggagccc |
| | | caggtgtacaccctgccccctagccaagaggagatgaccaagaaccaggtgtccct |
| | | gacctgcctggtgaagggcttctaccccagcgacatcgccgtggagtgggagagca |
| | | acggccagcccgagaacaactacaagaccacccccctgtgctggacagcgacggc |
| | | agcttcttcctgtacagccggctgaccgtggacaagagccggtggcaggagggcaa |
| | | cgtctttagctgctccgtgatgcacgaggccctgcacaaccactacacccagaaga |
| | | gcctgagcctgtccctgggcaagatggatatctacatctgggcgccttggccggg |
| | | acttgtggggtccttctcctgtcactggttatcacctttactgcaaacggggcag |
| | | aaagaaactcctgtatatattcaaacaaccatttatgagaccagtacaaactactc |
| | | aagaggaagatggctgtagctgccgatttccagaagaagaagaaggaggatgtgaa |
| | | ctgagagtgaagttcagcaggagcgcagacgcccccgcgtacaagcagggccagaa |
| | | ccagctctataacgagctcaatctaggacgaagagaggagtacgatgttttggaca |
| | | agagacgtggccgggaccctgagatgggggaaagccgagaaggaagaaccctcag |
| | | gaaggcctgtacaatgaactgcagaaagataagatggcggaggcctacagtgagat |
| | | tgggatgaaggcgagcgccggaggggcaaggggcacgatggcctttaccagggtc |
| | | tcagtacagccaccaaggacacctacgacgcccttcacatgcaggccctgccccct |
| | | cgc |
| pD-A(xs) CD123 CAR 1176-aa | 97 | malpvtalllplalllhaarpgsqvqlqqpgaelvrpgasvklsckasgytftsyw mnwvkqrpdqglewigridpydsethynqkfkdkailtvdkssstaymqlssltse dsavyycargnwddywgqgttltvssggggsggggssgggsdvqitqspsylaasp getitincrasksiskdlawyqekpgktnklliysgstlqsgipsrfsgsgsgtdf tltisslepedfamyycqqhnkypytfgggtkleikassgeskygppcppcpapef lggpsvflfppkpkdtlmisrtpevtcvvvdvsqedpevqfnwyvdgvevhnaktk preeqfnstyrvvsvltvlhqdwlngkeykckvsnkglpssiektiskakgqprep qvytlppsqeemtknqvsltclvkgfypsdiavewesngqpennyktttppvldsdg sfflysrltvdksrwqegnvfscsvmhealhnhytqkslslslgkmdiyiwaplag tcgvlllslvitlyckrgrkkllyifkqpfmrpvqttqeedgcscrfpeeeeggce lrvkfsrsadapaykqgqnqlynelnlgrreeydvldkrrgrdpemggkprrknpq eglynelqkdkmaeayseigmkgerrrgkghdglyqglstatkdtydalhmqalpp r |

In SEQ ID NO:94, capitalized bolded residues correspond to the T2A region; underlined residues correspond to the CD123 CAR region; and capitalized italicized residues correspond to the beta globulin UTR region.

Figure 28:
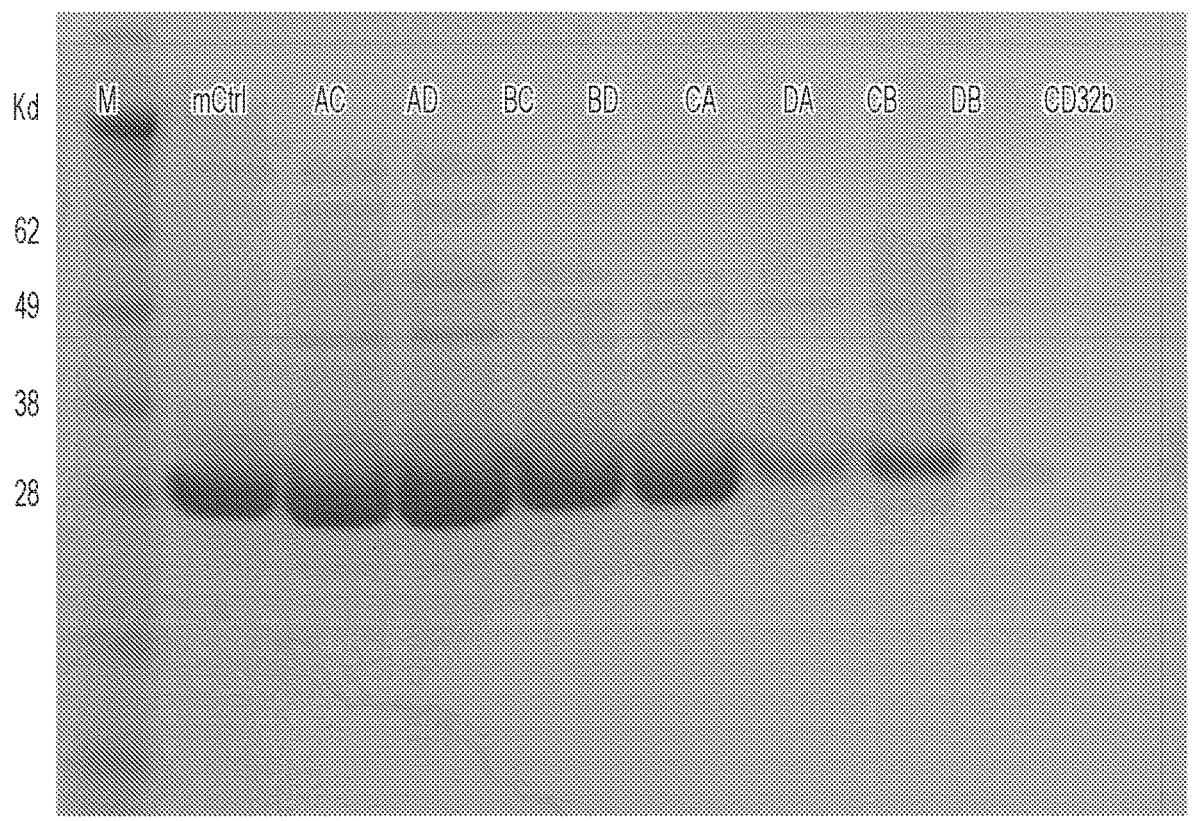
FIG. 28 is an image showing expression of humanized anti-CD123 scFv variants which were transiently expressed in HEK293 cells and were purified to near homogeneity via the C-terminal 6× His tag (SEQ ID NO: 128).
Figure 29A:
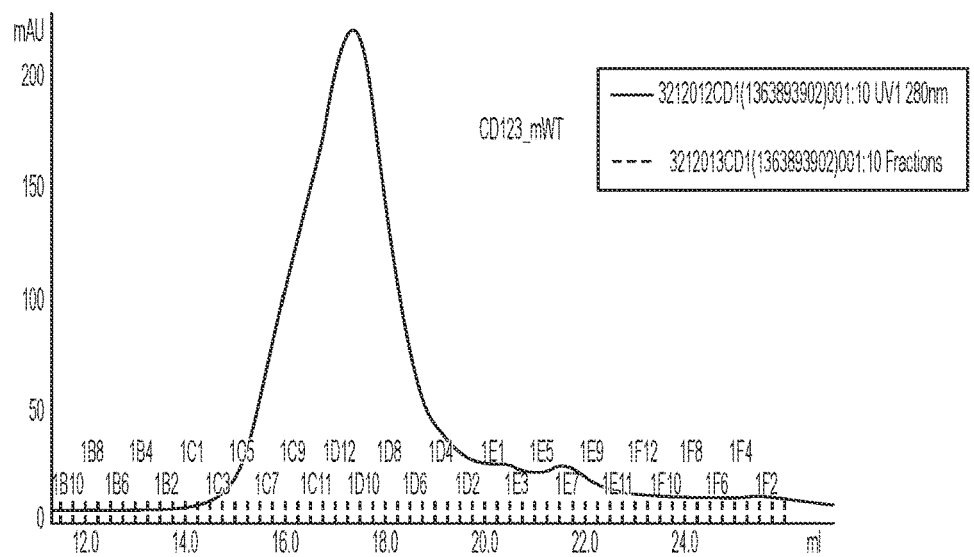
FIGS. 29A-29B is an image showing expression of humanized anti-CD123 scFv variants which were transiently expressed in HEK293 cells and were purified to near homogeneity via the C-terminal 6× His tag (SEQ ID NO: 128).
Figure 29A:
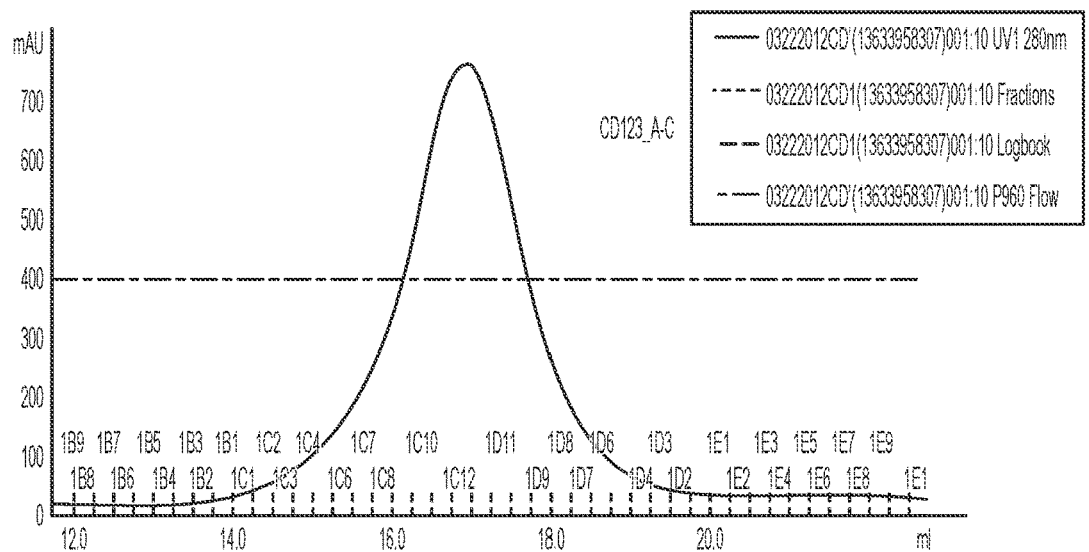
Figure 29A:
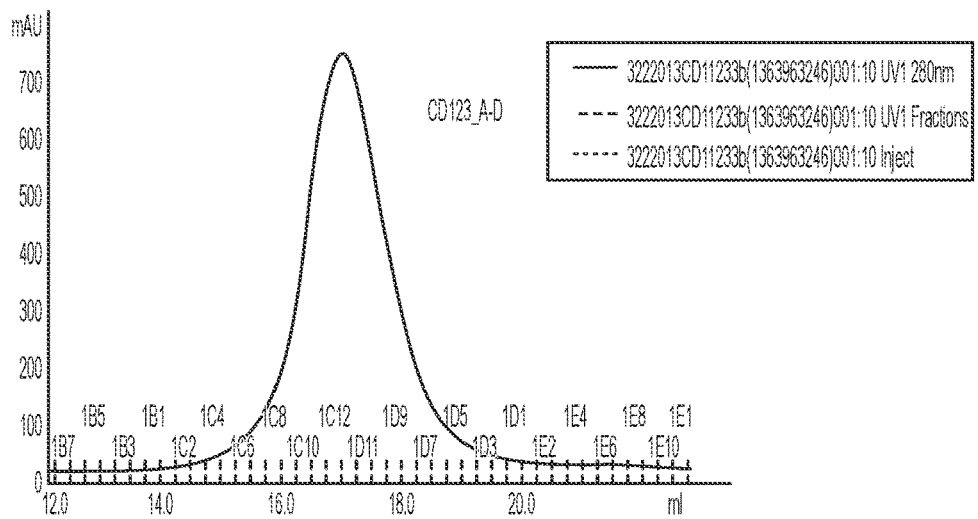
Figure 29B:
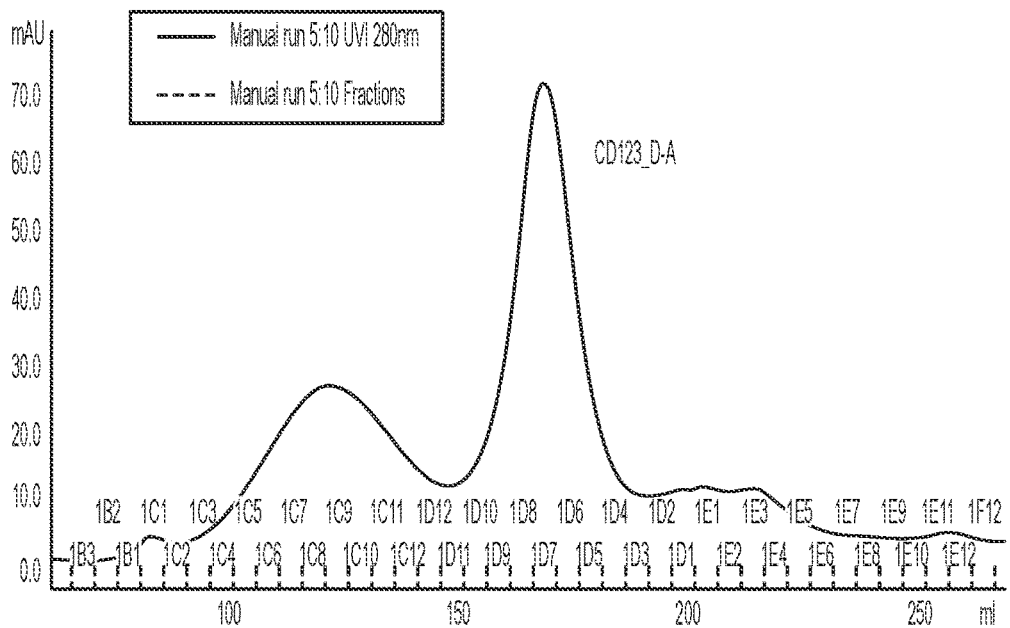
Figure 29B:
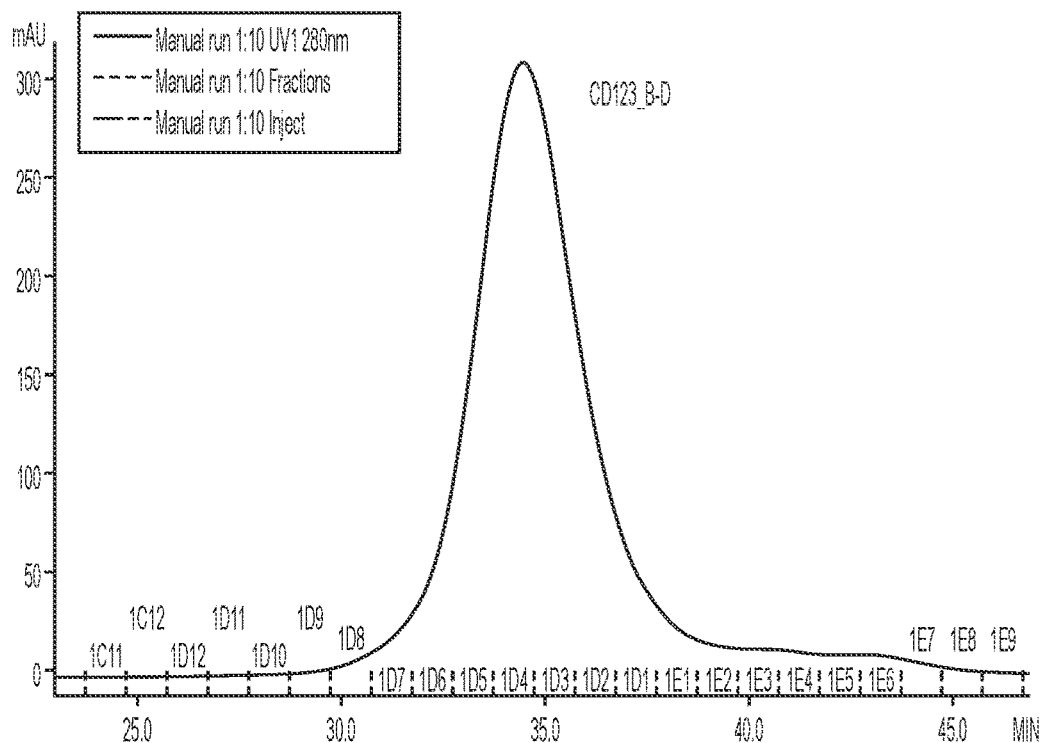
Figure 30A:
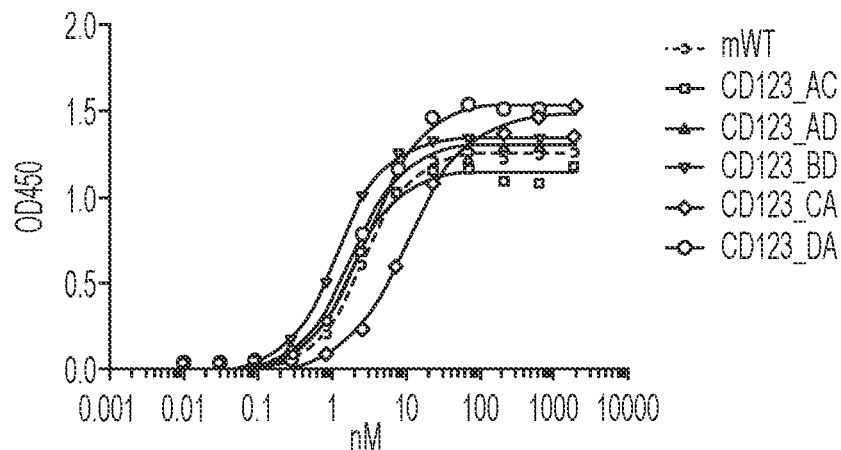
FIGS. 30A-30B is a graph showing binding of humanized anti-C123 scFv variants to immobilized CD123 determined by ELISA.
Figure 30B:
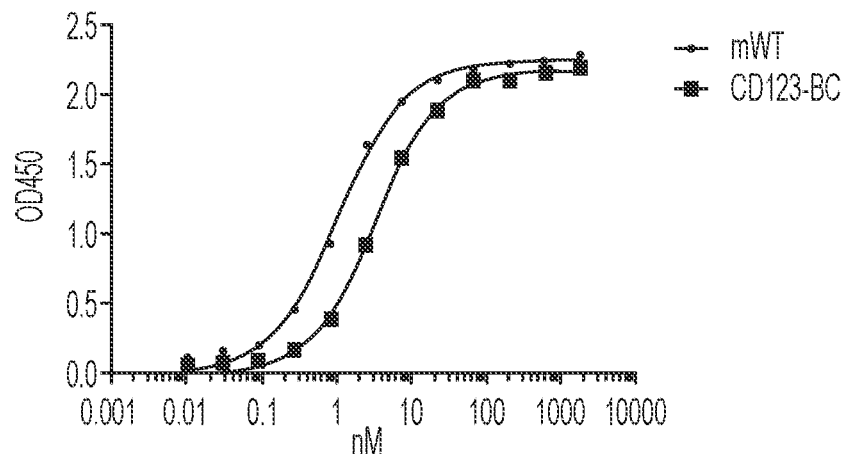
Figure 31:
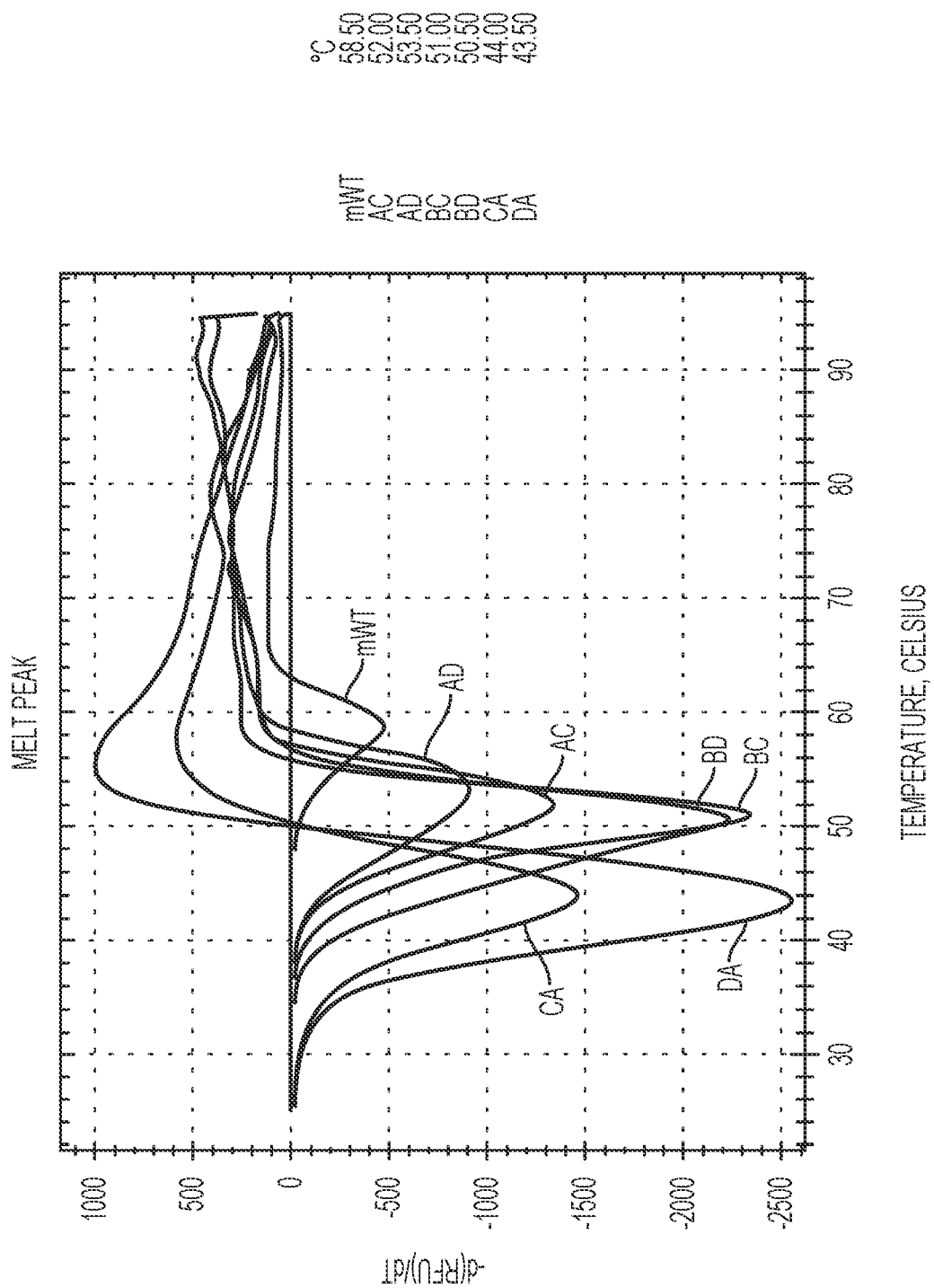
FIG. 31 is a graph showing melting temperatures of humanized anti-CD123 scFv variants measured using differential scanning fluorimetry (DSF).

The humanized anti-CD123 scFv variants were transiently expressed in HEK293 cells and were purified to near homogeneity via the C-terminal 6× His tag (SEQ ID NO: 128) (FIGS. 28 and 29A-29B). Expression levels of the variants were determined by UV280. Expression was compared to the mouse Ctrl scFv. Binding of the variants to the immobilized CD123 was confirmed by ELISA, and the estimated EC50 ranged from 1 to 10 nM as compared to that of the parent mouse scFv (~1.1-2.6 nM; FIGS. 30A and 30B). Thermal stability of the variants determined as melting temperatures was measured using the differential scanning fluorimetry (DSF). As shown in FIG. 31, the parent mouse scFv showed a melting temperature of 58.5° C., while the humanized anti-CD123 scFv variants had decreased melting temperatures ranging from 44° C. to 52° C. (FIG. 31).

Humanized sequence alignment with mouse sequences (SEQ ID NOS 92, 32, 31, 34, 33, and 93, respectively, in order of appearance):

```
VL
mouseV1      DIVLTQSPASLAVSLGQRATISCRASESVDNYGNTFMHWYQQKPGQPPKLLIYRASNLES

A_VK4_B3     DIVLTQSPDSLAVSLGERATINCRASESVDNYGNTFMHWYQQKPGQPPKLLIYRASNLES

B_VK3_L6     EIVLTQSPATLSLSPGERATLSCRASESVDNYGNTFMHWYQQKPGQAPRLLIYRASNLES
             :******:*::*.*:***.*************************.*:**********
```

```
mouseV1     GIPARFSGSGSRTDFTLTINPVEADDVATYYCQQSNEDPPTFGAGTKLELK

A_VK4_B3    GVPDRFSGSGSRTDFTLTISSLQAEDVAVYYCQQSNEDPPTFGQGTKLEIK

B_VK3_L6    GIPARFSGSGSRTDFTLTISSLEPEDVAVYYCQQSNEDPPTFGQGTKLEIK
            *:* **************.::..***.************** *****:*

VH
C_VH7_7-4.1 QIQLVQSGSELKKPGASVKVSCKASGYIFTNYGMNWVRQAPGQGLEWMGWINTYTGESTY

D_VH1_1-03  QIQLVQSGAEVKKPGASVKVSCKASGYIFTNYGMNWVRQAPGQRLEWMGWINTYTGESTY mouseVh     QIQLVQSGPELKKPGETVKISCKASGYIFTNYGMNWVKQAPGKSFKWMGWINTYTGESTY
            ********.*:**.::***********::.::**********

C_VH7_7-4.1 SADFKGRFVFSLDTSVSTAYLQINALKAEDTAVYYCARSGGYDPMDYWGQGTTVTVSS

D_VH1_1-03  SADFKGRVTITLDTSASTAYMELSSLRSEDTAVYYCARSGGYDPMDYWGQGTTVTVSS mouseVh     SADFKGRFAFSLETSASTAYLHINDLKNEDTATYFCARSGGYDPMDYWGQGTSVTVSS
            *******..::*:.**:..:.*:****.*:**************:**
```

Example 6

Characterization of Humanized CD123 CAR

Humanized anti-CD123 CAR constructs were generated based on the mouse anti-human CD123 scFv 32716 and inserted in a pELPS-41BB-CD3z backbone. Each plasmid was amplified by bacterial transformation using standard techniques in TOP10 cells, followed by a Maxiprep using the Qiagen Plasmid Maxi kit. Lentiviral supernatant was produced in 293T cells using standard techniques. Normal donor T cells were transduced with lentiviral supernatant and expanded using anti-CD3/CD28 beads and interleukin-2. Fold expansion of T cells transduced with each construct, or with a control mouse anti-human CD123 CAR (C1172) is shown in the following Table 3:

TABLE 3

Virus Production and T cell expansion

| Construct ID | Fold Expansion |
|---|---|
| NA (untransduced control) | 9 |
| C1172 | 21 |
| CAR8 (UL69-05CC) | 24 |
| CAR7 (WW88-24LB) | 23 |
| CAR3 (AW84-20CB) | 25 |
| CAR4 (QW85-24WB) | 24 |
| CAR5 (GW86-29RB) | 18 |
| CAR2 (KW82-25HB) | 23 |
| CAR6 (MW89-29GB) | 20 |
| CAR1 (UW81-20MB) | 20 |

Figure 32:
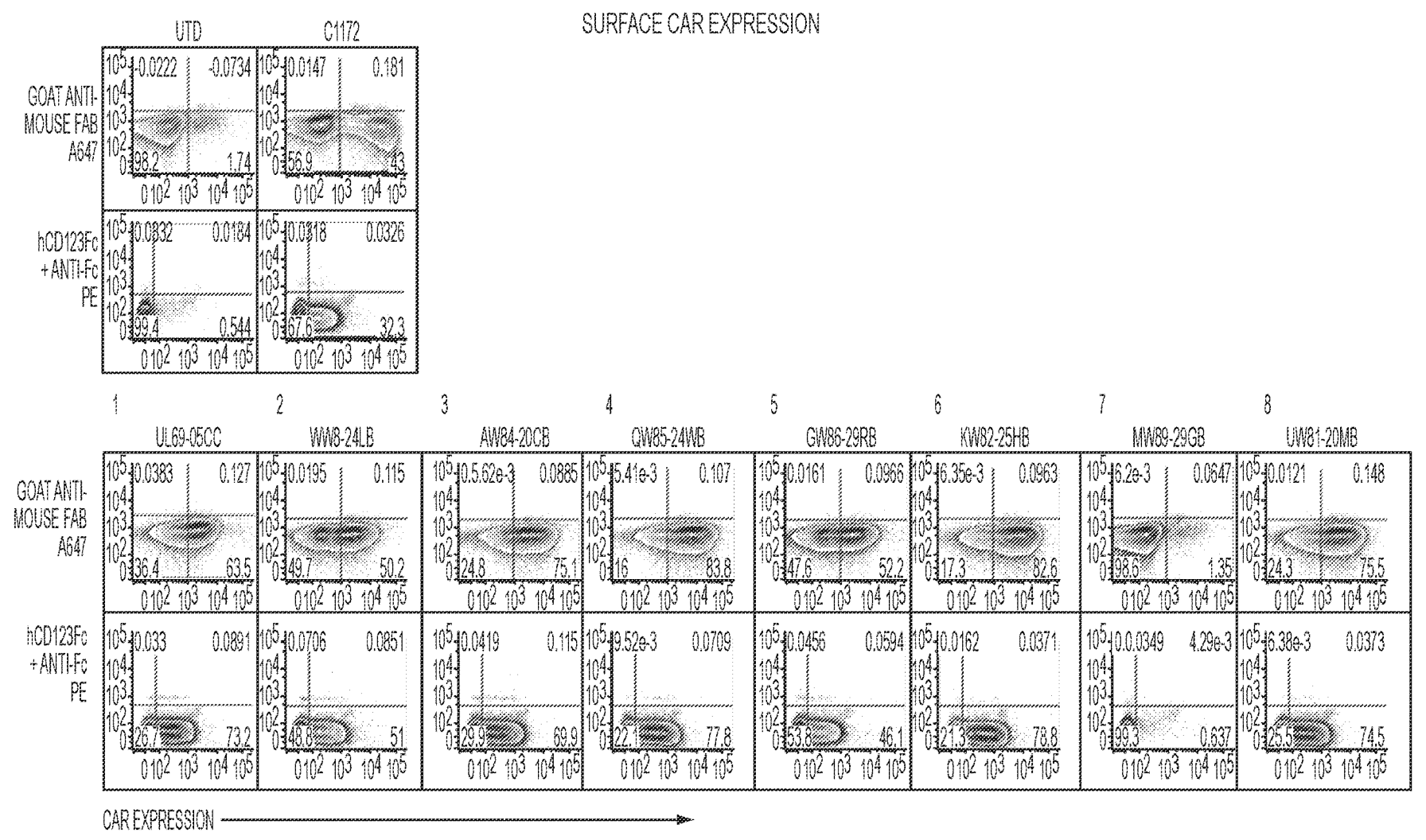

To detect the transduction efficiency and level of expression of each construct, transduced T cells on day 10 of expansion were stained with (i) Alexa fluor 647 goat anti-mouse F(ab) reagent, (ii) FITC goat anti-human F(ab), or (iii) human CD123-Fc primary followed by anti-human Fc PE. Anti-mouse F(ab) and CD123-Fc were found to have good correlation, suggesting that where CAR was expressed on the surface, it would be able to bind the target (FIG. 32). Anti-human F(ab) reagent did not detect CAR (data not shown).

TABLE 4

| Construct ID | Expression by Anti-Fab | Expression by CD123-Fc |
|---|---|---|
| NA (untransduced control) | 1.74 | 0.54 |
| C1172 | 43 | 32.3 |

TABLE 4-continued

| Construct ID | Expression by Anti-Fab | Expression by CD123-Fc |
|---|---|---|
| CAR8 (UL69-05CC) | 63.5 | 73.2 |
| CAR7 (WW88-24LB) | 50.2 | 51 |
| CAR3 (AW84-20CB) | 75.1 | 69.9 |
| CAR4 (QW85-24WB) | 83.8 | 77.8 |
| CAR5 (GW86-29RB) | 52.2 | 46.1 |
| CAR2 (KW82-25HB) | 82.6 | 78.6 |
| CAR6 (MW89-29GB) | 1.35 | 0.64 |
| CAR1 (UW81-20MB) | 75.5 | 74.5 |

Figure 33:
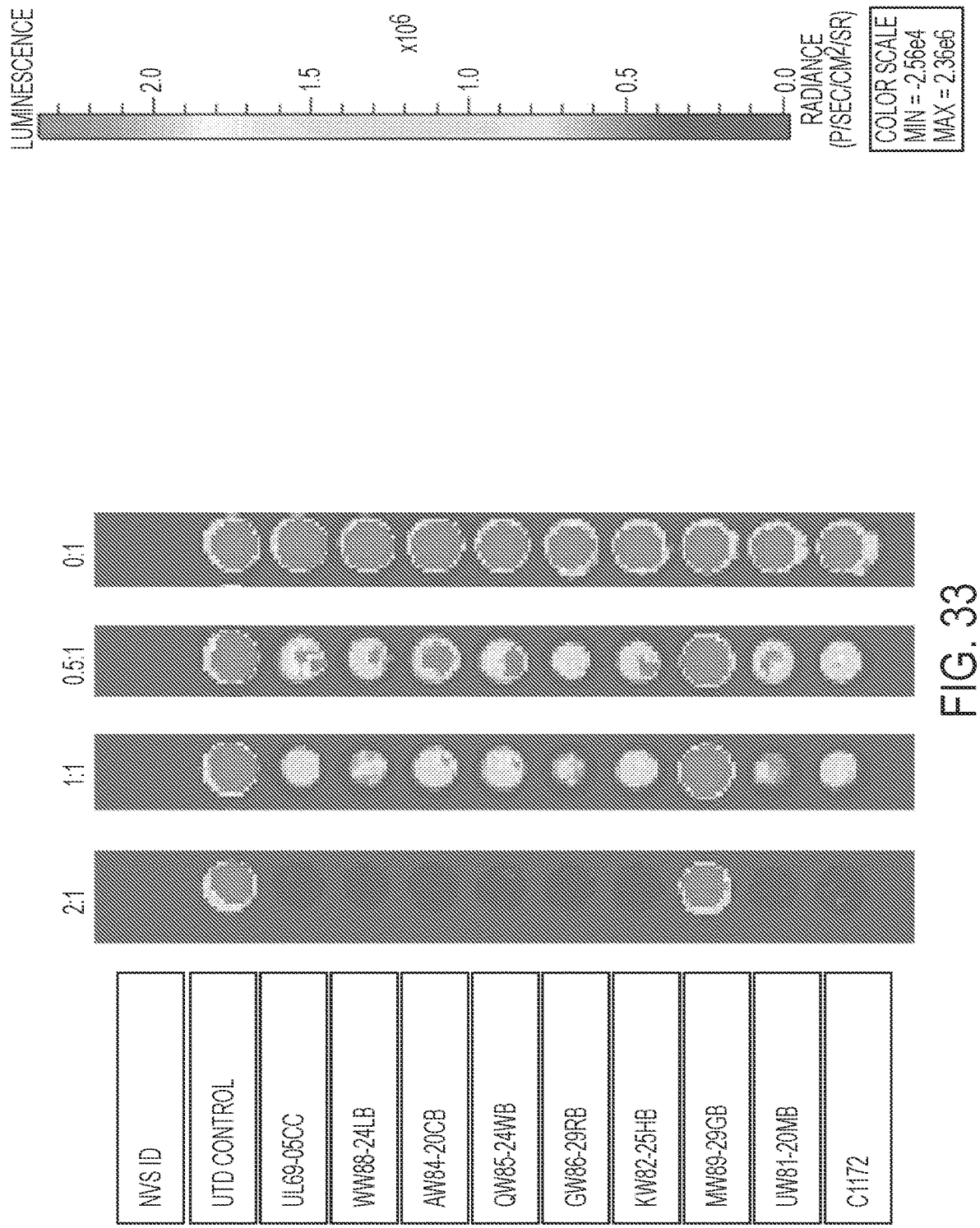
FIG. 33 is an image showing functional studies of T cells transduced with different humanized CAR constructs, or with control mouse anti-human CD123 CAR.
Figure 34:
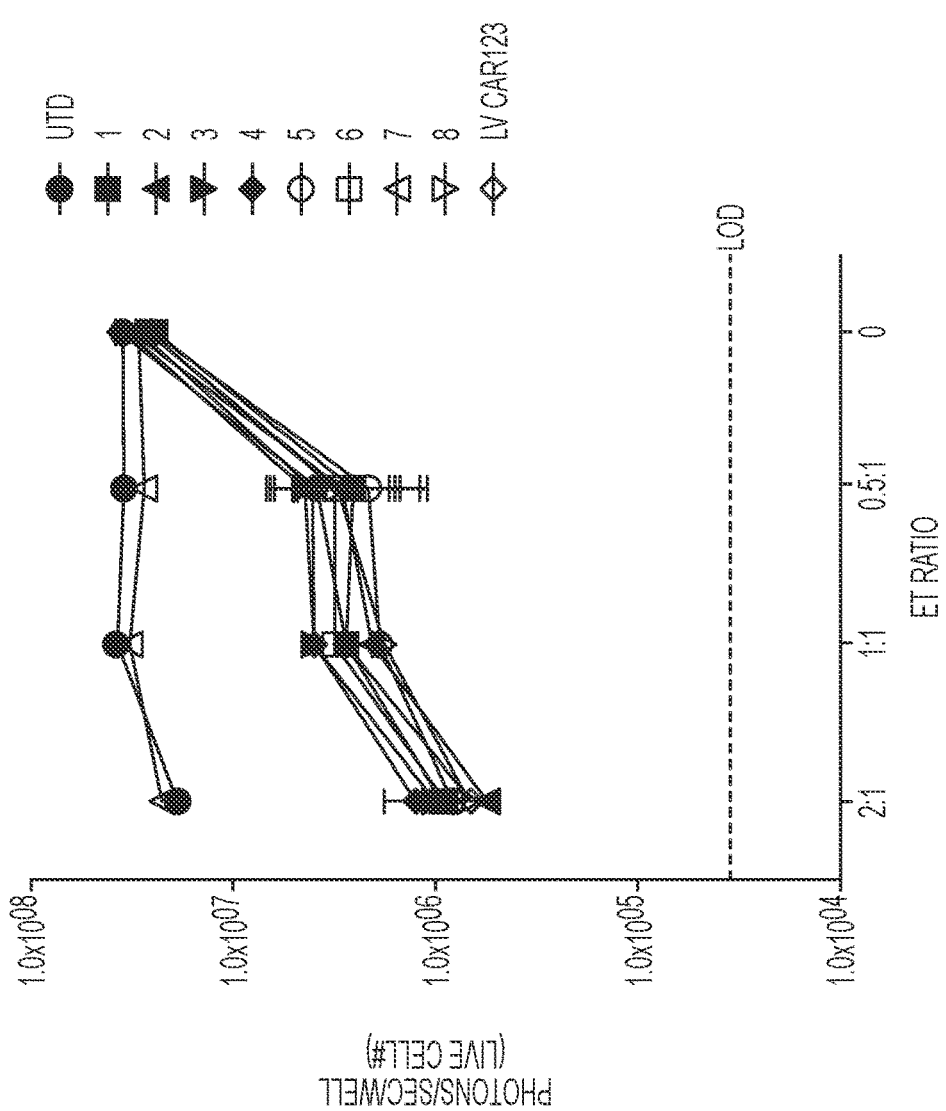
FIG. 34 is a graph showing results from killing assays with T cells transduced with different humanized CAR constructs, or with control mouse anti-human CD123 CAR.

MOLM14, a CD123-expression target cell line that had been previously transduced with firefly luciferase, was plated in a 96 well plate at $5 \times 10^4$ cells per well. T cells transduced with the different humanized CAR constructs, or with control mouse anti-human CD123 CAR, were plated at 2:1, 1:1, and 0.5:1 after correction for percent CAR expression. Specifically, all T cells were diluted to a CAR expression level of 40%, and therefore the effective E:T ratios were $2 \times 0.4 = 0.8:1$; $1 \times 0.4 = 0.4:1$; $0.5 \times 0.4 = 0.2:1$. Control wells contained MOLM14 cells alone (E:T=0:1), or MOLM14 cells killed with ETOH (MAX killing). After 16 hours, luciferin was added to each well and the plate was imaged for 10 seconds. Results are shown in FIG. 33. Results from a killing assay are presented in FIG. 34.

All constructs with the exception of MW89-29GB showed similar surface expression and anti-tumor efficacy. These constructs also show similar efficacy to the C1172 mouse anti-human CD123 construct.

Example 7

Anti-CD123 RNA CAR T Cell Therapy for AML and ALL

Figure 35:
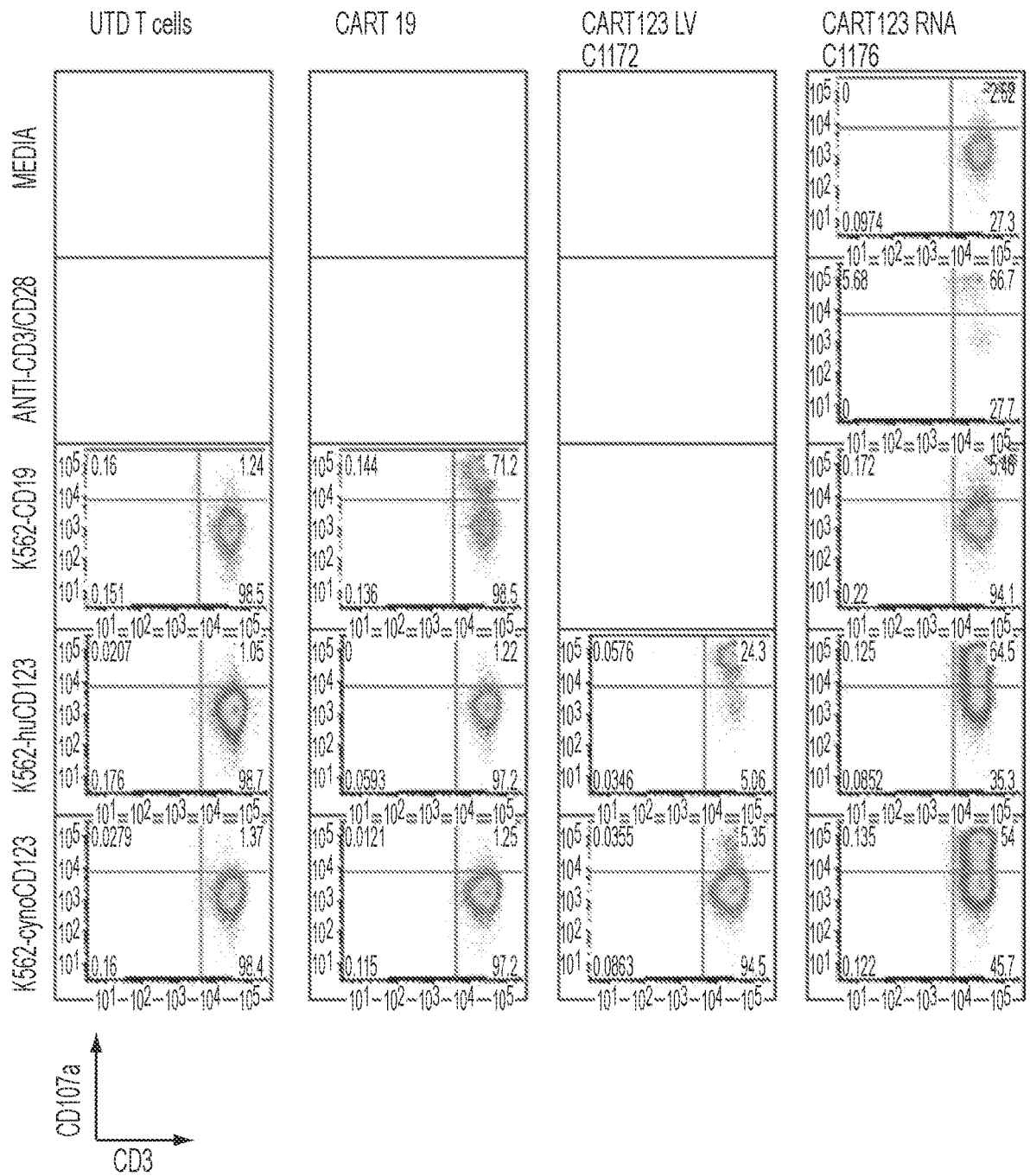
FIG. 35 is an image showing analysis of electroporated human T cells that were rested overnight, followed by a 2 hour co-incubation with targets in the presence of anti-CD107a, anti-CD49d and anti-CD28, and monensin, in a standard degranulation assay

Anti-CD123 CAR constructs C1172 (scFv 32716) and C1176 (scFv 26292) were cloned into a pDA vector. The nucleotide and amino acid sequences are provided in Table 2 as SEQ ID NOs:94-97. The constructs were subjected to in vitro transcription, and the resultant mRNA was electroporated into normal donor T cells. Human T cells were rested overnight, followed by a 2 hour co-incubation with targets (see FIG. 35), in the presence of anti-CD107a, anti-CD49d and anti-CD28, and monensin, in a standard degranulation assay. Controls were lentivirally transduced CART19, lentivirally transduced CART123 (construct C1172 based on the 32716 scFv), and anti-CD3/CD28 beads. Note C1176 recognizes cynomolgus CD123 as well as human CD123, whereas C1172 recognizes only human CD123.

These results show that T cells can be successfully electroporated with functional anti-CD123 CAR.

Figure 36:
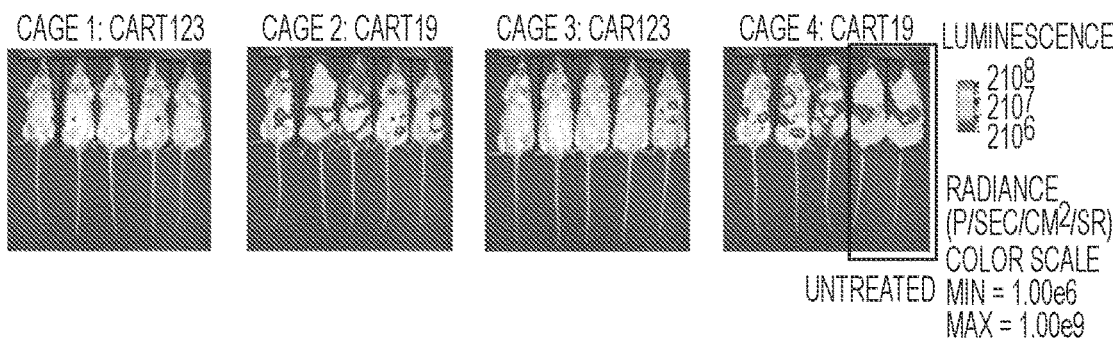
FIG. 36 is an image showing bioluminescence on D21 and D28 post-T cell injection into tumor-engrafted mice.
Figure 36:
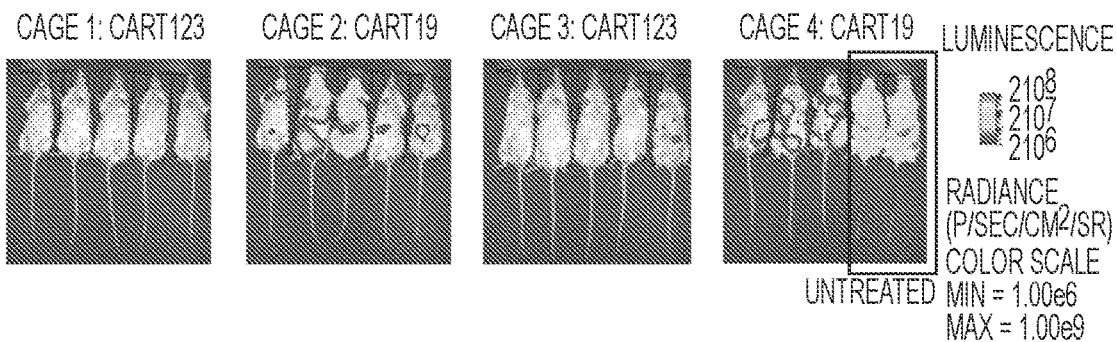
Figure 37:
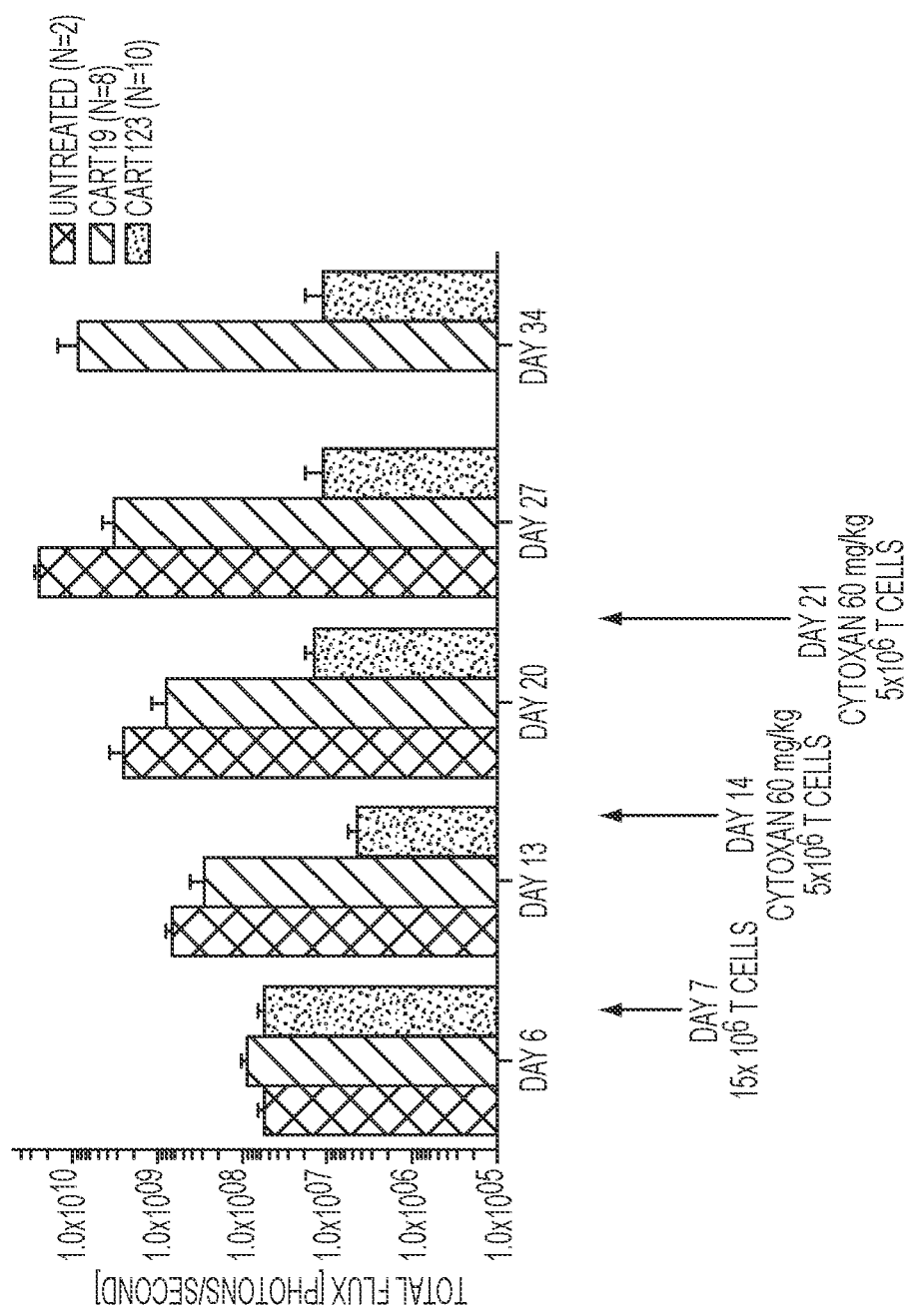
FIG. 37 is a graph showing that RNA-electroporated T cells can be used to induce an anti-tumor response in vivo in immunodeficient animals.

Normal donor T cells were expanded in vitro using anti-CD3/CD28 beads and rhIL2. Luciferase-expressing MOLM14 cells were injected iv (1×10$^6$ cells) into sublethally irradiated NSG mice on D0. Mice were imaged on D6 to confirm tumor engraftment (BLI). On D7, T cells were electroporated (EP) with RNA CD123 CAR or RNA CAR19 plasmid, or subjected to mock EP ("no treatment"), rested for 4 hours at 37 degrees, and then mice were treated with 15×10$^6$ engineered T cells. On D13, mice underwent BLI. On D14, thawed T cells were electroporated as above. On D14, mice were treated with cyclophosphamide 60 mg/kg i.v. for lymphodepletion, followed by an injection of 5×10$^6$ EP T cells iv. On D20, mice underwent BLI. On D21, thawed T cells were electroporated as above. On D21, mice were treated with cyclophosphamide 60 mg/kg i.v. for lymphodepletion, followed by an injection of 5×10$^6$ EP T cells i.v. Last imaging was performed on D34 to document the anti-tumor response. Bioluminescence on D21 and D28 post-T cell injection are shown in FIG. 36. Data demonstrating the anti-tumor effect are shown in FIG. 37.

These results show that RNA-electroporated CAR cells can be used to induce an anti-tumor response in vivo in immunodeficient animals.

Example 8

In Vivo Comparison of Anti-Tumor Efficacy of Anti-CD123 CAR T Cells

Figure 38:
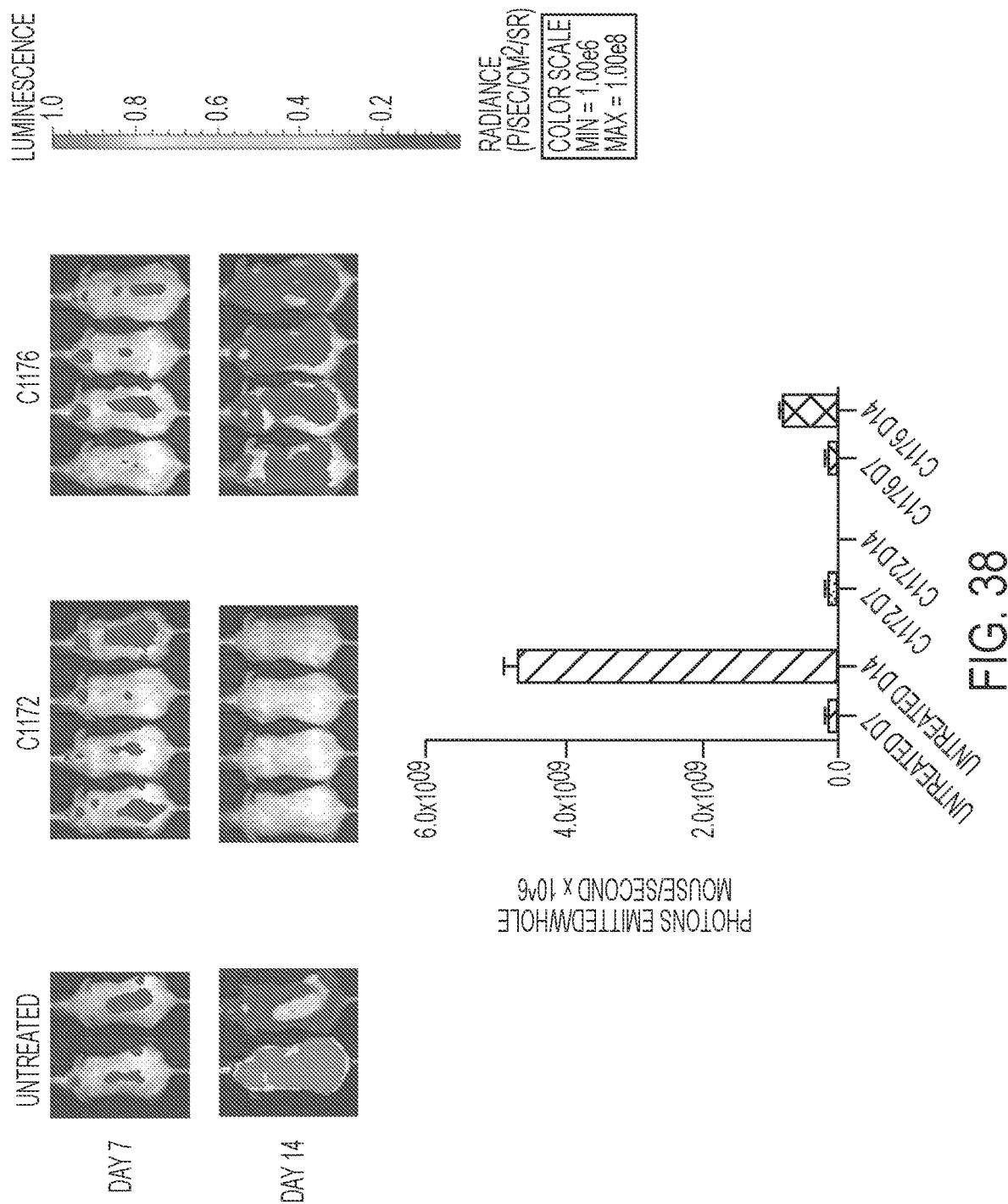
FIG. 38 is an image showing tumor burden by bioluminescent imaging of tumor engrafted mice injected with CD123 CART T cells.

T cells were transduced with the following constructs: C1172 (anti-CD123 32716 light-to-heavy chain CD8H 4-1BB CD3z; C1176 (anti-CD123 26292 light-to-heavy chain CD8H 4-1BB CD3z); 10 NSG mice were injected with MOLM14 Luc 1×10$^6$ on D0. Animals were imaged for tumor burden on D7, followed by injection of 1×10$^6$ T cells as follows: No T cells n=2; CART123_C1172 n=4 (50% CAR+ T cells); CART123_C1176 n=4 (50% CAR+ T cells). Tumor burden was followed serially by bioluminescent imaging (FIG. 38). Tumor burden as shown by bioluminescence 7 days after injection of T cells was lower in both T cell groups than in the untreated group, and CART123_C1172 appeared to be somewhat more potent than CART123_C1176.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of eradicating at least a portion of existing CD123-expressing cells in the bone marrow in a subject, the method comprising administering to the subject an effective amount of T cells expressing a chimeric antigen receptor (CAR) molecule comprising an anti-CD123 binding domain, a transmembrane domain, and an intracellular signaling domain, thereby eradicating at least a portion of the existing CD123-expressing cells in the bone marrow in a subject, wherein said anti-CD123 binding domain comprises:

(a) a light chain variable region comprising:
a light chain complementarity determining region 1 (LC CDR1) comprising the sequence of SEQ ID NO: 20, a light chain complementarity determining region 2 (LC CDR2) comprising the sequence of SEQ ID NO: 21, and a light chain complementarity determining region 3 (LC CDR3) comprising the sequence of SEQ ID NO: 22, and
a heavy chain variable region comprising:
a heavy chain complementarity determining region 1 (HC CDR1) comprising the sequence of SEQ ID NO: 16, a heavy chain complementarity determining region 2 (HC CDR2)

comprising the sequence of SEQ ID NO: 17, and a heavy chain complementarity determining region 3 (HC CDR3) comprising the sequence of SEQ ID NO: 18; or (b) a light chain variable region comprising:
a light chain complementarity determining region 1 (LC CDR1) comprising the sequence of SEQ ID NO: 28, a light chain complementarity determining region 2 (LC CDR2) comprising the sequence of SEQ ID NO: 29, and a light chain complementarity determining region 3 (LC CDR3) comprising the sequence of SEQ ID NO: 30, and
a heavy chain variable region comprising:
a heavy chain complementarity determining region 1 (HC CDR1) comprising the sequence of SEQ ID NO: 24, a heavy chain complementarity determining region 2 (HC CDR2) comprising the sequence of SEQ ID NO: 25, and a heavy chain complementarity determining region 3 (HC CDR3) comprising the sequence of SEQ ID NO: 26; or (c) a light chain variable region comprising:
a light chain complementarity determining region 1 (LC CDR1) comprising the sequence of SEQ ID NO: 87, a light chain complementarity determining region 2 (LC CDR2) comprising the sequence of SEQ ID NO: 88, and a light chain complementarity determining region 3 (LC CDR3) comprising the sequence of SEQ ID NO: 89, and
a heavy chain variable region comprising:
a heavy chain complementarity determining region 1 (HC CDR1) comprising the sequence of SEQ ID NO: 84, a heavy chain complementarity determining region 2 (HC CDR2) comprising the sequence of SEQ ID NO: 85, and a heavy chain complementarity determining region 3 (HC CDR3) comprising the sequence of SEQ ID NO: 86.

2. A method of treating a subject having cancer, the method comprising
administering to the subject an amount of T cells expressing a chimeric antigen receptor (CAR) molecule effective to eradicate at least a portion of existing CD123-expressing cells in the bone marrow in a subject, wherein said CAR molecule comprises an anti-CD123 binding domain, a transmembrane domain, and an intracellular signaling domain,
thereby treating the subject having cancer, wherein said anti-CD123 binding domain comprises:

(a) a light chain variable region comprising:
a light chain complementarity determining region 1 (LC CDR1) comprising the sequence of SEQ ID NO: 20, a light chain complementarity determining region 2 (LC CDR2) comprising the sequence of SEQ ID NO: 21, and a light chain complementarity determining region 3 (LC CDR3) comprising the sequence of SEQ ID NO: 22, and
a heavy chain variable region comprising:
a heavy chain complementarity determining region 1 (HC CDR1) comprising the sequence of SEQ ID NO: 16, a heavy chain complementarity determining region 2 (HC CDR2) comprising the sequence of SEQ ID NO: 17, and a heavy chain complementarity determining region 3 (HC CDR3) comprising the sequence of SEQ ID NO: 18; or (b) a light chain variable region comprising:
a light chain complementarity determining region 1 (LC CDR1) comprising the sequence of SEQ ID NO: 28, a light chain complementarity determining region 2 (LC CDR2) comprising the sequence of SEQ ID NO: 29, and a light chain complementarity determining region 3 (LC CDR3) comprising the sequence of SEQ ID NO: 30, and
a heavy chain variable region comprising:
a heavy chain complementarity determining region 1 (HC CDR1) comprising the sequence of SEQ ID NO: 24, a heavy chain complementarity determining region 2 (HC CDR2) comprising the sequence of SEQ ID NO: 25, and a heavy chain complementarity determining region 3 (HC CDR3) comprising the sequence of SEQ ID NO: 26; or (c) a light chain variable region comprising:
a light chain complementarity determining region 1 (LC CDR1) comprising the sequence of SEQ ID NO: 87, a light chain complementarity determining region 2 (LC CDR2) comprising the sequence of SEQ ID NO: 88, and a light chain complementarity determining region 3 (LC CDR3) comprising the sequence of SEQ ID NO: 89, and
a heavy chain variable region comprising:
a heavy chain complementarity determining region 1 (HC CDR1) comprising the sequence of SEQ ID NO: 84, a heavy chain complementarity determining region 2 (HC CDR2) comprising the sequence of SEQ ID NO: 85, and a heavy chain complementarity determining region 3 (HC CDR3) comprising the sequence of SEQ ID NO: 86.

3. A method of treating a subject having a disease, disorder or condition that is treatable with a bone marrow transplant or bone marrow reconditioning, the method comprising
administering to the subject an amount of T cells expressing a chimeric antigen receptor (CAR) molecule effective to eradicate at least a portion of existing CD123-expressing cells in the bone marrow in a subject, wherein said CAR molecule comprises an anti-CD123 binding domain, a transmembrane domain, and an intracellular signaling domain,
thereby treating the subject having a disease, disorder or condition that is treatable with a bone marrow transplant or bone marrow reconditioning, wherein said anti-CD123 binding domain comprises:

(a) a light chain variable region comprising:
a light chain complementarity determining region 1 (LC CDR1) comprising the sequence of SEQ ID NO: 20, a light chain complementarity determining region 2 (LC CDR2) comprising the sequence of SEQ ID NO: 21, and a light chain complementarity determining region 3 (LC CDR3) comprising the sequence of SEQ ID NO: 22, and
a heavy chain variable region comprising:
a heavy chain complementarity determining region 1 (HC CDR1) comprising the sequence of SEQ ID NO: 16, a heavy chain complementarity determining region 2 (HC CDR2) comprising the sequence of SEQ ID NO: 17, and a heavy chain complementarity determining region 3 (HC CDR3) comprising the sequence of SEQ ID NO: 18; or (b) a light chain variable region comprising:
a light chain complementarity determining region 1 (LC CDR1) comprising the sequence of SEQ ID NO: 28, a light chain complementarity determining region 2 (LC CDR2) comprising the sequence of SEQ ID NO: 29, and a light chain complementarity determining region 3 (LC CDR3) comprising the sequence of SEQ ID NO: 30, and
a heavy chain variable region comprising:
a heavy chain complementarity determining region 1 (HC CDR1) comprising the sequence of SEQ ID NO: 24, a heavy chain complementarity determining region 2

(HC CDR2) comprising the sequence of SEQ ID NO: 25, and a heavy chain complementarity determining region 3 (HC CDR3) comprising the sequence of SEQ ID NO: 26; or (c) a light chain variable region comprising:

a light chain complementarity determining region 1 (LC CDR1) comprising the sequence of SEQ ID NO: 87, a light chain complementarity determining region 2 (LC CDR2) comprising the sequence of SEQ ID NO: 88, and a light chain complementarity determining region 3 (LC CDR3) comprising the sequence of SEQ ID NO: 89, and a heavy chain variable region comprising:

a heavy chain complementarity determining region 1 (HC CDR1) comprising the sequence of SEQ ID NO: 84, a heavy chain complementarity determining region 2 (HC CDR2) comprising the sequence of SEQ ID NO: 85, and a heavy chain complementarity determining region 3 (HC CDR3) comprising the sequence of SEQ ID NO: 86.

4. The method of claim 1, wherein the method is a cellular conditioning method prior to bone marrow transplantation.

5. The method of claim 1, wherein the portion of existing CD123-expressing cells in the bone marrow eradicated comprises normal CD123-expressing bone marrow cells.

6. The method of claim 1, wherein the portion of existing CD123-epxressing cells in the bone marrow eradicated comprises CD123-expressing bone marrow myeloid progenitor cells.

7. The method of claim 1, wherein all or essentially all of the existing CD123-expressing cells in the bone marrow in the subject is eradicated.

8. The method of claim 1, wherein the number of CD123-expressing cells in bone marrow is reduced.

9. The method of claim 1, wherein the subject is in need of a bone marrow transplant or bone marrow reconditioning.

10. The method of claim 1, wherein the subject has a disease, disorder or condition that is treatable with a bone marrow transplant or bone marrow reconditioning.

11. The method of claim 10, wherein the disease, disorder or condition is selected from the group consisting of a hematological cancer, a solid tumor, a hematological disease, a metabolic disorder, HIV, HTLV, a lysosomal storage disorder and an immunodeficiency.

12. The method of claim 11, wherein the hematological cancer is a leukemia, lymphoma, or myeloma.

13. The method of claim 11, wherein the hematological cancer acute lymphoblastic leukemia (ALL), acute myeloid leukemia (AML), chronic lymphoid leukemia (CLL), chronic myelogenous leukemia (CML), Hodgkin's disease, Non-Hodgkin's lymphoma, or multiple myeloma.

14. The method of claim 1, wherein the method is performed prior to a bone marrow transplant.

15. The method of claim 1, further comprising administering a bone marrow transplant to the subject following the eradication of at least a portion of existing CD123-expressing cells in the bone marrow in the subject.

16. The method of claim 15, wherein the bone marrow transplant comprises transplantation of a stem cell.

17. The method of claim 15, wherein the bone marrow transplant comprises transplantation of autologous bone marrow cells or autologous stem cells.

18. The method of claim 15, wherein the bone marrow transplant comprises transplantation of allogeneic bone marrow cells or allogeneic stem cells.

19. The method of claim 1, wherein the subject has a hematological cancer or a solid tumor.

20. The method of claim 19, further comprising administering one or more anti-cancer therapy.

21. The method of claim 20, wherein the anti-cancer therapy is an anti-cancer CAR therapy, chemotherapy, or radiation.

22. The method of claim 1, wherein the T cells expressing the CAR molecule are CD8+ T cells.

23. The method of claim 1, wherein the T cells expressing the CAR molecule are human cells.

24. The method of claim 1, wherein the T cells expressing the CAR molecule are allogeneic T cells.

25. The method of claim 1, wherein the T cells expressing the CAR molecule are autologous T cells.

26. The method of claim 1, wherein the anti-CD123 binding domain comprises an antibody molecule.

27. The method of claim 26, wherein the antibody molecule comprises a scFv, a F(ab'), a F(ab')2, a Fv fragment, an immunoglobulin single domain antibody (sdAb), a single light chain variable domain (VL), a single heavy chain variable domain (VH), or a nanobody.

28. The method of claim 26, wherein the antibody molecule is a murine, human, or humanized antibody molecule.

29. The method of claim 1, wherein (a) the anti-CD123 binding domain comprises a light chain variable region comprising an amino acid sequence having at least one, two or three modifications but not more than 30, 20 or 10 modifications of an amino acid sequence of a light chain variable region provided in SEQ ID NO: 36, SEQ ID NO: 42, SEQ ID NO: 48, SEQ ID NO: 54, SEQ ID NO: 60, SEQ ID NO: 66, SEQ ID NO: 72, or SEQ ID NO: 78, or a sequence with 95-99% identity to an amino acid sequence provided in SEQ ID NO: 36, SEQ ID NO: 42, SEQ ID NO: 48, SEQ ID NO: 54, SEQ ID NO: 60, SEQ ID NO: 66, SEQ ID NO: 72, or SEQ ID NO: 78;

(b) the anti-CD123 binding domain comprises a heavy chain variable region comprising an amino acid sequence having at least one, two or three modifications but not more than 30, 20 or 10 modifications of an amino acid sequence of a heavy chain variable region provided in SEQ ID NO: 36, SEQ ID NO: 42, SEQ ID NO: 48, SEQ ID NO: 54, SEQ ID NO: 60, SEQ ID NO: 66, SEQ ID NO: 72, or SEQ ID NO: 78, or a sequence with 95-99% identity to an amino acid sequence provided in SEQ ID NO: 36, SEQ ID NO: 42, SEQ ID NO: 48, SEQ ID NO: 54, SEQ ID NO: 60, SEQ ID NO: 66, SEQ ID NO: 72, or SEQ ID NO: 78; or (c) both (a) and (b).

30. The method of claim 1, wherein the anti-CD123 binding domain comprises an amino acid sequence selected from the group consisting of SEQ ID NO: 36, SEQ ID NO: 42, SEQ ID NO: 48, SEQ ID NO: 54, SEQ ID NO: 60, SEQ ID NO: 66, SEQ ID NO: 72, and SEQ ID NO: 78, or a sequence with 95-99% identity thereof.

31. The method of claim 1, wherein the anti-CD123 binding domain comprises the amino acid sequence of SEQ ID NO: 101 or SEQ ID NO: 2, or an amino acid sequence with 95-99% identity thereto.

32. The method of claim 1, wherein the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154.

33. The method of claim 1, wherein the transmembrane domain comprises the amino acid sequence of SEQ ID NO: 5; an amino acid sequence comprising at least one, two or three modifications but not more than 20, 10 or 5 modifications of the amino acid sequence of SEQ ID NO: 5; or an amino acid sequence with 95-99% identity to the amino acid sequence of SEQ ID NO:5.

34. The method of claim 1, wherein the anti-CD123 binding domain is connected to the transmembrane domain by a hinge region.

35. The method of claim 34, wherein the hinge region comprises the amino acid sequence of any of SEQ ID NO: 4, 104, 122 or 124, or a sequence with 95-99% identity thereof.

36. The method of claim 1, wherein the intracellular signaling domain comprises a functional signaling domain of 4-1BB and a functional signaling domain of CD3 zeta.

37. The method of claim 1, wherein the intracellular signaling domain comprises a costimulatory domain.

38. The method of claim 1, wherein the intracellular signaling domain comprises a primary signaling domain.

39. The method of claim 1, wherein the intracellular signaling domain comprises a costimulatory domain and a primary signaling domain.

40. The method of claim 1, wherein the intracellular signaling domain comprises:
   (i) the amino acid sequence of SEQ ID NO: 6 or SEQ ID NO: 23;
   (ii) the amino acid sequence of SEQ ID NO: 7 or SEQ ID NO: 98; or
   (iii) both (i) and (ii).

41. The method of claim 37, wherein the costimulatory domain comprises a functional signaling domain of a protein selected from the group consisting of OX40, CD27, CD28, CDS, ICAM-1, LFA-1 (CD11a/CD18), ICOS (CD278), and 4-1BB (CD137).

42. The method of claim 37, wherein the costimulatory domain comprises
   (i) the amino acid sequence of SEQ ID NO: 6 or SEQ ID NO: 23; an amino acid sequence comprising at least one, two or three modifications but not more than 20, 10 or 5 modifications of the amino acid sequence of SEQ ID NO: 6 or SEQ ID NO: 23; or a sequence with 95-99% identity to the amino acid sequence of SEQ ID NO: 6 or SEQ ID NO: 23.

43. The method of claim 1, wherein intracellular signaling domain comprises:
   (i) a costimulatory domain comprising a functional signaling domain of a protein chosen from OX40, CD27, CD28, CDS, ICAM-1, LFA-1 (CD11a/CD18), ICOS (CD278), or 4-1BB (CD137);
   (ii) a primary signaling domain comprising a functional signaling domain derived from CD3 zeta, FcR gamma, FcR beta, CD3 gamma, CD3 delta, CD3 epsilon, CD5, CD22, CD79a, CD79b, CD278, CD66d, DAP10, or DAP12; or
   (iii) both (i) and (ii).

44. The method of claim 39, wherein the costimulatory domain comprises the amino acid sequence of SEQ ID NO: 6 or SEQ ID NO: 23; an amino acid sequence having at least one, two or three modifications but not more than 20, 10 or 5 modifications of the amino acid sequence of SEQ ID NO: 6 or SEQ ID NO: 23; or a sequence with 95-99% identity to the amino acid sequence of SEQ ID NO: 6 or SEQ ID NO: 23, and the primary signaling domain comprises the amino acid sequence of SEQ ID NO: 7 or SEQ ID NO: 98; an amino acid sequence having at least one, two or three modifications but not more than 20, 10 or 5 modifications of the amino acid sequence of SEQ ID NO: 7 or SEQ ID NO: 98; or a sequence with 95-99% identity to the amino acid sequence of SEQ ID NO: 7 or SEQ ID NO: 98.

45. The method of claim 1, wherein the CAR molecule comprises an amino acid sequence selected from the group consisting of SEQ ID NO:41, SEQ ID NO:47, SEQ ID NO:53, SEQ ID NO:59, SEQ ID NO:65, SEQ ID NO:71, SEQ ID NO:77, or SEQ ID NO:83, or a sequence with 95-99% identity thereof.

46. The method of claim 1, wherein the CAR molecule comprises an amino acid sequence of SEQ ID NO: 100, or a sequence with 95-99% identity thereof.

47. The method of claim 1, wherein the CAR molecule comprises an amino acid sequence of SEQ ID NO: 97, or a sequence with 95-99% identity thereof.

* * * * *

UNITED STATES PATENT AND TRADEMARK OFFICE
CERTIFICATE OF CORRECTION

| | | |
|---|---|---|
| PATENT NO. | : 11,028,177 B2 | Page 1 of 1 |
| APPLICATION NO. | : 15/400096 | |
| DATED | : June 8, 2021 | |
| INVENTOR(S) | : Brogdon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this
Thirty-first Day of January, 2023

*Katherine Kelly Vidal*

Katherine Kelly Vidal
*Director of the United States Patent and Trademark Office*